US008163474B2

(12) United States Patent
Lu et al.

(10) Patent No.: US 8,163,474 B2

(45) Date of Patent: Apr. 24, 2012

(54) NS1-NP DIAGNOSTICS OF INFLUENZA VIRUS INFECTION

(75) Inventors: Peter S. Lu, Palo Alto, CA (US); Michael P. Belmares, San Jose, CA (US); Carol Tan, Albany, CA (US); Linda McAllister, Sunnyvale, CA (US)

(73) Assignee: Arbor Vita Corporation, Fremont, CA (US)

( * ) Notice: Subject to any disclaimer, the term of this patent is extended or adjusted under 35 U.S.C. 154(b) by 0 days.

(21) Appl. No.: 12/405,150

(22) Filed: Mar. 16, 2009

(65) Prior Publication Data

US 2009/0280504 A1 Nov. 12, 2009

Related U.S. Application Data

(60) Provisional application No. 61/036,954, filed on Mar. 15, 2008.

(51) Int. Cl.
*C12Q 1/70* (2006.01)
*G01N 33/53* (2006.01)
*A61K 39/1451* (2006.01)

(52) U.S. Cl. ........................... 435/5; 435/7.1; 424/209.1

(58) Field of Classification Search ........................ None
See application file for complete search history.

(56) References Cited

U.S. PATENT DOCUMENTS

| | | | |
|---|---|---|---|
| 2004/0152142 | A1 | 8/2004 | Klepp et al. |
| 2007/0161078 | A1 | 7/2007 | Lu et al. |
| 2007/0224594 | A1 | 9/2007 | Lu et al. |

OTHER PUBLICATIONS

Lupiani et al. Proceeding of The Institute of Food Technologists First Annual Food Protection & Defense Research Conference, 2005, Atlanta Georgia, pp. 1-36.*
Julkunen et al. Vaccine, 2001, vol. 19, pp. S32-S37.*
Panshin et al. Virus Genes 2010, DOI 10.1007/s11262-010-0522-3.*
International search report dated Jun. 5, 2009 for PCT/US2009/037287.

* cited by examiner

*Primary Examiner* — Bao Li
(74) *Attorney, Agent, or Firm* — Wilson Sonsini Goodrich & Rosati

(57) ABSTRACT

The present application describes methods for assessing influenza infection, including prognosis. An assay that determines the amount of the NS1 and NP proteins of influenza virus shows enhanced sensitivity and reliability compared to either antigen alone. Many formats employ pan-specific antibodies (i.e., that react with all or at least with multiple strains within an influenza type).

22 Claims, 24 Drawing Sheets

MXXXXXXXFQVXCFLWXXRKXXXXXXXXDXPFXDRXXRXXXXXXGRXXTXXXX
IXXXXXXGXXIXXXXXXXXXXXXXXXXXXSXXXXXYXXXMXXXXXXXXXXXXX
XXXXXXXXXXXXXDQXXXXKXXXLXXXXXXXXXXXXXXXLXRXXXXXXXXXXG
XXXXXXXXXXXXXXXXXXXXXXXXXXXEXXXXXXXXXXXXXXXXXXXXXXEXX
XXXXXXXXXXXXXXXXXX

FIG. 1A

XXXXXXXXXXXXXXXXXVXXRFXDXEXGXAXXXXXXXXXQXXXXXXXXXXGLD
XXXXXXXXXXXXEXXXEXXXDXXXXXXIAXVXXXXXLXXXXLXXXXXXXXXXX
XXXXXXXSXXXXMXXXIMXXXXXXXXXXXXXXXXXXXXXXXXXXXXXXXXRXX
XXXXXXXXXXXXXXXXXXXXXXXXXXXXXXXXXXXENXXXXXXXXXXXXXXXX
XXXXXXXXXXXRXXE(S/P)EV

FIG. 1B

MDSNTVLSFQVDCFLWHVRKRFADQELGDAPFLDRLRRDQKSLRGRGNTLGLDIETATRAGK
QIVERILEEESDEALKMTIASVPASRYLTDMTLEEMSRDWFMLMPKQKVAGSLCIKMDQAIM
DKTIILKANFSVIFDRLETLILLRAFTEEGAIRVGEISPLPSLPGHTGEDVKNAIGVLIGGL
EWNDNTVRVSENTIQRFAWRGSDEDGRLPFPPNQKRKMARTIESEVEK

FIG. 2

MADNMTTTQIEVGPGATNATINFEAGILECYERLSWQRALDYPGQDRLNRLKRKLESRIKTH
NKSEPESKRMSLEERKAIGVKMMKVLLFMDPSAGIEGFEPYCMKNPSNSNCPKCNWADYPLT
PGKCLDDIEEEPEDVDDPTEIVLRDMNNKDARQKIKEEVNTQKEGKFRLTIKRDIRNVLSLR
VLVNGTFLKHPNGYKSLLTLHRLNAYDQSGRLVAKLVATDDLTVEDEEDGHRILNSLFERFN
EGHPKPIRAAETAMGVLSQFGQEHRLSPEEGDN

FIG. 3

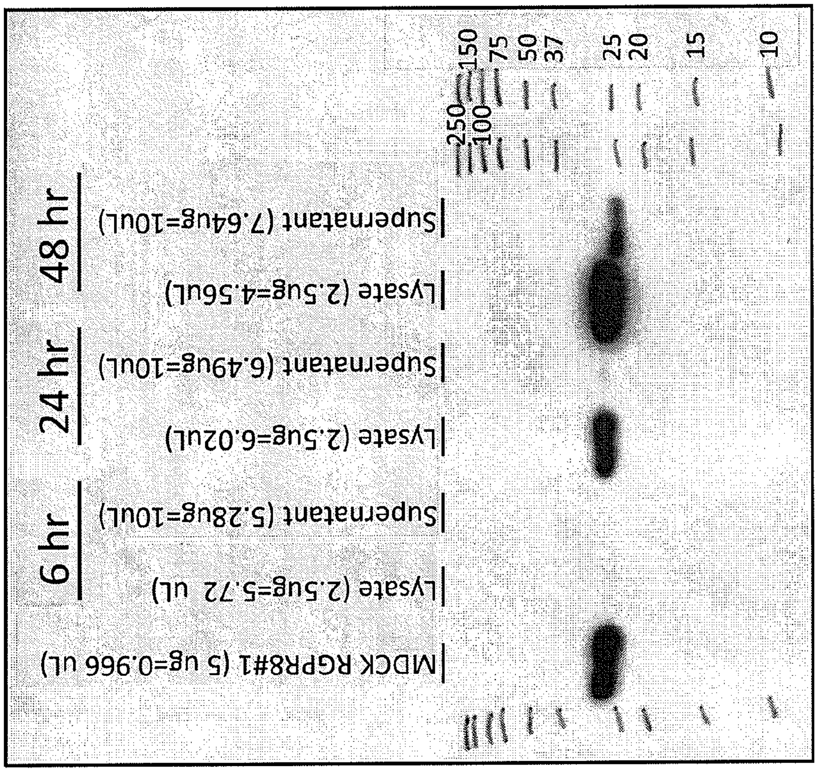
ECL+, 3min
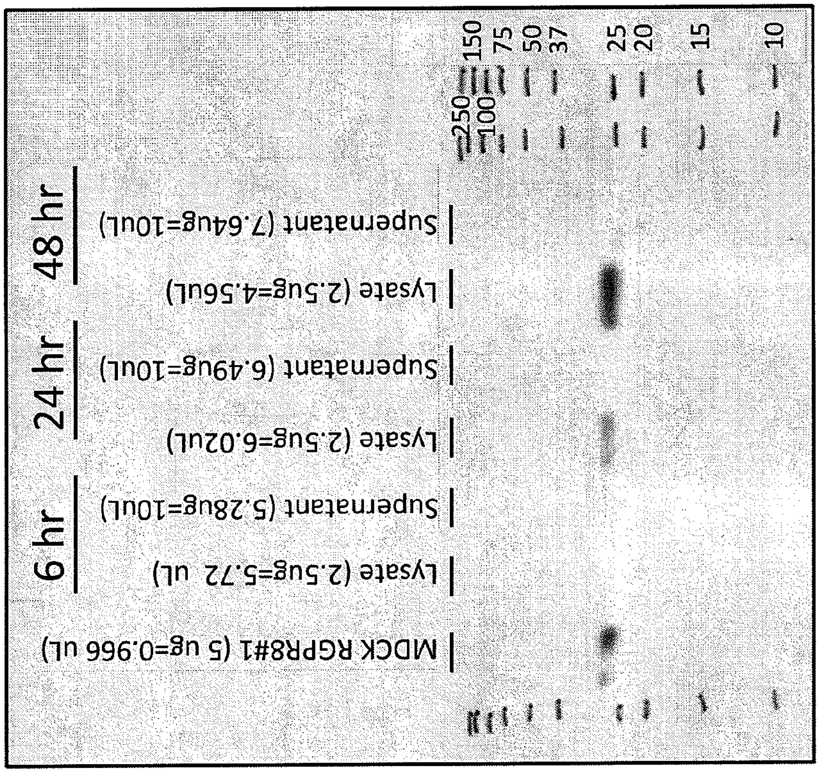
ECL+, 1sec
Figure 5

Sample 1 (+)
In saline

Sample 2 (+)
In saline

Sample 3 (+)
In saline

Pan-Flu A Test
In 80% M4 media, 20% buffer B3

Avian Flu Test
In 80% M4 media, 20% buffer B3

|        | F89-1F4 | F89-2A10 | F89-2F3 | F89-2H2 | F89-4D5 | F89-4G12 |
|--------|---------|----------|---------|---------|---------|----------|
| Detector | ☺ | x | x | x | ☺ | ☺ |
| Capture  | ☺ | x | x | x | ☺ | ☺ |

|        | F89-7H10 | F94-4C10 | F94-1F8 | F94-3A1 | F94-1F9 | F94-5E5 |
|--------|----------|----------|---------|---------|---------|---------|
| Detector | x | ☺⁺ | x | ☺ | x | x |
| Capture  | x | x | ☺* | ☺ | ☺* | ☺* |

\* With influenza 522
\+ With influenza 523

SEQUENCE OF MBP FUSION PEPTIDE COMPRISING 3 COPIES OF PSD95 DOMAIN 2:

1
*MSPILGYWKIKGLVQPTRLLLEYLEEKYEEHLYERDEGDKWRNKKFELGLEFPNLPYYID*

*61*
*GDVKLTQSMAIIRYIADKHNMLGGCPKERAEISMLEGAVLDIRYGVSRIAYSKDFETLKV*

*121*
*DFLSKLPEMLKMFEDRLCHKTYLNGDHVTHPDFMLYDALDVVLYMDPMCLDAFPKLVCFK*

*181*
*KRIEAIPQIDKYLKSSKYIAWPLQGWQATFGGGDHPPKSDLVPRGSPGISGGGGGLVPRG*

241
*SPGS*GTEPAEKVMEIKLIKGPKGLGFSIAGGVGNQHIPGDNSIYVTKIIEGGAAHKDGRL

301
QIGDKILAVNSVGLEDVMHEDAVAALKNTYDVVYLKVAKRKPPAEKVMEIKLIKGPKGLG

361
FSIAGGVGNQHIPGDNSIYVTKIIEGGAAHKDGRLQIGDKILAVNSVGLEDVMHEDAVAA

421
LKNTYDVVYLKVAKPSNAYLSDSYAPPDITTSYSQHLDNEISHSSYLGTDYPTAMTPTSP

481
RRYSPVAKDLLGEEDIPPAEKVMEIKLIKGPKGLGFSIAGGVGNQHIPGDNSIYVTKIIE

541
GGAAHKDGRLQIGDKILAVNSVGLEDVMHEDAVAALKNTYDVVYLKVAKPSNAYLSDSYA

Log(NS1_intensity/NP_intensity) over course of infection (Throat Samples)

| Patient number | DAY 1 3.0 mL | DAY 2 | DAY 3 | DAY 4 | DAY 5 | DAY 6 | DAY 7 |
|---|---|---|---|---|---|---|---|
| 1 | 0.383815366 | | | | | | |
| 2 | | | | | | | |
| 3 | | 0.881954971 | | -0.920818754 | | | |

Log(NS1_intensity/NP_intensity) over Course of Infection (Nasal Samples)

NASAL LOG(NS1/NP)

FIGURE 21

| | | THROAT | | | | NASAL | | | | | | | | | |
|---|---|---|---|---|---|---|---|---|---|---|---|---|---|---|---|
| | | DAY 1 | DAY 2 | DAY 3 | DAY 4 | DAY 1 | DAY 2 | DAY 3 | DAY 4 | DAY 5 | DAY 6 | DAY 7 | DAY 8 | DAY 9 | DAY 10 |
| NP | 1 | | 32.4 | | 90.1 | | 84.7 | | | | | | | | |
| | 2 | | | | | | 88.7 | 13.4 | | | | | | | |
| | 3 | | | | | | | | 56.9 | | 30.5 | | | | |
| | 4 | | | | | | | 18.5 | | | | | | | |
| | 5 | 9.3 | | | | | | | | | | | | | |
| | 6 | | | | | | | 17.1 | | 15 | | | | | 173.9 |
| | 9 | | | | | | | 15.3 | | | | | | | |
| | 10 | | | | | | 10.3 | | | | | | | | |
| NS1 | 1 | | 246.9 | | 10.6 | | 385.6 | | | | | | | | |
| | 2 | | | | | | 138.3 | 20.1 | | | | | | | |
| | 3 | | | | | | | | 4.4 | | 4.4 | | | | |
| | 4 | | | | | | | 6.9 | | | | | | | |
| | 5 | 22.5 | | | | | | | | | | | | | |
| | 6 | | | | | | | 6.1 | | 4.4 | | | | | 21.6 |
| | 9 | | | | | | | 8.4 | | | | | | | |
| | 10 | | | | | | 17.2 | | | | | | | | |

Summary of FluB Human Sample measurements with AVC Flu B NS1/NP double line test

| | N1 | N2 | N3 | N4 | N5 | N11 | N12 | N13 | N14 | N15 | N16 | N17 | N18 | N19 | N20 | 1603 | 1655 | 7145 | 7815 | 7862 | 4924 | B101 | B102 | B103 | B104 |
|---|---|---|---|---|---|---|---|---|---|---|---|---|---|---|---|---|---|---|---|---|---|---|---|---|---|
| Anti-NS1 | 3.4 | 4.7 | 2.7 | 2.6 | 7.2 | 2.5 | 3.3 | 8.3 | 1 | 7.3 | 3.1 | 1.7 | 2.2 | 1.3 | 17.2 | 544 | 34.2 | 190 | 261 | 603 | 33.4 | 112 | 493 | 281 | 4.1 |
| Anti-NP | 4.5 | 17.9 | 6.1 | 11.4 | 9.8 | 10.9 | 7.3 | 16.6 | 5.4 | 5.4 | 9.1 | 5.8 | 8 | 3.7 | 67.6 | 318 | 24.6 | 177 | 131 | 430 | 173 | 31.5 | 293 | 47.7 | 7.4 |

SEQUENCE LISTING

<160> NUMBER OF SEQ ID NOS: 1024

<210> SEQ ID NO 1
<211> LENGTH: 104
<212> TYPE: PRT
<213> ORGANISM: Artificial Sequence
<220> FEATURE:
<223> OTHER INFORMATION: Synthetic peptide of PDZ domain PSD95 d2

<400> SEQUENCE: 1

```
Val Met Arg Arg Lys Pro Pro Ala Glu Lys Val Met Glu Ile Lys Leu
1               5                   10                  15

Ile Lys Gly Pro Lys Gly Leu Gly Phe Ser Ile Ala Gly Gly Val Gly
            20                  25                  30

Asn Gln His Ile Pro Gly Asp Asn Ser Ile Tyr Val Thr Lys Ile Ile
        35                  40                  45

Glu Gly Gly Ala Ala His Lys Asp Gly Arg Leu Gln Ile Gly Asp Lys
    50                  55                  60

Ile Leu Ala Val Asn Ser Val Gly Leu Glu Asp Val Met His Glu Asp
65                  70                  75                  80

Ala Val Ala Ala Leu Lys Asn Thr Tyr Asp Val Val Tyr Leu Lys Val
                85                  90                  95

Ala Lys Pro Ser Asn Ala Tyr Leu
            100
```

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 2

```
Glu Ser Glu Val
1
```

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 3

```
Glu Ser Glu Ile
1
```

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 4

```
Glu Ser Lys Val
1
```

<210> SEQ ID NO 5
<211> LENGTH: 4
<212> TYPE: PRT
<213> ORGANISM: Artificial Sequence
<220> FEATURE:

<223> OTHER INFORMATION: Synthetic peptide of PDZ Ligand Motif

<400> SEQUENCE: 5

Thr Ser Glu Val
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 6

Gly Ser Glu Val
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 7

Arg Ser Glu Val
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 8

Arg Ser Lys Val
1

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 9

Gly Ser Glu Ile
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 10

Gly Ser Lys Val
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 11

Asn Ile Cys Ile
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 12

Thr Ile Cys Ile
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 13

Arg Ile Cys Ile
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 14

Asp Met Ala Leu
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 15

Asp Met Thr Leu
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 16

Asp Ile Ala Leu
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 17

-continued

Asp Leu Asp Tyr
1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide of PDZ Ligand Motif

<400> SEQUENCE: 18

Ser Ile Cys Leu
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide of PDZ Ligand Motif
<220> FEATURE:
<221> NAME/KEY: MISC_FEATURE
<222> LOCATION: (4)..(4)
<223> OTHER INFORMATION: Xaa = V, I or A

<400> SEQUENCE: 19

Glu Ser Glu Xaa
1

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 20

Pro Glu Ile Pro Lys Gly Arg Gly Leu Phe
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 21

Pro Glu Asn Pro Lys Gly Arg Gly Leu Phe
1 5 10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 22

Pro Glu Ile Pro Lys Lys Lys Lys Arg Gly Leu Phe
1 5 10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 23

Pro Glu Thr Pro Lys Arg Lys Arg Lys Arg Gly Leu Ser Phe
1 5 10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 24

Pro Glu Ile Pro Lys Lys Arg Glu Lys Arg Gly Leu Phe
1 5 10

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide of HA0 cleavage site sequence

<400> SEQUENCE: 25

Pro Glu Thr Pro Lys Arg Arg Arg Arg Gly Leu Phe
1 5 10

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide of PDZ domain motif

<400> SEQUENCE: 26

Gly Leu Gly Phe
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide of PL motif

<400> SEQUENCE: 27

Glu Pro Glu Val
1

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide of PL motif

<400> SEQUENCE: 28

Lys Met Ala Asp
1

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide of PDZ ligand motif

<400> SEQUENCE: 29

Arg Lys Tyr Leu
1

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide of PDZ ligand motif

<400> SEQUENCE: 30

Lys Lys Tyr Leu
1

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 31

Gln Asp Phe Val
1

<210> SEQ ID NO 32
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 32

Lys Ser Arg Val
1

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 33

Lys Ile Glu Leu
1

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 34

Lys Leu Ser Val
1

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 35

Ser Ala Val Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 36

Lys Val Leu Leu
1

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 37

Arg His Thr Cys
1

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 38

Leu Ser Leu Val
1

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide of Putative C-terminal PL motif

<400> SEQUENCE: 39

Val Lys Ser Cys
1

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide of Human PL sequence motif

<400> SEQUENCE: 40

Arg Ser Lys Ile
1

<210> SEQ ID NO 41
<211> LENGTH: 4
<212> TYPE: PRT
<213> ORGANISM: Artificial Sequence
<220> FEATURE:
<223> OTHER INFORMATION: Synthetic peptide of Human PL sequence motif

<400> SEQUENCE: 41

Lys Ser Glu Val
1

<210> SEQ ID NO 42
<211> LENGTH: 230
<212> TYPE: PRT
<213> ORGANISM: Influenza virus

<400> SEQUENCE: 42

```
Met Asp Ser Asn Thr Leu Ser Ser Phe Gln Val Asp Cys Phe Leu Trp
1               5                   10                  15

His Val Arg Lys Gln Val Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asn Ile Glu Thr Ala Thr Cys Val Gly Lys Gln Ile
    50                  55                  60

Val Glu Arg Ile Leu Lys Glu Glu Ser Asp Glu Ala Phe Lys Met Thr
65                  70                  75                  80

Met Ala Ser Ala Leu Ala Ser Arg Tyr Leu Thr Asp Met Thr Ile Glu
                85                  90                  95

Glu Met Ser Arg Asp Trp Phe Ile Val Met Pro Lys Gln Lys Val Ala
            100                 105                 110

Gly Pro Leu Cys Val Arg Met Asp Gln Ala Ile Thr Asp Lys Asn Ile
        115                 120                 125

Ile Leu Lys Ala Asn Phe Ser Val Ile Phe Asn Arg Leu Glu Thr Leu
    130                 135                 140

Thr Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Ile Leu Ile Gly Gly Leu Glu Trp Asn Asp Asn Thr Val
            180                 185                 190

Arg Val Ser Glu Ala Leu Gln Arg Phe Ala Trp Arg Ser Ser Asn Glu
        195                 200                 205

Asn Gly Arg Pro Pro Leu Thr Pro Thr Gln Lys Arg Lys Met Ala Gly
    210                 215                 220

Thr Ile Arg Ser Glu Val
225                 230
```

<210> SEQ ID NO 43
<211> LENGTH: 230
<212> TYPE: PRT
<213> ORGANISM: Influenza virus

<400> SEQUENCE: 43

```
Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
        35                  40                  45

Thr Leu Gly Leu Asp Ile Lys Ala Ala Thr His Val Gly Lys Gln Ile
    50                  55                  60
```

```
Val Glu Lys Ile Leu Lys Gly Glu Ser Asp Glu Ala Leu Lys Met Thr
65                  70                  75                  80

Met Ala Ser Thr Pro Ala Ser Arg Tyr Ile Thr Asp Met Thr Ile Glu
                85                  90                  95

Glu Leu Ser Arg Asn Trp Phe Met Leu Met Pro Lys Gln Lys Met Glu
            100                 105                 110

Gly Pro Leu Cys Ile Arg Met Asp Gln Ala Ile Met Glu Lys Asn Ile
        115                 120                 125

Met Leu Lys Ala Asn Phe Ser Val Ile Phe Asp Arg Leu Glu Asn Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
        195                 200                 205

Asn Gly Gly Pro Pro Leu Thr Pro Lys Gln Lys Arg Lys Met Ala Arg
    210                 215                 220

Thr Ala Arg Ser Lys Val
225                 230


<210> SEQ ID NO 44
<211> LENGTH: 230
<212> TYPE: PRT
<213> ORGANISM: Influenza virus

<400> SEQUENCE: 44

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205
```

Asn Gly Arg Ser Pro Leu Pro Pro Lys Gln Lys Arg Lys Met Glu Arg
    210                 215                 220

Thr Ile Glu Pro Glu Val
225                 230

<210> SEQ ID NO 45
<211> LENGTH: 225
<212> TYPE: PRT
<213> ORGANISM: Influenza virus

<400> SEQUENCE: 45

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Glu Ser Asp Lys Ala Leu Lys Met Pro
65                  70                  75                  80

Ala Ser Arg Tyr Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
        195                 200                 205

Leu Pro Pro Asn Gln Lys Arg Lys Met Ala Arg Thr Ile Glu Ser Glu
    210                 215                 220

Val
225

<210> SEQ ID NO 46
<211> LENGTH: 20
<212> TYPE: PRT
<213> ORGANISM: Influenza virus

<400> SEQUENCE: 46

Tyr Gly Arg Lys Lys Arg Arg Gln Arg Arg Arg Met Glu Arg Thr Ile
1               5                   10                  15

Glu Pro Glu Val
            20

<210> SEQ ID NO 47
<211> LENGTH: 20
<212> TYPE: PRT
<213> ORGANISM: Influenza virus

<400> SEQUENCE: 47

Tyr Gly Arg Lys Lys Arg Arg Gln Arg Arg Arg Met Ala Arg Thr Ile
1 5 10 15

Glu Ser Glu Val
20

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide of PSD95 binding peptide motif
<220> FEATURE:
<221> NAME/KEY: MISC_FEATURE
<222> LOCATION: (1)..(1)
<223> OTHER INFORMATION: Xaa = E or D or N or Q
<220> FEATURE:
<221> NAME/KEY: MISC_FEATURE
<222> LOCATION: (2)..(2)
<223> OTHER INFORMATION: Xaa = S or T
<220> FEATURE:
<221> NAME/KEY: MISC_FEATURE
<222> LOCATION: (3)..(3)
<223> OTHER INFORMATION: Xaa = D or E or Q or N
<220> FEATURE:
<221> NAME/KEY: MISC_FEATURE
<222> LOCATION: (4)..(4)
<223> OTHER INFORMATION: Xaa = V or L

<400> SEQUENCE: 48

Xaa Xaa Xaa Xaa
1

<210> SEQ ID NO 49
<211> LENGTH: 4
<212> TYPE: PRT
<213> ORGANISM: Artificial Sequence
<220> FEATURE:
<223> OTHER INFORMATION: Synthetic peptide of Preferred C-terminal sequence

<400> SEQUENCE: 49

Glu Ser Asp Val
1

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide of Preferred C-terminal sequence

<400> SEQUENCE: 50

Glu Thr Asp Val
1

<210> SEQ ID NO 51
<211> LENGTH: 4
<212> TYPE: PRT
<213> ORGANISM: Artificial Sequence
<220> FEATURE:
<223> OTHER INFORMATION: Synthetic peptide of Preferred C-terminal sequence

<400> SEQUENCE: 51

Glu Thr Glu Val
1

```
<210> SEQ ID NO 52
<211> LENGTH: 4
<212> TYPE: PRT
<213> ORGANISM: Artificial Sequence
<220> FEATURE:
<223> OTHER INFORMATION: Synthetic peptide of Preferred C-terminal
      sequence

<400> SEQUENCE: 52

Asp Thr Asp Val
1


<210> SEQ ID NO 53
<211> LENGTH: 4
<212> TYPE: PRT
<213> ORGANISM: Artificial Sequence
<220> FEATURE:
<223> OTHER INFORMATION: Synthetic peptide of Preferred C-terminal
      sequence

<400> SEQUENCE: 53

Asp Thr Glu Val
1


<210> SEQ ID NO 54
<211> LENGTH: 20
<212> TYPE: PRT
<213> ORGANISM: Artificial Sequence
<220> FEATURE:
<223> OTHER INFORMATION: Synthetic peptide of PL sequence

<400> SEQUENCE: 54

Gly Arg Trp Thr Gly Arg Ser Met Ser Ser Trp Lys Pro Thr Arg Arg
1               5                   10                  15

Glu Thr Glu Val
            20


<210> SEQ ID NO 55
<211> LENGTH: 20
<212> TYPE: PRT
<213> ORGANISM: Artificial Sequence
<220> FEATURE:
<223> OTHER INFORMATION: Synthetic peptide of PL sequence

<400> SEQUENCE: 55

Gln Ile Ser Pro Gly Gly Leu Glu Pro Pro Ser Glu Lys His Phe Arg
1               5                   10                  15

Glu Thr Glu Val
            20


<210> SEQ ID NO 56
<211> LENGTH: 20
<212> TYPE: PRT
<213> ORGANISM: Artificial Sequence
<220> FEATURE:
<223> OTHER INFORMATION: Synthetic peptide of PL sequence

<400> SEQUENCE: 56

Tyr Gly Arg Lys Lys Arg Arg Gln Arg Arg Arg Tyr Ile Pro Glu Ala
1               5                   10                  15

Gln Thr Arg Leu
            20


<210> SEQ ID NO 57
<211> LENGTH: 20
<212> TYPE: PRT
```

<213> ORGANISM: Artificial Sequence
<220> FEATURE:
<223> OTHER INFORMATION: Synthetic peptide of PL sequence

<400> SEQUENCE: 57

```
Tyr Gly Arg Lys Lys Arg Arg Gln Arg Arg Arg Arg Ile Ser Ser Ile
1               5                   10                  15

Glu Thr Asp Val
            20
```

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide of PL sequence

<400> SEQUENCE: 58

```
Tyr Gly Arg Lys Lys Arg Arg Gln Arg Arg Arg Lys Leu Ser Ser Ile
1               5                   10                  15

Glu Ser Asp Val
            20
```

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide of PL sequence

<400> SEQUENCE: 59

```
Tyr Gly Arg Lys Lys Arg Arg Gln Arg Arg Arg Thr Lys Asn Tyr Lys
1               5                   10                  15

Gln Thr Ser Val
            20
```

<210> SEQ ID NO 60
<211> LENGTH: 20
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 60

```
Ala Ala Gly Gly Arg Ser Ala Arg Gly Gly Arg Leu Gln Gly Arg Arg
1               5                   10                  15

Glu Thr Ala Leu
            20
```

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 61

```
Ala Gly Ala Val Arg Thr Pro Leu Ser Gln Val Asn Lys Val Trp Asp
1               5                   10                  15

Gln Ser Ser Val
            20
```

<210> SEQ ID NO 62

<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 62

Ala Val Gly Gly Arg Pro Ala Arg Gly Gly Arg Leu Gln Gly Arg Arg
1 5 10 15

Gln Thr Gln Val
20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 63

Asp Phe Arg Pro Ser Phe Lys His Ile Leu Phe Arg Arg Ala Arg Arg
1 5 10 15

Gly Phe Arg Gln
20

<210> SEQ ID NO 64
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 64

Asp Thr Leu Leu Leu Thr Glu Asn Glu Gly Asp Lys Thr Glu Glu Gln
1 5 10 15

Val Ser Tyr Val
20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 65

Gly Arg Trp Thr Gly Arg Ala Met Ser Ala Trp Lys Pro Thr Arg Arg
1 5 10 15

Glu Thr Glu Val
20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 66

His His Leu Val Ala Gln Arg Asp Ile Arg Gln Phe Gln Leu Gln His
1 5 10 15

Trp Leu Ala Ile
20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 67

Lys His Ser Arg Lys Ser Ser Ser Tyr Ser Ser Ser Ser Thr Thr Val
1 5 10 15

Lys Thr Ser Tyr
20

<210> SEQ ID NO 68
<211> LENGTH: 23
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 68

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 69

Leu Ala Val Leu Ala Tyr Ser Ile Thr Leu Val Met Leu Trp Ser Ile
1 5 10 15

Trp Gln Tyr Ala
20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 70

Leu Asn Ser Cys Ser Asn Arg Arg Val Tyr Lys Lys Met Pro Ser Ile
1 5 10 15

Glu Ser Asp Val
20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 71

Leu Asn Ser Ser Ser Asn Arg Arg Val Tyr Lys Lys Met Pro Ser Ile
1 5 10 15

Glu Ser Asp Val
20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 72

Pro Ile Pro Ala Gly Gly Cys Thr Phe Ser Gly Ile Phe Pro Thr Leu
1 5 10 15

Thr Ser Pro Leu
20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 73

Pro Tyr Ser Glu Leu Asn Tyr Glu Thr Ser His Tyr Pro Ala Ser Pro
1 5 10 15

Asp Ser Trp Val
20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 74

Gln Asp Phe Arg Arg Ala Phe Arg Arg Ile Leu Ala Arg Pro Trp Thr
1 5 10 15

Gln Thr Ala Trp
20

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 75

Gln Ile Ser Pro Gly Gly Leu Glu Pro Pro Ser Glu Lys His Phe Arg
1 5 10 15

Glu Thr Glu Val
20

<210> SEQ ID NO 76
<211> LENGTH: 20
<212> TYPE: PRT

<213> ORGANISM: Artificial Sequence
<220> FEATURE:
<223> OTHER INFORMATION: Synthetic peptide of PL sequence binding DLG2
d1

<400> SEQUENCE: 76

Arg Glu Leu Val Asp Arg Gly Glu Val Arg Gln Phe Thr Leu Arg His
1 5 10 15

Trp Leu Lys Val
20

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 77

Ser Phe Thr Ser Ile Leu Thr Cys His Gln Arg Arg Thr Gln Arg Lys
1 5 10 15

Glu Thr Val Ala
20

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 78

Ser Leu Lys Pro Gly Thr Val Leu Pro Pro Pro Pro Tyr Arg His Arg
1 5 10 15

Asn Thr Val Val
20

<210> SEQ ID NO 79
<211> LENGTH: 19
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 79

Ser Ser Lys Ser Lys Ser Ser Glu Glu Ser Gln Thr Phe Phe Gly Leu
1 5 10 15

Tyr Lys Leu

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide of PL sequence binding DLG2
d1

<400> SEQUENCE: 80

Ser Tyr Pro Thr Pro Arg Pro Tyr Pro Lys Pro Ala Pro Ser Ser Gly
1 5 10 15

Lys Asp Tyr Val
20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 81

Thr Gly Ser Ala Leu Gln Ala Trp Arg His Thr Ser Arg Gln Ala Thr
1 5 10 15

Glu Ser Thr Val
20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 82

Thr Gln Gly Phe Pro Gly Pro Ala Thr Trp Arg Arg Ile Ser Ser Leu
1 5 10 15

Glu Ser Glu Val
20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 83

Val Gly Thr Leu Leu Leu Glu Arg Val Ile Phe Pro Ser Val Lys Ile
1 5 10 15

Ala Thr Leu Val
20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 84

Val His Lys Val Arg Asn Lys Phe Lys Ala Lys Cys Ser Leu Cys Arg
1 5 10 15

Leu Tyr Ile Ile
20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide of PL sequence binding DLG2 d1

<400> SEQUENCE: 85

Tyr Gly Arg Lys Lys Arg Arg Gln Arg Arg Arg Gly Ala Ser Ala Asp

```
1               5                   10                  15

Ser Thr Gln Ala
            20


<210> SEQ ID NO 86
<211> LENGTH: 20
<212> TYPE: PRT
<213> ORGANISM: Artificial Sequence
<220> FEATURE:
<223> OTHER INFORMATION: Synthetic peptide of PL sequence binding DLG2
      d1

<400> SEQUENCE: 86

Tyr Gly Arg Lys Lys Arg Arg Gln Arg Arg Arg Lys Leu Ser Ser Ile
1               5                   10                  15

Glu Ser Asp Val
            20


<210> SEQ ID NO 87
<211> LENGTH: 20
<212> TYPE: PRT
<213> ORGANISM: Artificial Sequence
<220> FEATURE:
<223> OTHER INFORMATION: Synthetic peptide of PL sequence binding DLG2
      d1

<400> SEQUENCE: 87

Tyr Gly Arg Lys Lys Arg Arg Gln Arg Arg Arg Asn Asp Asn Ile Ala
1               5                   10                  15

Leu Leu Val Gln
            20


<210> SEQ ID NO 88
<211> LENGTH: 20
<212> TYPE: PRT
<213> ORGANISM: Artificial Sequence
<220> FEATURE:
<223> OTHER INFORMATION: Synthetic peptide of PL sequence binding DLG2
      d1

<400> SEQUENCE: 88

Tyr Gly Arg Lys Lys Arg Arg Gln Arg Arg Arg Ser Glu Gly Val Pro
1               5                   10                  15

Asp Leu Leu Val
            20


<210> SEQ ID NO 89
<211> LENGTH: 20
<212> TYPE: PRT
<213> ORGANISM: Artificial Sequence
<220> FEATURE:
<223> OTHER INFORMATION: Synthetic peptide of PL sequence binding GORASP
      d1

<400> SEQUENCE: 89

Asp Phe Ser Arg Gln Leu Gln Asn Ser Met Ser Gly Ala Ser Ala Asp
1               5                   10                  15

Ser Thr Gln Ala
            20


<210> SEQ ID NO 90
<211> LENGTH: 23
<212> TYPE: PRT
<213> ORGANISM: Artificial Sequence
<220> FEATURE:
<223> OTHER INFORMATION: Synthetic peptide of PL sequence binding GORASP
```

d1

<400> SEQUENCE: 90

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide of PL sequence binding GORASP d1

<400> SEQUENCE: 91

Asn Tyr Lys Leu Asn Thr Asp His Ala Gly Ser Asn Asp Asn Ile Ala
1 5 10 15

Leu Leu Val Gln
20

<210> SEQ ID NO 92
<211> LENGTH: 19
<212> TYPE: PRT
<213> ORGANISM: Artificial Sequence
<220> FEATURE:
<223> OTHER INFORMATION: Synthetic peptide of PL sequence binding GORASP d1

<400> SEQUENCE: 92

Ser Gly Gly Asn Arg Ala Arg Gln Glu Arg Leu Gln Arg Arg Arg Glu
1 5 10 15

Thr Gln Val

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide of PL sequence binding GORASP d1

<400> SEQUENCE: 93

Tyr Gly Arg Lys Lys Arg Arg Gln Arg Arg Arg Ala Arg Gly Asp Arg
1 5 10 15

Lys Arg Ile Val
20

<210> SEQ ID NO 94
<211> LENGTH: 20
<212> TYPE: PRT
<213> ORGANISM: Artificial Sequence
<220> FEATURE:
<223> OTHER INFORMATION: Synthetic peptide of PL sequence binding GORASP d1

<400> SEQUENCE: 94

Tyr Gly Arg Lys Lys Arg Arg Gln Arg Arg Arg Ala Val Ala Ala Thr
1 5 10 15

Ser Ile Asn Leu
20

<210> SEQ ID NO 95
<211> LENGTH: 20

<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 95

Tyr Gly Arg Lys Lys Arg Arg Gln Arg Arg Arg Glu Met Gln Val Thr
1               5                   10                  15

Leu Gly Leu His
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 96

Tyr Gly Arg Lys Lys Arg Arg Gln Arg Arg Arg Gly Ala Ser Ala Asp
1               5                   10                  15

Ser Thr Gln Ala
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 97

Tyr Gly Arg Lys Lys Arg Arg Gln Arg Arg Arg Ile Gly Glu Leu Gln
1               5                   10                  15

Leu Ser Ile Ala
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1
<220> FEATURE:
<221> NAME/KEY: misc_feature
<222> LOCATION: (20)..(20)
<223> OTHER INFORMATION: Xaa = any naturally occuring amino acid

<400> SEQUENCE: 98

Tyr Gly Arg Lys Lys Arg Arg Gln Arg Arg Arg Lys Leu Ser Ser Ile
1               5                   10                  15

Glu Ser Asp Xaa
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 99

```
Tyr Gly Arg Lys Lys Arg Arg Gln Arg Arg Arg Asn Asp Asn Ile Ala
1               5                   10                  15

Leu Leu Val Gln
            20


<210> SEQ ID NO 100
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 100

Tyr Gly Arg Lys Lys Arg Arg Gln Arg Arg Arg Gln Asp Glu Glu Glu
1               5                   10                  15

Gly Ile Trp Ala
            20


<210> SEQ ID NO 101
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 101

Tyr Gly Arg Lys Lys Arg Arg Gln Arg Arg Arg Ser Glu Gly Val Pro
1               5                   10                  15

Asp Leu Leu Val
            20


<210> SEQ ID NO 102
<211> LENGTH: 20
<212> TYPE: PRT
<213> ORGANISM: Artificial Sequence
<220> FEATURE:
<223> OTHER INFORMATION: Synthetic peptide of PL sequence binding
      GORASP d1

<400> SEQUENCE: 102

Tyr Val Tyr Ser Arg Val Lys Asn Leu Asn Ser Ser Glu Gly Val Pro
1               5                   10                  15

Asp Leu Leu Val
            20


<210> SEQ ID NO 103
<211> LENGTH: 20
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 103

Ala Val Gly Gly Arg Pro Ala Arg Gly Gly Arg Leu Gln Gly Arg Arg
1               5                   10                  15

Gln Thr Gln Val
            20


<210> SEQ ID NO 104
<211> LENGTH: 20
<212> TYPE: PRT
<213> ORGANISM: Artificial Sequence
<220> FEATURE:
```

<223> OTHER INFORMATION: Synthetic peptide of PL sequence binding
GRIP1 d4

<400> SEQUENCE: 104

Asp Phe Arg Pro Ser Phe Lys His Ile Leu Phe Arg Arg Ala Arg Arg
1               5                   10                  15

Gly Phe Arg Gln
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic peptide of PL sequence binding
GRIP1 d4

<400> SEQUENCE: 105

His His Leu Val Ala Gln Arg Asp Ile Arg Gln Phe Gln Leu Gln His
1               5                   10                  15

Trp Leu Ala Ile
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic peptide of PL sequence binding
GRIP1 d4

<400> SEQUENCE: 106

His Ser Cys Cys Asn Arg Ala Arg Gln Glu Arg Leu Gln Arg Arg Arg
1               5                   10                  15

Glu Thr Gln Val
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide of PL sequence binding
GRIP1 d4

<400> SEQUENCE: 107

Lys His Ser Arg Lys Ser Ser Ser Tyr Ser Ser Ser Ser Thr Thr Val
1               5                   10                  15

Lys Thr Ser Tyr
            20

<210> SEQ ID NO 108
<211> LENGTH: 23
<212> TYPE: PRT
<213> ORGANISM: Artificial Sequence
<220> FEATURE:
<223> OTHER INFORMATION: Synthetic peptide of PL sequence binding
GRIP1 d4

<400> SEQUENCE: 108

Lys Lys Lys Lys Gln Pro Gly Asn Ser Thr Lys Glu Ser Glu Ser Thr
1               5                   10                  15

Asn Ser Val Arg Leu Met Leu
            20

```
<210> SEQ ID NO 109
<211> LENGTH: 20
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 109

Lys Tyr Ser Ala Pro Arg Arg Pro Thr Ala Thr Gly Asp Tyr Asp Lys
1               5                   10                  15

Lys Asn Tyr Val
            20


<210> SEQ ID NO 110
<211> LENGTH: 20
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 110

Leu Ala Val Leu Ala Tyr Ser Ile Thr Leu Val Met Leu Trp Ser Ile
1               5                   10                  15

Trp Gln Tyr Ala
            20


<210> SEQ ID NO 111
<211> LENGTH: 20
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 111

Gln Asp Phe Arg Arg Ala Phe Arg Arg Ile Leu Ala Arg Pro Trp Thr
1               5                   10                  15

Gln Thr Ala Trp
            20


<210> SEQ ID NO 112
<211> LENGTH: 19
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 112

Ser Ser Lys Ser Lys Ser Ser Glu Glu Ser Gln Thr Phe Phe Gly Leu
1               5                   10                  15

Tyr Lys Leu


<210> SEQ ID NO 113
<211> LENGTH: 20
<212> TYPE: PRT
<213> ORGANISM: Artificial Sequence
<220> FEATURE:
<223> OTHER INFORMATION: Synthetic peptide of PL sequence binding
      GRIP1 d4

<400> SEQUENCE: 113

Ser Ser Pro Asp Ser Ser Tyr Gln Gly Lys Gly Phe Val Met Ser Arg
1               5                   10                  15
```

-continued

Ala Met Tyr Val
20

<210> SEQ ID NO 114
<211> LENGTH: 20
<212> TYPE: PRT
<213> ORGANISM: Artificial Sequence
<220> FEATURE:
<223> OTHER INFORMATION: Synthetic peptide of PL sequence binding GRIP1 d4

<400> SEQUENCE: 114

Val Asp Pro Asn Ser Pro Ala Ala Lys Lys Lys Tyr Val Ser Tyr Asn
1 5 10 15

Asn Leu Val Ile
20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptide of PL sequence binding GRIP1 d4

<400> SEQUENCE: 115

Val His Lys Val Arg Asn Lys Phe Lys Ala Lys Cys Ser Leu Cys Arg
1 5 10 15

Leu Tyr Ile Ile
20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide of PL sequence binding GRIP1 d4

<400> SEQUENCE: 116

Tyr Gly Arg Lys Lys Arg Arg Gln Arg Arg Arg Gly Ala Ser Ala Asp
1 5 10 15

Ser Thr Gln Ala
20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide of PL sequence binding GRIP1 d4

<400> SEQUENCE: 117

Tyr Gly Arg Lys Lys Arg Arg Gln Arg Arg Arg Asn Asp Asn Ile Ala
1 5 10 15

Leu Leu Val Gln
20

<210> SEQ ID NO 118
<211> LENGTH: 20
<212> TYPE: PRT
<213> ORGANISM: Artificial Sequence
<220> FEATURE:
<223> OTHER INFORMATION: Synthetic peptide of PL sequence binding GRIP1 d4

<400> SEQUENCE: 118

Tyr Gly Arg Lys Lys Arg Arg Gln Arg Arg Arg Ser Glu Gly Val Pro
1               5                   10                  15

Asp Leu Leu Val
            20

<210> SEQ ID NO 119
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 119

Ala Gly Ala Val Arg Thr Pro Leu Ser Gln Val Asn Lys Val Trp Asp
1               5                   10                  15

Gln Ser Ser Val
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 120

Ala Leu Val Leu Ile Ala Phe Cys Ile Ile Arg Arg Arg Pro Ser Ala
1               5                   10                  15

Tyr Gln Ala Leu
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 121

Ala Thr Asp Tyr Leu Val Gln Pro Phe Met Asp Gln Leu Ala Phe His
1               5                   10                  15

Gln Phe Tyr Ile
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 122

Ala Val Gly Gly Arg Pro Ala Arg Gly Gly Arg Leu Gln Gly Arg Arg
1               5                   10                  15

Gln Thr Gln Val
            20

<210> SEQ ID NO 123
<211> LENGTH: 20
<212> TYPE: PRT

<213> ORGANISM: Artificial Sequence
<220> FEATURE:
<223> OTHER INFORMATION: Synthetic peptide of PL sequence binding INADL d8

<400> SEQUENCE: 123

```
Asp Phe Arg Pro Ser Phe Lys His Ile Leu Phe Arg Arg Ala Arg Arg
1               5                   10                  15

Gly Phe Arg Gln
            20
```

<210> SEQ ID NO 124
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 124

```
Asp Ser Asp Pro Glu Asn Glu Pro Phe Asp Glu Asp Gln His Thr Gln
1               5                   10                  15

Ile Thr Lys Val
            20
```

<210> SEQ ID NO 125
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 125

```
Asp Thr Leu Leu Leu Thr Glu Asn Glu Gly Asp Lys Thr Glu Glu Gln
1               5                   10                  15

Val Ser Tyr Val
            20
```

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 126

```
Glu Leu Leu Gln Phe Cys Arg Thr Pro Asn Pro Ala Leu Lys Asn Gly
1               5                   10                  15

Gln Tyr Trp Val
            20
```

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 127

```
Glu Ser Ser Gly Thr Gln Ser Pro Lys Arg His Ser Gly Ser Tyr Leu
1               5                   10                  15

Val Thr Ser Val
            20
```

<210> SEQ ID NO 128
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 128

Gly Gly Gly Gly Gly Ser Gly Gly Gly Gly Ser Gly Leu Pro His Ser
1 5 10 15

Thr Thr Arg Val
20

<210> SEQ ID NO 129
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 129

Gly Gly Gly Gly Gly Ser Gly Gly Gly Gly Ser Gly Ser Arg Arg Pro
1 5 10 15

Lys Thr Arg Val
20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 130

Gly Arg Trp Thr Gly Arg Ala Met Ser Ala Trp Lys Pro Thr Arg Arg
1 5 10 15

Glu Thr Glu Val
20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 131

His His Leu Val Ala Gln Arg Asp Ile Arg Gln Phe Gln Leu Gln His
1 5 10 15

Trp Leu Ala Ile
20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 132

His Ser Cys Cys Asn Arg Ala Arg Gln Glu Arg Leu Gln Arg Arg Arg
1 5 10 15

Glu Thr Gln Val
20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 133

Ile Asn Ser Val Gly Ser Thr Ala Ser Ser Ser Gln Pro Leu Leu Val
1 5 10 15

His Asp Asp Val
20

<210> SEQ ID NO 134
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 134

Lys Ala Gly Tyr Arg Ala Pro Arg Ser Tyr Pro Lys Ser Asn Ser Ser
1 5 10 15

Lys Glu Tyr Val
20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 135

Lys His Ser Arg Lys Ser Ser Ser Tyr Ser Ser Ser Ser Thr Thr Val
1 5 10 15

Lys Thr Ser Tyr
20

<210> SEQ ID NO 136
<211> LENGTH: 23
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 136

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 137
<211> LENGTH: 20
<212> TYPE: PRT
<213> ORGANISM: Artificial Sequence
<220> FEATURE:

<223> OTHER INFORMATION: Synthetic peptide of PL sequence binding INADL
d8

<400> SEQUENCE: 137

Lys Thr Met Pro Ala Ala Met Tyr Arg Leu Leu Thr Ala Gln Glu Gln
1 5 10 15

Pro Val Tyr Ile
20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide of PL sequence binding INADL
d8

<400> SEQUENCE: 138

Leu Ala Val Leu Ala Tyr Ser Ile Thr Leu Val Met Leu Trp Ser Ile
1 5 10 15

Trp Gln Tyr Ala
20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide of PL sequence binding INADL
d8

<400> SEQUENCE: 139

Leu Gly Tyr Ser Ile Pro Ser Arg Ser Gly Ala Ser Gly Leu Asp Lys
1 5 10 15

Arg Asp Tyr Val
20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptide of PL sequence binding INADL
d8

<400> SEQUENCE: 140

Leu Asn Ser Cys Ser Asn Arg Arg Val Tyr Lys Lys Met Pro Ser Ile
1 5 10 15

Glu Ser Asp Val
20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptide of PL sequence binding INADL
d8

<400> SEQUENCE: 141

Leu Asn Ser Ser Ser Asn Arg Arg Val Tyr Lys Lys Met Pro Ser Ile
1 5 10 15

Glu Ser Asp Val
20

```
<210> SEQ ID NO 142
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 142

Pro Ile Pro Ala Gly Gly Cys Thr Phe Ser Gly Ile Phe Pro Thr Leu
1               5                   10                  15

Thr Ser Pro Leu
            20


<210> SEQ ID NO 143
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 143

Pro Tyr Ser Glu Leu Asn Tyr Glu Thr Ser His Tyr Pro Ala Ser Pro
1               5                   10                  15

Asp Ser Trp Val
            20


<210> SEQ ID NO 144
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 144

Gln Asp Phe Arg Arg Ala Phe Arg Arg Ile Leu Ala Arg Pro Trp Thr
1               5                   10                  15

Gln Thr Ala Trp
            20


<210> SEQ ID NO 145
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 145

Arg Glu Leu Val Asp Arg Gly Glu Val Arg Gln Phe Thr Leu Arg His
1               5                   10                  15

Trp Leu Lys Val
            20


<210> SEQ ID NO 146
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 146

Arg Asn Ile Glu Glu Val Tyr Val Gly Gly Lys Gln Val Val Pro Phe
1               5                   10                  15
```

Ser Ser Ser Val
20

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 147

Ser Phe Thr Ser Ile Leu Thr Cys His Gln Arg Arg Thr Gln Arg Lys
1 5 10 15

Glu Thr Val Ala
20

<210> SEQ ID NO 148
<211> LENGTH: 18
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 148

Ser Pro Gln Pro Asp Ser Thr Asp Asn Asp Asp Tyr Asp Asp Ile Ser
1 5 10 15

Ala Ala

<210> SEQ ID NO 149
<211> LENGTH: 19
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 149

Ser Ser Lys Ser Lys Ser Ser Glu Glu Ser Gln Thr Phe Phe Gly Leu
1 5 10 15

Tyr Lys Leu

<210> SEQ ID NO 150
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 150

Ser Ser Pro Asp Ser Ser Tyr Gln Gly Lys Gly Phe Val Met Ser Arg
1 5 10 15

Ala Met Tyr Val
20

<210> SEQ ID NO 151
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 151

```
Ser Tyr Pro Thr Pro Arg Pro Tyr Pro Lys Pro Ala Pro Ser Ser Gly
1               5                   10                  15

Lys Asp Tyr Val
            20


<210> SEQ ID NO 152
<211> LENGTH: 18
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 152

Thr Phe Ala Ala Gly Phe Asn Ser Thr Gly Leu Pro His Ser Thr Thr
1               5                   10                  15

Arg Val


<210> SEQ ID NO 153
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 153

Thr Phe Lys Gly Thr Pro Thr Ala Glu Asn Pro Glu Tyr Leu Gly Leu
1               5                   10                  15

Asp Val Pro Val
            20


<210> SEQ ID NO 154
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 154

Thr Gly Ser Ala Leu Gln Ala Trp Arg His Thr Ser Arg Gln Ala Thr
1               5                   10                  15

Glu Ser Thr Val
            20


<210> SEQ ID NO 155
<211> LENGTH: 20
<212> TYPE: PRT
<213> ORGANISM: Artificial Sequence
<220> FEATURE:
<223> OTHER INFORMATION: Synthetic peptide of PL sequence binding INADL
      d8

<400> SEQUENCE: 155

Thr Gln Gly Phe Pro Gly Pro Ala Thr Trp Arg Arg Ile Ser Ser Leu
1               5                   10                  15

Glu Ser Glu Val
            20


<210> SEQ ID NO 156
<211> LENGTH: 20
<212> TYPE: PRT
<213> ORGANISM: Artificial Sequence
<220> FEATURE:
```

<223> OTHER INFORMATION: Synthetic peptide of PL sequence binding INADL d8

<400> SEQUENCE: 156

Thr Arg Glu Asp Ile Tyr Val Asn Tyr Pro Thr Phe Ser Arg Arg Pro
1 5 10 15

Lys Thr Arg Val
20

<210> SEQ ID NO 157
<211> LENGTH: 19
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 157

Thr Thr Asn Asn Asn Pro Asn Ser Ala Val Asn Ile Lys Lys Ile Phe
1 5 10 15

Thr Asp Val

<210> SEQ ID NO 158
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 158

Val Asp Pro Asn Ser Pro Ala Ala Lys Lys Lys Tyr Val Ser Tyr Asn
1 5 10 15

Asn Leu Val Ile
20

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 159

Val Gly Thr Leu Leu Leu Glu Arg Val Ile Phe Pro Ser Val Lys Ile
1 5 10 15

Ala Thr Leu Val
20

<210> SEQ ID NO 160
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 160

Val His Lys Val Arg Asn Lys Phe Lys Ala Lys Cys Ser Leu Cys Arg
1 5 10 15

Leu Tyr Ile Ile
20

<210> SEQ ID NO 161

<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 161

```
Tyr Gly Arg Lys Lys Arg Arg Gln Arg Arg Arg Gly Ala Ser Ala Asp
1               5                   10                  15

Ser Thr Gln Ala
            20
```

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 162

```
Tyr Gly Arg Lys Lys Arg Arg Gln Arg Arg Arg Lys Leu Ser Ser Ile
1               5                   10                  15

Glu Ser Asp Val
            20
```

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 163

```
Tyr Gly Arg Lys Lys Arg Arg Gln Arg Arg Arg Met Ala Arg Thr Ala
1               5                   10                  15

Arg Ser Lys Val
            20
```

<210> SEQ ID NO 164
<211> LENGTH: 20
<212> TYPE: PRT
<213> ORGANISM: Artificial Sequence
<220> FEATURE:
<223> OTHER INFORMATION: Synthetic peptide of PL sequence binding INADL d8

<400> SEQUENCE: 164

```
Tyr Gly Arg Lys Lys Arg Arg Gln Arg Arg Arg Asn Asp Asn Ile Ala
1               5                   10                  15

Leu Leu Val Gln
            20
```

<210> SEQ ID NO 165
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 165

Tyr Gly Arg Lys Lys Arg Arg Gln Arg Arg Arg Lys Leu Ser Ser Ile
1 5 10 15

Glu Ser Asp Xaa
20

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 166

Ala Val Gly Gly Arg Pro Ala Arg Gly Gly Arg Leu Gln Gly Arg Arg
1 5 10 15

Gln Thr Gln Val
20

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 167

Asp Phe Arg Pro Ser Phe Lys His Ile Leu Phe Arg Arg Ala Arg Arg
1 5 10 15

Gly Phe Arg Gln
20

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 168

Asp Gly Gly Ala Arg Thr Glu Asp Glu Val Gln Ser Tyr Pro Ser Lys
1 5 10 15

His Asp Tyr Val
20

<210> SEQ ID NO 169
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 169

Phe His Ser Lys Thr Ala Gly Ala Asn Thr Thr Asp Lys Glu Leu Glu
1 5 10 15

Val Leu Ser Leu
20

<210> SEQ ID NO 170
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 170

Gly Gly Glu Asp Phe Lys Thr Thr Asn Pro Ser Lys Gln Phe Asp Lys
1 5 10 15

Asn Ala Tyr Val
20

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 171

Gly Arg Trp Thr Gly Arg Ala Met Ser Ala Trp Lys Pro Thr Arg Arg
1 5 10 15

Glu Thr Glu Val
20

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 172

His Asp Phe Arg Arg Ala Phe Lys Lys Ile Leu Ala Arg Gly Asp Arg
1 5 10 15

Lys Arg Ile Val
20

<210> SEQ ID NO 173
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 173

His His Leu Val Ala Gln Arg Asp Ile Arg Gln Phe Gln Leu Gln His
1 5 10 15

Trp Leu Ala Ile
20

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 174

His Ser Cys Cys Asn Arg Ala Arg Gln Glu Arg Leu Gln Arg Arg Arg
1 5 10 15

Glu Thr Gln Val
20

<210> SEQ ID NO 175
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 175

```
Ile Leu Asn Ser Ile Gln Val Met Arg Ala Gln Met Asn Gln Ile Gln
1               5                   10                  15

Ser Val Glu Val
            20
```

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 176

```
Lys Ala Gly Tyr Arg Ala Pro Arg Ser Tyr Pro Lys Ser Asn Ser Ser
1               5                   10                  15

Lys Glu Tyr Val
            20
```

<210> SEQ ID NO 177
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 177

```
Lys His Ser Arg Lys Ser Ser Ser Tyr Ser Ser Ser Ser Thr Thr Val
1               5                   10                  15

Lys Thr Ser Tyr
            20
```

<210> SEQ ID NO 178
<211> LENGTH: 23
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 178

```
Lys Lys Lys Lys Gln Pro Gly Asn Ser Thr Lys Glu Ser Glu Ser Thr
1               5                   10                  15

Asn Ser Val Arg Leu Met Leu
            20
```

<210> SEQ ID NO 179
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 179

```
Leu Ala Val Leu Ala Tyr Ser Ile Thr Leu Val Met Leu Trp Ser Ile
```

-continued

```
1               5                   10                  15

Trp Gln Tyr Ala
            20


<210> SEQ ID NO 180
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1284 d1

<400> SEQUENCE: 180

Leu Gly Tyr Ser Ile Pro Ser Arg Ser Gly Ala Ser Gly Leu Asp Lys
1               5                   10                  15

Arg Asp Tyr Val
            20


<210> SEQ ID NO 181
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1284 d1

<400> SEQUENCE: 181

Leu Asn Ser Cys Ser Asn Arg Arg Val Tyr Lys Lys Met Pro Ser Ile
1               5                   10                  15

Glu Ser Asp Val
            20


<210> SEQ ID NO 182
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1284 d1

<400> SEQUENCE: 182

Leu Ser Glu Lys Lys Thr Ser Gln Ser Pro His Arg Phe Gln Lys Thr
1               5                   10                  15

Ala Ser Pro Ile
            20


<210> SEQ ID NO 183
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1284 d1

<400> SEQUENCE: 183

Pro Gly Gln Pro Pro Lys Val Lys Ser Glu Phe Asn Ser Tyr Ser Leu
1               5                   10                  15

Thr Gly Tyr Val
            20


<210> SEQ ID NO 184
<211> LENGTH: 20
<212> TYPE: PRT
<213> ORGANISM: Artificial Sequence
<220> FEATURE:
<223> OTHER INFORMATION: Synthetic peptide of PL sequence binding
```

KIAA1284 d1

<400> SEQUENCE: 184

Pro Ile Pro Ala Gly Gly Cys Thr Phe Ser Gly Ile Phe Pro Thr Leu
1 5 10 15

Thr Ser Pro Leu
20

<210> SEQ ID NO 185
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 185

Gln Asp Phe Arg Arg Ala Phe Arg Arg Ile Leu Ala Arg Pro Trp Thr
1 5 10 15

Gln Thr Ala Trp
20

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 186

Arg Glu Leu Val Asp Arg Gly Glu Val Arg Gln Phe Thr Leu Arg His
1 5 10 15

Trp Leu Lys Val
20

<210> SEQ ID NO 187
<211> LENGTH: 19
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 187

Ser Ser Lys Ser Lys Ser Ser Glu Glu Ser Gln Thr Phe Phe Gly Leu
1 5 10 15

Tyr Lys Leu

<210> SEQ ID NO 188
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 188

Ser Ser Pro Asp Ser Ser Tyr Gln Gly Lys Gly Phe Val Met Ser Arg
1 5 10 15

Ala Met Tyr Val
20

<210> SEQ ID NO 189
<211> LENGTH: 20

-continued

<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 189

Thr Phe Lys Gly Thr Pro Thr Ala Glu Asn Pro Glu Tyr Leu Gly Leu
1 5 10 15

Asp Val Pro Val
20

<210> SEQ ID NO 190
<211> LENGTH: 19
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 190

Thr Thr Asn Asn Asn Pro Asn Ser Ala Val Asn Ile Lys Lys Ile Phe
1 5 10 15

Thr Asp Val

<210> SEQ ID NO 191
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 191

Val Asp Pro Asn Ser Pro Ala Ala Lys Lys Lys Tyr Val Ser Tyr Asn
1 5 10 15

Asn Leu Val Ile
20

<210> SEQ ID NO 192
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 192

Val His Lys Val Arg Asn Lys Phe Lys Ala Lys Cys Ser Leu Cys Arg
1 5 10 15

Leu Tyr Ile Ile
20

<210> SEQ ID NO 193
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 193

Tyr Gly Arg Lys Lys Arg Arg Gln Arg Arg Arg Glu Met Gln Val Thr
1 5 10 15

Leu Gly Leu His
20

<210> SEQ ID NO 194
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 194

Tyr Gly Arg Lys Lys Arg Arg Gln Arg Arg Arg Gly Ala Ser Ala Asp
1 5 10 15

Ser Thr Gln Ala
20

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 195

Tyr Gly Arg Lys Lys Arg Arg Gln Arg Arg Arg Ile Gly Glu Leu Gln
1 5 10 15

Leu Ser Ile Ala
20

<210> SEQ ID NO 196
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1

<400> SEQUENCE: 196

Tyr Gly Arg Lys Lys Arg Arg Gln Arg Arg Arg Lys Leu Ser Ser Ile
1 5 10 15

Glu Ser Asp Val
20

<210> SEQ ID NO 197
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1284 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 197

Tyr Gly Arg Lys Lys Arg Arg Gln Arg Arg Arg Lys Leu Ser Ser Ile
1 5 10 15

Glu Ser Asp Xaa
20

<210> SEQ ID NO 198
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 198

Tyr Gly Arg Lys Lys Arg Arg Gln Arg Arg Arg Asn Asp Asn Ile Ala
1 5 10 15

Leu Leu Val Gln
20

<210> SEQ ID NO 199
<211> LENGTH: 20
<212> TYPE: PRT
<213> ORGANISM: Artificial Sequence
<220> FEATURE:
<223> OTHER INFORMATION: Synthetic peptide of PL sequence binding KIAA1284 d1

<400> SEQUENCE: 199

Tyr Gly Arg Lys Lys Arg Arg Gln Arg Arg Arg Ser Glu Gly Val Pro
1 5 10 15

Asp Leu Leu Val
20

<210> SEQ ID NO 200
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 200

Asp Phe Arg Pro Ser Phe Lys His Ile Leu Phe Arg Arg Ala Arg Arg
1 5 10 15

Gly Phe Arg Gln
20

<210> SEQ ID NO 201
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 201

Asp Gly Gly Ala Arg Thr Glu Asp Glu Val Gln Ser Tyr Pro Ser Lys
1 5 10 15

His Asp Tyr Val
20

<210> SEQ ID NO 202
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 202

Glu Ala Leu Gln Pro Glu Pro Gly Arg Lys Arg Ile Pro Leu Thr Arg
1 5 10 15

Thr Thr Thr Phe
20

<210> SEQ ID NO 203

<211> LENGTH: 20
<212> TYPE: PRT
<213> ORGANISM: Artificial Sequence
<220> FEATURE:
<223> OTHER INFORMATION: Synthetic peptide of PL sequence binding
KIAA1415 d1

<400> SEQUENCE: 203

Phe His Ser Lys Thr Ala Gly Ala Asn Thr Thr Asp Lys Glu Leu Glu
1 5 10 15

Val Leu Ser Leu
20

<210> SEQ ID NO 204
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1415 d1

<400> SEQUENCE: 204

Gly Gly Glu Asp Phe Lys Thr Thr Asn Pro Ser Lys Gln Phe Asp Lys
1 5 10 15

Asn Ala Tyr Val
20

<210> SEQ ID NO 205
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1415 d1

<400> SEQUENCE: 205

His His Leu Val Ala Gln Arg Asp Ile Arg Gln Phe Gln Leu Gln His
1 5 10 15

Trp Leu Ala Ile
20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1415 d1

<400> SEQUENCE: 206

His Ser Cys Cys Asn Arg Ala Arg Gln Glu Arg Leu Gln Arg Arg Arg
1 5 10 15

Glu Thr Gln Val
20

<210> SEQ ID NO 207
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1415 d1

<400> SEQUENCE: 207

Ile Leu Asn Ser Ile Gln Val Met Arg Ala Gln Met Asn Gln Ile Gln
1 5 10 15

Ser Val Glu Val
20

<210> SEQ ID NO 208
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 208

Lys Ala Gly Tyr Arg Ala Pro Arg Ser Tyr Pro Lys Ser Asn Ser Ser
1 5 10 15

Lys Glu Tyr Val
20

<210> SEQ ID NO 209
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 209

Lys His Ser Arg Lys Ser Ser Ser Tyr Ser Ser Ser Ser Thr Thr Val
1 5 10 15

Lys Thr Ser Tyr
20

<210> SEQ ID NO 210
<211> LENGTH: 23
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 210

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 211
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 211

Leu Ala Val Leu Ala Tyr Ser Ile Thr Leu Val Met Leu Trp Ser Ile
1 5 10 15

Trp Gln Tyr Ala
20

<210> SEQ ID NO 212
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 212

Leu Gly Tyr Ser Ile Pro Ser Arg Ser Gly Ala Ser Gly Leu Asp Lys
1               5                   10                  15

Arg Asp Tyr Val
            20

<210> SEQ ID NO 213
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 213

Leu Asn Ser Cys Ser Asn Arg Arg Val Tyr Lys Lys Met Pro Ser Ile
1               5                   10                  15

Glu Ser Asp Val
            20

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 214

Pro Gly Gln Pro Pro Lys Val Lys Ser Glu Phe Asn Ser Tyr Ser Leu
1               5                   10                  15

Thr Gly Tyr Val
            20

<210> SEQ ID NO 215
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 215

Pro Ile Pro Ala Gly Gly Cys Thr Phe Ser Gly Ile Phe Pro Thr Leu
1               5                   10                  15

Thr Ser Pro Leu
            20

<210> SEQ ID NO 216
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 216

Gln Asp Phe Arg Arg Ala Phe Arg Arg Ile Leu Ala Arg Pro Trp Thr
1               5                   10                  15

Gln Thr Ala Trp
            20

<210> SEQ ID NO 217
<211> LENGTH: 20
<212> TYPE: PRT

<213> ORGANISM: Artificial Sequence
<220> FEATURE:
<223> OTHER INFORMATION: Synthetic peptide of PL sequence binding KIAA1415 d1

<400> SEQUENCE: 217

```
Arg Glu Leu Val Asp Arg Gly Glu Val Arg Gln Phe Thr Leu Arg His
1               5                   10                  15

Trp Leu Lys Val
            20
```

<210> SEQ ID NO 218
<211> LENGTH: 19
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 218

```
Ser Ser Lys Ser Lys Ser Ser Glu Glu Ser Gln Thr Phe Phe Gly Leu
1               5                   10                  15

Tyr Lys Leu
```

<210> SEQ ID NO 219
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 219

```
Ser Ser Pro Asp Ser Ser Tyr Gln Gly Lys Gly Phe Val Met Ser Arg
1               5                   10                  15

Ala Met Tyr Val
            20
```

<210> SEQ ID NO 220
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 220

```
Ser Ser Ser Arg Arg Asp Ser Ser Trp Ser Glu Thr Ser Glu Ala Ser
1               5                   10                  15

Tyr Ser Gly Leu
            20
```

<210> SEQ ID NO 221
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 221

```
Thr Ala Glu Asn Ala Glu Tyr Leu Arg Val Ala Pro Gln Ser Ser Glu
1               5                   10                  15

Phe Ile Gly Ala
            20
```

<210> SEQ ID NO 222
<211> LENGTH: 19
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 222

Thr Thr Asn Asn Asn Pro Asn Ser Ala Val Asn Ile Lys Lys Ile Phe
1 5 10 15

Thr Asp Val

<210> SEQ ID NO 223
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 223

Val Asp Pro Asn Ser Pro Ala Ala Lys Lys Lys Tyr Val Ser Tyr Asn
1 5 10 15

Asn Leu Val Ile
20

<210> SEQ ID NO 224
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 224

Val His Lys Val Arg Asn Lys Phe Lys Ala Lys Cys Ser Leu Cys Arg
1 5 10 15

Leu Tyr Ile Ile
20

<210> SEQ ID NO 225
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 225

Tyr Gly Arg Lys Lys Arg Arg Gln Arg Arg Arg Gly Ala Ser Ala Asp
1 5 10 15

Ser Thr Gln Ala
20

<210> SEQ ID NO 226
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 226

Tyr Gly Arg Lys Lys Arg Arg Gln Arg Arg Arg Asn Asp Asn Ile Ala
1 5 10 15

Leu Leu Val Gln
20

<210> SEQ ID NO 227
<211> LENGTH: 20
<212> TYPE: PRT
<213> ORGANISM: Artificial Sequence
<220> FEATURE:
<223> OTHER INFORMATION: Synthetic peptide of PL sequence binding KIAA1415 d1

<400> SEQUENCE: 227

Tyr Gly Arg Lys Lys Arg Arg Gln Arg Arg Arg Ser Glu Gly Val Pro
1 5 10 15

Asp Leu Leu Val
20

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 228

Asp Gly Gly Ala Arg Thr Glu Asp Glu Val Gln Ser Tyr Pro Ser Lys
1 5 10 15

His Asp Tyr Val
20

<210> SEQ ID NO 229
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 229

Phe His Ser Lys Thr Ala Gly Ala Asn Thr Thr Asp Lys Glu Leu Glu
1 5 10 15

Val Leu Ser Leu
20

<210> SEQ ID NO 230
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 230

His Asp Phe Arg Arg Ala Phe Lys Lys Ile Leu Ala Arg Gly Asp Arg
1 5 10 15

Lys Arg Ile Val
20

<210> SEQ ID NO 231
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 231

His His Leu Val Ala Gln Arg Asp Ile Arg Gln Phe Gln Leu Gln His
1 5 10 15

Trp Leu Ala Ile
20

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 232

His Ser Cys Cys Asn Arg Ala Arg Gln Glu Arg Leu Gln Arg Arg Arg
1 5 10 15

Glu Thr Gln Val
20

<210> SEQ ID NO 233
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 233

Lys Ala Gly Tyr Arg Ala Pro Arg Ser Tyr Pro Lys Ser Asn Ser Ser
1 5 10 15

Lys Glu Tyr Val
20

<210> SEQ ID NO 234
<211> LENGTH: 20
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 234

Lys His Ser Arg Lys Ser Ser Ser Tyr Ser Ser Ser Ser Thr Thr Val
1 5 10 15

Lys Thr Ser Tyr
20

<210> SEQ ID NO 235
<211> LENGTH: 23
<212> TYPE: PRT
<213> ORGANISM: Artificial Sequence
<220> FEATURE:
<223> OTHER INFORMATION: Synthetic peptide of PL sequence binding KIAA1719 d4

<400> SEQUENCE: 235

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 236
<211> LENGTH: 20

<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 236

Leu Ala Val Leu Ala Tyr Ser Ile Thr Leu Val Met Leu Trp Ser Ile
1 5 10 15

Trp Gln Tyr Ala
20

<210> SEQ ID NO 237
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 237

Asn Ser Tyr Val Arg Asp Asp Ala Ile Phe Ile Lys Ala Ile Val Asp
1 5 10 15

Leu Thr Gly Leu
20

<210> SEQ ID NO 238
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 238

Pro Gly Gln Pro Pro Lys Val Lys Ser Glu Phe Asn Ser Tyr Ser Leu
1 5 10 15

Thr Gly Tyr Val
20

<210> SEQ ID NO 239
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 239

Gln Asp Phe Arg Arg Ala Phe Arg Arg Ile Leu Ala Arg Pro Trp Thr
1 5 10 15

Gln Thr Ala Trp
20

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 240

Ser Pro Ala Ser Ile Pro His Ser Pro Gly Ala Phe Ala Tyr Glu Gly
1 5 10 15

Ala Ser Phe Tyr

20

<210> SEQ ID NO 241
<211> LENGTH: 19
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 241

Ser Ser Lys Ser Lys Ser Ser Glu Glu Ser Gln Thr Phe Phe Gly Leu
1 5 10 15

Tyr Lys Leu

<210> SEQ ID NO 242
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 242

Ser Ser Ser Arg Arg Asp Ser Ser Trp Ser Glu Thr Ser Glu Ala Ser
1 5 10 15

Tyr Ser Gly Leu
20

<210> SEQ ID NO 243
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 243

Val His Lys Val Arg Asn Lys Phe Lys Ala Lys Cys Ser Leu Cys Arg
1 5 10 15

Leu Tyr Ile Ile
20

<210> SEQ ID NO 244
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 244

Tyr Gly Arg Lys Lys Arg Arg Gln Arg Arg Arg Glu Met Gln Val Thr
1 5 10 15

Leu Gly Leu His
20

<210> SEQ ID NO 245
<211> LENGTH: 20
<212> TYPE: PRT
<213> ORGANISM: Artificial Sequence
<220> FEATURE:
<223> OTHER INFORMATION: Synthetic peptide of PL sequence binding
KIAA1719 d4

<400> SEQUENCE: 245

```
Tyr Gly Arg Lys Lys Arg Arg Gln Arg Arg Arg Asn Asp Asn Ile Ala
1               5                   10                  15

Leu Leu Val Gln
            20


<210> SEQ ID NO 246
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1719 d4

<400> SEQUENCE: 246

Tyr Gly Arg Lys Lys Arg Arg Gln Arg Arg Arg Arg Ile Ser Ser Ile
1               5                   10                  15

Glu Thr Asp Val
            20


<210> SEQ ID NO 247
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1719 d4

<400> SEQUENCE: 247

Tyr Gly Arg Lys Lys Arg Arg Gln Arg Arg Arg Arg Ile Ser Ser Leu
1               5                   10                  15

Glu Thr Gln Val
            20


<210> SEQ ID NO 248
<211> LENGTH: 20
<212> TYPE: PRT
<213> ORGANISM: Artificial Sequence
<220> FEATURE:
<223> OTHER INFORMATION: Synthetic peptide of PL sequence binding
      KIAA1719 d4

<400> SEQUENCE: 248

Tyr Gly Arg Lys Lys Arg Arg Gln Arg Arg Arg Ser Glu Gly Val Pro
1               5                   10                  15

Asp Leu Leu Val
            20


<210> SEQ ID NO 249
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 249

Ala Ala Gly Gly Arg Ser Ala Arg Gly Gly Arg Leu Gln Gly Arg Arg
1               5                   10                  15

Glu Thr Ala Leu
            20


<210> SEQ ID NO 250
<211> LENGTH: 20
<212> TYPE: PRT
<213> ORGANISM: Artificial Sequence
<220> FEATURE:
```

```
<223> OTHER INFORMATION: Synthetic peptide of PL sequence binding
      Lim Mystique d1

<400> SEQUENCE: 250

Ala Thr Asp Tyr Leu Val Gln Pro Phe Met Asp Gln Leu Ala Phe His
1               5                   10                  15

Gln Phe Tyr Ile
            20


<210> SEQ ID NO 251
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 251

Asp Phe Arg Pro Ser Phe Lys His Ile Leu Phe Arg Arg Ala Arg Arg
1               5                   10                  15

Gly Phe Arg Gln
            20


<210> SEQ ID NO 252
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 252

Glu Asp Pro Lys Asp Arg Pro Ser Ala Ala His Ile Val Glu Ala Leu
1               5                   10                  15

Glu Thr Asp Val
            20


<210> SEQ ID NO 253
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 253

Glu Leu Leu Gln Phe Cys Arg Thr Pro Asn Pro Ala Leu Lys Asn Gly
1               5                   10                  15

Gln Tyr Trp Val
            20


<210> SEQ ID NO 254
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 254

Phe His Ser Lys Thr Ala Gly Ala Asn Thr Thr Asp Lys Glu Leu Glu
1               5                   10                  15

Val Leu Ser Leu
            20
```

<210> SEQ ID NO 255
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 255

Phe Asn Gly Ser Ser Asn Gly His Val Tyr Glu Lys Leu Ser Ser Ile
1 5 10 15

Glu Ser Asp Val
20

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 256

Gly Arg Trp Thr Gly Arg Ala Met Ser Ala Trp Lys Pro Thr Arg Arg
1 5 10 15

Glu Thr Glu Val
20

<210> SEQ ID NO 257
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 257

His Asp Phe Arg Arg Ala Phe Lys Lys Ile Leu Ala Arg Gly Asp Arg
1 5 10 15

Lys Arg Ile Val
20

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 258

His His Leu Val Ala Gln Arg Asp Ile Arg Gln Phe Gln Leu Gln His
1 5 10 15

Trp Leu Ala Ile
20

<210> SEQ ID NO 259
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 259

His Ser Cys Cys Asn Arg Ala Arg Gln Glu Arg Leu Gln Arg Arg Arg
1 5 10 15

```
Glu Thr Gln Val
            20


<210> SEQ ID NO 260
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 260

Ile Leu Asn Ser Ile Gln Val Met Arg Ala Gln Met Asn Gln Ile Gln
1               5                   10                  15

Ser Val Glu Val
            20


<210> SEQ ID NO 261
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 261

Lys His Ser Arg Lys Ser Ser Ser Tyr Ser Ser Ser Ser Thr Thr Val
1               5                   10                  15

Lys Thr Ser Tyr
            20


<210> SEQ ID NO 262
<211> LENGTH: 23
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 262

Lys Lys Lys Lys Gln Pro Gly Asn Ser Thr Lys Glu Ser Glu Ser Thr
1               5                   10                  15

Asn Ser Val Arg Leu Met Leu
            20


<210> SEQ ID NO 263
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1

<400> SEQUENCE: 263

Leu Ala Ser Lys Ser Ala Glu Glu Gly Lys Gln Ile Pro Asp Ser Leu
1               5                   10                  15

Ser Thr Asp Leu
            20


<210> SEQ ID NO 264
<211> LENGTH: 20
<212> TYPE: PRT
<213> ORGANISM: Artificial Sequence
<220> FEATURE:
<223> OTHER INFORMATION: Synthetic peptide of PL sequence binding
      Lim Mystique d1
```

<400> SEQUENCE: 264

Leu Ala Val Leu Ala Tyr Ser Ile Thr Leu Val Met Leu Trp Ser Ile
1 5 10 15

Trp Gln Tyr Ala
20

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 265

Leu Met Asp Gly Leu Pro Pro Gly Asp Ser Asn Gln Leu Ala Trp Phe
1 5 10 15

Asp Thr Asp Leu
20

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 266

Leu Asn Ser Cys Ser Asn Arg Arg Val Tyr Lys Lys Met Pro Ser Ile
1 5 10 15

Glu Ser Asp Val
20

<210> SEQ ID NO 267
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 267

Leu Asn Ser Ser Ser Asn Arg Arg Val Tyr Lys Lys Met Pro Ser Ile
1 5 10 15

Glu Ser Asp Val
20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 268

Pro Ile Pro Ala Gly Gly Cys Thr Phe Ser Gly Ile Phe Pro Thr Leu
1 5 10 15

Thr Ser Pro Leu
20

<210> SEQ ID NO 269
<211> LENGTH: 20

<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 269

Pro Tyr Ser Glu Leu Asn Tyr Glu Thr Ser His Tyr Pro Ala Ser Pro
1 5 10 15

Asp Ser Trp Val
20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 270

Gln Asp Phe Arg Arg Ala Phe Arg Arg Ile Leu Ala Arg Pro Trp Thr
1 5 10 15

Gln Thr Ala Trp
20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 271

Gln Ile Ser Pro Gly Gly Leu Glu Pro Pro Ser Glu Lys His Phe Arg
1 5 10 15

Glu Thr Glu Val
20

<210> SEQ ID NO 272
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 272

Arg Glu Leu Val Asp Arg Gly Glu Val Arg Gln Phe Thr Leu Arg His
1 5 10 15

Trp Leu Lys Val
20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 273

Ser Pro Ala Ser Ile Pro His Ser Pro Gly Ala Phe Ala Tyr Glu Gly
1 5 10 15

Ala Ser Phe Tyr

20

<210> SEQ ID NO 274
<211> LENGTH: 19
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 274

Ser Ser Lys Ser Lys Ser Ser Glu Glu Ser Gln Thr Phe Phe Gly Leu
1 5 10 15

Tyr Lys Leu

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 275

Ser Ser Ser Arg Arg Asp Ser Ser Trp Ser Glu Thr Ser Glu Ala Ser
1 5 10 15

Tyr Ser Gly Leu
20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 276

Ser Tyr Pro Thr Pro Arg Pro Tyr Pro Lys Pro Ala Pro Ser Ser Gly
1 5 10 15

Lys Asp Tyr Val
20

<210> SEQ ID NO 277
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 277

Thr Phe Lys Gly Thr Pro Thr Ala Glu Asn Pro Glu Tyr Leu Gly Leu
1 5 10 15

Asp Val Pro Val
20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 278

Thr Gln Gly Phe Pro Gly Pro Ala Thr Trp Arg Arg Ile Ser Ser Leu
1 5 10 15

Glu Ser Glu Val
20

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 279

Val Asp Pro Asn Ser Pro Ala Ala Lys Lys Lys Tyr Val Ser Tyr Asn
1 5 10 15

Asn Leu Val Ile
20

<210> SEQ ID NO 280
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 280

Val His Asp Ala Glu Ser Ser Asp Glu Asp Gly Tyr Asp Trp Gly Pro
1 5 10 15

Ala Thr Asp Leu
20

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 281

Val His Lys Val Arg Asn Lys Phe Lys Ala Lys Cys Ser Leu Cys Arg
1 5 10 15

Leu Tyr Ile Ile
20

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 282

Val Pro Gly Ala Leu Asp Tyr Ala Ala Phe Ser Ser Ala Leu Tyr Gly
1 5 10 15

Glu Ser Asp Leu
20

<210> SEQ ID NO 283
<211> LENGTH: 20
<212> TYPE: PRT
<213> ORGANISM: Artificial Sequence
<220> FEATURE:

<223> OTHER INFORMATION: Synthetic peptide of PL sequence binding Lim Mystique d1

<400> SEQUENCE: 283

Tyr Gly Arg Lys Lys Arg Arg Gln Arg Arg Arg Ala Val Ala Ala Ala
1 5 10 15

Ser Ala Asn Leu
20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 284

Tyr Gly Arg Lys Lys Arg Arg Gln Arg Arg Arg Ala Val Ala Ala Thr
1 5 10 15

Ser Ala Asn Leu
20

<210> SEQ ID NO 285
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 285

Tyr Gly Arg Lys Lys Arg Arg Gln Arg Arg Arg Ala Val Ala Ala Thr
1 5 10 15

Ser Ile Asn Leu
20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 286

Tyr Gly Arg Lys Lys Arg Arg Gln Arg Arg Arg Glu Tyr Leu Gly Leu
1 5 10 15

Asp Val Pro Val
20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide of PL sequence binding Lim Mystique d1

<400> SEQUENCE: 287

Tyr Gly Arg Lys Lys Arg Arg Gln Arg Arg Arg Lys Leu Ser Ser Ile
1 5 10 15

Glu Ser Asp Val
20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide of PL sequence binding
Lim Mystique d1

<400> SEQUENCE: 288

Tyr Gly Arg Lys Lys Arg Arg Gln Arg Arg Arg Asn Asp Asn Ile Ala
1 5 10 15

Leu Leu Val Gln
20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 289

Ala Ala Gly Gly Arg Ser Ala Arg Gly Gly Arg Leu Gln Gly Arg Arg
1 5 10 15

Glu Thr Ala Leu
20

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 290

Ala Leu Val Leu Ile Ala Phe Cys Ile Ile Arg Arg Arg Pro Ser Ala
1 5 10 15

Tyr Gln Ala Leu
20

<210> SEQ ID NO 291
<211> LENGTH: 19
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 291

Ala Arg His Arg Val Thr Ser Tyr Thr Ser Ser Ser Val Asn Val Ser
1 5 10 15

Ser Asn Leu

<210> SEQ ID NO 292
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 292

Ala Thr Asp Tyr Leu Val Gln Pro Phe Met Asp Gln Leu Ala Phe His
1 5 10 15

Gln Phe Tyr Ile
20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 293

Ala Val Gly Gly Arg Pro Ala Arg Gly Gly Arg Leu Gln Gly Arg Arg
1 5 10 15

Gln Thr Gln Val
20

<210> SEQ ID NO 294
<211> LENGTH: 19
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 294

Ala Trp Asp Asp Ser Ala Arg Ala Ala Gly Gly Gln Gly Leu His Val
1 5 10 15

Thr Ala Leu

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 295

Asp Phe Arg Pro Ser Phe Lys His Ile Leu Phe Arg Arg Ala Arg Arg
1 5 10 15

Gly Phe Arg Gln
20

<210> SEQ ID NO 296
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 296

Glu Leu Leu Gln Phe Cys Arg Thr Pro Asn Pro Ala Leu Lys Asn Gly
1 5 10 15

Gln Tyr Trp Val
20

<210> SEQ ID NO 297
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 297

Glu Ser Ser Gly Thr Gln Ser Pro Lys Arg His Ser Gly Ser Tyr Leu
1 5 10 15

Val Thr Ser Val
20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 298

Phe Asn Gly Ser Ser Asn Gly His Val Tyr Glu Lys Leu Ser Ser Ile
1 5 10 15

Glu Ser Asp Val
20

<210> SEQ ID NO 299
<211> LENGTH: 19
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 299

Gly Gly Gly Gly Gly Ser Gly Gly Gly Gly Gly Ser Gly Ile Glu Ser
1 5 10 15

Val Lys Ile

<210> SEQ ID NO 300
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 300

Gly Gly Gly Gly Gly Ser Gly Gly Gly Gly Ser Gly Gly Gly His Ser
1 5 10 15

Thr Thr Arg Val
20

<210> SEQ ID NO 301
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 301

Gly Gly Gly Gly Gly Ser Gly Gly Gly Gly Ser Gly Leu Pro His Ser
1 5 10 15

Thr Thr Arg Val
20

<210> SEQ ID NO 302
<211> LENGTH: 20
<212> TYPE: PRT
<213> ORGANISM: Artificial Sequence
<220> FEATURE:

<223> OTHER INFORMATION: Synthetic peptide of PL sequence binding MAGI1 d1

<400> SEQUENCE: 302

Gly Gly Gly Gly Gly Ser Gly Gly Gly Gly Ser Gly Ser Arg Arg Pro
1 5 10 15

Lys Thr Arg Val
20

<210> SEQ ID NO 303
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 303

Gly Gly Gly Gly Gly Ser Gly Gly Gly Gly Thr Phe Ser Arg Arg Pro
1 5 10 15

Lys Thr Arg Val
20

<210> SEQ ID NO 304
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 304

Gly Arg Trp Ala Gly Arg Ser Ala Ala Ser Trp Arg Ser Arg Arg Arg
1 5 10 15

Glu Thr Ala Leu
20

<210> SEQ ID NO 305
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 305

Gly Arg Trp Thr Gly Arg Ala Met Ser Ala Trp Lys Pro Thr Arg Arg
1 5 10 15

Glu Thr Glu Val
20

<210> SEQ ID NO 306
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 306

Gly Arg Trp Thr Gly Arg Ser Ala Val Ser Trp Arg Pro Arg Arg Arg
1 5 10 15

Gln Thr Gln Val
20

<210> SEQ ID NO 307
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 307

Gly Arg Trp Thr Gly Arg Ser Met Ser Ser Trp Lys Pro Thr Arg Arg
1 5 10 15

Glu Thr Glu Val
20

<210> SEQ ID NO 308
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 308

His His Leu Val Ala Gln Arg Asp Ile Arg Gln Phe Gln Leu Gln His
1 5 10 15

Trp Leu Ala Ile
20

<210> SEQ ID NO 309
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 309

His Ser Cys Cys Asn Arg Ala Arg Gln Glu Arg Leu Gln Arg Arg Arg
1 5 10 15

Glu Thr Gln Val
20

<210> SEQ ID NO 310
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 310

Ile Ser Gly Thr Pro Thr Ser Thr Met Val His Gly Met Thr Ser Ser
1 5 10 15

Ser Ser Val Val
20

<210> SEQ ID NO 311
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 311

Lys Ala Gly Tyr Arg Ala Pro Arg Ser Tyr Pro Lys Ser Asn Ser Ser
1 5 10 15

Lys Glu Tyr Val
20

<210> SEQ ID NO 312
<211> LENGTH: 19
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 312

Lys Asp Ser Arg Pro Ser Phe Val Gly Ser Ser Ser Gly His Thr Ser
1 5 10 15

Thr Thr Leu

<210> SEQ ID NO 313
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 313

Lys His Ser Arg Lys Ser Ser Ser Tyr Ser Ser Ser Ser Thr Thr Val
1 5 10 15

Lys Thr Ser Tyr
20

<210> SEQ ID NO 314
<211> LENGTH: 23
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 314

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 315
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 315

Leu Ala Val Leu Ala Tyr Ser Ile Thr Leu Val Met Leu Trp Ser Ile
1 5 10 15

Trp Gln Tyr Ala
20

<210> SEQ ID NO 316
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 316

Leu His Asn Gln Ala Ser Val Pro Leu Glu Pro Arg Pro Leu Arg Arg
1 5 10 15

Glu Ser Glu Ile
20

<210> SEQ ID NO 317
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 317

Leu Asn Glu Thr Thr Glu Thr Gln Arg Thr Leu Leu Asn Gly Asp Leu
1 5 10 15

Gln Thr Ser Ile
20

<210> SEQ ID NO 318
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 318

Leu Asn Ser Cys Ser Asn Arg Arg Val Tyr Lys Lys Met Pro Ser Ile
1 5 10 15

Glu Ser Asp Val
20

<210> SEQ ID NO 319
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 319

Leu Asn Ser Ser Ser Asn Arg Arg Val Tyr Lys Lys Met Pro Ser Ile
1 5 10 15

Glu Ser Asp Val
20

<210> SEQ ID NO 320
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 320

Met Gly Arg Trp Thr Gly Arg Ser Ser Glu Ser Trp Arg Pro Arg Pro
1 5 10 15

Val Thr Gln Val
20

<210> SEQ ID NO 321
<211> LENGTH: 20
<212> TYPE: PRT

<213> ORGANISM: Artificial Sequence
<220> FEATURE:
<223> OTHER INFORMATION: Synthetic peptide of PL sequence binding MAGI1 d1

<400> SEQUENCE: 321

Asn Thr Ser Ser Asp Gln Ala Arg Gln Glu Arg Leu Arg Arg Arg Arg
1 5 10 15

Glu Thr Gln Val
20

<210> SEQ ID NO 322
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 322

Pro Gly Gln Pro Pro Lys Val Lys Ser Glu Phe Asn Ser Tyr Ser Leu
1 5 10 15

Thr Gly Tyr Val
20

<210> SEQ ID NO 323
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 323

Pro Ile Pro Ala Gly Gly Cys Thr Phe Ser Gly Ile Phe Pro Thr Leu
1 5 10 15

Thr Ser Pro Leu
20

<210> SEQ ID NO 324
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 324

Gln Asp Phe Arg Arg Ala Phe Arg Arg Ile Leu Ala Arg Pro Trp Thr
1 5 10 15

Gln Thr Ala Trp
20

<210> SEQ ID NO 325
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 325

Gln Ile Ser Pro Gly Gly Leu Glu Pro Pro Ser Glu Lys His Phe Arg
1 5 10 15

Glu Thr Glu Val
20

```
<210> SEQ ID NO 326
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 326

Gln Gln Tyr Gln Gln Arg Gln Ser Val Ile Phe His Lys Arg Ala Pro
1               5                   10                  15

Glu Gln Ala Leu
            20


<210> SEQ ID NO 327
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 327

Arg Glu Leu Val Asp Arg Gly Glu Val Arg Gln Phe Thr Leu Arg His
1               5                   10                  15

Trp Leu Lys Val
            20


<210> SEQ ID NO 328
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 328

Arg Asn Ile Glu Glu Val Tyr Val Gly Gly Lys Gln Val Val Pro Phe
1               5                   10                  15

Ser Ser Ser Val
            20


<210> SEQ ID NO 329
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 329

Ser Glu Gly Gly Arg Pro Thr Arg Gly Pro Arg Leu Gln Gly Arg Arg
1               5                   10                  15

Val Thr Gln Val
            20


<210> SEQ ID NO 330
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 330
```

Ser Phe Thr Ser Ile Leu Thr Cys His Gln Arg Arg Thr Gln Arg Lys
1 5 10 15

Glu Thr Val Ala
20

<210> SEQ ID NO 331
<211> LENGTH: 19
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 331

Ser Gly Gly Asn Arg Ala Arg Gln Glu Arg Leu Gln Arg Arg Arg Glu
1 5 10 15

Thr Gln Val

<210> SEQ ID NO 332
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 332

Ser Leu Ile Gly Pro Val Gln Lys Glu Tyr Gln Arg Glu Leu Gly Lys
1 5 10 15

Leu Ser Ser Pro
20

<210> SEQ ID NO 333
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 333

Ser Leu Lys Pro Gly Thr Val Leu Pro Pro Pro Pro Tyr Arg His Arg
1 5 10 15

Asn Thr Val Val
20

<210> SEQ ID NO 334
<211> LENGTH: 18
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 334

Ser Pro Gln Pro Asp Ser Thr Asp Asn Asp Asp Tyr Asp Asp Ile Ser
1 5 10 15

Ala Ala

<210> SEQ ID NO 335
<211> LENGTH: 19
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 335

Ser Ser Lys Ser Lys Ser Ser Glu Glu Ser Gln Thr Phe Phe Gly Leu
1 5 10 15

Tyr Lys Leu

<210> SEQ ID NO 336
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 336

Ser Ser Pro Asp Ser Ser Tyr Gln Gly Lys Gly Phe Val Met Ser Arg
1 5 10 15

Ala Met Tyr Val
20

<210> SEQ ID NO 337
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 337

Ser Ser Ser Arg Arg Asp Ser Ser Trp Ser Glu Thr Ser Glu Ala Ser
1 5 10 15

Tyr Ser Gly Leu
20

<210> SEQ ID NO 338
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 338

Ser Tyr Pro Thr Pro Arg Pro Tyr Pro Lys Pro Ala Pro Ser Ser Gly
1 5 10 15

Lys Asp Tyr Val
20

<210> SEQ ID NO 339
<211> LENGTH: 18
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 339

Thr Phe Ala Ala Gly Phe Asn Ser Thr Gly Leu Pro His Ser Thr Thr
1 5 10 15

Arg Val

<210> SEQ ID NO 340
<211> LENGTH: 19
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 340

Thr Gly Arg Gly Met Ser Gly Gly Arg Ser Ser Arg Thr Arg Arg Glu
1               5                   10                  15

Thr Gln Leu

<210> SEQ ID NO 341
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 341

Thr Gly Ser Ala Leu Gln Ala Trp Arg His Thr Ser Arg Gln Ala Thr
1               5                   10                  15

Glu Ser Thr Val
            20

<210> SEQ ID NO 342
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 342

Thr Gln Gly Phe Pro Gly Pro Ala Thr Trp Arg Arg Ile Ser Ser Leu
1               5                   10                  15

Glu Ser Glu Val
            20

<210> SEQ ID NO 343
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 343

Thr Arg Glu Asp Ile Tyr Val Asn Tyr Pro Thr Phe Ser Arg Arg Pro
1               5                   10                  15

Lys Thr Arg Val
            20

<210> SEQ ID NO 344
<211> LENGTH: 19
<212> TYPE: PRT
<213> ORGANISM: Artificial Sequence
<220> FEATURE:
<223> OTHER INFORMATION: Synthetic peptide of PL sequence binding
      MAGI1 d1

<400> SEQUENCE: 344

Thr Thr Asn Asn Asn Pro Asn Ser Ala Val Asn Ile Lys Lys Ile Phe
1               5                   10                  15

Thr Asp Val

<210> SEQ ID NO 345

<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 345

Val Asp Pro Asn Ser Pro Ala Ala Lys Lys Lys Tyr Val Ser Tyr Asn
1 5 10 15

Asn Leu Val Ile
20

<210> SEQ ID NO 346
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 346

Val Gly Thr Leu Leu Leu Glu Arg Val Ile Phe Pro Ser Val Lys Ile
1 5 10 15

Ala Thr Leu Val
20

<210> SEQ ID NO 347
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 347

Val His Lys Val Arg Asn Lys Phe Lys Ala Lys Cys Ser Leu Cys Arg
1 5 10 15

Leu Tyr Ile Ile
20

<210> SEQ ID NO 348
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 348

Trp Thr Gly Gln Ser Ala Asn Ser Arg Lys Pro Pro Arg Gln Arg Ser
1 5 10 15

Glu Thr Gln Val
20

<210> SEQ ID NO 349
<211> LENGTH: 20
<212> TYPE: PRT
<213> ORGANISM: Artificial Sequence
<220> FEATURE:
<223> OTHER INFORMATION: Synthetic peptide of PL sequence binding
MAGI1 d1

<400> SEQUENCE: 349

Tyr Gly Arg Lys Lys Arg Arg Gln Arg Arg Arg Glu Lys His Phe Arg
1 5 10 15

Glu Thr Glu Val
20

<210> SEQ ID NO 350
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 350

Tyr Gly Arg Lys Lys Arg Arg Gln Arg Arg Arg Gly Ala Ser Ala Asp
1 5 10 15

Ser Thr Gln Ala
20

<210> SEQ ID NO 351
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 351

Tyr Gly Arg Lys Lys Arg Arg Gln Arg Arg Arg Lys Leu Ser Ser Ile
1 5 10 15

Glu Ser Asp Val
20

<210> SEQ ID NO 352
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 352

Tyr Gly Arg Lys Lys Arg Arg Gln Arg Arg Arg Asn Asp Asn Ile Ala
1 5 10 15

Leu Leu Val Gln
20

<210> SEQ ID NO 353
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 353

Tyr Gly Arg Lys Lys Arg Arg Gln Arg Arg Arg Arg Ile Ser Ser Ile
1 5 10 15

Glu Thr Asp Val
20

<210> SEQ ID NO 354
<211> LENGTH: 20
<212> TYPE: PRT
<213> ORGANISM: Artificial Sequence
<220> FEATURE:
<223> OTHER INFORMATION: Synthetic peptide of PL sequence binding MAGI1 d1

<400> SEQUENCE: 354

Tyr Ser Ala Thr Tyr Ser Glu Leu Glu Asp Pro Gly Glu Met Ser Pro
1 5 10 15

Pro Ile Asp Leu
20

<210> SEQ ID NO 355
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 355

Ala Ala Gly Gly Arg Ser Ala Arg Gly Gly Arg Leu Gln Gly Arg Arg
1 5 10 15

Glu Thr Ala Leu
20

<210> SEQ ID NO 356
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 356

Ala Thr Asp Tyr Leu Val Gln Pro Phe Met Asp Gln Leu Ala Phe His
1 5 10 15

Gln Phe Tyr Ile
20

<210> SEQ ID NO 357
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 357

Ala Val Gly Gly Arg Pro Ala Arg Gly Gly Arg Leu Gln Gly Arg Arg
1 5 10 15

Gln Thr Gln Val
20

<210> SEQ ID NO 358
<211> LENGTH: 19
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 358

Ala Trp Asp Asp Ser Ala Arg Ala Ala Gly Gly Gln Gly Leu His Val
1 5 10 15

Thr Ala Leu

<210> SEQ ID NO 359
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 359

Asp Phe Arg Pro Ser Phe Lys His Ile Leu Phe Arg Arg Ala Arg Arg
1 5 10 15

Gly Phe Arg Gln
20

<210> SEQ ID NO 360
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 360

Asp Gly Gly Ala Arg Thr Glu Asp Glu Val Gln Ser Tyr Pro Ser Lys
1 5 10 15

His Asp Tyr Val
20

<210> SEQ ID NO 361
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 361

Asp Ser Asp Pro Glu Asn Glu Pro Phe Asp Glu Asp Gln His Thr Gln
1 5 10 15

Ile Thr Lys Val
20

<210> SEQ ID NO 362
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 362

Glu Leu Leu Gln Phe Cys Arg Thr Pro Asn Pro Ala Leu Lys Asn Gly
1 5 10 15

Gln Tyr Trp Val
20

<210> SEQ ID NO 363
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 363

Glu Ser Ser Gly Thr Gln Ser Pro Lys Arg His Ser Gly Ser Tyr Leu
1 5 10 15

Val Thr Ser Val
20

```
<210> SEQ ID NO 364
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 364

Phe His Ser Lys Thr Ala Gly Ala Asn Thr Thr Asp Lys Glu Leu Glu
1               5                   10                  15

Val Leu Ser Leu
            20


<210> SEQ ID NO 365
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 365

Phe Asn Gly Ser Ser Asn Gly His Val Tyr Glu Lys Leu Ser Ser Ile
1               5                   10                  15

Glu Ser Asp Val
            20


<210> SEQ ID NO 366
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 366

Gly Gly Glu Asp Phe Lys Thr Thr Asn Pro Ser Lys Gln Phe Asp Lys
1               5                   10                  15

Asn Ala Tyr Val
            20


<210> SEQ ID NO 367
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 367

Gly Arg Trp Thr Gly Arg Ala Met Ser Ala Trp Lys Pro Thr Arg Arg
1               5                   10                  15

Glu Thr Glu Val
            20


<210> SEQ ID NO 368
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 368

His Asp Phe Arg Arg Ala Phe Lys Lys Ile Leu Ala Arg Gly Asp Arg
```

```
1               5                   10                  15

Lys Arg Ile Val
            20


<210> SEQ ID NO 369
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 369

His His Leu Val Ala Gln Arg Asp Ile Arg Gln Phe Gln Leu Gln His
1               5                   10                  15

Trp Leu Ala Ile
            20


<210> SEQ ID NO 370
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 370

His Ser Cys Cys Asn Arg Ala Arg Gln Glu Arg Leu Gln Arg Arg Arg
1               5                   10                  15

Glu Thr Gln Val
            20


<210> SEQ ID NO 371
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 371

Ile Leu Asn Ser Ile Gln Val Met Arg Ala Gln Met Asn Gln Ile Gln
1               5                   10                  15

Ser Val Glu Val
            20


<210> SEQ ID NO 372
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI2 d5

<400> SEQUENCE: 372

Lys Ala Gly Tyr Arg Ala Pro Arg Ser Tyr Pro Lys Ser Asn Ser Ser
1               5                   10                  15

Lys Glu Tyr Val
            20


<210> SEQ ID NO 373
<211> LENGTH: 20
<212> TYPE: PRT
<213> ORGANISM: Artificial Sequence
<220> FEATURE:
<223> OTHER INFORMATION: Synthetic peptide of PL sequence binding
```

MAGI2 d5

<400> SEQUENCE: 373

Lys His Ser Arg Lys Ser Ser Ser Tyr Ser Ser Ser Ser Thr Thr Val
1 5 10 15

Lys Thr Ser Tyr
20

<210> SEQ ID NO 374
<211> LENGTH: 23
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 374

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 375
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 375

Lys Tyr Ser Ala Pro Arg Arg Pro Thr Ala Thr Gly Asp Tyr Asp Lys
1 5 10 15

Lys Asn Tyr Val
20

<210> SEQ ID NO 376
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 376

Leu Ala Ser Lys Ser Ala Glu Glu Gly Lys Gln Ile Pro Asp Ser Leu
1 5 10 15

Ser Thr Asp Leu
20

<210> SEQ ID NO 377
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 377

Leu Ala Val Leu Ala Tyr Ser Ile Thr Leu Val Met Leu Trp Ser Ile
1 5 10 15

Trp Gln Tyr Ala
20

<210> SEQ ID NO 378

<211> LENGTH: 20
<212> TYPE: PRT
<213> ORGANISM: Artificial Sequence
<220> FEATURE:
<223> OTHER INFORMATION: Synthetic peptide of PL sequence binding
MAGI2 d5

<400> SEQUENCE: 378

Leu Gly Tyr Ser Ile Pro Ser Arg Ser Gly Ala Ser Gly Leu Asp Lys
1 5 10 15

Arg Asp Tyr Val
20

<210> SEQ ID NO 379
<211> LENGTH: 20
<212> TYPE: PRT
<213> ORGANISM: Artificial Sequence
<220> FEATURE:
<223> OTHER INFORMATION: Synthetic peptide of PL sequence binding
MAGI2 d5

<400> SEQUENCE: 379

Leu Met Asp Gly Leu Pro Pro Gly Asp Ser Asn Gln Leu Ala Trp Phe
1 5 10 15

Asp Thr Asp Leu
20

<210> SEQ ID NO 380
<211> LENGTH: 20
<212> TYPE: PRT
<213> ORGANISM: Artificial Sequence
<220> FEATURE:
<223> OTHER INFORMATION: Synthetic peptide of PL sequence binding
MAGI2 d5

<400> SEQUENCE: 380

Leu Asn Ser Cys Ser Asn Arg Arg Val Tyr Lys Lys Met Pro Ser Ile
1 5 10 15

Glu Ser Asp Val
20

<210> SEQ ID NO 381
<211> LENGTH: 20
<212> TYPE: PRT
<213> ORGANISM: Artificial Sequence
<220> FEATURE:
<223> OTHER INFORMATION: Synthetic peptide of PL sequence binding
MAGI2 d5

<400> SEQUENCE: 381

Leu Asn Ser Ser Ser Asn Arg Arg Val Tyr Lys Lys Met Pro Ser Ile
1 5 10 15

Glu Ser Asp Val
20

<210> SEQ ID NO 382
<211> LENGTH: 20
<212> TYPE: PRT
<213> ORGANISM: Artificial Sequence
<220> FEATURE:
<223> OTHER INFORMATION: Synthetic peptide of PL sequence binding
MAGI2 d5

<400> SEQUENCE: 382

Pro Gly Gln Pro Pro Lys Val Lys Ser Glu Phe Asn Ser Tyr Ser Leu
1 5 10 15

Thr Gly Tyr Val
20

<210> SEQ ID NO 383
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 383

Pro Ile Pro Ala Gly Gly Cys Thr Phe Ser Gly Ile Phe Pro Thr Leu
1 5 10 15

Thr Ser Pro Leu
20

<210> SEQ ID NO 384
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 384

Pro Tyr Ser Glu Leu Asn Tyr Glu Thr Ser His Tyr Pro Ala Ser Pro
1 5 10 15

Asp Ser Trp Val
20

<210> SEQ ID NO 385
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 385

Gln Ala Thr Ser Arg Asn Gly His Ser Ala Arg Gln His Val Val Ala
1 5 10 15

Asp Thr Glu Leu
20

<210> SEQ ID NO 386
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 386

Gln Asp Phe Arg Arg Ala Phe Arg Arg Ile Leu Ala Arg Pro Trp Thr
1 5 10 15

Gln Thr Ala Trp
20

<210> SEQ ID NO 387
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 387

Gln Ile Ser Pro Gly Gly Leu Glu Pro Pro Ser Glu Lys His Phe Arg
1 5 10 15

Glu Thr Glu Val
20

<210> SEQ ID NO 388
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 388

Arg Glu Leu Val Asp Arg Gly Glu Val Arg Gln Phe Thr Leu Arg His
1 5 10 15

Trp Leu Lys Val
20

<210> SEQ ID NO 389
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 389

Arg Asn Ile Glu Glu Val Tyr Val Gly Gly Lys Gln Val Val Pro Phe
1 5 10 15

Ser Ser Ser Val
20

<210> SEQ ID NO 390
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 390

Ser Pro Ala Ser Ile Pro His Ser Pro Gly Ala Phe Ala Tyr Glu Gly
1 5 10 15

Ala Ser Phe Tyr
20

<210> SEQ ID NO 391
<211> LENGTH: 19
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 391

Ser Ser Lys Ser Lys Ser Ser Glu Glu Ser Gln Thr Phe Phe Gly Leu
1 5 10 15

Tyr Lys Leu

<210> SEQ ID NO 392
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 392

Ser Ser Pro Asp Ser Ser Tyr Gln Gly Lys Gly Phe Val Met Ser Arg
1 5 10 15

Ala Met Tyr Val
20

<210> SEQ ID NO 393
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 393

Ser Ser Ser Arg Arg Asp Ser Ser Trp Ser Glu Thr Ser Glu Ala Ser
1 5 10 15

Tyr Ser Gly Leu
20

<210> SEQ ID NO 394
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 394

Thr Gly Ser Ala Leu Gln Ala Trp Arg His Thr Ser Arg Gln Ala Thr
1 5 10 15

Glu Ser Thr Val
20

<210> SEQ ID NO 395
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 395

Thr Gln Gly Phe Pro Gly Pro Ala Thr Trp Arg Arg Ile Ser Ser Leu
1 5 10 15

Glu Ser Glu Val
20

<210> SEQ ID NO 396
<211> LENGTH: 19
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 396

Thr Thr Asn Asn Asn Pro Asn Ser Ala Val Asn Ile Lys Lys Ile Phe
1 5 10 15

Thr Asp Val

<210> SEQ ID NO 397
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 397

Val Asp Pro Asn Ser Pro Ala Ala Lys Lys Lys Tyr Val Ser Tyr Asn
1 5 10 15

Asn Leu Val Ile
20

<210> SEQ ID NO 398
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 398

Val Gly Thr Leu Leu Leu Glu Arg Val Ile Phe Pro Ser Val Lys Ile
1 5 10 15

Ala Thr Leu Val
20

<210> SEQ ID NO 399
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 399

Val His Asp Ala Glu Ser Ser Asp Glu Asp Gly Tyr Asp Trp Gly Pro
1 5 10 15

Ala Thr Asp Leu
20

<210> SEQ ID NO 400
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 400

Val His Lys Val Arg Asn Lys Phe Lys Ala Lys Cys Ser Leu Cys Arg
1 5 10 15

Leu Tyr Ile Ile
20

<210> SEQ ID NO 401
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 401

Val Pro Gly Ala Leu Asp Tyr Ala Ala Phe Ser Ser Ala Leu Tyr Gly
1 5 10 15

Glu Ser Asp Leu
20

<210> SEQ ID NO 402
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 402

Tyr Gly Arg Lys Lys Arg Arg Gln Arg Arg Arg Ala Val Ala Ala Thr
1 5 10 15

Ser Ala Asn Leu
20

<210> SEQ ID NO 403
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 403

Tyr Gly Arg Lys Lys Arg Arg Gln Arg Arg Arg Glu Tyr Leu Gly Leu
1 5 10 15

Asp Val Pro Val
20

<210> SEQ ID NO 404
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 404

Tyr Gly Arg Lys Lys Arg Arg Gln Arg Arg Arg Gly Ala Ser Ala Asp
1 5 10 15

Ser Thr Gln Ala
20

<210> SEQ ID NO 405
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 405

Tyr Gly Arg Lys Lys Arg Arg Gln Arg Arg Arg Lys Leu Ser Ser Ile
1 5 10 15

Glu Ser Asp Val
20

<210> SEQ ID NO 406
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 406

Tyr Gly Arg Lys Lys Arg Arg Gln Arg Arg Arg Asn Asp Asn Ile Ala
1 5 10 15

Leu Leu Val Gln
20

<210> SEQ ID NO 407
<211> LENGTH: 20
<212> TYPE: PRT
<213> ORGANISM: Artificial Sequence
<220> FEATURE:
<223> OTHER INFORMATION: Synthetic peptide of PL sequence binding MAGI2 d5

<400> SEQUENCE: 407

Tyr Gly Arg Lys Lys Arg Arg Gln Arg Arg Arg Ser Glu Gly Val Pro
1 5 10 15

Asp Leu Leu Val
20

<210> SEQ ID NO 408
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 408

Ala Ala Gly Gly Arg Ser Ala Arg Gly Gly Arg Leu Gln Gly Arg Arg
1 5 10 15

Glu Thr Ala Leu
20

<210> SEQ ID NO 409
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 409

Ala Leu Val Leu Ile Ala Phe Cys Ile Ile Arg Arg Arg Pro Ser Ala
1 5 10 15

Tyr Gln Ala Leu
20

<210> SEQ ID NO 410
<211> LENGTH: 19
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 410

Ala Arg His Arg Val Thr Ser Tyr Thr Ser Ser Ser Val Asn Val Ser
1 5 10 15

Ser Asn Leu

<210> SEQ ID NO 411
<211> LENGTH: 20
<212> TYPE: PRT

<213> ORGANISM: Artificial Sequence
<220> FEATURE:
<223> OTHER INFORMATION: Synthetic peptide of PL sequence binding
MAGI3 d1

<400> SEQUENCE: 411

Ala Thr Asp Tyr Leu Val Gln Pro Phe Met Asp Gln Leu Ala Phe His
1 5 10 15

Gln Phe Tyr Ile
20

<210> SEQ ID NO 412
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 412

Ala Val Gly Gly Arg Pro Ala Arg Gly Gly Arg Leu Gln Gly Arg Arg
1 5 10 15

Gln Thr Gln Val
20

<210> SEQ ID NO 413
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 413

Asp Phe Arg Pro Ser Phe Lys His Ile Leu Phe Arg Arg Ala Arg Arg
1 5 10 15

Gly Phe Arg Gln
20

<210> SEQ ID NO 414
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 414

Glu Leu Leu Gln Phe Cys Arg Thr Pro Asn Pro Ala Leu Lys Asn Gly
1 5 10 15

Gln Tyr Trp Val
20

<210> SEQ ID NO 415
<211> LENGTH: 17
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 415

Glu Asn Leu Ala Pro Val Thr Thr Phe Gly Lys Thr Asn Gly Tyr Ile
1 5 10 15

Ala

<210> SEQ ID NO 416
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 416

Glu Ser Ser Gly Thr Gln Ser Pro Lys Arg His Ser Gly Ser Tyr Leu
1 5 10 15

Val Thr Ser Val
20

<210> SEQ ID NO 417
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 417

Phe Asn Gly Ser Ser Asn Gly His Val Tyr Glu Lys Leu Ser Ser Ile
1 5 10 15

Glu Ser Asp Val
20

<210> SEQ ID NO 418
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 418

Gly Gly Asp Leu Gly Thr Arg Arg Gly Ser Ala His Phe Ser Ser Leu
1 5 10 15

Glu Ser Glu Val
20

<210> SEQ ID NO 419
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 419

Gly Gly Glu Asp Phe Lys Thr Thr Asn Pro Ser Lys Gln Phe Asp Lys
1 5 10 15

Asn Ala Tyr Val
20

<210> SEQ ID NO 420
<211> LENGTH: 19
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 420

Gly Gly Gly Gly Gly Ser Gly Gly Gly Gly Gly Ser Gly Ile Glu Ser 1 5 10 15

Val Lys Ile

<210> SEQ ID NO 421
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 421

Gly Gly Gly Gly Gly Ser Gly Gly Gly Gly Ser Gly Gly Gly His Ser
1 5 10 15

Thr Thr Arg Val
20

<210> SEQ ID NO 422
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 422

Gly Gly Gly Gly Gly Ser Gly Gly Gly Gly Ser Gly Leu Pro His Ser
1 5 10 15

Thr Thr Arg Val
20

<210> SEQ ID NO 423
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 423

Gly Gly Gly Gly Gly Ser Gly Gly Gly Gly Ser Gly Ser Arg Arg Pro
1 5 10 15

Lys Thr Arg Val
20

<210> SEQ ID NO 424
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 424

Gly Arg Trp Ala Gly Arg Ser Ala Ala Ser Trp Arg Ser Arg Arg Arg
1 5 10 15

Glu Thr Ala Leu
20

<210> SEQ ID NO 425
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

-continued

<400> SEQUENCE: 425

Gly Arg Trp Thr Gly Arg Ala Met Ser Ala Trp Lys Pro Thr Arg Arg
1 5 10 15

Glu Thr Glu Val
20

<210> SEQ ID NO 426
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 426

Gly Arg Trp Thr Gly Arg Cys Met Ser Cys Trp Lys Pro Thr Arg Arg
1 5 10 15

Glu Thr Glu Val
20

<210> SEQ ID NO 427
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 427

Gly Arg Trp Thr Gly Arg Ser Ala Val Ser Trp Arg Pro Arg Arg Arg
1 5 10 15

Gln Thr Gln Val
20

<210> SEQ ID NO 428
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 428

Gly Arg Trp Thr Gly Arg Ser Met Ser Ser Trp Lys Pro Thr Arg Arg
1 5 10 15

Glu Thr Glu Val
20

<210> SEQ ID NO 429
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 429

His Ala Met Asn Ala Ala Pro Arg Ala Met Glu Asn Ala Pro Ala Leu
1 5 10 15

Arg Thr Ser His
20

<210> SEQ ID NO 430
<211> LENGTH: 20

<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 430

His His Leu Val Ala Gln Arg Asp Ile Arg Gln Phe Gln Leu Gln His
1 5 10 15

Trp Leu Ala Ile
20

<210> SEQ ID NO 431
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 431

Ile Ser Gly Thr Pro Thr Ser Thr Met Val His Gly Met Thr Ser Ser
1 5 10 15

Ser Ser Val Val
20

<210> SEQ ID NO 432
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 432

Ile Ser Lys Leu Gly Ile Ser Gly Asp Ile Asp Leu Thr Ser Ala Ser
1 5 10 15

Tyr Thr Met Ile
20

<210> SEQ ID NO 433
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 433

Lys Ala Gly Tyr Arg Ala Pro Arg Ser Tyr Pro Lys Ser Asn Ser Ser
1 5 10 15

Lys Glu Tyr Val
20

<210> SEQ ID NO 434
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 434

Lys His Ser Arg Lys Ser Ser Ser Tyr Ser Ser Ser Ser Thr Thr Val
1 5 10 15

Lys Thr Ser Tyr

20

<210> SEQ ID NO 435
<211> LENGTH: 23
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 435

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 436
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 436

Leu Ala Ser Lys Ser Ala Glu Glu Gly Lys Gln Ile Pro Asp Ser Leu
1 5 10 15

Ser Thr Asp Leu
20

<210> SEQ ID NO 437
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 437

Leu Ala Val Leu Ala Tyr Ser Ile Thr Leu Val Met Leu Trp Ser Ile
1 5 10 15

Trp Gln Tyr Ala
20

<210> SEQ ID NO 438
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 438

Leu His Asn Gln Ala Ser Val Pro Leu Glu Pro Arg Pro Leu Arg Arg
1 5 10 15

Glu Ser Glu Ile
20

<210> SEQ ID NO 439
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 439

Leu Asn Ser Cys Ser Asn Arg Arg Val Tyr Lys Lys Met Pro Ser Ile
1 5 10 15

Glu Ser Asp Val
20

<210> SEQ ID NO 440
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 440

Leu Asn Ser Ser Ser Asn Arg Arg Val Tyr Lys Lys Met Pro Ser Ile
1 5 10 15

Glu Ser Asp Val
20

<210> SEQ ID NO 441
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 441

Leu Ser Glu Lys Lys Thr Ser Gln Ser Pro His Arg Phe Gln Lys Thr
1 5 10 15

Ser Ser Pro Ile
20

<210> SEQ ID NO 442
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 442

Met Gly Arg Trp Thr Gly Arg Ser Ser Glu Ser Trp Arg Pro Arg Pro
1 5 10 15

Val Thr Gln Val
20

<210> SEQ ID NO 443
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 443

Asn Thr Ser Ser Asp Gln Ala Arg Gln Glu Arg Leu Arg Arg Arg Arg
1 5 10 15

Glu Thr Gln Val
20

<210> SEQ ID NO 444
<211> LENGTH: 20
<212> TYPE: PRT
<213> ORGANISM: Artificial Sequence

```
<220> FEATURE:
<223> OTHER INFORMATION: Synthetic peptide of PL sequence binding
      MAGI3 d1

<400> SEQUENCE: 444

Pro Gly Gln Pro Pro Lys Val Lys Ser Glu Phe Asn Ser Tyr Ser Leu
1               5                   10                  15

Thr Gly Tyr Val
            20


<210> SEQ ID NO 445
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 445

Pro Ile Pro Ala Gly Gly Cys Thr Phe Ser Gly Ile Phe Pro Thr Leu
1               5                   10                  15

Thr Ser Pro Leu
            20


<210> SEQ ID NO 446
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 446

Pro Tyr Ser Glu Leu Asn Tyr Glu Thr Ser His Tyr Pro Ala Ser Pro
1               5                   10                  15

Asp Ser Trp Val
            20


<210> SEQ ID NO 447
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 447

Gln Asp Phe Arg Arg Ala Phe Arg Arg Ile Leu Ala Arg Pro Trp Thr
1               5                   10                  15

Gln Thr Ala Trp
            20


<210> SEQ ID NO 448
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 448

Gln Ile Ser Pro Gly Gly Leu Glu Pro Pro Ser Glu Lys His Phe Arg
1               5                   10                  15

Glu Thr Glu Val
            20
```

<210> SEQ ID NO 449
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 449

```
Arg Glu Leu Val Asp Arg Gly Glu Val Arg Gln Phe Thr Leu Arg His
1               5                   10                  15

Trp Leu Lys Val
            20
```

<210> SEQ ID NO 450
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 450

```
Arg Asn Ile Glu Glu Val Tyr Val Gly Gly Lys Gln Val Val Pro Phe
1               5                   10                  15

Ser Ser Ser Val
            20
```

<210> SEQ ID NO 451
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 451

```
Ser Phe Thr Ser Ile Leu Thr Cys His Gln Arg Arg Thr Gln Arg Lys
1               5                   10                  15

Glu Thr Val Ala
            20
```

<210> SEQ ID NO 452
<211> LENGTH: 19
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 452

```
Ser Gly Gly Asn Arg Ala Arg Gln Glu Arg Leu Gln Arg Arg Arg Glu
1               5                   10                  15

Thr Gln Val
```

<210> SEQ ID NO 453
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 453

```
Ser Leu Ile Gly Pro Val Gln Lys Glu Tyr Gln Arg Glu Leu Gly Lys
1               5                   10                  15
```

Leu Ser Ser Pro
20

<210> SEQ ID NO 454
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 454

Ser Leu Lys Pro Gly Thr Val Leu Pro Pro Pro Pro Tyr Arg His Arg
1 5 10 15

Asn Thr Val Val
20

<210> SEQ ID NO 455
<211> LENGTH: 18
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 455

Ser Pro Gln Pro Asp Ser Thr Asp Asn Asp Asp Tyr Asp Asp Ile Ser
1 5 10 15

Ala Ala

<210> SEQ ID NO 456
<211> LENGTH: 19
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 456

Ser Ser Lys Ser Lys Ser Ser Glu Glu Ser Gln Thr Phe Phe Gly Leu
1 5 10 15

Tyr Lys Leu

<210> SEQ ID NO 457
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 457

Ser Ser Pro Asp Ser Ser Tyr Gln Gly Lys Gly Phe Val Met Ser Arg
1 5 10 15

Ala Met Tyr Val
20

<210> SEQ ID NO 458
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 458

```
Ser Thr Asp Asn Leu Val Arg Pro Phe Met Asp Thr Leu Ala Ser His
1               5                   10                  15

Gln Leu Tyr Ile
            20


<210> SEQ ID NO 459
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 459

Ser Tyr Pro Thr Pro Arg Pro Tyr Pro Lys Pro Ala Pro Ser Ser Gly
1               5                   10                  15

Lys Asp Tyr Val
            20


<210> SEQ ID NO 460
<211> LENGTH: 18
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 460

Thr Phe Ala Ala Gly Phe Asn Ser Thr Gly Leu Pro His Ser Thr Thr
1               5                   10                  15

Arg Val


<210> SEQ ID NO 461
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 461

Thr Phe Lys Gly Thr Pro Thr Ala Glu Asn Pro Glu Tyr Leu Gly Leu
1               5                   10                  15

Asp Val Pro Val
            20


<210> SEQ ID NO 462
<211> LENGTH: 19
<212> TYPE: PRT
<213> ORGANISM: Artificial Sequence
<220> FEATURE:
<223> OTHER INFORMATION: Synthetic peptide of PL sequence binding
      MAGI3 d1

<400> SEQUENCE: 462

Thr Gly Arg Gly Met Ser Gly Gly Arg Ser Ser Arg Thr Arg Arg Glu
1               5                   10                  15

Thr Gln Leu


<210> SEQ ID NO 463
<211> LENGTH: 20
<212> TYPE: PRT
<213> ORGANISM: Artificial Sequence
<220> FEATURE:
<223> OTHER INFORMATION: Synthetic peptide of PL sequence binding
```

MAGI3 d1

<400> SEQUENCE: 463

Thr Gly Ser Ala Leu Gln Ala Trp Arg His Thr Ser Arg Gln Ala Thr
1 5 10 15

Glu Ser Thr Val
20

<210> SEQ ID NO 464
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 464

Thr Gln Gly Phe Pro Gly Pro Ala Thr Trp Arg Arg Ile Ser Ser Leu
1 5 10 15

Glu Ser Glu Val
20

<210> SEQ ID NO 465
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 465

Thr Arg Glu Asp Ile Tyr Val Asn Tyr Pro Thr Phe Ser Arg Arg Pro
1 5 10 15

Lys Thr Arg Val
20

<210> SEQ ID NO 466
<211> LENGTH: 19
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 466

Thr Thr Asn Asn Asn Pro Asn Ser Ala Val Asn Ile Lys Lys Ile Phe
1 5 10 15

Thr Asp Val

<210> SEQ ID NO 467
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 467

Val Asp Pro Asn Ser Pro Ala Ala Lys Lys Lys Tyr Val Ser Tyr Asn
1 5 10 15

Asn Leu Val Ile
20

<210> SEQ ID NO 468
<211> LENGTH: 20

<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 468

Val Gly Thr Leu Leu Leu Glu Arg Val Ile Phe Pro Ser Val Lys Ile
1 5 10 15

Ala Thr Leu Val
20

<210> SEQ ID NO 469
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 469

Val His Lys Val Arg Asn Lys Phe Lys Ala Lys Cys Ser Leu Cys Arg
1 5 10 15

Leu Tyr Ile Ile
20

<210> SEQ ID NO 470
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 470

Trp Thr Gly Gln Ser Ala Asn Ser Arg Lys Pro Pro Arg Gln Arg Ser
1 5 10 15

Glu Thr Gln Val
20

<210> SEQ ID NO 471
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 471

Tyr Gly Arg Lys Lys Arg Arg Gln Arg Arg Arg Lys Leu Ser Ser Ile
1 5 10 15

Glu Ser Asp Val
20

<210> SEQ ID NO 472
<211> LENGTH: 20
<212> TYPE: PRT
<213> ORGANISM: Artificial Sequence
<220> FEATURE:
<223> OTHER INFORMATION: Synthetic peptide of PL sequence binding
MAGI3 d1

<400> SEQUENCE: 472

Tyr Gly Arg Lys Lys Arg Arg Gln Arg Arg Arg Asn Asp Asn Ile Ala
1 5 10 15

Leu Leu Val Gln

20

<210> SEQ ID NO 473
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d1

<400> SEQUENCE: 473

Tyr Ser Ala Thr Tyr Ser Glu Leu Glu Asp Pro Gly Glu Met Ser Pro
1 5 10 15

Pro Ile Asp Leu
20

<210> SEQ ID NO 474
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 474

Ala Thr Asp Tyr Leu Val Gln Pro Phe Met Asp Gln Leu Ala Phe His
1 5 10 15

Gln Phe Tyr Ile
20

<210> SEQ ID NO 475
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 475

Ala Val Gly Gly Arg Pro Ala Arg Gly Gly Arg Leu Gln Gly Arg Arg
1 5 10 15

Gln Thr Gln Val
20

<210> SEQ ID NO 476
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 476

Asp Phe Arg Pro Ser Phe Lys His Ile Leu Phe Arg Arg Ala Arg Arg
1 5 10 15

Gly Phe Arg Gln
20

<210> SEQ ID NO 477
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 477

```
Asp Ser Asp Pro Glu Asn Glu Pro Phe Asp Glu Asp Gln His Thr Gln
1               5                   10                  15

Ile Thr Lys Val
            20


<210> SEQ ID NO 478
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 478

Asp Thr Leu Leu Leu Thr Glu Asn Glu Gly Asp Lys Thr Glu Glu Gln
1               5                   10                  15

Val Ser Tyr Val
            20


<210> SEQ ID NO 479
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 479

Glu Asp Pro Lys Asp Arg Pro Ser Ala Ala His Ile Val Glu Ala Leu
1               5                   10                  15

Glu Thr Asp Val
            20


<210> SEQ ID NO 480
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 480

Glu Ser Ser Gly Thr Gln Ser Pro Lys Arg His Ser Gly Ser Tyr Leu
1               5                   10                  15

Val Thr Ser Val
            20


<210> SEQ ID NO 481
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 481

Gly Gly Gly Gly Gly Ser Gly Gly Gly Gly Ser Gly Gly Gly His Ser
1               5                   10                  15

Thr Thr Arg Val
            20


<210> SEQ ID NO 482
<211> LENGTH: 20
<212> TYPE: PRT
<213> ORGANISM: Artificial Sequence
```

```
<220> FEATURE:
<223> OTHER INFORMATION: Synthetic peptide of PL sequence binding
      MAGI3 d2

<400> SEQUENCE: 482

Gly Gly Gly Gly Gly Ser Gly Gly Gly Gly Ser Gly Leu Pro His Ser
1               5                   10                  15

Thr Thr Arg Val
            20


<210> SEQ ID NO 483
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 483

Gly Arg Trp Thr Gly Arg Ala Met Ser Ala Trp Lys Pro Thr Arg Arg
1               5                   10                  15

Glu Thr Glu Val
            20


<210> SEQ ID NO 484
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 484

Gly Arg Trp Thr Gly Arg Cys Met Ser Cys Trp Lys Pro Thr Arg Arg
1               5                   10                  15

Glu Thr Glu Val
            20


<210> SEQ ID NO 485
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 485

His Asp Phe Arg Arg Ala Phe Lys Lys Ile Leu Ala Arg Gly Asp Arg
1               5                   10                  15

Lys Arg Ile Val
            20


<210> SEQ ID NO 486
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 486

His His Leu Val Ala Gln Arg Asp Ile Arg Gln Phe Gln Leu Gln His
1               5                   10                  15

Trp Leu Ala Ile
            20
```

<210> SEQ ID NO 487
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 487

His Pro Thr Asp Ile Thr Gly Leu Pro Asn Leu Ser Asp Pro Ser Val
1 5 10 15

Ser Thr Val Val
20

<210> SEQ ID NO 488
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 488

Ile Leu Asn Ser Ile Gln Val Met Arg Ala Gln Met Asn Gln Ile Gln
1 5 10 15

Ser Val Glu Val
20

<210> SEQ ID NO 489
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 489

Ile Ser Gly Thr Pro Thr Ser Thr Met Val His Gly Met Thr Ser Ser
1 5 10 15

Ser Ser Val Val
20

<210> SEQ ID NO 490
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 490

Ile Val Thr Val Val Thr Met Val Thr Asn Val Asp Phe Pro Pro Lys
1 5 10 15

Glu Ser Ser Leu
20

<210> SEQ ID NO 491
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 491

Lys Ala Gly Tyr Arg Ala Pro Arg Ser Tyr Pro Lys Ser Asn Ser Ser

```
1               5                   10                  15

Lys Glu Tyr Val
            20


<210> SEQ ID NO 492
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 492

Lys His Ser Arg Lys Ser Ser Ser Tyr Ser Ser Ser Ser Thr Thr Val
1               5                   10                  15

Lys Thr Ser Tyr
            20


<210> SEQ ID NO 493
<211> LENGTH: 23
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 493

Lys Lys Lys Lys Gln Pro Gly Asn Ser Thr Lys Glu Ser Glu Ser Thr
1               5                   10                  15

Asn Ser Val Arg Leu Met Leu
            20


<210> SEQ ID NO 494
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 494

Leu Ala Ser Lys Ser Ala Glu Glu Gly Lys Gln Ile Pro Asp Ser Leu
1               5                   10                  15

Ser Thr Asp Leu
            20


<210> SEQ ID NO 495
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 495

Leu Ala Val Leu Ala Tyr Ser Ile Thr Leu Val Met Leu Trp Ser Ile
1               5                   10                  15

Trp Gln Tyr Ala
            20


<210> SEQ ID NO 496
<211> LENGTH: 20
<212> TYPE: PRT
<213> ORGANISM: Artificial Sequence
<220> FEATURE:
<223> OTHER INFORMATION: Synthetic peptide of PL sequence binding
```

MAGI3 d2

<400> SEQUENCE: 496

Leu Asn Ser Cys Ser Asn Arg Arg Val Tyr Lys Lys Met Pro Ser Ile
1 5 10 15

Glu Ser Asp Val
20

<210> SEQ ID NO 497
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 497

Pro Gly Gln Pro Pro Lys Val Lys Ser Glu Phe Asn Ser Tyr Ser Leu
1 5 10 15

Thr Gly Tyr Val
20

<210> SEQ ID NO 498
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 498

Pro Ile Pro Ala Gly Gly Cys Thr Phe Ser Gly Ile Phe Pro Thr Leu
1 5 10 15

Thr Ser Pro Leu
20

<210> SEQ ID NO 499
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 499

Pro Tyr Gln Ser Gln Gly Phe Ser Thr Glu Glu Asp Glu Asp Glu Gln
1 5 10 15

Val Ser Ala Val
20

<210> SEQ ID NO 500
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 500

Gln Asp Phe Arg Arg Ala Phe Arg Arg Ile Leu Ala Arg Pro Trp Thr
1 5 10 15

Gln Thr Ala Trp
20

<210> SEQ ID NO 501

<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 501

Gln Ile Ser Pro Gly Gly Leu Glu Pro Pro Ser Glu Lys His Phe Arg
1 5 10 15

Glu Thr Glu Val
20

<210> SEQ ID NO 502
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 502

Arg Glu Leu Val Asp Arg Gly Glu Val Arg Gln Phe Thr Leu Arg His
1 5 10 15

Trp Leu Lys Val
20

<210> SEQ ID NO 503
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 503

Arg Ser Gly Ala Thr Ile Pro Leu Val Gly Gln Asp Ile Ile Asp Leu
1 5 10 15

Gln Thr Glu Val
20

<210> SEQ ID NO 504
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 504

Ser Phe Thr Ser Ile Leu Thr Cys His Gln Arg Arg Thr Gln Arg Lys
1 5 10 15

Glu Thr Val Ala
20

<210> SEQ ID NO 505
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 505

Ser Leu Lys Pro Gly Thr Val Leu Pro Pro Pro Pro Tyr Arg His Arg
1 5 10 15

Asn Thr Val Val
20

<210> SEQ ID NO 506
<211> LENGTH: 18
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 506

Ser Pro Gln Pro Asp Ser Thr Asp Asn Asp Asp Tyr Asp Asp Ile Ser
1 5 10 15

Ala Ala

<210> SEQ ID NO 507
<211> LENGTH: 19
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 507

Ser Ser Lys Ser Lys Ser Ser Glu Glu Ser Gln Thr Phe Phe Gly Leu
1 5 10 15

Tyr Lys Leu

<210> SEQ ID NO 508
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 508

Ser Ser Ser Arg Arg Asp Ser Ser Trp Ser Glu Thr Ser Glu Ala Ser
1 5 10 15

Tyr Ser Gly Leu
20

<210> SEQ ID NO 509
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 509

Ser Tyr Pro Thr Pro Arg Pro Tyr Pro Lys Pro Ala Pro Ser Ser Gly
1 5 10 15

Lys Asp Tyr Val
20

<210> SEQ ID NO 510
<211> LENGTH: 18
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 510

```
Thr Phe Ala Ala Gly Phe Asn Ser Thr Gly Leu Pro His Ser Thr Thr
1               5                   10                  15

Arg Val


<210> SEQ ID NO 511
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 511

Thr Gly Ser Ala Leu Gln Ala Trp Arg His Thr Ser Arg Gln Ala Thr
1               5                   10                  15

Glu Ser Thr Val
            20


<210> SEQ ID NO 512
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 512

Thr Gln Gly Phe Pro Gly Pro Ala Thr Trp Arg Arg Ile Ser Ser Leu
1               5                   10                  15

Glu Ser Glu Val
            20


<210> SEQ ID NO 513
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 513

Thr Arg Glu Asp Ile Tyr Val Asn Tyr Pro Thr Phe Ser Arg Arg Pro
1               5                   10                  15

Lys Thr Arg Val
            20


<210> SEQ ID NO 514
<211> LENGTH: 19
<212> TYPE: PRT
<213> ORGANISM: Artificial Sequence
<220> FEATURE:
<223> OTHER INFORMATION: Synthetic peptide of PL sequence binding
      MAGI3 d2

<400> SEQUENCE: 514

Thr Thr Asn Asn Asn Pro Asn Ser Ala Val Asn Ile Lys Lys Ile Phe
1               5                   10                  15

Thr Asp Val


<210> SEQ ID NO 515
<211> LENGTH: 20
<212> TYPE: PRT
<213> ORGANISM: Artificial Sequence
<220> FEATURE:
<223> OTHER INFORMATION: Synthetic peptide of PL sequence binding
      MAGI3 d2
```

<400> SEQUENCE: 515

Val Asp Pro Asn Ser Pro Ala Ala Lys Lys Lys Tyr Val Ser Tyr Asn
1 5 10 15

Asn Leu Val Ile
20

<210> SEQ ID NO 516
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 516

Val Gly Thr Leu Leu Leu Glu Arg Val Ile Phe Pro Ser Val Lys Ile
1 5 10 15

Ala Thr Leu Val
20

<210> SEQ ID NO 517
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 517

Val His Lys Val Arg Asn Lys Phe Lys Ala Lys Cys Ser Leu Cys Arg
1 5 10 15

Leu Tyr Ile Ile
20

<210> SEQ ID NO 518
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 518

Tyr Gly Arg Lys Lys Arg Arg Gln Arg Arg Arg Ala Arg Gly Arg Arg
1 5 10 15

Glu Thr Trp Val
20

<210> SEQ ID NO 519
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 519

Tyr Gly Arg Lys Lys Arg Arg Gln Arg Arg Arg Lys Leu Ser Ser Ile
1 5 10 15

Glu Ser Asp Val
20

<210> SEQ ID NO 520
<211> LENGTH: 20

<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 520

Tyr Gly Arg Lys Lys Arg Arg Gln Arg Arg Arg Asn Asp Asn Ile Ala
1 5 10 15

Leu Leu Val Gln
20

<210> SEQ ID NO 521
<211> LENGTH: 20
<212> TYPE: PRT
<213> ORGANISM: Artificial Sequence
<220> FEATURE:
<223> OTHER INFORMATION: Synthetic peptide of PL sequence binding MAGI3 d2

<400> SEQUENCE: 521

Tyr Gly Arg Lys Lys Arg Arg Gln Arg Arg Arg Ser Glu Gly Val Pro
1 5 10 15

Asp Leu Leu Val
20

<210> SEQ ID NO 522
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 522

Ala Ala Gly Gly Arg Ser Ala Arg Gly Gly Arg Leu Gln Gly Arg Arg
1 5 10 15

Glu Thr Ala Leu
20

<210> SEQ ID NO 523
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 523

Ala Gly Ala Val Arg Thr Pro Leu Ser Gln Val Asn Lys Val Trp Asp
1 5 10 15

Gln Ser Ser Val
20

<210> SEQ ID NO 524
<211> LENGTH: 19
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 524

Ala Arg His Arg Val Thr Ser Tyr Thr Ser Ser Ser Val Asn Val Ser
1 5 10 15

Ser Asn Leu

<210> SEQ ID NO 525
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 525

Ala Val Gly Gly Arg Pro Ala Arg Gly Gly Arg Leu Gln Gly Arg Arg
1 5 10 15

Gln Thr Gln Val
20

<210> SEQ ID NO 526
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 526

Asp Phe Arg Pro Ser Phe Lys His Ile Leu Phe Arg Arg Ala Arg Arg
1 5 10 15

Gly Phe Arg Gln
20

<210> SEQ ID NO 527
<211> LENGTH: 19
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 527

Glu Val Ile Gly Tyr Ile Glu Lys Pro Gly Val Glu Thr Leu Glu Asp
1 5 10 15

Ser Val Phe

<210> SEQ ID NO 528
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 528

Gly Gly Glu Asp Phe Lys Thr Thr Asn Pro Ser Lys Gln Phe Asp Lys
1 5 10 15

Asn Ala Tyr Val
20

<210> SEQ ID NO 529
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 529

Gly Arg Trp Thr Gly Arg Ala Met Ser Ala Trp Lys Pro Thr Arg Arg 1 5 10 15

Glu Thr Glu Val
20

<210> SEQ ID NO 530
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 530

Gly Arg Trp Thr Gly Arg Cys Met Ser Cys Trp Lys Pro Thr Arg Arg
1 5 10 15

Glu Thr Glu Val
20

<210> SEQ ID NO 531
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 531

His His Leu Val Ala Gln Arg Asp Ile Arg Gln Phe Gln Leu Gln His
1 5 10 15

Trp Leu Ala Ile
20

<210> SEQ ID NO 532
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 532

His Ser Cys Cys Asn Arg Ala Arg Gln Glu Arg Leu Gln Arg Arg Arg
1 5 10 15

Glu Thr Gln Val
20

<210> SEQ ID NO 533
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 533

Lys Ala Gly Tyr Arg Ala Pro Arg Ser Tyr Pro Lys Ser Asn Ser Ser
1 5 10 15

Lys Glu Tyr Val
20

<210> SEQ ID NO 534
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 534

Lys His Ser Arg Lys Ser Ser Ser Tyr Ser Ser Ser Ser Thr Thr Val
1 5 10 15

Lys Thr Ser Tyr
20

<210> SEQ ID NO 535
<211> LENGTH: 23
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 535

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 536
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 536

Lys Tyr Ser Ala Pro Arg Arg Pro Thr Ala Thr Gly Asp Tyr Asp Lys
1 5 10 15

Lys Asn Tyr Val
20

<210> SEQ ID NO 537
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 537

Leu Ala Val Leu Ala Tyr Ser Ile Thr Leu Val Met Leu Trp Ser Ile
1 5 10 15

Trp Gln Tyr Ala
20

<210> SEQ ID NO 538
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 538

Leu Met Asp Gly Leu Pro Pro Gly Asp Ser Asn Gln Leu Ala Trp Phe
1 5 10 15

Asp Thr Asp Leu
20

<210> SEQ ID NO 539

<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 539

Leu Asn Ser Cys Ser Asn Arg Arg Val Tyr Lys Lys Met Pro Ser Ile
1 5 10 15

Glu Ser Asp Val
20

<210> SEQ ID NO 540
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 540

Pro Gly Gln Pro Pro Lys Val Lys Ser Glu Phe Asn Ser Tyr Ser Leu
1 5 10 15

Thr Gly Tyr Val
20

<210> SEQ ID NO 541
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 541

Pro Ile Pro Ala Gly Gly Cys Thr Phe Ser Gly Ile Phe Pro Thr Leu
1 5 10 15

Thr Ser Pro Leu
20

<210> SEQ ID NO 542
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 542

Pro Tyr Ser Glu Leu Asn Tyr Glu Thr Ser His Tyr Pro Ala Ser Pro
1 5 10 15

Asp Ser Trp Val
20

<210> SEQ ID NO 543
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 543

Gln Asp Phe Arg Arg Ala Phe Arg Arg Ile Leu Ala Arg Pro Trp Thr
1 5 10 15

```
Gln Thr Ala Trp
            20


<210> SEQ ID NO 544
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d1

<400> SEQUENCE: 544

Arg Glu Leu Val Asp Arg Gly Glu Val Arg Gln Phe Thr Leu Arg His
1               5                   10                  15

Trp Leu Lys Val
            20


<210> SEQ ID NO 545
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d1

<400> SEQUENCE: 545

Arg Glu Leu Val Asp Arg Gly Glu Val Arg Gln Phe Thr Leu Arg His
1               5                   10                  15

Trp Leu Lys Val
            20


<210> SEQ ID NO 546
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d1

<400> SEQUENCE: 546

Ser Leu Ile Gly Pro Val Gln Lys Glu Tyr Gln Arg Glu Leu Gly Lys
1               5                   10                  15

Leu Ser Ser Pro
            20


<210> SEQ ID NO 547
<211> LENGTH: 19
<212> TYPE: PRT
<213> ORGANISM: Artificial Sequence
<220> FEATURE:
<223> OTHER INFORMATION: Synthetic peptide of PL sequence binding
      NeDLG d1

<400> SEQUENCE: 547

Ser Ser Lys Ser Lys Ser Ser Glu Glu Ser Gln Thr Phe Phe Gly Leu
1               5                   10                  15

Tyr Lys Leu


<210> SEQ ID NO 548
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d1

<400> SEQUENCE: 548
```

Ser Ser Pro Asp Ser Ser Tyr Gln Gly Lys Gly Phe Val Met Ser Arg
1               5                   10                  15

Ala Met Tyr Val
            20

<210> SEQ ID NO 549
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 549

Thr Ala Glu Asn Ala Glu Tyr Leu Arg Val Ala Pro Gln Ser Ser Glu
1               5                   10                  15

Phe Ile Gly Ala
            20

<210> SEQ ID NO 550
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 550

Thr Gly Ser Ala Leu Gln Ala Trp Arg His Thr Ser Arg Gln Ala Thr
1               5                   10                  15

Glu Ser Thr Val
            20

<210> SEQ ID NO 551
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 551

Thr Gln Gly Phe Pro Gly Pro Ala Thr Trp Arg Arg Ile Ser Ser Leu
1               5                   10                  15

Glu Ser Glu Val
            20

<210> SEQ ID NO 552
<211> LENGTH: 19
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 552

Thr Thr Asn Asn Asn Pro Asn Ser Ala Val Asn Ile Lys Lys Ile Phe
1               5                   10                  15

Thr Asp Val

<210> SEQ ID NO 553
<211> LENGTH: 20
<212> TYPE: PRT
<213> ORGANISM: Artificial Sequence
<220> FEATURE:

<223> OTHER INFORMATION: Synthetic peptide of PL sequence binding NeDLG d1

<400> SEQUENCE: 553

Val Asp Pro Asn Ser Pro Ala Ala Lys Lys Lys Tyr Val Ser Tyr Asn
1 5 10 15

Asn Leu Val Ile
20

<210> SEQ ID NO 554
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 554

Val Asp Ser Glu Arg Arg Pro His Phe Pro Gln Phe Ser Tyr Ser Ala
1 5 10 15

Ser Gly Thr Ala
20

<210> SEQ ID NO 555
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 555

Val Gly Thr Leu Leu Leu Glu Arg Val Ile Phe Pro Ser Val Lys Ile
1 5 10 15

Ala Thr Leu Val
20

<210> SEQ ID NO 556
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 556

Val His Lys Val Arg Asn Lys Phe Lys Ala Lys Cys Ser Leu Cys Arg
1 5 10 15

Leu Tyr Ile Ile
20

<210> SEQ ID NO 557
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d1

<400> SEQUENCE: 557

Tyr Gly Arg Lys Lys Arg Arg Gln Arg Arg Arg Asn Asp Asn Ile Ala
1 5 10 15

Leu Leu Val Gln
20

<210> SEQ ID NO 558
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 558

Ala Ala Gly Gly Arg Ser Ala Arg Gly Gly Arg Leu Gln Gly Arg Arg
1 5 10 15

Glu Thr Ala Leu
20

<210> SEQ ID NO 559
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 559

Ala Gly Ala Val Arg Thr Pro Leu Ser Gln Val Asn Lys Val Trp Asp
1 5 10 15

Gln Ser Ser Val
20

<210> SEQ ID NO 560
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 560

Ala Thr Asp Tyr Leu Val Gln Pro Phe Met Asp Gln Leu Ala Phe His
1 5 10 15

Gln Phe Tyr Ile
20

<210> SEQ ID NO 561
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 561

Ala Val Gly Gly Arg Pro Ala Arg Gly Gly Arg Leu Gln Gly Arg Arg
1 5 10 15

Gln Thr Gln Val
20

<210> SEQ ID NO 562
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 562

Asp Phe Arg Pro Ser Phe Lys His Ile Leu Phe Arg Arg Ala Arg Arg
1 5 10 15

```
Gly Phe Arg Gln
            20


<210> SEQ ID NO 563
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d2

<400> SEQUENCE: 563

Glu Asp Pro Lys Asp Arg Pro Ser Ala Ala His Ile Val Glu Ala Leu
1               5                   10                  15

Glu Thr Asp Val
            20


<210> SEQ ID NO 564
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d2

<400> SEQUENCE: 564

Glu Leu Leu Gln Phe Cys Arg Thr Pro Asn Pro Ala Leu Lys Asn Gly
1               5                   10                  15

Gln Tyr Trp Val
            20


<210> SEQ ID NO 565
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d2

<400> SEQUENCE: 565

Glu Ser Ser Gly Thr Gln Ser Pro Lys Arg His Ser Gly Ser Tyr Leu
1               5                   10                  15

Val Thr Ser Val
            20


<210> SEQ ID NO 566
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d2

<400> SEQUENCE: 566

Phe Asn Gly Ser Ser Asn Gly His Val Tyr Glu Lys Leu Ser Ser Ile
1               5                   10                  15

Glu Ser Asp Val
            20


<210> SEQ ID NO 567
<211> LENGTH: 20
<212> TYPE: PRT
<213> ORGANISM: Artificial Sequence
<220> FEATURE:
<223> OTHER INFORMATION: Synthetic peptide of PL sequence binding
      NeDLG d2
```

<400> SEQUENCE: 567

Gly Gly Asp Leu Gly Thr Arg Arg Gly Ser Ala His Phe Ser Ser Leu
1 5 10 15

Glu Ser Glu Val
20

<210> SEQ ID NO 568
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 568

Gly Arg Trp Thr Gly Arg Ala Met Ser Ala Trp Lys Pro Thr Arg Arg
1 5 10 15

Glu Thr Glu Val
20

<210> SEQ ID NO 569
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 569

Gly Arg Trp Thr Gly Arg Cys Met Ser Cys Trp Lys Pro Thr Arg Arg
1 5 10 15

Glu Thr Glu Val
20

<210> SEQ ID NO 570
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 570

His His Leu Val Ala Gln Arg Asp Ile Arg Gln Phe Gln Leu Gln His
1 5 10 15

Trp Leu Ala Ile
20

<210> SEQ ID NO 571
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 571

His Ser Cys Cys Asn Arg Ala Arg Gln Glu Arg Leu Gln Arg Arg Arg
1 5 10 15

Glu Thr Gln Val
20

<210> SEQ ID NO 572
<211> LENGTH: 20

<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 572

Ile Leu Asn Ser Ile Gln Val Met Arg Ala Gln Met Asn Gln Ile Gln
1 5 10 15

Ser Val Glu Val
20

<210> SEQ ID NO 573
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 573

Lys Ala Gly Tyr Arg Ala Pro Arg Ser Tyr Pro Lys Ser Asn Ser Ser
1 5 10 15

Lys Glu Tyr Val
20

<210> SEQ ID NO 574
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 574

Lys His Ser Arg Lys Ser Ser Ser Tyr Ser Ser Ser Ser Thr Thr Val
1 5 10 15

Lys Thr Ser Tyr
20

<210> SEQ ID NO 575
<211> LENGTH: 23
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 575

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 576
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 576

Lys Tyr Ser Ala Pro Arg Arg Pro Thr Ala Thr Gly Asp Tyr Asp Lys
1 5 10 15

Lys Asn Tyr Val

20

<210> SEQ ID NO 577
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 577

Leu Ala Val Leu Ala Tyr Ser Ile Thr Leu Val Met Leu Trp Ser Ile
1 5 10 15

Trp Gln Tyr Ala
20

<210> SEQ ID NO 578
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 578

Leu Gly Tyr Ser Ile Pro Ser Arg Ser Gly Ala Ser Gly Leu Asp Lys
1 5 10 15

Arg Asp Tyr Val
20

<210> SEQ ID NO 579
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 579

Leu Met Asp Gly Leu Pro Pro Gly Asp Ser Asn Gln Leu Ala Trp Phe
1 5 10 15

Asp Thr Asp Leu
20

<210> SEQ ID NO 580
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 580

Leu Asn Ser Cys Ser Asn Arg Arg Val Tyr Lys Lys Met Pro Ser Ile
1 5 10 15

Glu Ser Asp Val
20

<210> SEQ ID NO 581
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 581

Leu Asn Ser Ser Ser Asn Arg Arg Val Tyr Lys Lys Met Pro Ser Ile
1 5 10 15

Glu Ser Asp Val
20

<210> SEQ ID NO 582
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 582

Pro Gly Gln Pro Pro Lys Val Lys Ser Glu Phe Asn Ser Tyr Ser Leu
1 5 10 15

Thr Gly Tyr Val
20

<210> SEQ ID NO 583
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 583

Pro Ile Pro Ala Gly Gly Cys Thr Phe Ser Gly Ile Phe Pro Thr Leu
1 5 10 15

Thr Ser Pro Leu
20

<210> SEQ ID NO 584
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 584

Pro Tyr Ser Glu Leu Asn Tyr Glu Thr Ser His Tyr Pro Ala Ser Pro
1 5 10 15

Asp Ser Trp Val
20

<210> SEQ ID NO 585
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 585

Gln Asp Phe Arg Arg Ala Phe Arg Arg Ile Leu Ala Arg Pro Trp Thr
1 5 10 15

Gln Thr Ala Trp
20

<210> SEQ ID NO 586
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 586

Gln Ile Ser Pro Gly Gly Leu Glu Pro Pro Ser Glu Lys His Phe Arg
1 5 10 15

Glu Thr Glu Val
20

<210> SEQ ID NO 587
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 587

Arg Glu Leu Val Asp Arg Gly Glu Val Arg Gln Phe Thr Leu Arg His
1 5 10 15

Trp Leu Lys Val
20

<210> SEQ ID NO 588
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 588

Arg Glu Leu Val Asp Arg Gly Glu Val Arg Gln Phe Thr Leu Arg His
1 5 10 15

Trp Leu Lys Val
20

<210> SEQ ID NO 589
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 589

Arg Asn Ile Glu Glu Val Tyr Val Gly Gly Lys Gln Val Val Pro Phe
1 5 10 15

Ser Ser Ser Val
20

<210> SEQ ID NO 590
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 590

Ser Phe Thr Ser Ile Leu Thr Cys His Gln Arg Arg Thr Gln Arg Lys
1 5 10 15

Glu Thr Val Ala
20

<210> SEQ ID NO 591
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 591

Ser Leu Lys Pro Gly Thr Val Leu Pro Pro Pro Pro Tyr Arg His Arg
1 5 10 15

Asn Thr Val Val
20

<210> SEQ ID NO 592
<211> LENGTH: 18
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 592

Ser Pro Gln Pro Asp Ser Thr Asp Asn Asp Asp Tyr Asp Asp Ile Ser
1 5 10 15

Ala Ala

<210> SEQ ID NO 593
<211> LENGTH: 19
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 593

Ser Ser Lys Ser Lys Ser Ser Glu Glu Ser Gln Thr Phe Phe Gly Leu
1 5 10 15

Tyr Lys Leu

<210> SEQ ID NO 594
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 594

Ser Ser Pro Asp Ser Ser Tyr Gln Gly Lys Gly Phe Val Met Ser Arg
1 5 10 15

Ala Met Tyr Val
20

<210> SEQ ID NO 595
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 595

Thr Ala Glu Asn Ala Glu Tyr Leu Arg Val Ala Pro Gln Ser Ser Glu
1 5 10 15

Phe Ile Gly Ala
20

<210> SEQ ID NO 596
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 596

Thr Phe Lys Gly Thr Pro Thr Ala Glu Asn Pro Glu Tyr Leu Gly Leu
1 5 10 15

Asp Val Pro Val
20

<210> SEQ ID NO 597
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 597

Thr Gly Ser Ala Leu Gln Ala Trp Arg His Thr Ser Arg Gln Ala Thr
1 5 10 15

Glu Ser Thr Val
20

<210> SEQ ID NO 598
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 598

Thr Gln Gly Phe Pro Gly Pro Ala Thr Trp Arg Arg Ile Ser Ser Leu
1 5 10 15

Glu Ser Glu Val
20

<210> SEQ ID NO 599
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 599

Thr Arg Glu Asp Ile Tyr Val Asn Tyr Pro Thr Phe Ser Arg Arg Pro
1 5 10 15

Lys Thr Arg Val
20

<210> SEQ ID NO 600
<211> LENGTH: 19
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 600

Thr Thr Asn Asn Asn Pro Asn Ser Ala Val Asn Ile Lys Lys Ile Phe
1               5                   10                  15

Thr Asp Val

<210> SEQ ID NO 601
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 601

Val Asp Pro Asn Ser Pro Ala Ala Lys Lys Lys Tyr Val Ser Tyr Asn
1               5                   10                  15

Asn Leu Val Ile
            20

<210> SEQ ID NO 602
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 602

Val Gly Thr Leu Leu Leu Glu Arg Val Ile Phe Pro Ser Val Lys Ile
1               5                   10                  15

Ala Thr Leu Val
            20

<210> SEQ ID NO 603
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 603

Val His Lys Val Arg Asn Lys Phe Lys Ala Lys Cys Ser Leu Cys Arg
1               5                   10                  15

Leu Tyr Ile Ile
            20

<210> SEQ ID NO 604
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 604

Tyr Gly Arg Lys Lys Arg Arg Gln Arg Arg Arg Lys Leu Ser Ser Ile
1               5                   10                  15

Glu Ser Asp Val
            20

<210> SEQ ID NO 605
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 605

Tyr Gly Arg Lys Lys Arg Arg Gln Arg Arg Arg Asn Asp Asn Ile Ala
1 5 10 15

Leu Leu Val Gln
20

<210> SEQ ID NO 606
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 606

Tyr Gly Arg Lys Lys Arg Arg Gln Arg Arg Arg Ser Glu Gly Val Pro
1 5 10 15

Asp Leu Leu Val
20

<210> SEQ ID NO 607
<211> LENGTH: 20
<212> TYPE: PRT
<213> ORGANISM: Artificial Sequence
<220> FEATURE:
<223> OTHER INFORMATION: Synthetic peptide of PL sequence binding NeDLG d2

<400> SEQUENCE: 607

Tyr Ser Ala Thr Tyr Ser Glu Leu Glu Asp Pro Gly Glu Met Ser Pro
1 5 10 15

Pro Ile Asp Leu
20

<210> SEQ ID NO 608
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 608

Ala Ala Gly Gly Arg Ser Ala Arg Gly Gly Arg Leu Gln Gly Arg Arg
1 5 10 15

Glu Thr Ala Leu
20

<210> SEQ ID NO 609
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 609

Ala Gly Ala Val Arg Thr Pro Leu Ser Gln Val Asn Lys Val Trp Asp
1 5 10 15

Gln Ser Ser Val
20

<210> SEQ ID NO 610
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 610

Ala Val Gly Gly Arg Pro Ala Arg Gly Gly Arg Leu Gln Gly Arg Arg
1 5 10 15

Gln Thr Gln Val
20

<210> SEQ ID NO 611
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 611

Asp Phe Arg Pro Ser Phe Lys His Ile Leu Phe Arg Arg Ala Arg Arg
1 5 10 15

Gly Phe Arg Gln
20

<210> SEQ ID NO 612
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 612

Asp Gly Gly Ala Arg Thr Glu Asp Glu Val Gln Ser Tyr Pro Ser Lys
1 5 10 15

His Asp Tyr Val
20

<210> SEQ ID NO 613
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 613

Glu Leu Leu Gln Phe Cys Arg Thr Pro Asn Pro Ala Leu Lys Asn Gly
1 5 10 15

Gln Tyr Trp Val
20

<210> SEQ ID NO 614
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 614

Glu Ser Ser Gly Thr Gln Ser Pro Lys Arg His Ser Gly Ser Tyr Leu 1 5 10 15

Val Thr Ser Val
20

<210> SEQ ID NO 615
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 615

Phe Asn Gly Ser Ser Asn Gly His Val Tyr Glu Lys Leu Ser Ser Ile
1 5 10 15

Glu Ser Asp Val
20

<210> SEQ ID NO 616
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 616

Gly Gly Asp Leu Gly Thr Arg Arg Gly Ser Ala His Phe Ser Ser Leu
1 5 10 15

Glu Ser Glu Val
20

<210> SEQ ID NO 617
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 617

Gly Gly Glu Asp Phe Lys Thr Thr Asn Pro Ser Lys Gln Phe Asp Lys
1 5 10 15

Asn Ala Tyr Val
20

<210> SEQ ID NO 618
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 618

Gly Arg Trp Thr Gly Arg Ala Met Ser Ala Trp Lys Pro Thr Arg Arg
1 5 10 15

Glu Thr Glu Val
20

<210> SEQ ID NO 619
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 619

His His Leu Val Ala Gln Arg Asp Ile Arg Gln Phe Gln Leu Gln His
1 5 10 15

Trp Leu Ala Ile
20

<210> SEQ ID NO 620
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 620

His Ser Cys Cys Asn Arg Ala Arg Gln Glu Arg Leu Gln Arg Arg Arg
1 5 10 15

Glu Thr Gln Val
20

<210> SEQ ID NO 621
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 621

Ile Ser Gly Thr Pro Thr Ser Thr Met Val His Gly Met Thr Ser Ser
1 5 10 15

Ser Ser Val Val
20

<210> SEQ ID NO 622
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 622

Lys Ala Gly Tyr Arg Ala Pro Arg Ser Tyr Pro Lys Ser Asn Ser Ser
1 5 10 15

Lys Glu Tyr Val
20

<210> SEQ ID NO 623
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 623

Lys Glu Asn Asp Tyr Glu Ser Ile Ser Asp Leu Gln Gln Gly Arg Asp
1 5 10 15

Ile Thr Arg Leu
20

<210> SEQ ID NO 624

<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 624

Lys His Ser Arg Lys Ser Ser Ser Tyr Ser Ser Ser Ser Thr Thr Val
1 5 10 15

Lys Thr Ser Tyr
20

<210> SEQ ID NO 625
<211> LENGTH: 23
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 625

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 626
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 626

Lys Tyr Ser Ala Pro Arg Arg Pro Thr Ala Thr Gly Asp Tyr Asp Lys
1 5 10 15

Lys Asn Tyr Val
20

<210> SEQ ID NO 627
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 627

Leu Ala Val Leu Ala Tyr Ser Ile Thr Leu Val Met Leu Trp Ser Ile
1 5 10 15

Trp Gln Tyr Ala
20

<210> SEQ ID NO 628
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 628

Leu Gly Tyr Ser Ile Pro Ser Arg Ser Gly Ala Ser Gly Leu Asp Lys
1 5 10 15

Arg Asp Tyr Val
20

<210> SEQ ID NO 629
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 629

Leu His Asn Gln Ala Ser Val Pro Leu Glu Pro Arg Pro Leu Arg Arg
1 5 10 15

Glu Ser Glu Ile
20

<210> SEQ ID NO 630
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 630

Leu Asn Ser Cys Ser Asn Arg Arg Val Tyr Lys Lys Met Pro Ser Ile
1 5 10 15

Glu Ser Asp Val
20

<210> SEQ ID NO 631
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 631

Leu Asn Ser Ser Ser Asn Arg Arg Val Tyr Lys Lys Met Pro Ser Ile
1 5 10 15

Glu Ser Asp Val
20

<210> SEQ ID NO 632
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 632

Pro Gly Gln Pro Pro Lys Val Lys Ser Glu Phe Asn Ser Tyr Ser Leu
1 5 10 15

Thr Gly Tyr Val
20

<210> SEQ ID NO 633
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 633

Pro Ile Pro Ala Gly Gly Cys Thr Phe Ser Gly Ile Phe Pro Thr Leu
1 5 10 15

Thr Ser Pro Leu
20

<210> SEQ ID NO 634
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 634

Pro Tyr Ser Glu Leu Asn Tyr Glu Thr Ser His Tyr Pro Ala Ser Pro
1 5 10 15

Asp Ser Trp Val
20

<210> SEQ ID NO 635
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 635

Gln Ala Thr Ser Arg Asn Gly His Ser Ala Arg Gln His Val Val Ala
1 5 10 15

Asp Thr Glu Leu
20

<210> SEQ ID NO 636
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 636

Gln Asp Phe Arg Arg Ala Phe Arg Arg Ile Leu Ala Arg Pro Trp Thr
1 5 10 15

Gln Thr Ala Trp
20

<210> SEQ ID NO 637
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 637

Gln Ile Ser Pro Gly Gly Leu Glu Pro Pro Ser Glu Lys His Phe Arg
1 5 10 15

Glu Thr Glu Val
20

<210> SEQ ID NO 638
<211> LENGTH: 20
<212> TYPE: PRT

<213> ORGANISM: Artificial Sequence
<220> FEATURE:
<223> OTHER INFORMATION: Synthetic peptide of PL sequence binding Outer Membrane Protein

<400> SEQUENCE: 638

Gln Pro Thr Pro Thr Leu Gly Leu Asn Leu Gly Asn Asp Pro Asp Arg
1 5 10 15

Gly Thr Ser Ile
20

<210> SEQ ID NO 639
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 639

Arg Glu Leu Val Asp Arg Gly Glu Val Arg Gln Phe Thr Leu Arg His
1 5 10 15

Trp Leu Lys Val
20

<210> SEQ ID NO 640
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 640

Arg Glu Leu Val Asp Arg Gly Glu Val Arg Gln Phe Thr Leu Arg His
1 5 10 15

Trp Leu Lys Val
20

<210> SEQ ID NO 641
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 641

Arg Asn Ile Glu Glu Val Tyr Val Gly Gly Lys Gln Val Val Pro Phe
1 5 10 15

Ser Ser Ser Val
20

<210> SEQ ID NO 642
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 642

Arg Ser Gly Ala Thr Ile Pro Leu Val Gly Gln Asp Ile Ile Asp Leu
1 5 10 15

Gln Thr Glu Val
20

<210> SEQ ID NO 643
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 643

Ser Phe Thr Ser Ile Leu Thr Cys His Gln Arg Arg Thr Gln Arg Lys
1 5 10 15

Glu Thr Val Ala
20

<210> SEQ ID NO 644
<211> LENGTH: 19
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 644

Ser Gly Gly Asn Arg Ala Arg Gln Glu Arg Leu Gln Arg Arg Arg Glu
1 5 10 15

Thr Gln Val

<210> SEQ ID NO 645
<211> LENGTH: 18
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 645

Ser Pro Gln Pro Asp Ser Thr Asp Asn Asp Asp Tyr Asp Asp Ile Ser
1 5 10 15

Ala Ala

<210> SEQ ID NO 646
<211> LENGTH: 19
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 646

Ser Ser Lys Ser Lys Ser Ser Glu Glu Ser Gln Thr Phe Phe Gly Leu
1 5 10 15

Tyr Lys Leu

<210> SEQ ID NO 647
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 647

Ser Ser Pro Asp Ser Ser Tyr Gln Gly Lys Gly Phe Val Met Ser Arg
1 5 10 15

Ala Met Tyr Val
20

<210> SEQ ID NO 648
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 648

Ser Tyr Pro Thr Pro Arg Pro Tyr Pro Lys Pro Ala Pro Ser Ser Gly
1 5 10 15

Lys Asp Tyr Val
20

<210> SEQ ID NO 649
<211> LENGTH: 18
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 649

Thr Phe Ala Ala Gly Phe Asn Ser Thr Gly Leu Pro His Ser Thr Thr
1 5 10 15

Arg Val

<210> SEQ ID NO 650
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 650

Thr Phe Lys Gly Thr Pro Thr Ala Glu Asn Pro Glu Tyr Leu Gly Leu
1 5 10 15

Asp Val Pro Val
20

<210> SEQ ID NO 651
<211> LENGTH: 19
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 651

Thr Gly Arg Gly Met Ser Gly Gly Arg Ser Ser Arg Thr Arg Arg Glu
1 5 10 15

Thr Gln Leu

<210> SEQ ID NO 652
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 652

```
Thr Gly Ser Ala Leu Gln Ala Trp Arg His Thr Ser Arg Gln Ala Thr
1               5                   10                  15

Glu Ser Thr Val
            20


<210> SEQ ID NO 653
<211> LENGTH: 20
<212> TYPE: PRT
<213> ORGANISM: Artificial Sequence
<220> FEATURE:
<223> OTHER INFORMATION: Synthetic peptide of PL sequence binding
      Outer Membrane Protein

<400> SEQUENCE: 653

Thr Gln Gly Phe Pro Gly Pro Ala Thr Trp Arg Arg Ile Ser Ser Leu
1               5                   10                  15

Glu Ser Glu Val
            20


<210> SEQ ID NO 654
<211> LENGTH: 20
<212> TYPE: PRT
<213> ORGANISM: Artificial Sequence
<220> FEATURE:
<223> OTHER INFORMATION: Synthetic peptide of PL sequence binding
      Outer Membrane Protein

<400> SEQUENCE: 654

Thr Arg Glu Asp Ile Tyr Val Asn Tyr Pro Thr Phe Ser Arg Arg Pro
1               5                   10                  15

Lys Thr Arg Val
            20


<210> SEQ ID NO 655
<211> LENGTH: 19
<212> TYPE: PRT
<213> ORGANISM: Artificial Sequence
<220> FEATURE:
<223> OTHER INFORMATION: Synthetic peptide of PL sequence binding
      Outer Membrane Protein

<400> SEQUENCE: 655

Thr Thr Asn Asn Asn Pro Asn Ser Ala Val Asn Ile Lys Lys Ile Phe
1               5                   10                  15

Thr Asp Val


<210> SEQ ID NO 656
<211> LENGTH: 20
<212> TYPE: PRT
<213> ORGANISM: Artificial Sequence
<220> FEATURE:
<223> OTHER INFORMATION: Synthetic peptide of PL sequence binding
      Outer Membrane Protein

<400> SEQUENCE: 656

Val Asp Pro Asn Ser Pro Ala Ala Lys Lys Lys Tyr Val Ser Tyr Asn
1               5                   10                  15

Asn Leu Val Ile
            20


<210> SEQ ID NO 657
<211> LENGTH: 20
<212> TYPE: PRT
<213> ORGANISM: Artificial Sequence
<220> FEATURE:
<223> OTHER INFORMATION: Synthetic peptide of PL sequence binding
```

Outer Membrane Protein

<400> SEQUENCE: 657

Val Gly Thr Leu Leu Leu Glu Arg Val Ile Phe Pro Ser Val Lys Ile
1 5 10 15

Ala Thr Leu Val
20

<210> SEQ ID NO 658
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 658

Val His Asp Ala Glu Ser Ser Asp Glu Asp Gly Tyr Asp Trp Gly Pro
1 5 10 15

Ala Thr Asp Leu
20

<210> SEQ ID NO 659
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 659

Val His Lys Val Arg Asn Lys Phe Lys Ala Lys Cys Ser Leu Cys Arg
1 5 10 15

Leu Tyr Ile Ile
20

<210> SEQ ID NO 660
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 660

Val Pro Gly Ala Leu Asp Tyr Ala Ala Phe Ser Ser Ala Leu Tyr Gly
1 5 10 15

Glu Ser Asp Leu
20

<210> SEQ ID NO 661
<211> LENGTH: 20
<212> TYPE: PRT
<213> ORGANISM: Artificial Sequence
<220> FEATURE:
<223> OTHER INFORMATION: Synthetic peptide of PL sequence binding Outer Membrane Protein

<400> SEQUENCE: 661

Tyr Gly Arg Lys Lys Arg Arg Gln Arg Arg Arg Lys Leu Ser Ser Ile
1 5 10 15

Glu Ser Asp Val
20

<210> SEQ ID NO 662

<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 662

Tyr Gly Arg Lys Lys Arg Arg Gln Arg Arg Arg Asn Asp Asn Ile Ala
1 5 10 15

Leu Leu Val Gln
20

<210> SEQ ID NO 663
<211> LENGTH: 20
<212> TYPE: PRT
<213> ORGANISM: Artificial Sequence
<220> FEATURE:
<223> OTHER INFORMATION: Synthetic peptide of PL sequence binding
Outer Membrane Protein

<400> SEQUENCE: 663

Tyr Gly Arg Lys Lys Arg Arg Gln Arg Arg Arg Ser Glu Gly Val Pro
1 5 10 15

Asp Leu Leu Val
20

<210> SEQ ID NO 664
<211> LENGTH: 20
<212> TYPE: PRT
<213> ORGANISM: Artificial Sequence
<220> FEATURE:
<223> OTHER INFORMATION: Synthetic peptide of PL sequence binding PICK1
d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 664

Tyr Gly Arg Lys Lys Arg Arg Gln Arg Arg Arg Lys Leu Ser Ser Ile
1 5 10 15

Glu Ser Asp Xaa
20

<210> SEQ ID NO 665
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 665

Ala Leu Val Leu Ile Ala Phe Cys Ile Ile Arg Arg Arg Pro Ser Ala
1 5 10 15

Tyr Gln Ala Leu
20

<210> SEQ ID NO 666
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 666

Ala Thr Asp Tyr Leu Val Gln Pro Phe Met Asp Gln Leu Ala Phe His
1 5 10 15

Gln Phe Tyr Ile
20

<210> SEQ ID NO 667
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 667

Asp Phe Arg Pro Ser Phe Lys His Ile Leu Phe Arg Arg Ala Arg Arg
1 5 10 15

Gly Phe Arg Gln
20

<210> SEQ ID NO 668
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 668

Asp Gly Gly Ala Arg Thr Glu Asp Glu Val Gln Ser Tyr Pro Ser Lys
1 5 10 15

His Asp Tyr Val
20

<210> SEQ ID NO 669
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 669

Glu Leu Leu Gln Phe Cys Arg Thr Pro Asn Pro Ala Leu Lys Asn Gly
1 5 10 15

Gln Tyr Trp Val
20

<210> SEQ ID NO 670
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 670

Phe His Ser Lys Thr Ala Gly Ala Asn Thr Thr Asp Lys Glu Leu Glu
1 5 10 15

Val Leu Ser Leu
20

<210> SEQ ID NO 671
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 671

Gly Arg Trp Thr Gly Arg Ala Met Ser Ala Trp Lys Pro Thr Arg Arg
1 5 10 15

Glu Thr Glu Val
20

<210> SEQ ID NO 672
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 672

His Asp Phe Arg Arg Ala Phe Lys Lys Ile Leu Ala Arg Gly Asp Arg
1 5 10 15

Lys Arg Ile Val
20

<210> SEQ ID NO 673
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 673

His His Leu Val Ala Gln Arg Asp Ile Arg Gln Phe Gln Leu Gln His
1 5 10 15

Trp Leu Ala Ile
20

<210> SEQ ID NO 674
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 674

His Ser Cys Cys Asn Arg Ala Arg Gln Glu Arg Leu Gln Arg Arg Arg
1 5 10 15

Glu Thr Gln Val
20

<210> SEQ ID NO 675
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 675

Ile Leu Asn Ser Ile Gln Val Met Arg Ala Gln Met Asn Gln Ile Gln
1 5 10 15

Ser Val Glu Val
20

<210> SEQ ID NO 676
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 676

```
Lys Ala Gly Tyr Arg Ala Pro Arg Ser Tyr Pro Lys Ser Asn Ser Ser
1               5                   10                  15

Lys Glu Tyr Val
            20
```

<210> SEQ ID NO 677
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 677

```
Lys His Ser Arg Lys Ser Ser Ser Tyr Ser Ser Ser Ser Thr Thr Val
1               5                   10                  15

Lys Thr Ser Tyr
            20
```

<210> SEQ ID NO 678
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 678

```
Lys Thr Met Pro Ala Ala Met Tyr Arg Leu Leu Thr Ala Gln Glu Gln
1               5                   10                  15

Pro Val Tyr Ile
            20
```

<210> SEQ ID NO 679
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 679

```
Lys Tyr Ser Ala Pro Arg Arg Pro Thr Ala Thr Gly Asp Tyr Asp Lys
1               5                   10                  15

Lys Asn Tyr Val
            20
```

<210> SEQ ID NO 680
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 680

```
Leu Ala Val Leu Ala Tyr Ser Ile Thr Leu Val Met Leu Trp Ser Ile
```

1 5 10 15

Trp Gln Tyr Ala
20

<210> SEQ ID NO 681
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 681

Leu Ser Glu Lys Lys Thr Ser Gln Ser Pro His Arg Phe Gln Lys Thr
1 5 10 15

Ser Ser Pro Ile
20

<210> SEQ ID NO 682
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 682

Pro Gly Gln Pro Pro Lys Val Lys Ser Glu Phe Asn Ser Tyr Ser Leu
1 5 10 15

Thr Gly Tyr Val
20

<210> SEQ ID NO 683
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 683

Pro Ile Pro Ala Gly Gly Cys Thr Phe Ser Gly Ile Phe Pro Thr Leu
1 5 10 15

Thr Ser Pro Leu
20

<210> SEQ ID NO 684
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 684

Pro Tyr Ser Glu Leu Asn Tyr Glu Thr Ser His Tyr Pro Ala Ser Pro
1 5 10 15

Asp Ser Trp Val
20

<210> SEQ ID NO 685
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 685

Gln Asp Phe Arg Arg Ala Phe Arg Arg Ile Leu Ala Arg Pro Trp Thr
1 5 10 15

Gln Thr Ala Trp
20

<210> SEQ ID NO 686
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 686

Arg Glu Leu Val Asp Arg Gly Glu Val Arg Gln Phe Thr Leu Arg His
1 5 10 15

Trp Leu Lys Val
20

<210> SEQ ID NO 687
<211> LENGTH: 18
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 687

Ser Pro Gln Pro Asp Ser Thr Asp Asn Asp Asp Tyr Asp Asp Ile Ser
1 5 10 15

Ala Ala

<210> SEQ ID NO 688
<211> LENGTH: 19
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 688

Ser Ser Lys Ser Lys Ser Ser Glu Glu Ser Gln Thr Phe Phe Gly Leu
1 5 10 15

Tyr Lys Leu

<210> SEQ ID NO 689
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 689

Ser Ser Pro Asp Ser Ser Tyr Gln Gly Lys Gly Phe Val Met Ser Arg
1 5 10 15

Ala Met Tyr Val
20

<210> SEQ ID NO 690
<211> LENGTH: 20
<212> TYPE: PRT

<213> ORGANISM: Artificial Sequence
<220> FEATURE:
<223> OTHER INFORMATION: Synthetic peptide of PL sequence binding
PICK1 d1

<400> SEQUENCE: 690

Ser Tyr Pro Thr Pro Arg Pro Tyr Pro Lys Pro Ala Pro Ser Ser Gly
1 5 10 15

Lys Asp Tyr Val
20

<210> SEQ ID NO 691
<211> LENGTH: 19
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 691

Thr Thr Asn Asn Asn Pro Asn Ser Ala Val Asn Ile Lys Lys Ile Phe
1 5 10 15

Thr Asp Val

<210> SEQ ID NO 692
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 692

Val Asp Pro Asn Ser Pro Ala Ala Lys Lys Lys Tyr Val Ser Tyr Asn
1 5 10 15

Asn Leu Val Ile
20

<210> SEQ ID NO 693
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 693

Val His Lys Val Arg Asn Lys Phe Lys Ala Lys Cys Ser Leu Cys Arg
1 5 10 15

Leu Tyr Ile Ile
20

<210> SEQ ID NO 694
<211> LENGTH: 20
<212> TYPE: PRT
<213> ORGANISM: Artificial Sequence
<220> FEATURE:
<223> OTHER INFORMATION: Synthetic peptide of PL sequence binding
PICK1 d1

<400> SEQUENCE: 694

Tyr Gly Arg Lys Lys Arg Arg Gln Arg Arg Arg Glu Met Gln Val Thr
1 5 10 15

Leu Gly Leu His
20

<210> SEQ ID NO 695
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 695

Tyr Gly Arg Lys Lys Arg Arg Gln Arg Arg Arg Glu Tyr Leu Gly Leu
1 5 10 15

Asp Val Pro Val
20

<210> SEQ ID NO 696
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1

<400> SEQUENCE: 696

Tyr Gly Arg Lys Lys Arg Arg Gln Arg Arg Arg Ile Gly Glu Leu Gln
1 5 10 15

Leu Ser Ile Ala
20

<210> SEQ ID NO 697
<211> LENGTH: 20
<212> TYPE: PRT
<213> ORGANISM: Artificial Sequence
<220> FEATURE:
<223> OTHER INFORMATION: Synthetic peptide of PL sequence binding PICK1 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 697

Tyr Gly Arg Lys Lys Arg Arg Gln Arg Arg Arg Lys Leu Ser Ser Ile
1 5 10 15

Glu Ser Asp Xaa
20

<210> SEQ ID NO 698
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 698

Ala Ala Gly Gly Arg Ser Ala Arg Gly Gly Arg Leu Gln Gly Arg Arg
1 5 10 15

Glu Thr Ala Leu
20

<210> SEQ ID NO 699
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 699

Ala Val Gly Gly Arg Pro Ala Arg Gly Gly Arg Leu Gln Gly Arg Arg
1 5 10 15

Gln Thr Gln Val
20

<210> SEQ ID NO 700
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 700

Asp Phe Arg Pro Ser Phe Lys His Ile Leu Phe Arg Arg Ala Arg Arg
1 5 10 15

Gly Phe Arg Gln
20

<210> SEQ ID NO 701
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 701

Asp Gly Gly Ala Arg Thr Glu Asp Glu Val Gln Ser Tyr Pro Ser Lys
1 5 10 15

His Asp Tyr Val
20

<210> SEQ ID NO 702
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 702

Glu Leu Leu Gln Phe Cys Arg Thr Pro Asn Pro Ala Leu Lys Asn Gly
1 5 10 15

Gln Tyr Trp Val
20

<210> SEQ ID NO 703
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 703

Phe Asn Gly Ser Ser Asn Gly His Val Tyr Glu Lys Leu Ser Ser Ile
1 5 10 15

Glu Ser Asp Val
20

<210> SEQ ID NO 704
<211> LENGTH: 20

<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 704

Gly Gly Asp Leu Gly Thr Arg Arg Gly Ser Ala His Phe Ser Ser Leu
1 5 10 15

Glu Ser Glu Val
20

<210> SEQ ID NO 705
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 705

Gly Gly Glu Asp Phe Lys Thr Thr Asn Pro Ser Lys Gln Phe Asp Lys
1 5 10 15

Asn Ala Tyr Val
20

<210> SEQ ID NO 706
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 706

Gly Arg Trp Ala Gly Arg Ser Ala Ala Ser Trp Arg Ser Arg Arg Arg
1 5 10 15

Glu Thr Ala Leu
20

<210> SEQ ID NO 707
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 707

Gly Arg Trp Thr Gly Arg Ala Met Ser Ala Trp Lys Pro Thr Arg Arg
1 5 10 15

Glu Thr Glu Val
20

<210> SEQ ID NO 708
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 708

His His Leu Val Ala Gln Arg Asp Ile Arg Gln Phe Gln Leu Gln His
1 5 10 15

Trp Leu Ala Ile

20

<210> SEQ ID NO 709
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 709

Lys Ala Gly Tyr Arg Ala Pro Arg Ser Tyr Pro Lys Ser Asn Ser Ser
1 5 10 15

Lys Glu Tyr Val
20

<210> SEQ ID NO 710
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 710

Lys His Ser Arg Lys Ser Ser Ser Tyr Ser Ser Ser Ser Thr Thr Val
1 5 10 15

Lys Thr Ser Tyr
20

<210> SEQ ID NO 711
<211> LENGTH: 23
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 711

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 712
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 712

Lys Tyr Ser Ala Pro Arg Arg Pro Thr Ala Thr Gly Asp Tyr Asp Lys
1 5 10 15

Lys Asn Tyr Val
20

<210> SEQ ID NO 713
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 713

Leu Ala Val Leu Ala Tyr Ser Ile Thr Leu Val Met Leu Trp Ser Ile
1 5 10 15

Trp Gln Tyr Ala
20

<210> SEQ ID NO 714
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 714

Leu Gly Tyr Ser Ile Pro Ser Arg Ser Gly Ala Ser Gly Leu Asp Lys
1 5 10 15

Arg Asp Tyr Val
20

<210> SEQ ID NO 715
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 715

Leu Asn Ser Cys Ser Asn Arg Arg Val Tyr Lys Lys Met Pro Ser Ile
1 5 10 15

Glu Ser Asp Val
20

<210> SEQ ID NO 716
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 716

Leu Asn Ser Ser Ser Asn Arg Arg Val Tyr Lys Lys Met Pro Ser Ile
1 5 10 15

Glu Ser Asp Val
20

<210> SEQ ID NO 717
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 717

Pro Gly Gln Pro Pro Lys Val Lys Ser Glu Phe Asn Ser Tyr Ser Leu
1 5 10 15

Thr Gly Tyr Val
20

<210> SEQ ID NO 718
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 718

Pro Ile Pro Ala Gly Gly Cys Thr Phe Ser Gly Ile Phe Pro Thr Leu
1 5 10 15

Thr Ser Pro Leu
20

<210> SEQ ID NO 719
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 719

Pro Tyr Ser Glu Leu Asn Tyr Glu Thr Ser His Tyr Pro Ala Ser Pro
1 5 10 15

Asp Ser Trp Val
20

<210> SEQ ID NO 720
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 720

Gln Asp Phe Arg Arg Ala Phe Arg Arg Ile Leu Ala Arg Pro Trp Thr
1 5 10 15

Gln Thr Ala Trp
20

<210> SEQ ID NO 721
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 721

Gln Ile Ser Pro Gly Gly Leu Glu Pro Pro Ser Glu Lys His Phe Arg
1 5 10 15

Glu Thr Glu Val
20

<210> SEQ ID NO 722
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 722

Arg Glu Leu Val Asp Arg Gly Glu Val Arg Gln Phe Thr Leu Arg His
1 5 10 15

Trp Leu Lys Val
20

<210> SEQ ID NO 723
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 723

Arg Asn Ile Glu Glu Val Tyr Val Gly Gly Lys Gln Val Val Pro Phe
1 5 10 15

Ser Ser Ser Val
20

<210> SEQ ID NO 724
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 724

Ser Phe Thr Ser Ile Leu Thr Cys His Gln Arg Arg Thr Gln Arg Lys
1 5 10 15

Glu Thr Val Ala
20

<210> SEQ ID NO 725
<211> LENGTH: 19
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 725

Ser Ser Lys Ser Lys Ser Ser Glu Glu Ser Gln Thr Phe Phe Gly Leu
1 5 10 15

Tyr Lys Leu

<210> SEQ ID NO 726
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 726

Ser Ser Pro Asp Ser Ser Tyr Gln Gly Lys Gly Phe Val Met Ser Arg
1 5 10 15

Ala Met Tyr Val
20

<210> SEQ ID NO 727
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 727

Ser Tyr Pro Thr Pro Arg Pro Tyr Pro Lys Pro Ala Pro Ser Ser Gly
1 5 10 15

```
Lys Asp Tyr Val
            20


<210> SEQ ID NO 728
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 728

Thr Gly Ser Ala Leu Gln Ala Trp Arg His Thr Ser Arg Gln Ala Thr
1               5                   10                  15

Glu Ser Thr Val
            20


<210> SEQ ID NO 729
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 729

Thr Gln Gly Phe Pro Gly Pro Ala Thr Trp Arg Arg Ile Ser Ser Leu
1               5                   10                  15

Glu Ser Glu Val
            20


<210> SEQ ID NO 730
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 730

Thr Arg Glu Asp Ile Tyr Val Asn Tyr Pro Thr Phe Ser Arg Arg Pro
1               5                   10                  15

Lys Thr Arg Val
            20


<210> SEQ ID NO 731
<211> LENGTH: 19
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 731

Thr Thr Asn Asn Asn Pro Asn Ser Ala Val Asn Ile Lys Lys Ile Phe
1               5                   10                  15

Thr Asp Val


<210> SEQ ID NO 732
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1
```

<400> SEQUENCE: 732

Val Asp Pro Asn Ser Pro Ala Ala Lys Lys Lys Tyr Val Ser Tyr Asn
1               5                   10                  15

Asn Leu Val Ile
            20

<210> SEQ ID NO 733
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 733

Val Gly Thr Leu Leu Leu Glu Arg Val Ile Phe Pro Ser Val Lys Ile
1               5                   10                  15

Ala Thr Leu Val
            20

<210> SEQ ID NO 734
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 734

Val His Lys Val Arg Asn Lys Phe Lys Ala Lys Cys Ser Leu Cys Arg
1               5                   10                  15

Leu Tyr Ile Ile
            20

<210> SEQ ID NO 735
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 735

Tyr Gly Arg Lys Lys Arg Arg Gln Arg Arg Arg Ala Leu Lys Ser Ile
1               5                   10                  15

Glu Thr Glu Val
            20

<210> SEQ ID NO 736
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1

<400> SEQUENCE: 736

Tyr Gly Arg Lys Lys Arg Arg Gln Arg Arg Arg Ala Arg Gly Arg Arg
1               5                   10                  15

Glu Thr Trp Val
            20

<210> SEQ ID NO 737
<211> LENGTH: 20
<212> TYPE: PRT

<213> ORGANISM: Artificial Sequence
<220> FEATURE:
<223> OTHER INFORMATION: Synthetic peptide of PL sequence binding
PSD95 d1

<400> SEQUENCE: 737

Tyr Gly Arg Lys Lys Arg Arg Gln Arg Arg Arg Glu Lys His Phe Arg
1 5 10 15

Glu Thr Glu Val
20

<210> SEQ ID NO 738
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 738

Tyr Gly Arg Lys Lys Arg Arg Gln Arg Arg Arg Gly Ala Ser Ala Asp
1 5 10 15

Ser Thr Gln Ala
20

<210> SEQ ID NO 739
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 739

Tyr Gly Arg Lys Lys Arg Arg Gln Arg Arg Arg Gly Met Thr Ser Ser
1 5 10 15

Ser Ser Val Val
20

<210> SEQ ID NO 740
<211> LENGTH: 16
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 740

Tyr Gly Arg Lys Lys Arg Arg Gln Arg Arg Arg Ile Glu Thr Glu Val
1 5 10 15

<210> SEQ ID NO 741
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 741

Tyr Gly Arg Lys Lys Arg Arg Gln Arg Arg Arg Lys Leu Ser Ser Ile
1 5 10 15

Glu Ser Asp Val
20

<210> SEQ ID NO 742

<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 742

Tyr Gly Arg Lys Lys Arg Arg Gln Arg Arg Arg Lys Leu Ser Ser Ile
1 5 10 15

Glu Ser Asp Val
20

<210> SEQ ID NO 743
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 743

Tyr Gly Arg Lys Lys Arg Arg Gln Arg Arg Arg Lys Leu Ser Ser Ile
1 5 10 15

Glu Ser Asp Xaa
20

<210> SEQ ID NO 744
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 744

Tyr Gly Arg Lys Lys Arg Arg Gln Arg Arg Arg Lys Leu Ser Ser Ile
1 5 10 15

Glu Ser Asp Xaa
20

<210> SEQ ID NO 745
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 745

Tyr Gly Arg Lys Lys Arg Arg Gln Arg Arg Arg Lys Leu Ser Ser Ile
1 5 10 15

Glu Ser Asp Xaa
20

<210> SEQ ID NO 746

<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1
<220> FEATURE:
<221> NAME/KEY: misc_feature
<222> LOCATION: (19)..(19)
<223> OTHER INFORMATION: Xaa = any naturally occurring amino acid

<400> SEQUENCE: 746

Tyr Gly Arg Lys Lys Arg Arg Gln Arg Arg Arg Lys Leu Ser Ser Ile
1 5 10 15

Glu Ser Xaa Val
20

<210> SEQ ID NO 747
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 747

Tyr Gly Arg Lys Lys Arg Arg Gln Arg Arg Arg Lys Leu Ser Ser Ile
1 5 10 15

Glu Ser Tyr Val
20

<210> SEQ ID NO 748
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 748

Tyr Gly Arg Lys Lys Arg Arg Gln Arg Arg Arg Lys Leu Ser Ser Ile
1 5 10 15

Glu Thr Asp Val
20

<210> SEQ ID NO 749
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1
<220> FEATURE:
<221> NAME/KEY: misc_feature
<222> LOCATION: (20)..(20)
<223> OTHER INFORMATION: Xaa = any naturally occurring amino acid

<400> SEQUENCE: 749

Tyr Gly Arg Lys Lys Arg Arg Gln Arg Arg Arg Lys Leu Ser Ser Ile
1 5 10 15

Glu Thr Asp Xaa
20

<210> SEQ ID NO 750
<211> LENGTH: 20
<212> TYPE: PRT
<213> ORGANISM: Artificial Sequence
<220> FEATURE:

<223> OTHER INFORMATION: Synthetic peptide of PL sequence binding PSD95 d1

<400> SEQUENCE: 750

Tyr Gly Arg Lys Lys Arg Arg Gln Arg Arg Arg Lys Leu Ser Ser Ile
1 5 10 15

Glu Tyr Asp Val
20

<210> SEQ ID NO 751
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 751

Tyr Gly Arg Lys Lys Arg Arg Gln Arg Arg Arg Asn Asp Asn Ile Ala
1 5 10 15

Leu Leu Val Gln
20

<210> SEQ ID NO 752
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 752

Tyr Gly Arg Lys Lys Arg Arg Gln Arg Arg Arg Gln Asp Glu Arg Val
1 5 10 15

Glu Thr Arg Val
20

<210> SEQ ID NO 753
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 753

Tyr Gly Arg Lys Lys Arg Arg Gln Arg Arg Arg Gln Asp Ser Arg Glu
1 5 10 15

Glu Thr Gln Leu
20

<210> SEQ ID NO 754
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 754

Tyr Gly Arg Lys Lys Arg Arg Gln Arg Arg Arg Arg Ile Ser Ser Ile
1 5 10 15

Glu Thr Asp Val
20

<210> SEQ ID NO 755
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 755

Tyr Gly Arg Lys Lys Arg Arg Gln Arg Arg Arg Arg Ile Ser Ser Ile
1 5 10 15

Gln Thr Asp Val
20

<210> SEQ ID NO 756
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 756

Tyr Gly Arg Lys Lys Arg Arg Gln Arg Arg Arg Arg Ile Ser Ser Leu
1 5 10 15

Glu Ser Glu Val
20

<210> SEQ ID NO 757
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 757

Tyr Gly Arg Lys Lys Arg Arg Gln Arg Arg Arg Arg Ile Ser Ser Leu
1 5 10 15

Glu Thr Glu Val
20

<210> SEQ ID NO 758
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 758

Tyr Gly Arg Lys Lys Arg Arg Gln Arg Arg Arg Arg Ile Ser Ser Leu
1 5 10 15

Glu Thr Gln Val
20

<210> SEQ ID NO 759
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1

<400> SEQUENCE: 759

Tyr Gly Arg Lys Lys Arg Arg Gln Arg Arg Arg Arg Ser Arg Arg Arg
1 5 10 15

Glu Thr Ala Leu
20

<210> SEQ ID NO 760
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 760

Tyr Gly Arg Lys Lys Arg Arg Gln Arg Arg Arg Thr Lys Asn Tyr Lys
1 5 10 15

Gln Thr Ser Val
20

<210> SEQ ID NO 761
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1

<400> SEQUENCE: 761

Tyr Ser Ala Thr Tyr Ser Glu Leu Glu Asp Pro Gly Glu Met Ser Pro
1 5 10 15

Pro Ile Asp Leu
20

<210> SEQ ID NO 762
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 762

Ala Ala Gly Gly Arg Ser Ala Arg Gly Gly Arg Leu Gln Gly Arg Arg
1 5 10 15

Glu Thr Ala Leu
20

<210> SEQ ID NO 763
<211> LENGTH: 19
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 763

Ala Arg His Arg Val Thr Ser Tyr Thr Ser Ser Ser Val Asn Val Ser
1 5 10 15

Ser Asn Leu

<210> SEQ ID NO 764
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 764

Ala Val Gly Gly Arg Pro Ala Arg Gly Gly Arg Leu Gln Gly Arg Arg
1 5 10 15

Gln Thr Gln Val
20

<210> SEQ ID NO 765
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 765

Asp Phe Arg Pro Ser Phe Lys His Ile Leu Phe Arg Arg Ala Arg Arg
1 5 10 15

Gly Phe Arg Gln
20

<210> SEQ ID NO 766
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 766

Glu Asp Pro Lys Asp Arg Pro Ser Ala Ala His Ile Val Glu Ala Leu
1 5 10 15

Glu Thr Asp Val
20

<210> SEQ ID NO 767
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 767

Glu Leu Leu Gln Phe Cys Arg Thr Pro Asn Pro Ala Leu Lys Asn Gly
1 5 10 15

Gln Tyr Trp Val
20

<210> SEQ ID NO 768
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 768

Glu Ser Ser Gly Thr Gln Ser Pro Lys Arg His Ser Gly Ser Tyr Leu
1 5 10 15

Val Thr Ser Val
20

<210> SEQ ID NO 769
<211> LENGTH: 20
<212> TYPE: PRT

<213> ORGANISM: Artificial Sequence
<220> FEATURE:
<223> OTHER INFORMATION: Synthetic peptide of PL sequence binding PSD95 d1, d2

<400> SEQUENCE: 769

Phe Asn Gly Ser Ser Asn Gly His Val Tyr Glu Lys Leu Ser Ser Ile
1 5 10 15

Glu Ser Asp Val
20

<210> SEQ ID NO 770
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 770

Gly Gly Asp Leu Gly Thr Arg Arg Gly Ser Ala His Phe Ser Ser Leu
1 5 10 15

Glu Ser Glu Val
20

<210> SEQ ID NO 771
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 771

Gly Gly Glu Asp Phe Lys Thr Thr Asn Pro Ser Lys Gln Phe Asp Lys
1 5 10 15

Asn Ala Tyr Val
20

<210> SEQ ID NO 772
<211> LENGTH: 19
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 772

Gly Gly Gly Gly Gly Ser Gly Gly Gly Gly Gly Ser Gly Ile Glu Ser
1 5 10 15

Val Lys Ile

<210> SEQ ID NO 773
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 773

Gly Arg Trp Ala Gly Arg Ser Ala Ala Ser Trp Arg Ser Arg Arg Arg
1 5 10 15

Glu Thr Ala Leu
20

```
<210> SEQ ID NO 774
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1, d2

<400> SEQUENCE: 774

Gly Arg Trp Thr Gly Arg Ala Met Ser Ala Trp Lys Pro Thr Arg Arg
1               5                   10                  15

Glu Thr Glu Val
            20


<210> SEQ ID NO 775
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1, d2

<400> SEQUENCE: 775

Gly Arg Trp Thr Gly Arg Ser Ala Val Ser Trp Arg Pro Arg Arg Arg
1               5                   10                  15

Gln Thr Gln Val
            20


<210> SEQ ID NO 776
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1, d2

<400> SEQUENCE: 776

His His Leu Val Ala Gln Arg Asp Ile Arg Gln Phe Gln Leu Gln His
1               5                   10                  15

Trp Leu Ala Ile
            20


<210> SEQ ID NO 777
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1, d2

<400> SEQUENCE: 777

His Pro Thr Asp Ile Thr Gly Leu Pro Asn Leu Ser Asp Pro Ser Val
1               5                   10                  15

Ser Thr Val Val
            20


<210> SEQ ID NO 778
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95 d1, d2

<400> SEQUENCE: 778

His Ser Cys Cys Asn Arg Ala Arg Gln Glu Arg Leu Gln Arg Arg Arg
```

1 5 10 15

Glu Thr Gln Val
20

<210> SEQ ID NO 779
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 779

Ile Leu Asn Ser Ile Gln Val Met Arg Ala Gln Met Asn Gln Ile Gln
1 5 10 15

Ser Val Glu Val
20

<210> SEQ ID NO 780
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 780

Ile Ser Gly Thr Pro Thr Ser Thr Met Val His Gly Met Thr Ser Ser
1 5 10 15

Ser Ser Val Val
20

<210> SEQ ID NO 781
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 781

Lys Ala Gly Tyr Arg Ala Pro Arg Ser Tyr Pro Lys Ser Asn Ser Ser
1 5 10 15

Lys Glu Tyr Val
20

<210> SEQ ID NO 782
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 782

Lys Asp Ile Thr Ser Asp Ser Glu Asn Ser Asn Phe Arg Asn Glu Ile
1 5 10 15

Gln Ser Leu Val
20

<210> SEQ ID NO 783
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 783

Lys Asp Ile Thr Ser Asp Ser Glu Asn Ser Asn Phe Arg Asn Glu Ile
1 5 10 15

Gln Ser Leu Val
20

<210> SEQ ID NO 784
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 784

Lys His Ser Arg Lys Ser Ser Ser Tyr Ser Ser Ser Ser Thr Thr Val
1 5 10 15

Lys Thr Ser Tyr
20

<210> SEQ ID NO 785
<211> LENGTH: 23
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 785

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 786
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 786

Leu Ala Val Leu Ala Tyr Ser Ile Thr Leu Val Met Leu Trp Ser Ile
1 5 10 15

Trp Gln Tyr Ala
20

<210> SEQ ID NO 787
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 787

Leu His Asn Gln Ala Ser Val Pro Leu Glu Pro Arg Pro Leu Arg Arg
1 5 10 15

Glu Ser Glu Ile
20

<210> SEQ ID NO 788

<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 788

Leu Asn Ser Cys Ser Asn Arg Arg Val Tyr Lys Lys Met Pro Ser Ile
1 5 10 15

Glu Ser Asp Val
20

<210> SEQ ID NO 789
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 789

Leu Asn Ser Ser Ser Asn Arg Arg Val Tyr Lys Lys Met Pro Ser Ile
1 5 10 15

Glu Ser Asp Val
20

<210> SEQ ID NO 790
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 790

Met Gly Arg Trp Thr Gly Arg Ser Ser Glu Ser Trp Arg Pro Arg Pro
1 5 10 15

Val Thr Gln Val
20

<210> SEQ ID NO 791
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 791

Asn Thr Ser Ser Asp Gln Ala Arg Gln Glu Arg Leu Arg Arg Arg Arg
1 5 10 15

Glu Thr Gln Val
20

<210> SEQ ID NO 792
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 792

Pro Ile Pro Ala Gly Gly Cys Thr Phe Ser Gly Ile Phe Pro Thr Leu
1 5 10 15

Thr Ser Pro Leu
20

<210> SEQ ID NO 793
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 793

Pro Tyr Ser Glu Leu Asn Tyr Glu Thr Ser His Tyr Pro Ala Ser Pro
1 5 10 15

Asp Ser Trp Val
20

<210> SEQ ID NO 794
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 794

Gln Asp Phe Arg Arg Ala Phe Arg Arg Ile Leu Ala Arg Pro Trp Thr
1 5 10 15

Gln Thr Ala Trp
20

<210> SEQ ID NO 795
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 795

Gln Ile Ser Pro Gly Gly Leu Glu Pro Pro Ser Glu Lys His Phe Arg
1 5 10 15

Glu Thr Glu Val
20

<210> SEQ ID NO 796
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 796

Arg Glu Leu Val Asp Arg Gly Glu Val Arg Gln Phe Thr Leu Arg His
1 5 10 15

Trp Leu Lys Val
20

<210> SEQ ID NO 797
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 797

Arg Asn Ile Glu Glu Val Tyr Val Gly Gly Lys Gln Val Val Pro Phe
1 5 10 15

Ser Ser Ser Val
20

<210> SEQ ID NO 798
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 798

Arg Ser Gly Ala Thr Ile Pro Leu Val Gly Gln Asp Ile Ile Asp Leu
1 5 10 15

Gln Thr Glu Val
20

<210> SEQ ID NO 799
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 799

Ser Phe Thr Ser Ile Leu Thr Cys His Gln Arg Arg Thr Gln Arg Lys
1 5 10 15

Glu Thr Val Ala
20

<210> SEQ ID NO 800
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 800

Ser Leu Ile Gly Pro Val Gln Lys Glu Tyr Gln Arg Glu Leu Gly Lys
1 5 10 15

Leu Ser Ser Pro
20

<210> SEQ ID NO 801
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 801

Ser Leu Lys Pro Gly Thr Val Leu Pro Pro Pro Pro Tyr Arg His Arg
1 5 10 15

Asn Thr Val Val
20

<210> SEQ ID NO 802
<211> LENGTH: 20
<212> TYPE: PRT

<213> ORGANISM: Artificial Sequence
<220> FEATURE:
<223> OTHER INFORMATION: Synthetic peptide of PL sequence binding PSD95 d1, d2

<400> SEQUENCE: 802

Ser Leu Lys Pro Gly Thr Val Leu Pro Pro Pro Pro Tyr Arg His Arg
1               5                   10                  15

Asn Thr Val Val
            20

<210> SEQ ID NO 803
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 803

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 804
<211> LENGTH: 18
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 804

Thr Phe Ala Ala Gly Phe Asn Ser Thr Gly Leu Pro His Ser Thr Thr
1               5                   10                  15

Arg Val

<210> SEQ ID NO 805
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 805

Thr Phe Lys Gly Thr Pro Thr Ala Glu Asn Pro Glu Tyr Leu Gly Leu
1               5                   10                  15

Asp Val Pro Val
            20

<210> SEQ ID NO 806
<211> LENGTH: 19
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 806

Thr Gly Arg Gly Met Ser Gly Gly Arg Ser Ser Arg Thr Arg Arg Glu
1               5                   10                  15

Thr Gln Leu

<210> SEQ ID NO 807
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 807

Thr Gly Ser Ala Leu Gln Ala Trp Arg His Thr Ser Arg Gln Ala Thr
1 5 10 15

Glu Ser Thr Val
20

<210> SEQ ID NO 808
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 808

Thr Gln Gly Phe Pro Gly Pro Ala Thr Trp Arg Arg Ile Ser Ser Leu
1 5 10 15

Glu Ser Glu Val
20

<210> SEQ ID NO 809
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 809

Thr Arg Glu Asp Ile Tyr Val Asn Tyr Pro Thr Phe Ser Arg Arg Pro
1 5 10 15

Lys Thr Arg Val
20

<210> SEQ ID NO 810
<211> LENGTH: 19
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 810

Thr Thr Asn Asn Asn Pro Asn Ser Ala Val Asn Ile Lys Lys Ile Phe
1 5 10 15

Thr Asp Val

<210> SEQ ID NO 811
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d1, d2

<400> SEQUENCE: 811

Val Asp Pro Asn Ser Pro Ala Ala Lys Lys Lys Tyr Val Ser Tyr Asn
1 5 10 15

Asn Leu Val Ile
20

<210> SEQ ID NO 812
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 812

Val Gly Thr Leu Leu Leu Glu Arg Val Ile Phe Pro Ser Val Lys Ile
1 5 10 15

Ala Thr Leu Val
20

<210> SEQ ID NO 813
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 813

Val His Lys Val Arg Asn Lys Phe Lys Ala Lys Cys Ser Leu Cys Arg
1 5 10 15

Leu Tyr Ile Ile
20

<210> SEQ ID NO 814
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 814

Trp Thr Gly Gln Ser Ala Asn Ser Arg Lys Pro Pro Arg Gln Arg Ser
1 5 10 15

Glu Thr Gln Val
20

<210> SEQ ID NO 815
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 815

Tyr Gly Arg Lys Lys Arg Arg Gln Arg Arg Arg Gly Ala Ser Ala Asp
1 5 10 15

Ser Thr Gln Ala
20

<210> SEQ ID NO 816
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 816

Tyr Gly Arg Lys Lys Arg Arg Gln Arg Arg Arg Lys Leu Ser Ser Ile
1 5 10 15

Glu Ser Asp Val
20

<210> SEQ ID NO 817
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 817

Tyr Gly Arg Lys Lys Arg Arg Gln Arg Arg Arg Met Ala Gly Thr Ile
1 5 10 15

Arg Ser Glu Val
20

<210> SEQ ID NO 818
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 818

Tyr Gly Arg Lys Lys Arg Arg Gln Arg Arg Arg Met Ala Arg Thr Ile
1 5 10 15

Glu Ser Glu Ile
20

<210> SEQ ID NO 819
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 819

Tyr Gly Arg Lys Lys Arg Arg Gln Arg Arg Arg Met Ala Arg Thr Ile
1 5 10 15

Glu Ser Glu Val
20

<210> SEQ ID NO 820
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d1, d2

<400> SEQUENCE: 820

Tyr Gly Arg Lys Lys Arg Arg Gln Arg Arg Arg Met Glu Arg Thr Ile
1 5 10 15

Glu Pro Glu Val
20

<210> SEQ ID NO 821
<211> LENGTH: 20
<212> TYPE: PRT

<213> ORGANISM: Artificial Sequence
<220> FEATURE:
<223> OTHER INFORMATION: Synthetic peptide of PL sequence binding PSD95 d1, d2

<400> SEQUENCE: 821

Tyr Gly Arg Lys Lys Arg Arg Gln Arg Arg Arg Asn Asp Asn Ile Ala
1 5 10 15

Leu Leu Val Gln
20

<210> SEQ ID NO 822
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 822

Ala Ala Gly Gly Arg Ser Ala Arg Gly Gly Arg Leu Gln Gly Arg Arg
1 5 10 15

Glu Thr Ala Leu
20

<210> SEQ ID NO 823
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 823

Ala Val Gly Gly Arg Pro Ala Arg Gly Gly Arg Leu Gln Gly Arg Arg
1 5 10 15

Gln Thr Gln Val
20

<210> SEQ ID NO 824
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 824

Phe Asn Gly Ser Ser Asn Gly His Val Tyr Glu Lys Leu Ser Ser Ile
1 5 10 15

Glu Ser Asp Val
20

<210> SEQ ID NO 825
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 825

Gly Gly Asp Leu Gly Thr Arg Arg Gly Ser Ala His Phe Ser Ser Leu
1 5 10 15

Glu Ser Glu Val
20

<210> SEQ ID NO 826
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 826

Gly Arg Trp Ala Gly Arg Ser Ala Ala Ser Trp Arg Ser Arg Arg Arg
1 5 10 15

Glu Thr Ala Leu
20

<210> SEQ ID NO 827
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 827

Gly Arg Trp Thr Gly Arg Ala Met Ser Ala Trp Lys Pro Thr Arg Arg
1 5 10 15

Glu Thr Glu Val
20

<210> SEQ ID NO 828
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 828

Gly Arg Trp Thr Gly Arg Ser Ala Val Ser Trp Arg Pro Arg Arg Arg
1 5 10 15

Gln Thr Gln Val
20

<210> SEQ ID NO 829
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 829

Lys Asp Ile Thr Ser Asp Ser Glu Asn Ser Asn Phe Arg Asn Glu Ile
1 5 10 15

Gln Ser Leu Val
20

<210> SEQ ID NO 830
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 830

```
Lys His Ser Arg Lys Ser Ser Ser Tyr Ser Ser Ser Ser Thr Thr Val
1               5                   10                  15

Lys Thr Ser Tyr
            20


<210> SEQ ID NO 831
<211> LENGTH: 23
<212> TYPE: PRT
<213> ORGANISM: Artificial Sequence
<220> FEATURE:
<223> OTHER INFORMATION: Synthetic peptide of PL sequence binding
      PSD95  d2

<400> SEQUENCE: 831

Lys Lys Lys Lys Gln Pro Gly Asn Ser Thr Lys Glu Ser Glu Ser Thr
1               5                   10                  15

Asn Ser Val Arg Leu Met Leu
            20


<210> SEQ ID NO 832
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95  d2

<400> SEQUENCE: 832

Leu Asn Ser Cys Ser Asn Arg Arg Val Tyr Lys Lys Met Pro Ser Ile
1               5                   10                  15

Glu Ser Asp Val
            20


<210> SEQ ID NO 833
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95  d2

<400> SEQUENCE: 833

Leu Asn Ser Ser Ser Asn Arg Arg Val Tyr Lys Lys Met Pro Ser Ile
1               5                   10                  15

Glu Ser Asp Val
            20


<210> SEQ ID NO 834
<211> LENGTH: 20
<212> TYPE: PRT
<213> ORGANISM: Artificial Sequence
<220> FEATURE:
<223> OTHER INFORMATION: Synthetic peptide of PL sequence binding
      PSD95  d2

<400> SEQUENCE: 834

Asn Thr Ser Ser Asp Gln Ala Arg Gln Glu Arg Leu Arg Arg Arg Arg
1               5                   10                  15

Glu Thr Gln Val
            20


<210> SEQ ID NO 835
<211> LENGTH: 20
<212> TYPE: PRT
<213> ORGANISM: Artificial Sequence
<220> FEATURE:
```

<223> OTHER INFORMATION: Synthetic peptide of PL sequence binding
PSD95 d2

<400> SEQUENCE: 835

Gln Ile Ser Pro Gly Gly Leu Glu Pro Pro Ser Glu Lys His Phe Arg
1 5 10 15

Glu Thr Glu Val
20

<210> SEQ ID NO 836
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 836

Arg Glu Leu Val Asp Arg Gly Glu Val Arg Gln Phe Thr Leu Arg His
1 5 10 15

Trp Leu Lys Val
20

<210> SEQ ID NO 837
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 837

Arg Ser Gly Ala Thr Ile Pro Leu Val Gly Gln Asp Ile Ile Asp Leu
1 5 10 15

Gln Thr Glu Val
20

<210> SEQ ID NO 838
<211> LENGTH: 18
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 838

Ser Pro Gln Pro Asp Ser Thr Asp Asn Asp Asp Tyr Asp Asp Ile Ser
1 5 10 15

Ala Ala

<210> SEQ ID NO 839
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 839

Ser Ser Ser Arg Arg Asp Ser Ser Trp Ser Glu Thr Ser Glu Ala Ser
1 5 10 15

Tyr Ser Gly Leu
20

<210> SEQ ID NO 840

<211> LENGTH: 19
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 840

Thr Gly Arg Gly Met Ser Gly Gly Arg Ser Ser Arg Thr Arg Arg Glu
1 5 10 15

Thr Gln Leu

<210> SEQ ID NO 841
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 841

Thr Gln Gly Phe Pro Gly Pro Ala Thr Trp Arg Arg Ile Ser Ser Leu
1 5 10 15

Glu Ser Glu Val
20

<210> SEQ ID NO 842
<211> LENGTH: 19
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 842

Thr Thr Asn Asn Asn Pro Asn Ser Ala Val Asn Ile Lys Lys Ile Phe
1 5 10 15

Thr Asp Val

<210> SEQ ID NO 843
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 843

Val His Lys Val Arg Asn Lys Phe Lys Ala Lys Cys Ser Leu Cys Arg
1 5 10 15

Leu Tyr Ile Ile
20

<210> SEQ ID NO 844
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 844

Tyr Gly Arg Lys Lys Arg Arg Gln Arg Arg Arg Ala Leu Lys Ser Ile
1 5 10 15

Glu Thr Glu Val
20

<210> SEQ ID NO 845
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 845

Tyr Gly Arg Lys Lys Arg Arg Gln Arg Arg Arg Ala Arg Gly Arg Arg
1 5 10 15

Glu Thr Trp Val
20

<210> SEQ ID NO 846
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 846

Tyr Gly Arg Lys Lys Arg Arg Gln Arg Arg Arg Asp Lys Glu Leu Glu
1 5 10 15

Val Leu Ser Leu
20

<210> SEQ ID NO 847
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 847

Tyr Gly Arg Lys Lys Arg Arg Gln Arg Arg Arg Glu Lys His Phe Arg
1 5 10 15

Glu Ala Glu Ala
20

<210> SEQ ID NO 848
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 848

Tyr Gly Arg Lys Lys Arg Arg Gln Arg Arg Arg Glu Lys His Phe Arg
1 5 10 15

Glu Thr Glu Val
20

<210> SEQ ID NO 849
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 849

Tyr Gly Arg Lys Lys Arg Arg Gln Arg Arg Arg Glu Tyr Leu Gly Leu
1 5 10 15

Asp Val Pro Val
20

<210> SEQ ID NO 850
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 850

Tyr Gly Arg Lys Lys Arg Arg Gln Arg Arg Arg Gly Met Thr Ser Ser
1 5 10 15

Ser Ser Val Val
20

<210> SEQ ID NO 851
<211> LENGTH: 16
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 851

Tyr Gly Arg Lys Lys Arg Arg Gln Arg Arg Arg Ile Glu Thr Glu Val
1 5 10 15

<210> SEQ ID NO 852
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 852

Tyr Gly Arg Lys Lys Arg Arg Gln Arg Arg Arg Lys Leu Ser Ser Ile
1 5 10 15

Glu Ser Asp Leu
20

<210> SEQ ID NO 853
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 853

Tyr Gly Arg Lys Lys Arg Arg Gln Arg Arg Arg Lys Leu Ser Ser Ile
1 5 10 15

Glu Ser Asp Val
20

<210> SEQ ID NO 854
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 854

Tyr Gly Arg Lys Lys Arg Arg Gln Arg Arg Arg Lys Leu Ser Ser Ile
1 5 10 15

Glu Ser Asp Val
20

<210> SEQ ID NO 855
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 855

Tyr Gly Arg Lys Lys Arg Arg Gln Arg Arg Arg Lys Leu Ser Ser Ile
1 5 10 15

Glu Ser Asp Xaa
20

<210> SEQ ID NO 856
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 856

Tyr Gly Arg Lys Lys Arg Arg Gln Arg Arg Arg Lys Leu Ser Ser Ile
1 5 10 15

Glu Ser Asp Xaa
20

<210> SEQ ID NO 857
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 857

Tyr Gly Arg Lys Lys Arg Arg Gln Arg Arg Arg Lys Leu Ser Ser Ile
1 5 10 15

Glu Ser Asp Xaa
20

<210> SEQ ID NO 858
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:

<221> NAME/KEY: misc_feature
<222> LOCATION: (20)..(20)
<223> OTHER INFORMATION: Xaa = any naturally occurring amino acid

<400> SEQUENCE: 858

Tyr Gly Arg Lys Lys Arg Arg Gln Arg Arg Arg Lys Leu Ser Ser Ile
1               5                   10                  15

Glu Ser Asp Xaa
            20

<210> SEQ ID NO 859
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 859

Tyr Gly Arg Lys Lys Arg Arg Gln Arg Arg Arg Lys Leu Ser Ser Ile
1               5                   10                  15

Glu Ser Asp Xaa
            20

<210> SEQ ID NO 860
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 860

Tyr Gly Arg Lys Lys Arg Arg Gln Arg Arg Arg Lys Leu Ser Ser Ile
1               5                   10                  15

Glu Ser Asp Xaa
            20

<210> SEQ ID NO 861
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2
<220> FEATURE:
<221> NAME/KEY: misc_feature
<222> LOCATION: (19)..(19)
<223> OTHER INFORMATION: Xaa = any naturally occurring amino acid

<400> SEQUENCE: 861

Tyr Gly Arg Lys Lys Arg Arg Gln Arg Arg Arg Lys Leu Ser Ser Ile
1               5                   10                  15

Glu Ser Xaa Val
            20

<210> SEQ ID NO 862
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 862

Tyr Gly Arg Lys Lys Arg Arg Gln Arg Arg Arg Lys Leu Ser Ser Ile
1 5 10 15

Glu Ser Tyr Val
20

<210> SEQ ID NO 863
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

<400> SEQUENCE: 863

Tyr Gly Arg Lys Lys Arg Arg Gln Arg Arg Arg Lys Leu Ser Ser Ile
1 5 10 15

Glu Thr Asp Val
20

<210> SEQ ID NO 864
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:
<221> NAME/KEY: misc_feature
<222> LOCATION: (20)..(20)
<223> OTHER INFORMATION: Xaa = any naturally occurring amino acid

<400> SEQUENCE: 864

Tyr Gly Arg Lys Lys Arg Arg Gln Arg Arg Arg Lys Leu Ser Ser Ile
1 5 10 15

Glu Thr Asp Xaa
20

<210> SEQ ID NO 865
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2
<220> FEATURE:
<221> NAME/KEY: misc_feature
<222> LOCATION: (18)..(18)
<223> OTHER INFORMATION: Xaa = any naturally occurring amino acid

<400> SEQUENCE: 865

Tyr Gly Arg Lys Lys Arg Arg Gln Arg Arg Arg Lys Leu Ser Ser Ile
1 5 10 15

Glu Xaa Asp Val
20

<210> SEQ ID NO 866
<211> LENGTH: 20
<212> TYPE: PRT
<213> ORGANISM: Artificial Sequence
<220> FEATURE:
<223> OTHER INFORMATION: Synthetic peptide of PL sequence binding
PSD95 d2

-continued

<400> SEQUENCE: 866

Tyr Gly Arg Lys Lys Arg Arg Gln Arg Arg Arg Lys Leu Ser Ser Ile
1 5 10 15

Glu Tyr Asp Val
20

<210> SEQ ID NO 867
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 867

Tyr Gly Arg Lys Lys Arg Arg Gln Arg Arg Arg Met Ala Arg Thr Ile
1 5 10 15

Glu Ser Glu Ile
20

<210> SEQ ID NO 868
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 868

Tyr Gly Arg Lys Lys Arg Arg Gln Arg Arg Arg Met Ala Arg Thr Ile
1 5 10 15

Glu Ser Glu Val
20

<210> SEQ ID NO 869
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 869

Tyr Gly Arg Lys Lys Arg Arg Gln Arg Arg Arg Met Glu Arg Thr Ile
1 5 10 15

Glu Pro Glu Val
20

<210> SEQ ID NO 870
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 870

Tyr Gly Arg Lys Lys Arg Arg Gln Arg Arg Arg Asn Asp Asn Ile Ala
1 5 10 15

Leu Leu Val Gln
20

<210> SEQ ID NO 871
<211> LENGTH: 20
<212> TYPE: PRT

<213> ORGANISM: Artificial Sequence
<220> FEATURE:
<223> OTHER INFORMATION: Synthetic peptide of PL sequence binding PSD95 d2

<400> SEQUENCE: 871

Tyr Gly Arg Lys Lys Arg Arg Gln Arg Arg Arg Gln Asp Glu Arg Val
1 5 10 15

Glu Thr Arg Val
20

<210> SEQ ID NO 872
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 872

Tyr Gly Arg Lys Lys Arg Arg Gln Arg Arg Arg Gln Asp Ser Arg Glu
1 5 10 15

Glu Thr Gln Leu
20

<210> SEQ ID NO 873
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 873

Tyr Gly Arg Lys Lys Arg Arg Gln Arg Arg Arg Arg Ile Ser Ser Ile
1 5 10 15

Glu Thr Asp Val
20

<210> SEQ ID NO 874
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 874

Tyr Gly Arg Lys Lys Arg Arg Gln Arg Arg Arg Arg Ile Ser Ser Ile
1 5 10 15

Gln Thr Asp Val
20

<210> SEQ ID NO 875
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 875

Tyr Gly Arg Lys Lys Arg Arg Gln Arg Arg Arg Arg Ile Ser Ser Leu
1 5 10 15

Glu Ser Glu Val
20

<210> SEQ ID NO 876
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 876

Tyr Gly Arg Lys Lys Arg Arg Gln Arg Arg Arg Arg Ile Ser Ser Leu
1 5 10 15

Glu Thr Glu Val
20

<210> SEQ ID NO 877
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 877

Tyr Gly Arg Lys Lys Arg Arg Gln Arg Arg Arg Arg Ile Ser Ser Leu
1 5 10 15

Glu Thr Gln Val
20

<210> SEQ ID NO 878
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 878

Tyr Gly Arg Lys Lys Arg Arg Gln Arg Arg Arg Arg Ser Arg Arg Arg
1 5 10 15

Glu Thr Ala Leu
20

<210> SEQ ID NO 879
<211> LENGTH: 20
<212> TYPE: PRT
<213> ORGANISM: Artificial Sequence
<220> FEATURE:
<223> OTHER INFORMATION: Synthetic peptide of PL sequence binding PSD95 d2

<400> SEQUENCE: 879

Tyr Gly Arg Lys Lys Arg Arg Gln Arg Arg Arg Thr Lys Asn Tyr Lys
1 5 10 15

Gln Thr Ser Val
20

<210> SEQ ID NO 880
<211> LENGTH: 23
<212> TYPE: PRT
<213> ORGANISM: Artificial Sequence
<220> FEATURE:
<223> OTHER INFORMATION: Synthetic peptide of PL sequence binding PTN-3

<400> SEQUENCE: 880

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 881
<211> LENGTH: 20
<212> TYPE: PRT
<213> ORGANISM: Artificial Sequence
<220> FEATURE:
<223> OTHER INFORMATION: Synthetic peptide of PL sequence binding PTN-3

<400> SEQUENCE: 881

Leu Met Asp Gly Leu Pro Pro Gly Asp Ser Asn Gln Leu Ala Trp Phe
1 5 10 15

Asp Thr Asp Leu
20

<210> SEQ ID NO 882
<211> LENGTH: 20
<212> TYPE: PRT
<213> ORGANISM: Artificial Sequence
<220> FEATURE:
<223> OTHER INFORMATION: Synthetic peptide of PL sequence binding PTN-3

<400> SEQUENCE: 882

Tyr Gly Arg Lys Lys Arg Arg Gln Arg Arg Arg Ala Val Ala Ala Thr
1 5 10 15

Ser Ala Asn Leu
20

<210> SEQ ID NO 883
<211> LENGTH: 20
<212> TYPE: PRT
<213> ORGANISM: Artificial Sequence
<220> FEATURE:
<223> OTHER INFORMATION: Synthetic peptide of PL sequence binding PTN-3

<400> SEQUENCE: 883

Tyr Gly Arg Lys Lys Arg Arg Gln Arg Arg Arg Glu Tyr Leu Gly Leu
1 5 10 15

Asp Val Pro Val
20

<210> SEQ ID NO 884
<211> LENGTH: 20
<212> TYPE: PRT
<213> ORGANISM: Artificial Sequence
<220> FEATURE:
<223> OTHER INFORMATION: Synthetic peptide of PL sequence binding PTN-3

<400> SEQUENCE: 884

Tyr Gly Arg Lys Lys Arg Arg Gln Arg Arg Arg Gly Ala Ser Ala Asp
1 5 10 15

Ser Thr Gln Ala
20

<210> SEQ ID NO 885
<211> LENGTH: 20
<212> TYPE: PRT
<213> ORGANISM: Artificial Sequence
<220> FEATURE:

<223> OTHER INFORMATION: Synthetic peptide of PL sequence binding
      PTN-3

<400> SEQUENCE: 885

Tyr Gly Arg Lys Lys Arg Arg Gln Arg Arg Arg Asn Asp Asn Ile Ala
1               5                   10                  15

Leu Leu Val Gln
            20

<210> SEQ ID NO 886
<211> LENGTH: 20
<212> TYPE: PRT
<213> ORGANISM: Artificial Sequence
<220> FEATURE:
<223> OTHER INFORMATION: Synthetic peptide of PL sequence binding
      PTN-3

<400> SEQUENCE: 886

Tyr Gly Arg Lys Lys Arg Arg Gln Arg Arg Arg Ser Glu Gly Val Pro
1               5                   10                  15

Asp Leu Leu Val
            20

<210> SEQ ID NO 887
<211> LENGTH: 20
<212> TYPE: PRT
<213> ORGANISM: Artificial Sequence
<220> FEATURE:
<223> OTHER INFORMATION: Synthetic peptide of PL sequence binding
      SHANK 1

<400> SEQUENCE: 887

Ala Ala Gly Gly Arg Ser Ala Arg Gly Gly Arg Leu Gln Gly Arg Arg
1               5                   10                  15

Glu Thr Ala Leu
            20

<210> SEQ ID NO 888
<211> LENGTH: 20
<212> TYPE: PRT
<213> ORGANISM: Artificial Sequence
<220> FEATURE:
<223> OTHER INFORMATION: Synthetic peptide of PL sequence binding
      SHANK 1

<400> SEQUENCE: 888

Ala Leu Val Leu Ile Ala Phe Cys Ile Ile Arg Arg Arg Pro Ser Ala
1               5                   10                  15

Tyr Gln Ala Leu
            20

<210> SEQ ID NO 889
<211> LENGTH: 19
<212> TYPE: PRT
<213> ORGANISM: Artificial Sequence
<220> FEATURE:
<223> OTHER INFORMATION: Synthetic peptide of PL sequence binding
      SHANK 1

<400> SEQUENCE: 889

Ala Trp Asp Asp Ser Ala Arg Ala Ala Gly Gly Gln Gly Leu His Val
1               5                   10                  15

Thr Ala Leu

<210> SEQ ID NO 890

<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 890

Asp Ala Lys Leu Lys Ser Asp Gly Thr Ile Ala Ala Ile Thr Glu Lys
1 5 10 15

Glu Thr His Phe
20

<210> SEQ ID NO 891
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 891

Asp Phe Arg Pro Ser Phe Lys His Ile Leu Phe Arg Arg Ala Arg Arg
1 5 10 15

Gly Phe Arg Gln
20

<210> SEQ ID NO 892
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 892

Asp Gly Gly Ala Arg Thr Glu Asp Glu Val Gln Ser Tyr Pro Ser Lys
1 5 10 15

His Asp Tyr Val
20

<210> SEQ ID NO 893
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 893

Asp Ser Asp Pro Glu Asn Glu Pro Phe Asp Glu Asp Gln His Thr Gln
1 5 10 15

Ile Thr Lys Val
20

<210> SEQ ID NO 894
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 894

Glu Ala Leu Gln Pro Glu Pro Gly Arg Lys Arg Ile Pro Leu Thr Arg
1 5 10 15

Thr Thr Thr Phe
20

<210> SEQ ID NO 895
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 895

Glu Leu Leu Gln Phe Cys Arg Thr Pro Asn Pro Ala Leu Lys Asn Gly
1 5 10 15

Gln Tyr Trp Val
20

<210> SEQ ID NO 896
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 896

Gly Gly Glu Asp Phe Lys Thr Thr Asn Pro Ser Lys Gln Phe Asp Lys
1 5 10 15

Asn Ala Tyr Val
20

<210> SEQ ID NO 897
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 897

Gly Gly Gly Gly Gly Ser Gly Gly Gly Gly Ser Gly Gly Gly His Ser
1 5 10 15

Thr Thr Arg Val
20

<210> SEQ ID NO 898
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 898

Gly Gly Gly Gly Gly Ser Gly Gly Gly Gly Ser Gly Leu Pro His Ser
1 5 10 15

Thr Thr Arg Val
20

<210> SEQ ID NO 899
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 899

Gly Gly Gly Gly Gly Ser Gly Gly Gly Gly Ser Gly Ser Arg Arg Pro
1 5 10 15

Lys Thr Arg Val
20

<210> SEQ ID NO 900
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 900

His His Leu Val Ala Gln Arg Asp Ile Arg Gln Phe Gln Leu Gln His
1 5 10 15

Trp Leu Ala Ile
20

<210> SEQ ID NO 901
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 901

His Ser Cys Cys Asn Arg Ala Arg Gln Glu Arg Leu Gln Arg Arg Arg
1 5 10 15

Glu Thr Gln Val
20

<210> SEQ ID NO 902
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 902

Lys Ala Gly Tyr Arg Ala Pro Arg Ser Tyr Pro Lys Ser Asn Ser Ser
1 5 10 15

Lys Glu Tyr Val
20

<210> SEQ ID NO 903
<211> LENGTH: 19
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 903

Lys Asp Ser Arg Pro Ser Phe Val Gly Ser Ser Ser Gly His Thr Ser
1 5 10 15

Thr Thr Leu

<210> SEQ ID NO 904
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 904

Lys Glu Asn Asp Tyr Glu Ser Ile Ser Asp Leu Gln Gln Gly Arg Asp
1 5 10 15

Ile Thr Arg Leu
20

<210> SEQ ID NO 905
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 905

Lys His Ser Arg Lys Ser Ser Ser Tyr Ser Ser Ser Ser Thr Thr Val
1 5 10 15

Lys Thr Ser Tyr
20

<210> SEQ ID NO 906
<211> LENGTH: 23
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 906

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 907
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 907

Lys Pro Gln Ile Ala Ala Leu Lys Glu Glu Thr Glu Glu Glu Val Gln
1 5 10 15

Asp Thr Arg Leu
20

<210> SEQ ID NO 908
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 908

Lys Tyr Ser Ala Pro Arg Arg Pro Thr Ala Thr Gly Asp Tyr Asp Lys
1 5 10 15

Lys Asn Tyr Val
20

<210> SEQ ID NO 909
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 909

```
Leu Ala Ser Lys Ser Ala Glu Glu Gly Lys Gln Ile Pro Asp Ser Leu
1               5                   10                  15

Ser Thr Asp Leu
            20
```

<210> SEQ ID NO 910
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 910

```
Leu Ala Val Leu Ala Tyr Ser Ile Thr Leu Val Met Leu Trp Ser Ile
1               5                   10                  15

Trp Gln Tyr Ala
            20
```

<210> SEQ ID NO 911
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 911

```
Leu Gly Tyr Ser Ile Pro Ser Arg Ser Gly Ala Ser Gly Leu Asp Lys
1               5                   10                  15

Arg Asp Tyr Val
            20
```

<210> SEQ ID NO 912
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 912

```
Leu Met Asp Gly Leu Pro Pro Gly Asp Ser Asn Gln Leu Ala Trp Phe
1               5                   10                  15

Asp Thr Asp Leu
            20
```

<210> SEQ ID NO 913
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 913

```
Leu Asn Glu Thr Thr Glu Thr Gln Arg Thr Leu Leu Asn Gly Asp Leu
```

1 5 10 15

Gln Thr Ser Ile
20

<210> SEQ ID NO 914
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 914

Leu Asn Ser Cys Ser Asn Arg Arg Val Tyr Lys Lys Met Pro Ser Ile
1 5 10 15

Glu Ser Asp Val
20

<210> SEQ ID NO 915
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 915

Leu Gln Phe His Arg Gly Ser Arg Ala Gln Ser Phe Leu Gln Thr Glu
1 5 10 15

Thr Ser Val Ile
20

<210> SEQ ID NO 916
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 916

Pro Gly Gln Pro Pro Lys Val Lys Ser Glu Phe Asn Ser Tyr Ser Leu
1 5 10 15

Thr Gly Tyr Val
20

<210> SEQ ID NO 917
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 917

Pro Ile Pro Ala Gly Gly Cys Thr Phe Ser Gly Ile Phe Pro Thr Leu
1 5 10 15

Thr Ser Pro Leu
20

<210> SEQ ID NO 918
<211> LENGTH: 20
<212> TYPE: PRT
<213> ORGANISM: Artificial Sequence
<220> FEATURE:
<223> OTHER INFORMATION: Synthetic peptide of PL sequence binding

SHANK 1

<400> SEQUENCE: 918

Pro Pro Ala Thr Pro Ser Pro Arg Leu Ala Leu Pro Ala His His Asn
1 5 10 15

Ala Thr Arg Leu
20

<210> SEQ ID NO 919
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 919

Pro Ser Trp Arg Arg Ser Ser Leu Ser Glu Ser Glu Asn Ala Thr Ser
1 5 10 15

Leu Thr Thr Phe
20

<210> SEQ ID NO 920
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 920

Pro Tyr Ser Glu Leu Asn Tyr Glu Thr Ser His Tyr Pro Ala Ser Pro
1 5 10 15

Asp Ser Trp Val
20

<210> SEQ ID NO 921
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 921

Gln Asp Phe Arg Arg Ala Phe Arg Arg Ile Leu Ala Arg Pro Trp Thr
1 5 10 15

Gln Thr Ala Trp
20

<210> SEQ ID NO 922
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 922

Arg Glu Leu Val Asp Arg Gly Glu Val Arg Gln Phe Thr Leu Arg His
1 5 10 15

Trp Leu Lys Val
20

<210> SEQ ID NO 923

<211> LENGTH: 11
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 923

Arg Arg Ala Ser Thr Ser Arg Glu Thr Trp Val
1 5 10

<210> SEQ ID NO 924
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 924

Arg Ser Gly Ala Thr Ile Pro Leu Val Gly Gln Asp Ile Ile Asp Leu
1 5 10 15

Gln Thr Glu Val
20

<210> SEQ ID NO 925
<211> LENGTH: 19
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 925

Ser Ser Lys Ser Lys Ser Ser Glu Glu Ser Gln Thr Phe Phe Gly Leu
1 5 10 15

Tyr Lys Leu

<210> SEQ ID NO 926
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 926

Ser Ser Pro Asp Ser Ser Tyr Gln Gly Lys Gly Phe Val Met Ser Arg
1 5 10 15

Ala Met Tyr Val
20

<210> SEQ ID NO 927
<211> LENGTH: 20
<212> TYPE: PRT
<213> ORGANISM: Artificial Sequence
<220> FEATURE:
<223> OTHER INFORMATION: Synthetic peptide of PL sequence binding
SHANK 1

<400> SEQUENCE: 927

Ser Ser Ser Arg Arg Asp Ser Ser Trp Ser Glu Thr Ser Glu Ala Ser
1 5 10 15

Tyr Ser Gly Leu
20

<210> SEQ ID NO 928
<211> LENGTH: 18
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 928

```
Thr Phe Ala Ala Gly Phe Asn Ser Thr Gly Leu Pro His Ser Thr Thr
1               5                   10                  15

Arg Val
```

<210> SEQ ID NO 929
<211> LENGTH: 19
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 929

```
Thr Gly Arg Gly Met Ser Gly Gly Arg Ser Ser Arg Thr Arg Arg Glu
1               5                   10                  15

Thr Gln Leu
```

<210> SEQ ID NO 930
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 930

```
Thr Arg Glu Asp Ile Tyr Val Asn Tyr Pro Thr Phe Ser Arg Arg Pro
1               5                   10                  15

Lys Thr Arg Val
            20
```

<210> SEQ ID NO 931
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 931

```
Val Asp Pro Asn Ser Pro Ala Ala Lys Lys Lys Tyr Val Ser Tyr Asn
1               5                   10                  15

Asn Leu Val Ile
            20
```

<210> SEQ ID NO 932
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 932

```
Val His Lys Val Arg Asn Lys Phe Lys Ala Lys Cys Ser Leu Cys Arg
1               5                   10                  15

Leu Tyr Ile Ile
```

20

<210> SEQ ID NO 933
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 933

Val Pro Gly Ala Leu Asp Tyr Ala Ala Phe Ser Ser Ala Leu Tyr Gly
1 5 10 15

Glu Ser Asp Leu
20

<210> SEQ ID NO 934
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 934

Tyr Gly Arg Lys Lys Arg Arg Gln Arg Arg Arg Asp Lys Glu Leu Glu
1 5 10 15

Val Leu Ser Leu
20

<210> SEQ ID NO 935
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 935

Tyr Gly Arg Lys Lys Arg Arg Gln Arg Arg Arg Leu Leu Lys Glu Arg
1 5 10 15

Ser Thr Glu Leu
20

<210> SEQ ID NO 936
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 936

Tyr Gly Arg Lys Lys Arg Arg Gln Arg Arg Arg Asn Asp Asn Ile Ala
1 5 10 15

Leu Leu Val Gln
20

<210> SEQ ID NO 937
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 937

Tyr Gly Arg Lys Lys Arg Arg Gln Arg Arg Arg Pro Ser Arg Lys Leu
1 5 10 15

Asn Thr Glu Ile
20

<210> SEQ ID NO 938
<211> LENGTH: 20
<212> TYPE: PRT
<213> ORGANISM: Artificial Sequence
<220> FEATURE:
<223> OTHER INFORMATION: Synthetic peptide of PL sequence binding SHANK 1

<400> SEQUENCE: 938

Tyr Gly Arg Lys Lys Arg Arg Gln Arg Arg Arg Tyr Ile Pro Glu Ala
1 5 10 15

Gln Thr Arg Leu
20

<210> SEQ ID NO 939
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 939

Ala Ala Gly Gly Arg Ser Ala Arg Gly Gly Arg Leu Gln Gly Arg Arg
1 5 10 15

Glu Thr Ala Leu
20

<210> SEQ ID NO 940
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 940

Phe His Ser Lys Thr Ala Gly Ala Asn Thr Thr Asp Lys Glu Leu Glu
1 5 10 15

Val Leu Ser Leu
20

<210> SEQ ID NO 941
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 941

Phe Asn Gly Ser Ser Asn Gly His Val Tyr Glu Lys Leu Ser Ser Ile
1 5 10 15

Glu Ser Asp Val
20

<210> SEQ ID NO 942
<211> LENGTH: 20
<212> TYPE: PRT
<213> ORGANISM: Artificial Sequence
<220> FEATURE:
<223> OTHER INFORMATION: Synthetic peptide of PL sequence binding
TIP43 d1

<400> SEQUENCE: 942

Gly Gly Asp Leu Gly Thr Arg Arg Gly Ser Ala His Phe Ser Ser Leu
1 5 10 15

Glu Ser Glu Val
20

<210> SEQ ID NO 943
<211> LENGTH: 20
<212> TYPE: PRT
<213> ORGANISM: Artificial Sequence
<220> FEATURE:
<223> OTHER INFORMATION: Synthetic peptide of PL sequence binding
TIP43 d1

<400> SEQUENCE: 943

Gly Arg Trp Thr Gly Arg Ala Met Ser Ala Trp Lys Pro Thr Arg Arg
1 5 10 15

Glu Thr Glu Val
20

<210> SEQ ID NO 944
<211> LENGTH: 20
<212> TYPE: PRT
<213> ORGANISM: Artificial Sequence
<220> FEATURE:
<223> OTHER INFORMATION: Synthetic peptide of PL sequence binding
TIP43 d1

<400> SEQUENCE: 944

Lys His Ser Arg Lys Ser Ser Ser Tyr Ser Ser Ser Ser Thr Thr Val
1 5 10 15

Lys Thr Ser Tyr
20

<210> SEQ ID NO 945
<211> LENGTH: 23
<212> TYPE: PRT
<213> ORGANISM: Artificial Sequence
<220> FEATURE:
<223> OTHER INFORMATION: Synthetic peptide of PL sequence binding
TIP43 d1

<400> SEQUENCE: 945

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 946
<211> LENGTH: 20
<212> TYPE: PRT
<213> ORGANISM: Artificial Sequence
<220> FEATURE:
<223> OTHER INFORMATION: Synthetic peptide of PL sequence binding
TIP43 d1

<400> SEQUENCE: 946

Leu Ala Ser Lys Ser Ala Glu Glu Gly Lys Gln Ile Pro Asp Ser Leu
1 5 10 15

Ser Thr Asp Leu
20

<210> SEQ ID NO 947
<211> LENGTH: 20
<212> TYPE: PRT
<213> ORGANISM: Artificial Sequence
<220> FEATURE:
<223> OTHER INFORMATION: Synthetic peptide of PL sequence binding
      TIP43 d1

<400> SEQUENCE: 947

```
Leu Asn Ser Ser Ser Asn Arg Arg Val Tyr Lys Lys Met Pro Ser Ile
1               5                   10                  15

Glu Ser Asp Val
            20
```

<210> SEQ ID NO 948
<211> LENGTH: 20
<212> TYPE: PRT
<213> ORGANISM: Artificial Sequence
<220> FEATURE:
<223> OTHER INFORMATION: Synthetic peptide of PL sequence binding
      TIP43 d1

<400> SEQUENCE: 948

```
Arg Ser Gly Ala Thr Ile Pro Leu Val Gly Gln Asp Ile Ile Asp Leu
1               5                   10                  15

Gln Thr Glu Val
            20
```

<210> SEQ ID NO 949
<211> LENGTH: 20
<212> TYPE: PRT
<213> ORGANISM: Artificial Sequence
<220> FEATURE:
<223> OTHER INFORMATION: Synthetic peptide of PL sequence binding
      TIP43 d1

<400> SEQUENCE: 949

```
Ser Phe Thr Ser Ile Leu Thr Cys His Gln Arg Arg Thr Gln Arg Lys
1               5                   10                  15

Glu Thr Val Ala
            20
```

<210> SEQ ID NO 950
<211> LENGTH: 20
<212> TYPE: PRT
<213> ORGANISM: Artificial Sequence
<220> FEATURE:
<223> OTHER INFORMATION: Synthetic peptide of PL sequence binding
      TIP43 d1

<400> SEQUENCE: 950

```
Ser Ser Ser Arg Arg Asp Ser Ser Trp Ser Glu Thr Ser Glu Ala Ser
1               5                   10                  15

Tyr Ser Gly Leu
            20
```

<210> SEQ ID NO 951
<211> LENGTH: 20
<212> TYPE: PRT
<213> ORGANISM: Artificial Sequence
<220> FEATURE:
<223> OTHER INFORMATION: Synthetic peptide of PL sequence binding
      TIP43 d1

<400> SEQUENCE: 951

```
Thr Gln Gly Phe Pro Gly Pro Ala Thr Trp Arg Arg Ile Ser Ser Leu
```

1 5 10 15

Glu Ser Glu Val
20

<210> SEQ ID NO 952
<211> LENGTH: 19
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 952

Thr Thr Asn Asn Asn Pro Asn Ser Ala Val Asn Ile Lys Lys Ile Phe
1 5 10 15

Thr Asp Val

<210> SEQ ID NO 953
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 953

Val His Lys Val Arg Asn Lys Phe Lys Ala Lys Cys Ser Leu Cys Arg
1 5 10 15

Leu Tyr Ile Ile
20

<210> SEQ ID NO 954
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 954

Tyr Gly Arg Lys Lys Arg Arg Gln Arg Arg Arg Glu Tyr Leu Gly Leu
1 5 10 15

Asp Val Pro Val
20

<210> SEQ ID NO 955
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 955

Tyr Gly Arg Lys Lys Arg Arg Gln Arg Arg Arg Gly Ala Ser Ala Asp
1 5 10 15

Ser Thr Gln Ala
20

<210> SEQ ID NO 956
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 956

Tyr Gly Arg Lys Lys Arg Arg Gln Arg Arg Arg Lys Leu Ser Ser Ile
1 5 10 15

Glu Ser Asp Val
20

<210> SEQ ID NO 957
<211> LENGTH: 20
<212> TYPE: PRT
<213> ORGANISM: Artificial Sequence
<220> FEATURE:
<223> OTHER INFORMATION: Synthetic peptide of PL sequence binding TIP43 d1

<400> SEQUENCE: 957

Tyr Gly Arg Lys Lys Arg Arg Gln Arg Arg Arg Asn Asp Asn Ile Ala
1 5 10 15

Leu Leu Val Gln
20

<210> SEQ ID NO 958
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 958

Ala Ala Gly Gly Arg Ser Ala Arg Gly Gly Arg Leu Gln Gly Arg Arg
1 5 10 15

Glu Thr Ala Leu
20

<210> SEQ ID NO 959
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 959

Ala Gly Ala Val Arg Thr Pro Leu Ser Gln Val Asn Lys Val Trp Asp
1 5 10 15

Gln Ser Ser Val
20

<210> SEQ ID NO 960
<211> LENGTH: 19
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 960

Ala Arg His Arg Val Thr Ser Tyr Thr Ser Ser Ser Val Asn Val Ser
1 5 10 15

Ser Asn Leu

<210> SEQ ID NO 961
<211> LENGTH: 20
<212> TYPE: PRT

<213> ORGANISM: Artificial Sequence
<220> FEATURE:
<223> OTHER INFORMATION: Synthetic peptide of PL sequence binding Vartul d2

<400> SEQUENCE: 961

Ala Thr Asp Tyr Leu Val Gln Pro Phe Met Asp Gln Leu Ala Phe His
1 5 10 15

Gln Phe Tyr Ile
20

<210> SEQ ID NO 962
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 962

Asp Phe Arg Pro Ser Phe Lys His Ile Leu Phe Arg Arg Ala Arg Arg
1 5 10 15

Gly Phe Arg Gln
20

<210> SEQ ID NO 963
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 963

Glu Leu Leu Gln Phe Cys Arg Thr Pro Asn Pro Ala Leu Lys Asn Gly
1 5 10 15

Gln Tyr Trp Val
20

<210> SEQ ID NO 964
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 964

Glu Ser Ser Gly Thr Gln Ser Pro Lys Arg His Ser Gly Ser Tyr Leu
1 5 10 15

Val Thr Ser Val
20

<210> SEQ ID NO 965
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 965

Gly Arg Trp Thr Gly Arg Ala Met Ser Ala Trp Lys Pro Thr Arg Arg
1 5 10 15

Glu Thr Glu Val
20

```
<210> SEQ ID NO 966
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 966

His His Leu Val Ala Gln Arg Asp Ile Arg Gln Phe Gln Leu Gln His
1               5                   10                  15

Trp Leu Ala Ile
            20


<210> SEQ ID NO 967
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 967

Lys His Ser Arg Lys Ser Ser Ser Tyr Ser Ser Ser Ser Thr Thr Val
1               5                   10                  15

Lys Thr Ser Tyr
            20


<210> SEQ ID NO 968
<211> LENGTH: 23
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 968

Lys Lys Lys Lys Gln Pro Gly Asn Ser Thr Lys Glu Ser Glu Ser Thr
1               5                   10                  15

Asn Ser Val Arg Leu Met Leu
            20


<210> SEQ ID NO 969
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 969

Leu Ala Val Leu Ala Tyr Ser Ile Thr Leu Val Met Leu Trp Ser Ile
1               5                   10                  15

Trp Gln Tyr Ala
            20


<210> SEQ ID NO 970
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 970
```

```
Leu Asn Ser Cys Ser Asn Arg Arg Val Tyr Lys Lys Met Pro Ser Ile
1               5                   10                  15

Glu Ser Asp Val
            20


<210> SEQ ID NO 971
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 971

Pro Ile Pro Ala Gly Gly Cys Thr Phe Ser Gly Ile Phe Pro Thr Leu
1               5                   10                  15

Thr Ser Pro Leu
            20


<210> SEQ ID NO 972
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 972

Pro Val Tyr Ile Val Gln Glu Met Pro Pro Gln Ser Pro Ala Asn Ile
1               5                   10                  15

Tyr Tyr Lys Val
            20


<210> SEQ ID NO 973
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 973

Pro Tyr Ser Glu Leu Asn Tyr Glu Thr Ser His Tyr Pro Ala Ser Pro
1               5                   10                  15

Asp Ser Trp Val
            20


<210> SEQ ID NO 974
<211> LENGTH: 20
<212> TYPE: PRT
<213> ORGANISM: Artificial Sequence
<220> FEATURE:
<223> OTHER INFORMATION: Synthetic peptide of PL sequence binding
      Vartul d2

<400> SEQUENCE: 974

Gln Asp Phe Arg Arg Ala Phe Arg Arg Ile Leu Ala Arg Pro Trp Thr
1               5                   10                  15

Gln Thr Ala Trp
            20


<210> SEQ ID NO 975
<211> LENGTH: 20
<212> TYPE: PRT
<213> ORGANISM: Artificial Sequence
<220> FEATURE:
```

<223> OTHER INFORMATION: Synthetic peptide of PL sequence binding
Vartul d2

<400> SEQUENCE: 975

Gln Ile Ser Pro Gly Gly Leu Glu Pro Pro Ser Glu Lys His Phe Arg
1 5 10 15

Glu Thr Glu Val
20

<210> SEQ ID NO 976
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 976

Arg Glu Leu Val Asp Arg Gly Glu Val Arg Gln Phe Thr Leu Arg His
1 5 10 15

Trp Leu Lys Val
20

<210> SEQ ID NO 977
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 977

Ser Leu Ile Gly Pro Val Gln Lys Glu Tyr Gln Arg Glu Leu Gly Lys
1 5 10 15

Leu Ser Ser Pro
20

<210> SEQ ID NO 978
<211> LENGTH: 19
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 978

Ser Ser Lys Ser Lys Ser Ser Glu Glu Ser Gln Thr Phe Phe Gly Leu
1 5 10 15

Tyr Lys Leu

<210> SEQ ID NO 979
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 979

Ser Tyr Pro Thr Pro Arg Pro Tyr Pro Lys Pro Ala Pro Ser Ser Gly
1 5 10 15

Lys Asp Tyr Val
20

<210> SEQ ID NO 980

<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 980

Thr Gln Gly Phe Pro Gly Pro Ala Thr Trp Arg Arg Ile Ser Ser Leu
1 5 10 15

Glu Ser Glu Val
20

<210> SEQ ID NO 981
<211> LENGTH: 19
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 981

Thr Thr Asn Asn Asn Pro Asn Ser Ala Val Asn Ile Lys Lys Ile Phe
1 5 10 15

Thr Asp Val

<210> SEQ ID NO 982
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 982

Val Asp Pro Asn Ser Pro Ala Ala Lys Lys Lys Tyr Val Ser Tyr Asn
1 5 10 15

Asn Leu Val Ile
20

<210> SEQ ID NO 983
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 983

Val His Lys Val Arg Asn Lys Phe Lys Ala Lys Cys Ser Leu Cys Arg
1 5 10 15

Leu Tyr Ile Ile
20

<210> SEQ ID NO 984
<211> LENGTH: 20
<212> TYPE: PRT
<213> ORGANISM: Artificial Sequence
<220> FEATURE:
<223> OTHER INFORMATION: Synthetic peptide of PL sequence binding
Vartul d2

<400> SEQUENCE: 984

Tyr Gly Arg Lys Lys Arg Arg Gln Arg Arg Arg Gly Ala Ser Ala Asp
1 5 10 15

Ser Thr Gln Ala

20

<210> SEQ ID NO 985
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 985

Tyr Gly Arg Lys Lys Arg Arg Gln Arg Arg Arg Lys Leu Ser Ser Ile
1 5 10 15

Glu Ser Asp Val
20

<210> SEQ ID NO 986
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 986

Tyr Gly Arg Lys Lys Arg Arg Gln Arg Arg Arg Asn Asp Asn Ile Ala
1 5 10 15

Leu Leu Val Gln
20

<210> SEQ ID NO 987
<211> LENGTH: 20
<212> TYPE: PRT
<213> ORGANISM: Artificial Sequence
<220> FEATURE:
<223> OTHER INFORMATION: Synthetic peptide of PL sequence binding Vartul d2

<400> SEQUENCE: 987

Tyr Ser Ala Thr Tyr Ser Glu Leu Glu Asp Pro Gly Glu Met Ser Pro
1 5 10 15

Pro Ile Asp Leu
20

<210> SEQ ID NO 988
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 988
attgagtcag aagtttgaag a 21

<210> SEQ ID NO 989
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 989
attgagccag aagtttgaag a 21

<210> SEQ ID NO 990
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 990
attgagtcaa aagtttgaag a 21

<210> SEQ ID NO 991
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 991
gctaggtcaa aagtttgaag a 21

<210> SEQ ID NO 992
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 992
attaagtcag aagtttgaag a 21

<210> SEQ ID NO 993
<211> LENGTH: 21
<212> TYPE: DNA
<213> ORGANISM: Artificial Sequence
<220> FEATURE:
<223> OTHER INFORMATION: Synthetic oligonucleotide of NS1 C-Term Coding Region

<400> SEQUENCE: 993
attaggtcag aagtttgaag a 21

<210> SEQ ID NO 994
<211> LENGTH: 7
<212> TYPE: PRT
<213> ORGANISM: Artificial Sequence
<220> FEATURE:
<223> OTHER INFORMATION: Synthetic peptide of NS2 Region

<400> SEQUENCE: 994

Gln Leu Ser Gln Lys Phe Glu
1 5

<210> SEQ ID NO 995
<211> LENGTH: 7
<212> TYPE: PRT
<213> ORGANISM: Artificial Sequence
<220> FEATURE:
<223> OTHER INFORMATION: Synthetic peptide of NS2 Region

<400> SEQUENCE: 995

Gln Leu Gly Gln Lys Phe Glu
1 5

<210> SEQ ID NO 996
<211> LENGTH: 4

<212> TYPE: PRT
<213> ORGANISM: Artificial Sequence
<220> FEATURE:
<223> OTHER INFORMATION: Synthetic peptide of Preferred C-terminal sequence

<400> SEQUENCE: 996

Asp Ser Asp Val
1

<210> SEQ ID NO 997
<211> LENGTH: 4
<212> TYPE: PRT
<213> ORGANISM: Artificial Sequence
<220> FEATURE:
<223> OTHER INFORMATION: Synthetic peptide of Preferred C-terminal sequence

<400> SEQUENCE: 997

Asp Ser Glu Val
1

<210> SEQ ID NO 998
<211> LENGTH: 230
<212> TYPE: PRT
<213> ORGANISM: Artificial Sequence
<220> FEATURE:
<223> OTHER INFORMATION: Synthetic peptide of invariant amino acid residues between NS1 proteins from three subtypes of influenza A: H1N1, H3N2 and H5N1
<220> FEATURE:
<221> NAME/KEY: MOD_RES
<222> LOCATION: (1)..(230)
<223> OTHER INFORMATION: Synthetic peptide of Xaa = any naturally occuring amino acid

<400> SEQUENCE: 998

```
Met Xaa Xaa Xaa Xaa Xaa Xaa Xaa Phe Gln Val Xaa Cys Phe Leu Trp
1               5                   10                  15

Xaa Xaa Arg Lys Xaa Xaa Xaa Xaa Xaa Xaa Xaa Xaa Asp Xaa Pro Phe
            20                  25                  30

Xaa Asp Arg Xaa Xaa Arg Xaa Xaa Xaa Xaa Xaa Xaa Gly Arg Xaa Xaa
        35                  40                  45

Thr Xaa Xaa Xaa Xaa Ile Xaa Xaa Xaa Xaa Xaa Xaa Gly Xaa Xaa Ile
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Ser Xaa Xaa Xaa Xaa Xaa Tyr Xaa Xaa Xaa Met Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Asp Gln Xaa Xaa Xaa Xaa Lys Xaa Xaa
        115                 120                 125

Xaa Leu Xaa Xaa Xaa Xaa Xaa Xaa Xaa Xaa Xaa Xaa Xaa Xaa Xaa Xaa
    130                 135                 140

Xaa Leu Xaa Arg Xaa Xaa Xaa Xaa Xaa Xaa Xaa Xaa Xaa Xaa Gly Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Glu Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205
```

```
Xaa Glu Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa
225                 230


<210> SEQ ID NO 999
<211> LENGTH: 230
<212> TYPE: PRT
<213> ORGANISM: Artificial Sequence
<220> FEATURE:
<223> OTHER INFORMATION: Synthetic peptide of amino acid residues
      found in the NS1 protein of H5N1 but not found in H3N2 or H1N1
<220> FEATURE:
<221> NAME/KEY: MOD_RES
<222> LOCATION: (1)..(226)
<223> OTHER INFORMATION: Synthetic peptide of Xaa = any naturally
      occurring amino acid
<220> FEATURE:
<221> NAME/KEY: MOD_RES
<222> LOCATION: (228)..(228)
<223> OTHER INFORMATION: Synthetic peptide of Xaa = S or P

<400> SEQUENCE: 999

Xaa Xaa Xaa Xaa Xaa Xaa Xaa Xaa Xaa Xaa Xaa Xaa Xaa Xaa Xaa Xaa
1               5                   10                  15

Xaa Val Xaa Xaa Arg Phe Xaa Asp Xaa Glu Xaa Gly Xaa Ala Xaa Xaa
            20                  25                  30

Xaa Xaa Xaa Xaa Xaa Xaa Xaa Gln Xaa Xaa Xaa Xaa Xaa Xaa Xaa Xaa
        35                  40                  45

Xaa Xaa Gly Leu Asp Xaa Xaa Xaa Xaa Xaa Xaa Xaa Xaa Xaa Xaa Xaa
    50                  55                  60

Xaa Glu Xaa Xaa Xaa Glu Xaa Xaa Xaa Asp Xaa Xaa Xaa Xaa Xaa Xaa
65                  70                  75                  80

Ile Ala Xaa Val Xaa Xaa Xaa Xaa Xaa Leu Xaa Xaa Xaa Xaa Leu Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Ser Xaa Xaa Xaa Xaa Met Xaa Xaa Xaa Ile Met Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Arg Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Glu Asn Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Arg
    210                 215                 220

Xaa Xaa Glu Xaa Glu Val
225                 230


<210> SEQ ID NO 1000
<211> LENGTH: 234
<212> TYPE: PRT
<213> ORGANISM: Artificial Sequence
<220> FEATURE:
<223> OTHER INFORMATION: Synthetic peptide of consensus sequence of
      residues of the NS1 protein from different strains of influenza
```

A

<400> SEQUENCE: 1000

Met Asp Ser Asn Thr Val Leu Ser Phe Gln Val Asp Cys Phe Leu Trp
1 5 10 15

His Val Arg Lys Arg Phe Ala Asp Gln Glu Leu Gly Asp Ala Pro Phe
20 25 30

Leu Asp Arg Leu Arg Arg Asp Gln Lys Ser Leu Arg Gly Arg Gly Asn
35 40 45

Thr Leu Gly Leu Asp Ile Glu Thr Ala Thr Arg Ala Gly Lys Gln Ile
50 55 60

Val Glu Arg Ile Leu Glu Glu Glu Ser Asp Glu Ala Leu Lys Met Thr
65 70 75 80

Ile Ala Ser Val Pro Ala Ser Arg Tyr Leu Thr Asp Met Thr Leu Glu
85 90 95

Glu Met Ser Arg Asp Trp Phe Met Leu Met Pro Lys Gln Lys Val Ala
100 105 110

Gly Ser Leu Cys Ile Lys Met Asp Gln Ala Ile Met Asp Lys Thr Ile
115 120 125

Ile Leu Lys Ala Asn Phe Ser Val Ile Phe Asp Arg Leu Glu Thr Leu
130 135 140

Ile Leu Leu Arg Ala Phe Thr Glu Glu Gly Ala Ile Arg Val Gly Glu
145 150 155 160

Ile Ser Pro Leu Pro Ser Leu Pro Gly His Thr Gly Glu Asp Val Lys
165 170 175

Asn Ala Ile Gly Val Leu Ile Gly Gly Leu Glu Trp Asn Asp Asn Thr
180 185 190

Val Arg Val Ser Glu Asn Thr Ile Gln Arg Phe Ala Trp Arg Gly Ser
195 200 205

Asp Glu Asp Gly Arg Leu Pro Phe Pro Pro Asn Gln Lys Arg Lys Met
210 215 220

Ala Arg Thr Ile Glu Ser Glu Val Glu Lys
225 230

<210> SEQ ID NO 1001
<211> LENGTH: 281
<212> TYPE: PRT
<213> ORGANISM: Artificial Sequence
<220> FEATURE:
<223> OTHER INFORMATION: Synthetic peptide of consensus sequence of residues of the NS1 protein form different strains of influenza B

<400> SEQUENCE: 1001

Met Ala Asp Asn Met Thr Thr Thr Gln Ile Glu Val Gly Pro Gly Ala
1 5 10 15

Thr Asn Ala Thr Ile Asn Phe Glu Ala Gly Ile Leu Glu Cys Tyr Glu
20 25 30

Arg Leu Ser Trp Gln Arg Ala Leu Asp Tyr Pro Gly Gln Asp Arg Leu
35 40 45

Asn Arg Leu Lys Arg Lys Leu Glu Ser Arg Ile Lys Thr His Asn Lys
50 55 60

Ser Glu Pro Glu Ser Lys Arg Met Ser Leu Glu Glu Arg Lys Ala Ile
65 70 75 80

Gly Val Lys Met Met Lys Val Leu Leu Phe Met Asp Pro Ser Ala Gly
85 90 95

Ile Glu Gly Phe Glu Pro Tyr Cys Met Lys Asn Pro Ser Asn Ser Asn
100 105 110

Cys Pro Lys Cys Asn Trp Ala Asp Tyr Pro Leu Thr Pro Gly Lys Cys
115 120 125

Leu Asp Asp Ile Glu Glu Glu Pro Glu Asp Val Asp Asp Pro Thr Glu
130 135 140

Ile Val Leu Arg Asp Met Asn Asn Lys Asp Ala Arg Gln Lys Ile Lys
145 150 155 160

Glu Glu Val Asn Thr Gln Lys Glu Gly Lys Phe Arg Leu Thr Ile Lys
165 170 175

Arg Asp Ile Arg Asn Val Leu Ser Leu Arg Val Leu Val Asn Gly Thr
180 185 190

Phe Leu Lys His Pro Asn Gly Tyr Lys Ser Leu Leu Thr Leu His Arg
195 200 205

Leu Asn Ala Tyr Asp Gln Ser Gly Arg Leu Val Ala Lys Leu Val Ala
210 215 220

Thr Asp Asp Leu Thr Val Glu Asp Glu Glu Asp Gly His Arg Ile Leu
225 230 235 240

Asn Ser Leu Phe Glu Arg Phe Asn Glu Gly His Pro Lys Pro Ile Arg
245 250 255

Ala Ala Glu Thr Ala Met Gly Val Leu Ser Gln Phe Gly Gln Glu His
260 265 270

Arg Leu Ser Pro Glu Glu Gly Asp Asn
275 280

<210> SEQ ID NO 1002
<211> LENGTH: 601
<212> TYPE: PRT
<213> ORGANISM: Artificial Sequence
<220> FEATURE:
<223> OTHER INFORMATION: Synthetic peptide of MBP FUSION PEPTIDE COMPRISING 3 COPIES OF PSD95 DOMAIN 2

<400> SEQUENCE: 1002

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Ser Gly Gly Gly Gly Gly Leu Val Pro Arg Gly
225                 230                 235                 240

Ser Pro Gly Ser Gly Thr Glu Pro Ala Glu Lys Val Met Glu Ile Lys
                245                 250                 255

Leu Ile Lys Gly Pro Lys Gly Leu Gly Phe Ser Ile Ala Gly Gly Val
            260                 265                 270

Gly Asn Gln His Ile Pro Gly Asp Asn Ser Ile Tyr Val Thr Lys Ile
        275                 280                 285

Ile Glu Gly Gly Ala Ala His Lys Asp Gly Arg Leu Gln Ile Gly Asp
    290                 295                 300

Lys Ile Leu Ala Val Asn Ser Val Gly Leu Glu Asp Val Met His Glu
305                 310                 315                 320

Asp Ala Val Ala Ala Leu Lys Asn Thr Tyr Asp Val Val Tyr Leu Lys
                325                 330                 335

Val Ala Lys Arg Lys Pro Pro Ala Glu Lys Val Met Glu Ile Lys Leu
            340                 345                 350

Ile Lys Gly Pro Lys Gly Leu Gly Phe Ser Ile Ala Gly Gly Val Gly
        355                 360                 365

Asn Gln His Ile Pro Gly Asp Asn Ser Ile Tyr Val Thr Lys Ile Ile
    370                 375                 380

Glu Gly Gly Ala Ala His Lys Asp Gly Arg Leu Gln Ile Gly Asp Lys
385                 390                 395                 400

Ile Leu Ala Val Asn Ser Val Gly Leu Glu Asp Val Met His Glu Asp
                405                 410                 415

Ala Val Ala Ala Leu Lys Asn Thr Tyr Asp Val Val Tyr Leu Lys Val
            420                 425                 430

Ala Lys Pro Ser Asn Ala Tyr Leu Ser Asp Ser Tyr Ala Pro Pro Asp
        435                 440                 445

Ile Thr Thr Ser Tyr Ser Gln His Leu Asp Asn Glu Ile Ser His Ser
    450                 455                 460

Ser Tyr Leu Gly Thr Asp Tyr Pro Thr Ala Met Thr Pro Thr Ser Pro
465                 470                 475                 480

Arg Arg Tyr Ser Pro Val Ala Lys Asp Leu Leu Gly Glu Glu Asp Ile
                485                 490                 495

Pro Pro Ala Glu Lys Val Met Glu Ile Lys Leu Ile Lys Gly Pro Lys
            500                 505                 510

Gly Leu Gly Phe Ser Ile Ala Gly Gly Val Gly Asn Gln His Ile Pro
        515                 520                 525

Gly Asp Asn Ser Ile Tyr Val Thr Lys Ile Ile Glu Gly Gly Ala Ala
    530                 535                 540

His Lys Asp Gly Arg Leu Gln Ile Gly Asp Lys Ile Leu Ala Val Asn
545                 550                 555                 560

Ser Val Gly Leu Glu Asp Val Met His Glu Asp Ala Val Ala Ala Leu
                565                 570                 575

Lys Asn Thr Tyr Asp Val Val Tyr Leu Lys Val Ala Lys Pro Ser Asn
            580                 585                 590

Ala Tyr Leu Ser Asp Ser Tyr Ala Pro
        595                 600
```

<210> SEQ ID NO 1003
<211> LENGTH: 866
<212> TYPE: DNA
<213> ORGANISM: Influenza A virus

<400> SEQUENCE: 1003

```
caaaagcagg gtgacaaaga cataatggat tccaacactg tgtcaagttt ccaggtagat     60

tgctttcttt ggcatatccg gaaacaagtt gtagaccaag aactgagtga tgccccattc    120

cttgatcggc ttcgccgaga tcagaggtcc ctaagaggaa gaggcaatac tctcggtcta    180

gacatcaaag cagccaccca tgttggaaag caaattgtag aaaagattct gaaagaagaa    240

tctgatgagg cacttaaaat gaccatggtc tccacacctg cttcgcgata cataactgac    300

atgactattg aggaattgtc aagaaactgg ttcatgctga tgcccaagca gaaagtagaa    360

ggacctcttt gcatcagaat ggaccaggca atcatggaga aaaacatcat gttgaaagcg    420

aatttcagtg tgatttttga ccgactagag accatagtat tactaagggc tttcaccgaa    480

gagggagcaa ttgttggcga aatctcacca ttgccttctt ttccaggaca tactattgag    540

gatgtcaaaa atgcaattgg ggtcctcatc ggaggacttg aatggaatga taacacagtt    600

cgagtctcta aaaatctaca gagattcgct tggagaagca gtaatgagaa tgggggacct    660

ccacttactc caaaacagaa acggaaaatg gcgagaacag ctaggtcaaa agtttgaaga    720

gataagatgg ctgattgaag aagtgagaca cagactaaaa acaactgaaa atagctttga    780

acaaataaca ttcatgcaag cattacaact gctgtttgaa gtggaacagg agataagaac    840

tttctcattt cagcttattt aatgat                                         866
```

<210> SEQ ID NO 1004
<211> LENGTH: 230
<212> TYPE: PRT
<213> ORGANISM: Influenza A virus

<400> SEQUENCE: 1004

```
Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
        35                  40                  45

Thr Leu Gly Leu Asp Ile Lys Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Val Ser Thr Pro Ala Ser Arg Tyr Ile Thr Asp Met Thr Ile Glu
                85                  90                  95

Glu Leu Ser Arg Asn Trp Phe Met Leu Met Pro Lys Gln Lys Val Glu
            100                 105                 110

Gly Pro Leu Cys Ile Arg Met Asp Gln Ala Ile Met Glu Lys Asn Ile
        115                 120                 125

Met Leu Lys Ala Asn Phe Ser Val Ile Phe Asp Arg Leu Glu Thr Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190
```

Arg Val Ser Lys Asn Leu Gln Arg Phe Ala Trp Arg Ser Ser Asn Glu
195 200 205

Asn Gly Gly Pro Pro Leu Thr Pro Lys Gln Lys Arg Lys Met Ala Arg
210 215 220

Thr Ala Arg Ser Lys Val
225 230

<210> SEQ ID NO 1005
<211> LENGTH: 855
<212> TYPE: DNA
<213> ORGANISM: Influenza A virus

<400> SEQUENCE: 1005
agcaaaagca gggtggcaaa gacataatgg attcccacac tgtgtcaagc tttcaggtag 60
attgcttcct ttggcatgtc cgcaaacaag ttgcagacca aggtctaggc gatgccccct 120
tccttgatcg gcttcgccga gatcagaagt ctctaaaggg aagaggcagc actctcggtc 180
tgaacatcga aacagccact tgtgttggaa agcaaatagt agagaggatt ctgaaagaag 240
aatccgatga ggcattcaaa atgaccatgg cctccgcact tgcttcgcgg tacctaactg 300
acatgactat tgaagaaatg tcaagggact ggttcatgct catgcccaag cagaaagtgg 360
ctggccctct ttgtgtcaaa atggaccagg cgataatgga taagaacatc atactgaaag 420
cgaatttcag tgtgattttt gatcggttgg agaatctgac attactaagg gctttcaccg 480
aagagggagc aattgttggc gaaatttcac cattgccttc tcttccagga catactaatg 540
aggatgtcaa aaatgcaatt ggggtcctca tcgggggact tgaatggaat gataacacag 600
ttcgagtctc tgaaactcta cagagattcg cttggagaag cagtaatgag actgggggac 660
ctccattcac tccaacacag aaacggaaaa tggcgggaac aattaggtca gaagtttgaa 720
gaaataagat ggctgattga agaagtgagg cataaattga agacgacaga gaatagtttt 780
gagcaaataa catttatgca agcattacag ctattgtttg aagtggaaca agagattaga 840
acgttttcat ttcag 855

<210> SEQ ID NO 1006
<211> LENGTH: 230
<212> TYPE: PRT
<213> ORGANISM: Influenza A virus

<400> SEQUENCE: 1006

Met Asp Ser His Thr Val Ser Ser Phe Gln Val Asp Cys Phe Leu Trp
1 5 10 15

His Val Arg Lys Gln Val Ala Asp Gln Gly Leu Gly Asp Ala Pro Phe
20 25 30

Leu Asp Arg Leu Arg Arg Asp Gln Lys Ser Leu Lys Gly Arg Gly Ser
35 40 45

Thr Leu Gly Leu Asn Ile Glu Thr Ala Thr Cys Val Gly Lys Gln Ile
50 55 60

Val Glu Arg Ile Leu Lys Glu Glu Ser Asp Glu Ala Phe Lys Met Thr
65 70 75 80

Met Ala Ser Ala Leu Ala Ser Arg Tyr Leu Thr Asp Met Thr Ile Glu
85 90 95

Glu Met Ser Arg Asp Trp Phe Met Leu Met Pro Lys Gln Lys Val Ala
100 105 110

Gly Pro Leu Cys Val Lys Met Asp Gln Ala Ile Met Asp Lys Asn Ile
115 120 125

Ile Leu Lys Ala Asn Phe Ser Val Ile Phe Asp Arg Leu Glu Asn Leu
    130                 135                 140

Thr Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Thr Gly Gly Pro Pro Phe Thr Pro Thr Gln Lys Arg Lys Met Ala Gly
    210                 215                 220

Thr Ile Arg Ser Glu Val
225                 230

<210> SEQ ID NO 1007
<211> LENGTH: 890
<212> TYPE: DNA
<213> ORGANISM: Influenza A virus

<400> SEQUENCE: 1007
agcaaaagca gggtgacaaa aacataatgg attccaacac tgtatcaagc tttcaggtag 60
actgctttct ttggcatgtc cgcaaacgat ttgcagacca agaactgggt gatgccccat 120
tccttgaccg gcttcgccga gatcagaaat ctctaagagg aagaggcagc actcttggtc 180
tggacatcga aacagccact cgtgctggaa aacagatagt ggagcggatt ctgaaggaag 240
aatccgatga ggcactcaaa atgactattg cctctgtacc tgcttcacgc tacctaactg 300
acatgactct tgaagagatg tcaagagact ggttcatgct catgccaaag caaaaagtag 360
caggctccct ctgtatcaga atggaccagg cgatcatgga taagaacatc atgctgaaag 420
cgaacttcag tgtgatcttc gatcggctgg agacactaat actgctcagg gctttcaccg 480
aagaaggagc aattgtcggc gaaatttcac cattgccttc tcttccagga catactgatg 540
aggatgtcaa aaatgcaatt ggggtcctca tcggaggact tgaatggaat gataacacag 600
ttcgagtctc tgaaactcta cagagattcg cttggagaag cagtaatgag gatgggagac 660
ctccactccc tccaaagcag aaacggaaaa tggcgagaac aattgagtca gaagtttgaa 720
gaaataaggt ggctgattga agaagtgcga catagactaa agattacaga gaatagtttt 780
gagcaaataa catttatgca agccttacaa ctactgcttg aagtagagca agagataaga 840
actttctcgt ttcagcttat ttaatgataa aaaacaccct tgtttctact 890

<210> SEQ ID NO 1008
<211> LENGTH: 230
<212> TYPE: PRT
<213> ORGANISM: Influenza A virus

<400> SEQUENCE: 1008

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr

```
65                  70                  75                  80

Ile Ala Ser Val Pro Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Leu Pro Pro Lys Gln Lys Arg Lys Met Ala Arg
    210                 215                 220

Thr Ile Glu Ser Glu Val
225                 230
```

<210> SEQ ID NO 1009
<211> LENGTH: 1068
<212> TYPE: DNA
<213> ORGANISM: Influenza B virus

<400> SEQUENCE: 1009

```
gcaaacggaa aaaaatggcg gacaacatga ccacaacaca aattgaggtg ggtccgggag      60

caaccaatgc caccataaac tttgaagcag gaattttgga gtgctatgaa aggctttcat     120

ggcaaagagc ccttgactac cctggtcaag accgcctaaa cagactaaag agaaaattag     180

aatcaagaat aaagactcac aacaaaagtg agcctgaaag taaaaggatg tctcttgaag     240

agagaaaagc aattggggta aaaatgatga aagtgctcct atttatgaac ccatctgctg     300

gaattgaagg gtttgagcca tactgtatga aaaatccctc caatagcaac tgtccaaact     360

gcaattgggc cgattaccct ccaacaccag gaaagtgcct tgatgacata gaagaagaac     420

cggagaatgt tgatgaccca actgaaatag tattaaggga catgaacaac aaagatgcaa     480

ggcaaaagat aaaagaggaa gtaaacactc agaaagaagg gaagttccgt ttgacaataa     540

aaagggatat acgtaatgtg ttgtccttga gagtgctagt aaacggaaca ttcctcaagc     600

accctaatgg atacaagacc ttatcaactc tgcatagatt gaatgcatat gaccagagtg     660

gaaggcttgt tgctaaactt gttgctactg atgatcttac agtggaggat gaagaagatg     720

gccatcggat cctcaactca ctcttcgagc gttttaatga aggacattca aagccaattc     780

gagcagctga aactgcggtg ggagtcttat cccaatttgg tcaagagcac cgattatcac     840

cagaggaggg agacaattag actggttacg gaagaacttt atcttttaag taaaagaatt     900

gatgataaca tattgttcca caaaacagta atagctaaca gctccataat agctgacatg     960

attgtatcat tatcattatt ggaaacattg tatgaaatga aggatgtggt tgaagtgtac    1020

agcaggcagt gcttgtgaat ttaaaataaa aatcctcttg ttactact                1068
```

<210> SEQ ID NO 1010
<211> LENGTH: 281
<212> TYPE: PRT

<213> ORGANISM: Influenza B virus

<400> SEQUENCE: 1010

Met Ala Asp Asn Met Thr Thr Thr Gln Ile Glu Val Gly Pro Gly Ala
1 5 10 15

Thr Asn Ala Thr Ile Asn Phe Glu Ala Gly Ile Leu Glu Cys Tyr Glu
20 25 30

Arg Leu Ser Trp Gln Arg Ala Leu Asp Tyr Pro Gly Gln Asp Arg Leu
35 40 45

Asn Arg Leu Lys Arg Lys Leu Glu Ser Arg Ile Lys Thr His Asn Lys
50 55 60

Ser Glu Pro Glu Ser Lys Arg Met Ser Leu Glu Glu Arg Lys Ala Ile
65 70 75 80

Gly Val Lys Met Met Lys Val Leu Leu Phe Met Asn Pro Ser Ala Gly
85 90 95

Ile Glu Gly Phe Glu Pro Tyr Cys Met Lys Asn Pro Ser Asn Ser Asn
100 105 110

Cys Pro Asn Cys Asn Trp Ala Asp Tyr Pro Pro Thr Pro Gly Lys Cys
115 120 125

Leu Asp Asp Ile Glu Glu Glu Pro Glu Asn Val Asp Asp Pro Thr Glu
130 135 140

Ile Val Leu Arg Asp Met Asn Asn Lys Asp Ala Arg Gln Lys Ile Lys
145 150 155 160

Glu Glu Val Asn Thr Gln Lys Glu Gly Lys Phe Arg Leu Thr Ile Lys
165 170 175

Arg Asp Ile Arg Asn Val Leu Ser Leu Arg Val Leu Val Asn Gly Thr
180 185 190

Phe Leu Lys His Pro Asn Gly Tyr Lys Thr Leu Ser Thr Leu His Arg
195 200 205

Leu Asn Ala Tyr Asp Gln Ser Gly Arg Leu Val Ala Lys Leu Val Ala
210 215 220

Thr Asp Asp Leu Thr Val Glu Asp Glu Glu Asp Gly His Arg Ile Leu
225 230 235 240

Asn Ser Leu Phe Glu Arg Phe Asn Glu Gly His Ser Lys Pro Ile Arg
245 250 255

Ala Ala Glu Thr Ala Val Gly Val Leu Ser Gln Phe Gly Gln Glu His
260 265 270

Arg Leu Ser Pro Glu Glu Gly Asp Asn
275 280

<210> SEQ ID NO 1011
<211> LENGTH: 1024
<212> TYPE: DNA
<213> ORGANISM: Influenza B virus

<400> SEQUENCE: 1011
atggcggaca acatgaccac aacacaaatc gaggtgggtc cgggagcaac caatgccacc 60
ataaactttg aagcaggaat tctggagtgc tatgaaagac tttcatggca aagagccctt 120
gactaccctg gtcaagaccg cctaaacaga ctaaagagaa agttagagtc aagaataaag 180
actcacaaca aaagtgagcc tgaaagtaaa aggatgtctc ttgaagagag aaaagcaatt 240
ggagtaaaaa tgatgaaagt gctcctattt atggatccat ctgctggaat tgaagggttt 300
gagccatact gtatgaaaag ctcttcaaat agcaactgtc cgaaatacaa ttggatcaat 360
taccctctaa caccaggaag gtgccttgat gacatagaag aagaaccaga ggatgttgat 420

```
ggcccaactg aaatagtatt aagggacatg aacaacaaag atgcaagaca aaagataaag    480

gaggaagtaa acactcagaa agaagggaag ttccgtttga caataaaaag ggatatacgt    540

aatgtgttgt ccttgagagt gttagtaaac ggaacattcc tcaaacatcc caatggatat    600

aagtccttat taactctgca tagattgaat acatatgacc agagtggaag gcttgttgct    660

aaacttgttg ctactgatga tcttacagtg gaggatgaag aagatggcca tcggatcctc    720

aactcactct tcgagcgtct taatgaagga catccaaagc caattcgagc agctgaaact    780

gcgatgggag tcttatccca atttggtcaa gagcaccgat tatcaccaga agagggagac    840

aattagactg gtcacggaag aactttatct tttaagtaaa agaattgatg ataacatatt    900

gtttcacaaa acagtaatag ctaacagctc cataatagct gacatgattg tatcattatc    960

attattagaa acactgtatg aaataaagga tgtggttgaa gtgtacagca ggcagtgctt   1020

gtga                                                                1024


<210> SEQ ID NO 1012
<211> LENGTH: 281
<212> TYPE: PRT
<213> ORGANISM: Influenza B virus

<400> SEQUENCE: 1012

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asp Pro Ser Ala Gly
                85                  90                  95

Ile Glu Gly Phe Glu Pro Tyr Cys Met Lys Ser Ser Ser Asn Ser Asn
            100                 105                 110

Cys Pro Lys Tyr Asn Trp Ile Asn Tyr Pro Leu Thr Pro Gly Arg Cys
        115                 120                 125

Leu Asp Asp Ile Glu Glu Glu Pro Glu Asp Val Asp Gly Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Leu Thr Leu His Arg
        195                 200                 205

Leu Asn Thr Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Pro Lys Pro Ile Arg
                245                 250                 255

Ala Ala Glu Thr Ala Met Gly Val Leu Ser Gln Phe Gly Gln Glu His
            260                 265                 270
```

```
Arg Leu Ser Pro Glu Glu Gly Asp Asn
        275                 280


<210> SEQ ID NO 1013
<211> LENGTH: 1565
<212> TYPE: DNA
<213> ORGANISM: Influenza A virus

<400> SEQUENCE: 1013

agcaaaagca gggtagataa tcactcactg agtgacatca aaatcatggc gtcccaaggc     60

accaaacggt cttacgaaca gatggagact gatggagaac gccagaatgc cactgaaatc    120

agagcatccg tcggaaaaat gattggtgga attggacgat tctacatcca aatgtgcaca    180

gaacttaaac tcagtgatta tgagggacgg ttgatccaaa acagcttaac aatagagaga    240

atggtgctct ctgcttttga cgaaaggaga aataaatacc tggaagaaca tcccagtgcg    300

gggaaggatc ctaagaaaac tggaggacct atatacagaa gagtaaacgg aaagtggatg    360

agagaactca tcctttatga caaagaagaa ataaggcgaa tctggcgcca agctaataat    420

ggtgacgatg caacggctgg tctgactcac atgatgatct ggcattccaa tttgaatgat    480

gcaacttatc agaggacaag ggctcttgtt cgcaccggaa tggatcccag gatgtgctct    540

ctgatgcaag gttcaactct ccctaggagg tctggagccg caggtgctgc agtcaaagga    600

gttggaacaa tggtgatgga attggtcagg atgatcaaac gtgggatcaa tgatcggaac    660

ttctggaggg gtgagaatgg acgaaaaaca agaattgctt atgaaagaat gtgcaacatt    720

ctcaaaggga aatttcaaac tgctgcacaa aaagcaatga tggatcaagt gagagagagc    780

cgggacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagagaggga tactctctag tcggaataga ccctttcaga    960

ctgcttcaaa acagccaagt gtacagccta atcagaccaa atgagaatcc agcacacaag   1020

agtcaactgg tgtggatggc atgccattct gccgcatttg aagatctaag agtattgagc   1080

ttcatcaaag ggacgaaggt ggtcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccgtt   1320

atggcagcat tcactgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                                1565


<210> SEQ ID NO 1014
<211> LENGTH: 498
<212> TYPE: PRT
<213> ORGANISM: Influenza A virus

<400> SEQUENCE: 1014

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30
```

-continued

```
Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460
```

```
Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 1015
<211> LENGTH: 1566
<212> TYPE: DNA
<213> ORGANISM: Influenza A virus

<400> SEQUENCE: 1015

agcaaaagca gggttaataa tcactcaccg agtgacatca aaatcatggc gtcccaaggc     60

accaaacggt cttatgaaca gatggaaact gatggggatc gccagaatgc aactgagatt    120

agggcatccg tcgggaagat gattgatgga attgggagat tctacatcca aatgtgcact    180

gaacttaaac tcagtgatca tgaagggcgg ttgatccaga acagcttgac aatagagaaa    240

atggtgctct ctgcttttga tgaaagaagg aataaatacc tggaagaaca ccccagcgcg    300

gggaaagatc ccaagaaaac tgggggggccc atatacagga gagtagatgg aaaatggatg    360

agggaactcg tcctttatga caaagaagag ataaggcgaa tctggcgcca agccaacaat    420

ggtgaggatg cgacagctgg tctaactcac ataatgatct ggcattccaa tttgaatgat    480

gcaacatacc agaggacaag agctcttgtt cgaactggaa tggatcccag aatgtgctct    540

ctgatgcagg gctcgactct ccctagaagg tccggagctg caggtgctgc agtcaaagga    600

atcgggacaa tggtgatgga actgatcaga atggtcaaac gggggatcaa cgatcgaaat    660

ttctggagag gtgagaatgg gcggaaaaca agaagtgctt atgagagaat gtgcaacatt    720

cttaaaggaa aatttcaaac agctgcacaa agagcaatgg tggatcaagt gagagaaagt    780

cggaacccag gaaatgctga gatcgaagat ctcatatttt tggcaagatc tgcattgata    840

ttgagagggt cagttgctca caaatcttgc ctacctgcct gtgcgtatgg acctgcagta    900

tccagtgggt acgacttcga aaaagaggga tattccttgg tgggaataga ccctttcaaa    960

ctacttcaaa atagccaaat atacagccta atcagaccta acgagaatcc agcacacaag   1020

agtcagctgg tgtggatggc atgccattct gctgcatttg aagatttaag attgttaagc   1080

ttcatcagag ggacaaaagt atctccgcgg gggaaactgt caactagagg agtacaaatt   1140

gcttcaaatg agaacatgga taatatggga tcgagcactc ttgaactgag aagcgggtac   1200

tgggccataa ggaccaggag tggaggaaac actaatcaac agagggcctc cgcaggccaa   1260

accagtgtgc aacctacgtt ttctgtacaa agaaacctcc catttgaaaa gtcaaccatc   1320

atggcagcat tcactggaaa tacggaggga aggacttcag acatgagggc agaaatcata   1380

agaatgatgg aaggtgcaaa accagaagaa gtgtcattcc gggggagggg agttttcgag   1440

ctctcagacg agaaggcaac gaacccgatc gtgccctctt ttgatatgag taatgaagga   1500

tcttatttct tcggagacaa tgcagaagag tacgacaatt aaggaaaaaa taccottgtt   1560

tctact                                                              1566


<210> SEQ ID NO 1016
<211> LENGTH: 498
<212> TYPE: PRT
<213> ORGANISM: Influenza A virus

<400> SEQUENCE: 1016

Met Ala Ser Gln Gly Thr Lys Arg Ser Tyr Glu Gln Met Glu Thr Asp
```

-continued

```
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp His Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430
```

Thr Glu Gly Arg Thr Ser Asp Met Arg Ala Glu Ile Ile Arg Met Met
435 440 445

Glu Gly Ala Lys Pro Glu Glu Val Ser Phe Arg Gly Arg Gly Val Phe
450 455 460

Glu Leu Ser Asp Glu Lys Ala Thr Asn Pro Ile Val Pro Ser Phe Asp
465 470 475 480

Met Ser Asn Glu Gly Ser Tyr Phe Phe Gly Asp Asn Ala Glu Glu Tyr
485 490 495

Asp Asn

<210> SEQ ID NO 1017
<211> LENGTH: 1565
<212> TYPE: DNA
<213> ORGANISM: Influenza A virus

<400> SEQUENCE: 1017
agcaaaagca gggtagataa tcactcaccg agtgacatca acatcatggc gtctcaaggc 60
accaaacgat cttatgaaca gatggaaact ggtggagaac gccagaatgc tactgagatt 120
agggcatctg ttggaagaat ggttagtggc attgggaggt tctacataca gatgtgcaca 180
gaactcaaac tcagtgacta tgaagggagg ctgatccaga acagcataac aatagagaga 240
atggtgctct ctgcatttga tgaaagaagg aacagatacc tggaagaaca ccccagtgcg 300
gggaaggacc cgaagaaaac tggaggtcca atttatcgga ggagagacgg gaaatgggtg 360
agagagctga ttctgtatga caaagaggag atcaggagga tttggcgtca agcgaacaat 420
ggagaggacg cgactgctgg tcttacccac ctgatgatat ggcattccaa cctaaatgat 480
gccacatatc agagaacgag agctctcgtg cgtactggaa tggatcccag gatgtgctct 540
ctgatgcaag gatcaactct cccgaggaga tctggagctg ccggtgcagc agtaaagggg 600
gtagggacaa tggtgatgga gctgattcgg atgataaagc gagggatcaa cgaccggaat 660
ttctggagag gtgaaaatgg aagaagaaca aggattgcat atgagagaat gtgtaacatc 720
ctcaaaggga aattccaaac agcagcacaa agagcaatga tggatcaagt gcgagagagc 780
agaaatcctg ggaatgctga aattgaagat ctcatttttc tggcacggtc tgcactcatc 840
ctgagaggat cagtggccca taaatcctgc ttgcctgctt gtgtgtacgg acttgcagtg 900
gccagtggat atgactttga gagagaaggg tactctctgg ttggaataga tcctttccgt 960
ctgcttcaaa acagccaggt ctttagtctc attagaccaa atgagaatcc agcacataag 1020
agtcaattag tgtggatggc atgccactct gcagcatttg aggaccttag agtctcaagt 1080
ttcatcagag ggacaagagt ggtcccaaga ggacagctat ccaccagagg ggttcaaatt 1140
gcctcaaatg agaacatgga agcaatggac tccaacactc ttgaactgag aagtagatat 1200
tgggctataa gaaccagaag cggaggaaac accaaccagc ggagggcatc tgcaggacag 1260
atcagcgttc agcccacttt ctcagtacag agaaatcttc ccttcgaaag agcaaccatt 1320
atggcagcat ttacagggaa tactgagggc agaacgtctg acatgaggac tgaaatcata 1380
ggaatgatgg aaagtgccag accagaagat gtgtcattcc aggggcgggg agtcttcgag 1440
ctctcggacg aaaaggcaac gaacccgatc gtgccttcct ttgacatgaa taatgaagga 1500
tcttatttct tcggagacaa tgcagaggag tatgacaatt aaagaaaaat acccttgttt 1560
ctact 1565

<210> SEQ ID NO 1018
<211> LENGTH: 498
<212> TYPE: PRT

<213> ORGANISM: Influenza A virus

<400> SEQUENCE: 1018

Met Ala Ser Gln Gly Thr Lys Arg Ser Tyr Glu Gln Met Glu Thr Gly
1 5 10 15

Gly Glu Arg Gln Asn Ala Thr Glu Ile Arg Ala Ser Val Gly Arg Met
20 25 30

Val Ser Gly Ile Gly Arg Phe Tyr Ile Gln Met Cys Thr Glu Leu Lys
35 40 45

Leu Ser Asp Tyr Glu Gly Arg Leu Ile Gln Asn Ser Ile Thr Ile Glu
50 55 60

Arg Met Val Leu Ser Ala Phe Asp Glu Arg Arg Asn Arg Tyr Leu Glu
65 70 75 80

Glu His Pro Ser Ala Gly Lys Asp Pro Lys Lys Thr Gly Gly Pro Ile
85 90 95

Tyr Arg Arg Arg Asp Gly Lys Trp Val Arg Glu Leu Ile Leu Tyr Asp
100 105 110

Lys Glu Glu Ile Arg Arg Ile Trp Arg Gln Ala Asn Asn Gly Glu Asp
115 120 125

Ala Thr Ala Gly Leu Thr His Leu Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Met Val Met Glu
180 185 190

Leu Ile Arg Met Ile Lys Arg Gly Ile Asn Asp Arg Asn Phe Trp Arg
195 200 205

Gly Glu Asn Gly Arg Arg Thr Arg Ile Ala Tyr Glu Arg Met Cys Asn
210 215 220

Ile Leu Lys Gly Lys Phe Gln Thr Ala Ala Gln Arg Ala Met Met Asp
225 230 235 240

Gln Val Arg Glu Ser Arg Asn Pro Gly Asn Ala Glu Ile Glu Asp Leu
245 250 255

Ile Phe Leu Ala Arg Ser Ala Leu Ile Leu Arg Gly Ser Val Ala His
260 265 270

Lys Ser Cys Leu Pro Ala Cys Val Tyr Gly Leu Ala Val Ala Ser Gly
275 280 285

Tyr Asp Phe Glu Arg Glu Gly Tyr Ser Leu Val Gly Ile Asp Pro Phe
290 295 300

Arg Leu Leu Gln Asn Ser Gln Val Phe Ser Leu Ile Arg Pro Asn Glu
305 310 315 320

Asn Pro Ala His Lys Ser Gln Leu Val Trp Met Ala Cys His Ser Ala
325 330 335

Ala Phe Glu Asp Leu Arg Val Ser Ser Phe Ile Arg Gly Thr Arg Val
340 345 350

Val Pro Arg Gly Gln Leu Ser Thr Arg Gly Val Gln Ile Ala Ser Asn
355 360 365

Glu Asn Met Glu Ala Met Asp Ser Asn Thr Leu Glu Leu Arg Ser Arg
370 375 380

Tyr Trp Ala Ile Arg Thr Arg Ser Gly Gly Asn Thr Asn Gln Arg Arg
385 390 395 400

Ala Ser Ala Gly Gln Ile Ser Val Gln Pro Thr Phe Ser Val Gln Arg

```
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Gly Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn


<210> SEQ ID NO 1019
<211> LENGTH: 1515
<212> TYPE: DNA
<213> ORGANISM: Influenza A virus

<400> SEQUENCE: 1019

tgagtgacat caacatcatg gcgtctcaag gcaccaaacg atcttatgaa cagatggaaa     60

ctggtggaga acgccagaat gccactgaga tcagggcatc cgttggaaga atggttggtg    120

gaattgggag gttttacata cagatgtgca ctgaactcaa actcagcgac caggaaggaa    180

ggttgatcca gaacagtata acagtagaga gaatggttct ctctgcattt gatgaaagga    240

ggaacaggta cctagaggaa catcccagtg cggggaagga cccgaagaag accggaggtc    300

caatctaccg aagaagaaac gggaaatggg tgagagagct gattctgtat gacaaagagg    360

agataaggag aatttggcgc caagcgaaca atggagaaga cgcaactgct ggtctcactc    420

acatgatgat ttggcattcc aacctaaatg atgccacata ccagagaaca agagccctcg    480

tgcggactgg aatggacccc agaatgtgct ctctgatgca aggatcaacc ctcccgagga    540

gatctggagc tgctggtgca gcaataaagg gagtcgggac gatggtaatg gaactaattc    600

ggatgataaa gcgaggcatt aatgaccgga acttctggag aggcgagaat ggacgaagaa    660

caaggattgc atatgagaga atgtgcaaca tcctcaaagg gaaatttcaa acagcagcac    720

aaaaagcaat gatggatcag gtgcgagaaa gcagaaatcc tgggaatgct gaaattgaag    780

atctcatttt tctggcacgg tctgcactca tcctgagagg atccgtagcc cataagtcct    840

gcttgcctgc ttgtgtgtac ggactcgctg tggccagtgg atatgatttt gagagggaag    900

ggtactctct ggttgggata gatcctttcc gtctgcttca gaacagtcag gtcttcagtc    960

tcattagacc aaaagagaat ccagcacata aaagtcaatt ggtatggatg gcatgccatt   1020

ctgcagcatt tgaggacctg agagtctcaa gtttcattag aggaacaaga gtaatcccaa   1080

gaggacaact atccactaga ggagttcaga ttgcttcaaa tgagaacgtg gaagcaatgg   1140

actccagcac tcttgaactg agaagcagat attgggctat aaggaccagg agtggaggaa   1200

acaccaacca acagagagca tctgcaggac aaatcagtgt acagcccact ttctcagtac   1260

agagaaatct tcccttcgaa agagtgacca ttatggccgc gtttaagggg aataccgagg   1320

gcagaacatc tgacatgagg actgaaatca taagaatgat ggaaagtgcc agaccagaag   1380

atgtgtcttt ccaggggcgg ggagtcttcg agctctcaga cgaaaaggca acgaacccga   1440

tcgtgccttc ctttgacatg agtaatgaag gatcttattt cttcggagac aatgcagagg   1500

aatatgacaa ttgaa                                                    1515
```

<210> SEQ ID NO 1020
<211> LENGTH: 498
<212> TYPE: PRT
<213> ORGANISM: Influenza A virus

<400> SEQUENCE: 1020

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Gln Glu Gly Arg Leu Ile Gln Asn Ser Ile Thr Val Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asn Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Ile Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Ile Pro Arg Gly Gln Leu Ser Thr Arg Gly Val Gln Ile Ala Ser Asn
        355                 360                 365

Glu Asn Val Glu Ala Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg

```
385                 390                 395                 400

Ala Ser Ala Gly Gln Ile Ser Val Gln Pro Thr Phe Ser Val Gln Arg
                405                 410                 415

Asn Leu Pro Phe Glu Arg Val Thr Ile Met Ala Ala Phe Lys Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 1021
<211> LENGTH: 1811
<212> TYPE: DNA
<213> ORGANISM: Influenza B virus

<400> SEQUENCE: 1021

```
gcagaagcag agcattttct tgtgaactta aagtaccaac aaaaactgaa aaatcaaaat      60
gtccaacatg gatattgacg gcatcaacgc tggaacaatt gacaaaacac cagaagaaac     120
aacttctgga accagtggag caaccagacc aatcatcaga ccagcaaccc ttgccccacc     180
aagcaacaaa cggacccgga acccatcccc ggaaagggca accacaagca gtgaagctga     240
tatcggaagg agaacccaaa agaaacaaac cccgacagag ataaagaaga gcgtctacaa     300
tatggtagtg aaactgggtg aattctacaa ccagatgatg gtcaaagctg gactcaacga     360
tgacatggag agaaacctaa tccaaaatgc acatgctgtg gaaagaattc tattggctgc     420
tacggatgac aagaaaactg aattccagaa gaaaaagaat gccagagatg tcaaagaagg     480
gaaagaagaa atagaccaca acaaaacagg aggcaccttt tacaagatgg taagagatga     540
taaaaccatc tacttcagcc ctataagaat tacctttta aaagaagagg tgaaaacaat     600
gtacaaaacc accatgggga gtgatggttt cagtggacta aatcacatca tgattgggca     660
ttcacagatg aacgatgtct gcttccaaag gtcaaaggca ttaaaaagag ttggacttga     720
cccttcatta atcagcactt ttgcagggag cacgctcccc agaagatcag gtacaactgg     780
tgttgcgacc aaaggaggtg gaactttagt agcagaagcc attcgattta taggaagagc     840
aatggcagat agagggctat tgagagacat caaagccaag acggcctatg aaaagattct     900
tctgaatctg aaaaacaagt gctctgcgcc ccaacaaaag gctctagttg atcaagtgat     960
tggaagtaga aatccaggga ttgcagacat agaagaccta accctgcttg ctcgaagtat    1020
ggtcgttgtt aggccctctg tggcgagcaa agtggtgctt cccataagca tttatgctaa    1080
aataccccaa ctagggttca atgttgaaga atactctatg gttgggtatg aagccatggc    1140
tctttataat atggcaacac ctgtttccat attaagaatg ggagatgatg caaaagataa    1200
atcacaacta ttcttcatgt cttgcttcgg agctgcctat gaagacctaa gagttttgtc    1260
tgcactaaca ggcacagaat tcaagcccag gtcagcatta aagtgcaagg gtttccacgt    1320
tccagcaaag gagcaagtgg aaggaatggg ggcagctctg atgtccatca agctccagtt    1380
ttgggctcca atgaccagat ctgggggaaa tgaagtaggt ggagacggag ggtctggcca    1440
aataagttgc aacccagtgt ttgcagtaga aagacctatt gctctaagca aacaagctgt    1500
```

```
aagaagaatg ctgtcaatga atattgaggg acgtgatgca gatgtcaaag gaaatctact   1560

caagatgatg aatgattcaa tggctaagaa aaccaatggg aatgctttca ttgggaagaa   1620

aatgtttcaa atatcagaca aaaacaaaac caatcccatt gagattcaaa ttaagcagac   1680

catccccaat ttcttctttg ggagggacac agcagaggat tatgatgacc tcgactatta   1740

aagcaacaaa atagacacta tggctgtgat tgtttcagta cgtttgggat gtgggtgttt   1800

actcttatta a                                                        1811
```

<210> SEQ ID NO 1022
<211> LENGTH: 560
<212> TYPE: PRT
<213> ORGANISM: Influenza B virus

<400> SEQUENCE: 1022

```
Met Ser Asn Met Asp Ile Asp Gly Ile Asn Ala Gly Thr Ile Asp Lys
1               5                   10                  15

Thr Pro Glu Glu Thr Thr Ser Gly Thr Ser Gly Ala Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Ile Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Thr Thr
225                 230                 235                 240

Gly Val Ala Thr Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320
```

```
Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Asn Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Ile Glu Ile Gln Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 1023
<211> LENGTH: 1683
<212> TYPE: DNA
<213> ORGANISM: Influenza B virus

<400> SEQUENCE: 1023

atgtccaaca tggatattga cggcatcaac gctggaacaa ttgacaaaac accagaagaa      60

acaacttctg gaaccagtgg agcaaccaga ccaatcatca gaccagcaac ccttgcccca     120

ccaagcaaca aacggacccg gaacccatcc ccggaaaggg caaccacaag cagtgaagct     180

gatatcggaa ggagaaccca aaagaaacaa accccgacag agataaagaa gagcgtctac     240

aatatggtag tgaaactggg tgaattctac aaccagatga tggtcaaagc tggactcaac     300

gatgacatgg agagaaacct aatccaaaat gcacatgctg tggaaagaat tctattggct     360

gctacggatg acaagaaaac tgaattccag aagaaaaaga atgccagaga tgtcaaagaa     420

gggaaagaag aaatagacca caacaaaaca ggaggcacct tttacaagat ggtaagagat     480

gataaaacca tctacttcag ccctataaga attacctttt taaaagaaga ggtgaaaaca     540

atgtacaaaa ccaccatggg gagtgatggt ttcagtggac taaatcacat catgattggg     600

cattcacaga tgaacgatgt ctgcttccaa aggtcaaagg cattaaaaag agttggactt     660

gacccttcat taatcagcac ttttgcaggg agcacgctcc ccagaagatc aggtacaact     720

ggtgttgcga ccaaaggagg tggaacttta gtagcagaag ccattcgatt tataggaaga     780

gcaatggcag atagagggct attgagagac atcaaagcca agacggccta tgaaaagatt     840
```

```
cttctgaatc tgaaaaacaa gtgctctgcg ccccaacaaa aggctctagt tgatcaagtg    900

attggaagta gaaatccagg gattgcagac atagaagacc taaccctgct tgctcgaagt    960

atggtcgttg ttaggccctc tgtggcgagc aaagtggtgc ttcccataag catttatgct   1020

aaaatacccc aactagggtt caatgttgaa gaatactcta tggttgggta tgaagccatg   1080

gctctttata atatggcaac acctgtttcc atattaagaa tgggagatga tgcaaaagat   1140

aaatcacaac tattcttcat gtcttgcttc ggagctgcct atgaagacct aagagttttg   1200

tctgcactaa caggcacaga attcaagccc aggtcagcat taaagtgcaa gggtttccac   1260

gttccagcaa aggagcaagt ggaaggaatg gggcagctc tgatgtccat caagctccag   1320

ttttgggctc caatgaccag atctggggga aatgaagtag gtggagacgg agggtctggc   1380

caaataagtt gcagcccagt gtttgcagta gaaagaccta ttgctctaag caaacaagct   1440

gtaagaagaa tgctgtcaat gaatattgag ggacgtgatg cagatgtcaa aggaaatcta   1500

ctcaagatga tgaatgattc aatggctaag aaaaccaatg ggaatgcttt cattgggaag   1560

aaaatgtttc aaatatcaga caaaaacaaa accaatccca ttgagattca aattaagcag   1620

accatcccca atttcttctt tgggagggac acagcagagg attatgatga cctcgactat   1680

taa                                                                 1683
```

<210> SEQ ID NO 1024
<211> LENGTH: 560
<212> TYPE: PRT
<213> ORGANISM: Influenza B virus

<400> SEQUENCE: 1024

```
Met Ser Asn Met Asp Ile Asp Gly Ile Asn Ala Gly Thr Ile Asp Lys
1               5                   10                  15

Thr Pro Glu Glu Thr Thr Ser Gly Thr Ser Gly Ala Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Ile Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220
```

-continued

```
Ile Ser Thr Phe Ala Gly Ser Thr Leu Pro Arg Arg Ser Gly Thr Thr
225                 230                 235                 240

Gly Val Ala Thr Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Ile Glu Ile Gln Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```

NS1-NP DIAGNOSTICS OF INFLUENZA VIRUS INFECTION

This application claims priority to U.S. Provisional App. No. 61/036,954 (filed Mar. 15, 2008), which is incorporated by reference in its entirety. In addition, International patent applications PCT/US06/26155, filed Jul. 3, 2006, PCT/US06/41748 filed Oct. 21, 2006, and PCT/US08/01123 filed on Jan. 28, 2008, as well as U.S. applications Nos. 11/698,798 filed Jan. 26, 2007; 11/481,411 filed Jul. 3, 2006, 60/792,274, filed Apr. 14, 2006, 60/765,292, filed Feb. 2, 2006, 60/726,377, filed Oct. 13, 2005; and 60/696,221, filed Jul. 1, 2005, are directed to related subject matter and each application is incorporated by reference in its entirety for all purposes.

REFERENCE TO A SEQUENCE LISTING

This application includes a Sequence Listing provided in ASCII text file 6610SEQLIST.txt, of size 375,278 bytes and created on Mar. 16, 2009, which is hereby incorporated by reference in its entirety for all purposes.

BACKGROUND OF THE INVENTION

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza type C viruses also infect only humans. They infect most people when they are young and rarely causes serious illness.

Current rapid immunodiagnostic tests for influenza antigens like the Tauns Capilia™ assay (Tauns Laboratories, Inc., Japan), "Binax NOW FluA and FluB™" (Binax, Inc., Portland, Me.), "Directigen Flu A+B™" (Becton Dickinson, Franklin Lakes, N.J.), "Flu OIA™" (Biostar Inc., Boulder, Colo.), "Quick Vue™" (Quidel, Sand Diego, Calif.), "Influ AB Quick™" (Denka Sieken Co., Ltd., Japan) and "Xpect Flu A & B" (Remel Inc., Lenexa, Kans.), can reportedly either detect influenza A or distinguish between influenza A and B. The complexity of the test formats may require special training. In addition, significant amounts of virion particles are commonly required to obtain a positive test result, limiting their use to a short window of time when virus shedding is at its highest levels. Assay sensitivity is also variable with up to 20% false negative test results in certain assays being of significant current concern (e.g., see "WHO recommendations on the use of rapid testing for influenza diagnosis," July 2005). Reverse-transcriptase PCR-based diagnostics (RT-PCR) has resulted in advances in capabilities, but is laborious and requires highly trained personnel making on-site or field-testing difficult. Because of the relative inefficiency of the reverse transcriptase enzyme, significant amounts of virus (e.g., $10^4$ virion particles) and as many as 20 primers may be required effectively to detect viral RNA. Unfortunately, RT-PCR is not easily adapted to high throughput screening of subjects in an epidemic setting or to field uses in an agricultural or point-of-care setting.

BRIEF SUMMARY OF THE INVENTION

Among other things, the invention provides a method of determining the presence of and/or assessing an influenza virus infection, comprising: (a) determining an amount of influenza virus non-structural 1 (NS1) protein in a sample from a subject, and (b) determining an amount of influenza virus nucleoprotein (NP) in the sample, wherein a detectable amount of NS1 protein and/or NP protein indicates that the subject is infected with an influenza virus and/or a ratio of an amount of NS1 protein to an amount of NP protein indicates a prognosis of the subject.

Optionally, the method further comprises comparing the amount of NS1 with the amount of NP in the sample. Optionally, the prognosis includes stage of infection, progress of infection over time, severity of infection, outcome of infection under a treatment of interest, and/or amenability to treatment. Optionally, the method further comprises determining the stage of infection from the ratio, a relatively higher ratio indicating a relatively earlier stage of infection. Optionally, the method further comprises selecting a treatment regime from the ratio, a relatively high ratio favoring administering an anti-viral agent that inhibits viral reproduction and/or isolating the patient. Optionally, the method is performed at different times, wherein changes in the ratio with time provide an indication of the course of infection.

Optionally, the amount of NS1 and/or NP protein is determined using at least one antibody that specifically binds to NS1 or NP. Optionally, the amount of NS1 is determined using at least one NS1 antibody and the amount of NP is determined using at least one NP antibody. Optionally, determining the amount of NS1 or NP comprises: contacting the sample with at least one NS1 or NP antibody, and determining the amount of a complex of the at least antibody specifically bound to the NS1 or NP protein, wherein the amount of the complex is an indication of the amount of NS1 or NP in the sample.

Optionally, the at least one NS1 antibody or at least one NP antibody comprises an antibody that is pan-specific to influenza virus type A. Optionally, the at least one NS1 antibody competes with an antibody selected from the group consisting of F64 3H3, F68 8E6, F64 6G12, F68 10A5, F80 7E8, F80 8F6, F80 9B1, F81 1C12, F81 1F3, F81 4D5, and F64 1A10.

Optionally, determining the amount of the antigen (NS1 and/or NP) comprises contacting the sample with first and second pan specific antibodies that bind to different epitopes of the antigen; and determining the amount of a complex between the first and second antibodies and the antigen, wherein the amount of the complex is an indication of the amount of the antigen in the sample. Optionally, the method is performed using a lateral flow format.

Optionally, the pan-specific antibodies for NS1 each bind to an epitope within residues 8-21, 9-20, 29-38 or 45-49 of NS1. Optionally, the first and/or second pan-specific antibodies for NS1 comprises a mixture of antibodies. Optionally, the first and second pan-specific antibodies for NS1 each compete with one or more antibodies selected from the group consisting of F64 3H3, F68 4H9, F68 8E6, F64 6G12, F68 10A5, F80 3D5, F80 7E8, F80 8F6, F80 9B1, F81 1C12, F81 1F3, F81 4D5, F64 1A10, F89 6B5, F94 1F9 and F94 3A1 wherein the first pan-specific antibody binds to a different epitope than the second pan-specific antibody. Optionally, the first and second antibodies are pan-specific for NS1 from influenza A, wherein the first antibody competes with or is derived from the monoclonal antibody F64 3H3 and/or F68 4H9 and is optionally immobilized on a solid substrate, and the second antibody competes with or is derived from the monoclonal antibody F68 8E6 and/or F80 3D5 and is optionally gold-conjugated.

Optionally, the first and second antibodies are pan-specific for NS1 from influenza B, the first antibody competes with or is derived from the monoclonal antibody F89 6B5 and is optionally immobilized on a solid substrate, and the second antibody competes with or is derived from the monoclonal antibody F94 1F9 and/or F94 3A1 and is optionally gold-conjugated.

Optionally, the sample is a nasal or throat sample. Optionally, the subject is a human showing symptoms of influenza. Optionally, the amount of NS1 and/or NP is determined using at least one post synaptic density protein (PSD95), Drosophila discs large tumor suppressor (DlgA), and zonula occludens 1 protein (ZO1) (PDZ polypeptide that binds specifically to NS1 or NP. Optionally, the PDZ polypeptide is immobilized to a solid phase and the NS1 and/or NP antibody is a detection antibody. Optionally, the at least one PDZ polypeptide that binds specifically to NS1 is selected from the group consisting of PSD95 domain 2, InaD-like (INADL) domain 8, or combinations thereof.

Optionally, the method is performed on samples from a test subject and a control subject, the test subject being treated with a test agent, and the control subject being untreated with the test agent, and the method further comprises comparing the change in the NS1:NP ratio in the two subjects over time. A quicker decrease in NS1:NP ratio over time in one or more test subjects kept in the presence of the test agent can indicate that the test agent is effective in treating influenza during the early stages of infection.

Optionally, the amount of NS1 and/or NP and/or the NS1:NP ratio in the sample(s) ("test sample(s)") is compared to that measured in a control sample. The control sample can be taken from a control subject believed to be infected with influenza virus. The control subject for example at a known (or believed) stage of infection. Examples of subjects at an early stage of infection include subjects infected within the last 72 hours, e.g., within the last 48 or 24 hours. Examples of subjects at a late stage of infection include those infected at least 5 days ago, e.g., to have been infected at least 1 week ago.

Optionally, the amount of NS1 and/or NP and/or the NS1:NP ratio in the sample(s) is compared to that measured in multiple control samples taken at different timepoints of an influenza virus infection in a control subject. For example, the amount of NS1 and/or NP in the test sample(s) and control sample(s) is measured by contacting the test sample(s) and control sample(s) with the same solution of an NS1-binding agent and/or an NP-binding agent. The amount of NS1 and/or NP and/or the NS1:NP ratio in the sample(s) can be measured using a lateral flow assay in which an NS1-capture agent and an NP-capture agent are both immobilized within the same area of a solid support.

Optionally, the method further comprises determining an amount of an NA, and/or an HA protein and/or an M1 protein the sample, wherein a detectable amount of NA protein and/or HA protein and/or M1 protein indicates the subject is infected with influenza virus. Optionally, the method further comprises determining a subtype of and NA protein and/or an HA protein and/or type of M1 protein or an NS1 protein or and M1 protein in the sample, wherein the subtype of HA or NA protein indicates the strain of the influenza virus, and the type of the NS1 protein and/or NP protein and/or M1 protein indicates the type of influenza virus the subject is infected with.

Optionally, the method further comprises contacting the sample with first and second PDZ domains, and the method further comprises determining relative binding of the first and second PDZ domains to NS1 protein the sample and typing the influenza virus infection as pathogenic or nonpathogenic from the relative binding. Optionally, the first and second PDZ domains are PSD95 and INADL.

Optionally, determining an amount of influenza virus antigen (e.g., NS1 and/or NP) in a sample comprises contacting the sample with first and second binding agents specific for the influenza A and influenza B type of that antigen, and the method further comprises determining relative binding to the first and second binding agents, and characterizing the influenza virus infection as A or B based on the relative binding.

The invention further provides an array comprising at least one first agent that binds to influenza virus NS1 and at least one agent that binds to NP. Optionally, at least one NS1-binding agent and/or at least one NP-binding agent is an antibody or a PDZ polypeptide. Optionally, the array comprises at least two pan-specific NS1 antibodies and/or at least two pan-specific NP antibodies. Optionally, the array comprises at least two subtype-specific NS1 antibodies and/or at least two subtype-specific NP antibodies. Optionally, the array comprises at least one antibody specific for influenza A NS1 and at least one antibody specific for influenza B NS1. Optionally, the array comprises at least one antibody specific for influenza A NP and at least one antibody specific for influenza B NP. Optionally, the array further comprises at least one agent that binds to an M1 protein and at least one agent that binds to an HA protein.

The invention also provides a kit for the assessment of an influenza virus infection in a subject, comprising: (a) a first agent for determining the amount of influenza virus NS1 protein, and (b) a second agent for determining the amount of influenza virus NP protein. Optionally the first agent or the second agent comprises at least one antibody.

BRIEF DESCRIPTION OF THE DRAWINGS

FIG. 1A (SEQ ID NO:998) shows the invariant amino acid residues between NS1 proteins from three subtypes of influenza A: H1N1, H3N2 and H5N1. As described below, segments of NS1 protein including clusters of invariant amino acid residues are useful for inducing pan-specific antibodies.

FIG. 1B (SEQ ID NO:999) shows amino acid residues found in the NS1 protein of H5N1 but not found in H3N2 or H1N1. Clusters of these residues, particularly the clusters at positions 21-28 and at the C-terminus, are useful for preparing an antibody that binds to H5N1 without binding to the other two subtypes.

FIG. 2 (SEQ ID NO:1000) shows a consensus sequence of residues of the NS1 protein from different strains of influenza A.

FIG. 3 (SEQ ID NO: 1001) shows a consensus sequence of residues of the NS1 protein form different strains of influenza B. Underlined residues are invariable between different strains.

FIG. 5 shows NS1 expression in MDCK cells infected with A/PR/8/34.

FIG. 14: Sequence of a GST fusion peptide comprising 3 copies of PSD95 domain 2 (SEQ ID NO: 1002). GST-derived sequence, including GST peptide sequence and cloning linker sequence, is italicized (amino acids 1-242 and 243-244 respectively). Native PSD95 domain 2 sequence is in bold (corresponding to amino acids 197 to 288 of NCBI Acc. No. AAC52113); native PSD95 sequence other than domain 2 is shown in normal (i.e., non-bold, non-italicized) font (any such sequence that is repeated/relocated is also underlined).

FIG. 21: CAMAG absorbance unit values for AVC Flu A/B Tests (NS1) and AVC Flu A NP Tests of patients as a function of time.

DEFINITIONS

Figure 4:
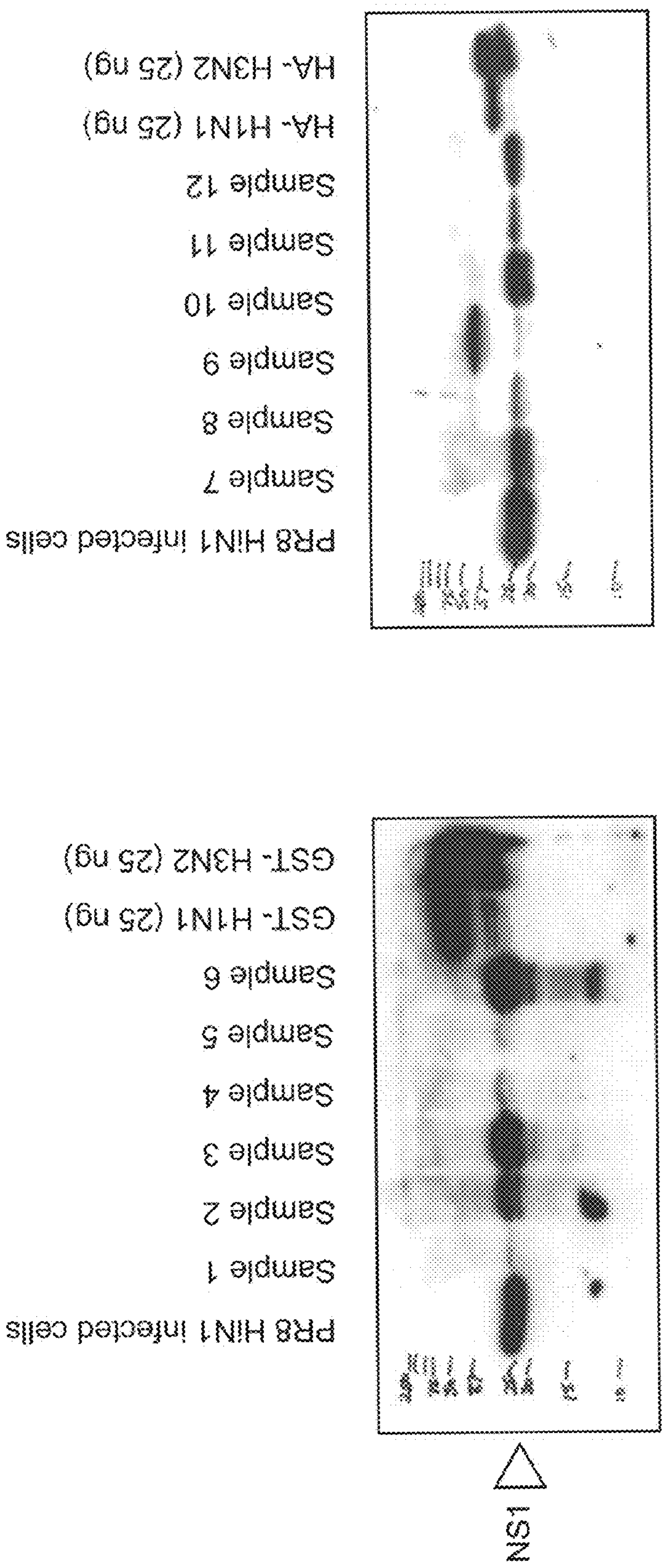
FIG. 4 shows the results of testing nasal secretions from six human Flu A positive samples.

"Avian influenza A" means an influenza A subtype that infects an avian subject and is transmissible between avian subjects. Representative examples of avian influenza hemmagglutinin subtypes include H5, H6, H7, H9 and H10 and representative strains include H5N1, H6N2, H7N3, H7N7, H9N2, H10N4 and H10N5. Some strains of Avian influenza can also infect humans.

"Avian subject" means a subject suitable for testing or treatment including all species of birds, including both wild birds (such as wildfowl) and domesticated species (such as poultry). Preferably, the avian subject to be tested or treated is selected from the group consisting of chickens, turkeys, ducks, geese, quail, ostrich, emus and exotic birds such as parrots, cockatoos and cockatiels. More preferably, the avian subject to be tested is a chicken, turkey, goose or quail.

"Pathogenic strain of influenza A" when used in the context of distinguishing between different strains of influenza virus means a "notifiable avian influenza" (NAI) virus according to the guidelines set forth by the OIE World Organization for Animal Health, World Health Organization or their designated representatives e.g., as set forth in the OIE "Manual of Diagnostic Tests and Vaccines for Terrestrial Animals, 5th edition, 2004 (www.oie.int). Further, the subject pathogenic strain has "high pathogenicity" in a representative test for virulence or an H5 or H7 virus with an influenza A hemmagglutinin (HA) precursor protein HA0 cleavage site amino acid sequence that is similar to any of those that have been observed in virulent viruses, i.e., as defined by the OIE or a representative similar national or international organization or trade association. Representative examples of HA0 cleavage site amino acid sequences in virulent H5 and H7 strains of influenza A comprise multiple basic amino acids (arginine or lysine) at the cleavage site of the viral precursor hemagglutinin protein, e.g., where low virulence strains of H7 viruses have PEIPKGR*GLF (SEQ ID NO:20) or PENPKGR*GLF (SEQ ID NO:21) highly pathogenic strains have – PEIPKKKKR*GLF (SEQ ID NO:22), PETPKRKRKR*GLSF (SEQ ID NO:23), PEIPKKREKR*GLF (SEQ ID NO:24) or PETPKRRRR*GLF (SEQ ID NO:25). Current representative tests for virulence include inoculation of 4-8 week old chickens with infectious virus wherein strains are considered to be highly pathogenic if they cause more than 75% mortality within 10 days; and/or, any virus that has an intravenous pathogenicity index (IVPI) greater than 1.2, wherein intravenously inoculated birds are examined at 24-hour intervals over a 10-day period; scored for "0", normal; "1" sick; "2" severely sick"; "3" dead; and, the mean score calculated as the IVPI. The latter highly pathogenic strains are referred to by the OIE as a "highly pathogenic NAI virus" (HPNIA). Current representative examples of NAI include the H5 and H7 strains of influenza A. Current representative examples of HPNIA include H5N1.

"Less Pathogenic strain of influenza A" means an avian influenza A that is notifiable, i.e., an NAI isolate (supra), but which is not pathogenic for chickens and does not have an HA0 cleavage site amino acid sequence similar to any of those that have been observed in virulent viruses, i.e., a strain referred to by the OIE as a "low pathogenicity avian influenza (LPAI).

Strains of influenza A that are not classified as highly pathogenic or less pathogenic are referred to as seasonal flu. Most strains of influenza A H1N1 are seasonal flu. However, one strain responsible for the 1918 Spanish flu is highly pathogenic.

"PDZ domain" means an amino acid sequence homologous over about 90 contiguous amino acids; preferably about 80-90; more preferably, about 70-80, more preferably about 50-70 amino acids with the brain synaptic protein PSD95, the Drosophila septate junction protein Discs-Large (DLG) and/or the epithelial tight junction protein ZO1 (ZO1). Representative examples of PDZ domains are also known in the art as Discs-Large homology repeats ("DHRs") and "GLGF" repeats (SEQ ID NO:26). Examples of PDZ domains are found in diverse membrane-associated proteins including members of the MAGUK family of guanylate kinase homologs, several protein phosphatases and kinases, neuronal nitric oxide synthase, tumor suppressor proteins, and several dystrophin-associated proteins, collectively known as syntrophins. The instant PDZ domains encompass both natural and non-natural amino acid sequences. Representative examples of PDZ domains include: (a) polymorphic variants of PDZ proteins, (b) chimeric PDZ domains containing portions of two different PDZ proteins or a PDZ-derived portion and a non-PDZ portion, (c) fragments of a PDZ domain that are capable of binding specifically to a cognate PL, and the like. A "PDZ polypeptide" is any peptide derived from a PDZ domain, including sequence variants, chimeric polypeptides containing portions of two different PDZ proteins or a PDZ-derived portion and a non-PDZ portion, fragments of a PDZ domain that are capable of binding specifically to a cognate PL, and the like. Preferably, the instant PDZ domains contain amino acid sequences which are substantially identical to those disclosed in U.S. patent application Ser. No. 10/485,788 (filed Feb. 3, 2004), International patent application PCT/US03/285/28508 (filed Sep. 9, 2003), International patent application PCT/US01/44138 (filed Nov. 9, 2001), incorporated herein by reference in their entirety. Representative non-natural PDZ domains include those in which the corresponding genetic code for the amino acid sequence has been mutated, e.g., to produce amino acid changes that alter (strengthen or weaken) either binding or specificity of binding to PL. *Optionally a PDZ domain or a variant thereof has at least* 50, 60, 70, 80 or 90% sequence identity with a PDZ domain from at least one of brain synaptic protein PSD95, the Drosophila septate junction protein Discs-Large (DLG) and/or the epithelial tight junction protein ZO1 (ZO1), and animal homologs. Optionally a variant of a natural PDZ domain has at least 90% sequence identity with the natural PDZ domain. Sequence identities of PDZ domains are determined over at least 70 amino acids within the PDZ domain, preferably 80 amino acids, and more preferably 80-90 or 80-100 amino acids. Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. The term "allelic variant" is used to refer to variations between genes of different individuals in the same species and corresponding variations in proteins encoded by the genes. An exemplary PDZ domain for PSD95 d2 is provided as SEQ ID NO: 1.

"PDZ protein", used interchangeably with "PDZ-domain containing polypeptides" and "PDZ polypeptides", means a naturally occurring or non-naturally occurring protein having a PDZ domain (supra). Representative examples of PDZ proteins have been disclosed previously (supra) and include CASK, MPP1, DLG1, DLG2, PSD95, NeDLG, TIP-33, TIP-43, LDP, LIM, LIMK1, LIMK2, MPP2, AF6, GORASP1, INADL, KIAA0316, KIAA1284, MAG11, MAST2, MINT1, NSP, NOS1, PAR3, PAR3L, PAR6 beta, PICK1, Shank 1, Shank 2, Shank 3, SITAC-18, TIP1, and ZO-1. The instant non-natural PDZ domain polypeptides useful in screening assays may contain e.g. a PDZ domain that is smaller than a natural PDZ domain. For example a non-natural PDZ domain may optionally contain a "GLGF" motif, i.e., a motif having the GLGF amino acid sequence (SEQ ID NO:26), which typically resides proximal, e.g. usually within about 10-20 amino acids N-terminal, to an PDZ domain. The latter GLGF motif (SEQ ID NO:26), and the 3 amino acids immediately N-terminal to the GLGF motif (SEQ ID NO:26) are often required for PDZ binding activity. Similarly, non-natural PDZ domains may be constructed that lack the P-sheet at the C-terminus of a PDZ domain, i.e., this region may often be deleted from the natural PDZ domain without affecting the binding of a PL. Some exemplary PDZ proteins are provided and the GI or accession numbers are provided in parenthesis: PSMD9 (9184389), af6 (430993), AIPC (12751451), ALP (2773059), APXL-1 (13651263), MAGI2 (2947231), CARDI1 (1282772), CARDI4 (13129123), CASK (3087815), CNK1 (3930780), CBP (3192908), Densin 180 (16755892), DLG1 (475816), DLG2 (12736552), DLG5 (3650451), DLG6 splice var 1 (14647140), DLG6 splice var 2 (AB053303), DVL1 (2291005), DVL2 (2291007), DVL3 (6806886), ELFIN 1 (2957144), ENIGMA (561636), ERBIN (8923908), EZRIN binding protein 50 (3220018), FLJ00011 (10440342), FLJ11215 (11436365), FLJ12428 (BC012040), FLJ12615 (10434209), FLJ20075 Semcap2 (7019938), FLJ21687 (10437836), FLJ31349 (AK055911), FLJ32798 (AK057360), GoRASP1 (NM031899), GoRASP2 (13994253), GRIP1 (4539083), GTPase Activating Enzyme (2389008), Guanine Exchange Factor (6650765), HEMBA 1000505 (10436367), HEMBA 1003117 (7022001), HSPC227 (7106843), HTRA3 (AY040094), HTRA4 (AL576444), INADL (2370148), KIAA0147 Vartul (1469875), KIAA0303 MAST4 (2224546), KIAA0313 (7657260), KIAA0316 (6683123), KIAA0340 (2224620), KIAA0380 (2224700), KIAA0382 (7662087), KIAA0440 (2662160), KIAA0545 (14762850), KIAA0559 (3043641), KIAA0561 MAST3 (3043645), KIAA0613 (3327039), KIAA0751 RIM2 (12734165), KIAA0807 MAST2 (3882334), KIAA0858 (4240204), KIAA0902 (4240292), KIAA0967 (4589577), KIAA0973 SEMCAP3 (5889526), KIAA1202 (6330421), KIAA1222 (6330610), KIAA1284 (6331369), KIAA1389 (7243158), KIAA1415 (7243210), KIAA1526 (5817166), KIAA1620 (10047316), KIAA1634 MAGI3 (10047344), KIAA1719 (1267982), LIM Mystique (12734250), LIM (3108092), LIMK1 (4587498), LIMK2 (1805593), LIM-RIL (1085021), LU-1 (U52111), MAGI1 (3370997), MGC5395 (BC012477), MINT1 (2625024), MINT3 (3169808) MPP1 (189785), MPP2 (939884), MPP3 (1022812), MUPP1 (2104784), NeDLG (10853920), Neurabin II (AJ401189), NOS1 (642525), novel PDZ gene (7228177), Novel Serine Protease (1621243), Numb Binding Protein (AK056823), Outer Membrane Protein (7023825), p55T (12733367), PAR3 (8037914), PAR3-like (AF428250), PAR6 (2613011), PAR6BETA (13537116), PAR6GAMMA (13537118), PDZ-73 (5031978), PDZK1 (2944188), PICK1 (4678411), PIST (98394330), prIL16 (1478492), PSAP (6409315), PSD95 (3318652), PTN-3 (179912), PTN-4 (190747), PTPL1 (515030), RGS12 (3290015), RGS3 (18644735), Rho-GAP10 (NM020824), Rhophilin-like (14279408), Serine Protease (2738914), Shank 2 (6049185), Shank 3 (AC000036), Shroom (18652858), Similar to GRASP65 (14286261), Similar to Ligand of Numb px2 (BC036755), Similar to PTP Homolog (21595065), SIP1 (2047327), SITAC-18 (8886071), SNPCIIA (20809633), Shank 1 (7025450), Syntenin (2795862), Syntrophin 1 alpha (1145727), Syntrophin beta 2 (476700), Syntrophin gamma 1 (9507162), Syntrophin gamma 2 (9507164), TAX2-like protein (3253116), TIAM 1 (4507500), TIAM 2 (6912703), TIP 1 (2613001), TIP2 (2613003), TIP33 (2613007), TIP43 (2613011), X-11 beta (3005559), ZO-1 (292937), ZO-2 (12734763), ZO-3 (10092690).

"PDZ ligand", abbreviated "PL", means a naturally occurring protein that has an amino acid sequence which binds to and forms a molecular interaction complex with a PDZ-domain. Representative examples of PL have been provided previously in prior US and International patent applications (supra).

"Specific binding" between a binding agent, e.g., an antibody or a PDZ domain, and an NS1 protein refers to the ability of a capture- or detection-agent to preferentially bind to a particular viral analyte that is present in a mixture of different viral analytes The particular analyte is for example an influenzaviral analyte in a mixture of other influenzaviral and/or non-influenzaviral analytes. Analgous considerations apply to other analytes. A binding agent preferentially binds to a particular analyte in a mixture of analytes, some of which may be present in excess compared to the particular analyte. Optionally, the agent binds specifically to the particular analyte at least 2×, 5×, 10×, 30×, 100, 300× or 1000× higher affinity than unrelated control proteins. Specific binding is often the result of interaction between specific surface structure of the binding agent and/or ligand (e.g., hydrogen bonds), whereas non-specific binding is relatively independent of specific surface structures (e.g., van der Waals forces). Specific binding to a particular analyte over unrelated proteins may or may not mean that that a binding agent preferentially binds to the analyte over closely related analytes. Some binding agents are type- or subtype-specific, e.g., the agent binds preferentially to a protein from influenzavirus of a given type or subtype over the same protein from influenzavirus of a different type or subtype. Other binding agents bind multiple types or subtypes of analytes. For example, some antibodies described in the application specifically bind to NS1 from influenza B without specifically binding to NS1 from influenza A, and vice versa. Specific binding also means a dissociation constant (KD) that is less than about $10^{-6}$ M; preferably, less than about $10^{-7}$ M; and, most preferably, less than about $10^{-8}$ M, In some methods, specific binding interaction is capable of discriminating between proteins having or lacking a PL with a discriminatory capacity greater than about 10- to about 100-fold; and, preferably greater than about 1000- to about 10,000-fold. Specific binding can readily be distinguished from nonspecific binding, by for example, by subtracting from a test signal a background signal from a control sample known to lack analyte and/or by generating a signal from binding of two binding agents to different epitopes of the same analyte as in a sandwich assay.

"Capture agent/analyte complex" is a complex that results from the specific binding of a capture agent, with an analyte, e.g. an influenza viral NS1 protein. A capture agent and an analyte specifically bind, i.e., the one to the other, under conditions suitable for specific binding, wherein such physicochemical conditions are conveniently expressed e.g. in terms of salt concentration, pH, detergent concentration, protein concentration, temperature and time. The subject conditions are suitable to allow binding to occur e.g. in a solution; or alternatively, where one of the binding members is immobilized on a solid phase. Representative conditions so-suitable are described in e.g., Harlow and Lane, "Antibodies: A Laboratory Manual", Cold Spring Harbor Laboratory, Cold Spring Harbor, N.Y. (1989). Suitable conditions preferably result in binding interactions having dissociation constants (KD) that are less than about $10^{-6}$ M; preferably, less than about $10^{-7}$ M; and, most preferably less than about $10^{-8}$ M.

"Solid phase" means a surface to which one or more reactants may be attached electrostatically, hydrophobically, or covalently. Representative solid phases include e.g.: nylon 6; nylon 66; polystyrene; latex beads; magnetic beads; glass beads; polyethylene; polypropylene; polybutylene; butadiene-styrene copolymers; silastic rubber; polyesters; polyamides; cellulose and derivatives; acrylates; methacrylates; polyvinyl; vinyl chloride; polyvinyl chloride; polyvinyl fluoride; copolymers of polystyrene; silica gel; silica wafers glass; agarose; dextrans; liposomes; insoluble protein metals; and, nitrocellulose. Representative solid phases include those formed as beads, tubes, strips, disks, filter papers, plates and the like. Filters may serve to capture analyte e.g. as a filtrate, or act by entrapment, or act by covalently binding. A solid phase capture reagent for distribution to a user may consist of a solid phase coated with a "capture reagent", and packaged (e.g., under a nitrogen atmosphere) to preserve and/or maximize binding of the capture reagent to an influenza NS1 analyte in a biological sample.

Samples include tissue fluids, tissue sections, biological materials carried in the air or in water and/or collected there from e.g. by filtration, centrifugation and the like, e.g., for assessing bioterror threats and the like. Alternative biological samples can be taken from fetus or egg, egg yolk, and amniotic fluids. Representative biological fluids include urine, blood, plasma, serum, cerebrospinal fluid, semen, lung lavage fluid, feces, sputum, mucus, water carrying biological materials and the like, as well as material taken or derived from these biological fluids. Alternatively, biological samples include nasopharyngeal or oropharyngeal swabs, nasal lavage fluid, tissue from trachea, lungs, air sacs, intestine, spleen, kidney, brain, liver and heart, sputum, mucus, water carrying biological materials, cloacal swabs, sputum, nasal and oral mucus, and the like. Samples can be analyzed with or without further processing. Further processing can add or remove materials present in a sample as originally removed from a subject. Representative biological samples also include foodstuffs, e.g., samples of meats, processed foods, poultry, swine and the like. Biological samples also include contaminated solutions (e.g., food processing solutions and the like), swab samples from out-patient sites, hospitals, clinics, food preparation facilities (e.g., restaurants, slaughter houses, cold storage facilities, supermarket packaging and the like). Biological samples may also include in situ tissues and bodily fluids (i.e., samples not collected for testing), e.g., the instant methods may be useful in detecting the presence or severity or viral infection in the eye e.g., using eye drops, test strips applied directly to the conjunctiva; or, the presence or extent of lung infection by e.g. placing an indicator capsule in the mouth or nasopharynx of the test subject. Alternatively, a swab or test strip can be placed in the mouth. The biological sample may be derived from any tissue, organ or group of cells of the subject. In some embodiments a scrape, biopsy, or lavage is obtained from a subject. Biological samples may include bodily fluids such as blood, urine, sputum, and oral fluid; and samples such as nasal washes, swabs or aspirates, tracheal aspirates, chancre swabs, and stool samples, or materials derived from such samples. Methods are known to those of skill in the art for the collection of biological specimens suitable for the detection of individual pathogens of interest, for example, nasopharyngeal specimens such as nasal swabs, washes or aspirates, or tracheal aspirates in the case of high risk influenza A viruses involved in respiratory disease, oral swabs and the like. Optionally, the biological sample may be suspended in an isotonic solution containing antibiotics such as penicillin, streptomycin, gentamycin, and mycostatin.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample that is not found naturally.

"Subject", is used herein to refer to an organism such as a human or to an animal such as a domesticated animal, e.g. mammals, fishes, birds, reptiles, amphibians and the like. If so desired, the subject can be cells maintained in vitro or ex vivo (for example cultured or isolated or recombinant cells infected with influenza virus). Some subjects have influenza or at least one symptom thereof. Some subjects are at increased risk of influenza, e.g., previously exposed to influenza virus or to another organism suspected to have influenza.

Some subjects not exhibit any symptom of influenza, or not suspected of having influenza, or is not at increased risk for influenza.

"Signal generating compound", abbreviated "SGC", means a molecule that can be linked to an an antibody or a PL or a PDZ (e.g. using a chemical linking method as disclosed further below and is capable of reacting to form a chemical or physical entity (i.e., a reaction product) detectable in an assay according to the instant disclosure. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds, radioisotopes (e.g., $^{131}I$, $^{125}I$, $^{14}C$, $^{3}H$, $^{35}S$, $^{32}P$ and the like), enzymes (e.g., below), binding proteins (e.g., biotin, avidin, streptavidin and the like), magnetic particles, chemically reactive compounds (e.g., colored stains), labeled oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative SGC's useful in a signal generating conjugate include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); IUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); IUB Class 4 (e.g., lyases); IUB Class 5 especially 5.3 and 5.4 (e.g., phosphoglucose isomerase, trios phosphatase isomerase, phosphoglucose mutase and the like.) Signal generating compounds also include SGC whose products are detectable by fluorescent and chemiluminescent wavelengths, e.g., luciferase, fluorescence emitting metals such as $^{152}Eu$, or others of the lanthanide series; compounds such as luminol, isoluminol, acridinium salts, and the like; bioluminescent compounds such as luciferin; fluorescent proteins; and the like. Fluorescent proteins include, but are not limited to the following: namely, (i) green fluorescent protein (GFP), i.e., including, but not limited to, a "humanized" versions of GFP wherein codons of the naturally-occurring nucleotide sequence are exchanged to more closely match human codon bias; (ii) GFP derived from *Aequoria victoria* and derivatives thereof, e.g., a "humanized" derivative such as Enhanced GFP, which are available commercially, e.g., from Clontech, Inc.; (iii) GFP from other species such as *Renilla reniformis, Renilla mulleri*, or *Ptilosarcus guernyi*, as described in, e.g., WO 99/49019 and Peelle et al. (2001) J. Protein Chem. 20:507-519; (iv) "humanized" recombinant GFP (hrGFP) (Stratagene); and, (v) other fluorescent and colored proteins from Anthozoan species, such as those described in Matz et al. (1999) Nature Biotechnol. 17:969-973; and the like. The subject signal generating compounds can be coupled to a PL or PDZ domain polypeptide. SGCs can also be attached to any agent of interest, e.g., antibodies. Attaching certain SGC to agents can be accomplished through metal chelating groups such as EDTA. The subject SGC share the common property of allowing detection and/or quantification of an influenza PL analyte in a test sample. The subject SGC are detectable using a visual method; preferably, with a method amenable to automation such as a spectrophotometric method, a fluorescence method, a chemiluminescent method, a electrical nanometric method involving e.g., a change in conductance, impedance, resistance and the like and a magnetic field method. Some SGC's are detectable with the naked eye. Some SGC's are detecable with a signal detection apparatus, such as those described herein. Some SGCs are not themselves detectable but become detectable when subject to further treatment with e.g.

The SGC can be attached in any manner (e.g., through covalent or non-covalent bonds) to a binding agent of interest (e.g., an antibody or a PDZ polypeptide). SGCs suitable for attachment to agents such as antibodies include colloidal gold, fluorescent antibodies, Europium, latex particles, and enzymes. The agents that bind to NS1 and NP can each comprise distinct SGCs. For example, red latex particles can be conjugated to anti-NS1 antibodies and blue latex particles can be conjugated to anti-NP antibodies. Other detectable SGCs suitable for use in a lateral flow format include any moiety that is detectable by spectroscopic, photochemical, biochemical, immunochemical, electrical, optical, chemical, or other means. For example, suitable SGCs include biotin for staining with labeled streptavidin conjugate, fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric SGCss such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic SGCs are typically detected by providing the enzyme with a substrate and detecting the reaction product produced by the action of the enzyme on the substrate, and colorimetric labels are detected by simply visualizing the colored label.

Determining the presence and/or amount of an analyte such as influenza NS1 or NP can be achieved by determining the presence and/or amount of specific binding between a binding agent and the analyte. The binding agent for example comprises an antibody or a PDZ domain that can bind specifically to a site on the analyte (e.g., influenza NS1 or NP). Suitable binding sites on the analyte include an epitope or a C-terminal PL site. Detection can be achieved in many ways. The presence and/or amount of NS1 or NP in a sample can be determined with or without immuno-PCR amplification. Immuno-PCR amplification is a technique in which a protein immunogen is detected using a binding agent labeled with a nucleic acid. PCR amplification of the nucleic acid with labeled primers which are not attached to the binding agent generates a detectable amount labeled PCR amplification product. The amount of labeled amplification product is amplified through multiple rounds of amplification in exponential fashion, where the rate of amplification of the is influenced by the amount of PCR product present, which itself increases during the course of each round of amplification. Although immuno-PCR provides a sensitive means to detect NS1 or NP, either antigen can be present at sufficient amounts to be detected by less sensitive but more simple-to-perform methods.

Optionally, detection is achieved through the use of a SGC that itself emits or can generate a detectable signal. Optionally, the SGC is attached to (or attachable to) an agent that can bind specifically to an analyte of interest. The agent is for example an antibody or a PDZ polypeptide that can bind specifically to influenza NS1 or NP. The SGC can be directly attached (or attachable) to the agent. The SGC can also be attached or attachable to a second agent that can attach to the first agent (e.g., an antibody to an anti-NS1 antibody). Optionally, the second agent specifically binds to the first agent. In an example, the first agent is first allowed to bind specifically to the analyte of interest, and a second agent is then allowed to bind specifically to the agent, where the second agent optionally comprised the SGC, or is attachable to the SGC. In other examples, the SGC is not attached or attachable to the agent.

Optionally, the SGC itself can emit or can generate a detectable signal. In an example, the SGC intrinsically emits a detectable signal, so that the presence and/or amount of the SGC can be directly determined (i.e., the presence and/or amount of the SGC need not be not inferred by determining the presence and/or amount of another detectable molecule). Optionally, the SGC can conditionally emit a detectable signal under certain conditions (e.g., fluorescent light). Optionally, the SGC does not emit a detectable signal but can be modified to emit a detectable signal. For example, the SGC does not emit a detectable signal when originally attached to the agent but can be modified later to emit a detectable signal. Optionally, the SGC converts or allows the conversion of another substance (substrate) to a product that emits a detectable signal that is not emitted by the substrate itself. Optionally, the SGC can undergo a detectable change or enable a detectable change in another molecule. For example, the SGC can catalyze or co-catalyze a detectable reaction, or act as an activator or inhibitor of a detectable reaction. An SGC can for example comprise an enzyme, a coenzyme, a cofactor, a peptide, or protein or an inorganic molecule. Optionally, the SGC does not comprise a nucleic acid. Optionally, the presence of the SGC is not detected using PCR amplification if the SGC comprises a nucleic acid.

The term "label" is synonymous with SGC. A label (or SGC) optionally emits a detectable signal by itself, e.g., under proper conditions. A labeled agent includes an agent which is attached to a label so that the presence and/or amount of the agent can be determined by detecting or measuring the detectable signal emitted by the SGC (without having to determine the presence and/or amount of another detectable molecule).

Optionally, the presence and/or amount of a detectable entity can be amplified for greater sensitivity. Optionally, the signal amplification is increased in non-exponential fashion, e.g., the rate of signal amplification does not change depending upon the current amount of the signal present. Optionally, the signal amplification is achieved by more than one round of amplification using the same amplification method. Optionally, the amplification does not involve PCR amplification if the detectable entity comprises a nucleic acid.

The binding site on an analyte includes the region of the analyte to which a binding agent specifically binds and/or at least partially prevents specific binding between the analyte and other binding agents. Binding sites include epitopes of a monoclonal antibody (mAb) and PL sites recognized by a PDZ polypeptide. For example, two antibodies bind to the same or overlapping epitope if one competitively inhibits (blocks) binding of a prototypical antibody defining the competition group to the antigen (an NS1 protein of influenza A or influenza B, in the assays below). That is, a 3-fold or 5-fold excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference). Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other. Conversely, two binding agents have different binding sites on an analyte if the specific binding of one agent to the analyte has no inhibitory effect on the specific binding of the other agent to the analyte.

DETAILED DESCRIPTION OF THE INVENTION

I. General Introduction

The present application in part provides methods for assessing an influenza virus infection, including infection with influenza A and/or influenza B. Existing assays are generally based upon the detection of a single influenza antigen within a sample of interest. The present inventors have found that the amounts of influenza virus antigens such as nonstructural protein 1 ("NS1") and nucleoprotein (NP), as described below, can vary widely in samples from infected subjects. For example, the amounts of NS1 and/or NP can vary between different infected subjects and can also vary within the same infected subject over time. As an example, a sample taken from an infected subject can have higher amounts of NS1 than NP, while another sample taken from the same subject (e.g., at a different timepoint) or taken from a different infected subject can by contrast have higher amounts of NP than NS1. Accordingly, the invention provides a method of assessment of an influenza virus infection in a subject, by determining the amounts of both NS1 and NP in a sample. The amount of NS1 and/or NP can be measured by any method, including those discussed herein.

The "amount" of an analyte such as NS1 or NP need not be a precise, actual or absolute measure of the total amount of analyte present. For example, a relative or comparative estimate of the level or concentration of an analyte can be sufficient. The relative amount can optionally be determined by comparison to the same analyte in a different sample, or by comparison to a different analyte in the same sample, or by comparison to a different analyte in a different sample, or by comparison to a control containing a known amount of the analyte. An amount can be a quantitative or qualitative measurement. A quantitative measurement can be relative or absolute. A qualitative measurement indicates whether or not an analyte is present at a detectable level. An analyte is present at a detectable level if a higher signal (with appropriate allowance for experimental error) is generated in a sample relative to a control in which the analyte is absent. Optionally, the signal from a positive sample is at least about 1.5× higher than background, e.g., about 2×, 5×, 10×, 30×, 10×, 300× or 1000× higher, The observed presence of either NS1 or NP or both indicates that the subject is infected with influenza virus.

The amounts of NS1 and NP can be measured by contacting the sample with a combination of a NS1-binding agent and an NP-binding agent, and measuring the specific binding between the sample and the NS1-binding agent, and the specific binding between the sample and NP-binding agent. The amount of specific binding between the sample and the NS1- (or NP-)binding agent can be indicative of the amount of NS1 (or NP) present in the sample. The presence of a significant amount of NS1 (or NP, or both) in the sample indicates that the subject is infected with influenza virus. Significance can be measured from an increase (with due allowance for experimental error) relative to a suitable control lacking the analyte(s) being measured.

The NS1-binding agent and the NP-binding agent can be contacted with the sample in contact with one another or separately. In the former situation for a solid phase assay, both binding agents can be deposited in the same area of a support. The agents can be deposited from separate solutions or together as mixture. Alternatively, for a liquid assay, the binding agents can be provided as a mixture in solution.

In assays in which the binding agent are kept separate, they can be deposited in different regions of the same support, such as in an array, or on different supports, such as beads. The separated binding agents can be contacted with the sample together (e.g., in an array format) or in separate assays. If separate assays are performed, a sample can be split or two samples can be obtained from the same subject.
Regardless of format, both agents can be contacted with a sample at substantially the same time (e.g., within the same hour, optionally within the same minute).

The measured amount of NS1 or NP in the sample can be compared to the amount of NS1 or NP in a control sample. The control sample can be a negative control lacking the analyte(s) being measured, optionally taken from a subject that is known or believed to be free from an influenza virus infection, e.g., is not showing at least one symptom of infection. As well as or instead of a negative control, comparison can be performed with a positive control, e.g., from a subject known or believed to have an influenza infection. Use of one or more positive controls from different times of infection can be used. For example the control sample can be known or believed to have been taken before 1, 2, 3, 4, 5, 6, 7, 8, 9 or 10 days of infection, or optionally before 2 or 3 weeks of infection. Also for example, the control sample can be known or believed to have been taken at least after 0, 1, 2, 3, 4, 5, 6, 7, 8, 9 or 10 days of infection, or after 2 or 3 weeks of infection. Any combination of such parameters can be used. For example, the control sample can be known or believed to have been taken after at least 1 day and before 3 days; or after 3 days and before 3 weeks of infection. Also for example, the control sample can be known or believed to have been taken after at least 4 days of infection and before 2 weeks. Optionally, the control sample is taken from the same subject, but at a different timepoint (e.g., before, or within 1 or 2 days after, or at least 5 days after, the time at which infection is believed to have begun). Optionally, the control sample contains a known amount of NS1 and/or NP.

Lateral flow provides one convenient format for contacting the control and/or test sample with a binding agent. Such a format uses a detection agent and/or a capture agent. Usually, the detection agent is labeled and in solution and the capture agent is immobilized or immobilizable.

In another format, the test and control samples are immobilized and the samples are contacted with a binding agent in solution form, e.g., a solution of detection agent and/or capture agent. Optionally, the control sample can be contacted with the same solution of binding agent that the test sample is contacted with. For example, any viral proteins in the control sample and test sample can be immobilized onto solid support—for example, the control and test samples can be attached to separate beads or separate areas of a flat surface (e.g., in an array). The optionally-immobilized test and control samples can then be contacted with the same solution of the binding agent.

The test and control sample can be regarded as being contacted with the "same solution" of reagents (e.g., binding agents or SGC substrates) when the samples are contacted with a continuous body of reagent solution in a single vessel, or when the samples are contacted with divided aliquots of the reagent solution in separate vessel irrespective of whether the divided aliquots have been subjected to different processing between collection and analysis. For example, an aliquot of solution can be deposited onto (or into) a solid support or vessel (e.g., onto a membrane, for example as an array, or into a well of a multiwell plate) and evaporated to dryness, before the solid support is contacted to the sample, yet the test and control samples can be regarded as being contacted with the same "solution" of binding agent.

Binding agents can be regarded as being contacted with the same sample, if the binding agents are contacted with a continuous body of sample in a single vessel, or if the binding agents are contacted with divided aliquots of a sample in separate vessel irrespective whether the divided aliquots have been subject to different processing between collection and analysis, or if the binding agents are contacted with separate samples from the same individual collected at about the same time (i.e., within an hour of one another) again irrespective of whether the different samples have been separately processed between collection and analysis.

Contacting the test and/or control sample with the same solution of binding agent allows standardization of results to enable more reliable comparison of the amounts of NS1 and/or NP (e.g., the NS1:NP ratio) in test and control samples. When the sample is contacted with two or more binding agents (e.g., NS1-binding agent and NP-binding agent), the test and control samples are both optionally contacted with the same solution of the first binding agent and the same solution of the second binding agent. For example, the test and control can be contacted with a single co-solution of the first and second binding agents. Optionally, the test and control samples are also exposed to the same solutions of reagents and processed in substantially identical fashion. Optionally, the test and control samples are processed simultaneously.

The assessment of infection can include identifying one or more infected subjects in a population, and/or determining whether a particular subject is infected with influenza virus. Because the claimed methods comprise determining amounts of two "independent" influenza virus antigens (NS1 and NP), each of which individually are present in widely varying amounts within infected subjects, the overall sensitivity and reliability of the assay is increased. A combined NS1 and NP test is also less susceptible to false negatives by antigen mutations. In addition, in assays where a cosolution or mixture of detection agents for NS1 and/or NP is used, the combined signal generated by both reagents in the mixture can be stronger than either one alone. For example, antibodies to NS1 and NP can each be deposited onto two separate areas (e.g., as "stripes" in a lateral-flow assay) such that neither antibody is in contact with each other. Also for example, both antibodies can be deposited onto a single area or overlapping areas, e.g., as a single stripe. When both NS1 and NP antibodies are deposited together onto the same area, the binding of both NS1 and NP present in the sample to that area can generate a stronger signal than binding of NS1 alone or NP alone. Where both NS1 and NP capture agents are deposited in two separate areas, then infected samples in which one antigen is present in detectable amounts but the other antigen is not can also be detected.

As well as or instead of determining whether a subject is infected or not, the present invention provides methods that further characterize the nature of the infection (if present). The present inventors have discovered that the relative amounts of NS1 and NP vary during the progression of an infection. An increased or relatively higher NS1:NP ratio indicates an early stage of infection. Early stage of infection means that the infection began approximately less than one week ago, for example within the last three days, e.g., within the last 48 hours, optionally within the last 24 hours. Optionally, detection of NS1 indicates that the infection began at least about 6 hours ago. NS1 antigen appears early after infection relative to NP. The timing of antigen expression (during viral infection) of the two viral antigens appears to differ: NS1 is expressed very early, whereas NP is expressed later, although there is some overlap in expression.

Accordingly, one can monitor the course of infection and/or determine the stage of the infection by comparing the amounts of NS1 and NP in an infected subject. This information can be put to a wide variety of uses, including determination of the prognosis of an infected subject. Many anti-influenza treatments (e.g., TAMIFLU and Relenza) are more effective at an earlier stage of infection when viral reproduction is intensive (e.g. within 48 hours of infection), so that a higher NS1:NP ratio indicates a greater likelihood that such a treatment will be effective (e.g., in inhibiting the replication or propagation of virus). Conversely, a decreased or relatively lower NS1:NP ratio indicates a late or advanced stage of infection, with a lower chance that such drugs will be effective. Optionally, subjects who are found to be at a later stage of infection can be treated with agents known to have a therapeutic effect at the later stages of infection. Such treatments can include anti-inflammatories and regulators of the immune system, or inhibitors of airway congestion such as disodium cromoglycate. Antioxidants such as superoxide dismutase can also be effective in treating lung edema at late stages of infection.

The present method can be useful in a variety of ways. One can identify subjects at an early stage of infection from a population of infected subjects. Optionally, subjects in early stages of infection can be selectively administered a drug or test agent of interest. Such subjects with an early stage of infection can optionally be segregated or quarantined from a population of subjects, e.g., showing no symptoms of influenza infection. Asymptomatic or symptomatic subjects can also be tested for infection. One can also determine the variation in the efficacy of a treatment of interest at different stages of infection in order to determine an optimal time of administration for the treatment. Similarly, one can assess the efficacy of an anti-influenza drug by comparing the change in NS1:NP ratio over time in treated and untreated subjects. One can also screen one or more test agents for therapeutic efficacy against influenza.

Optionally, the detection assay is a non-PCR assay. A non-PCR assay is one that does not comprise the exponential amplification of a nucleic acid, for example by PCR (polymerase chain reaction) or other procedures. Accordingly, assays such as RT-PCR and immuno-PCR are considered to be PCR assays.

II. Influenza Viruses and their Proteins

The influenza viruses belong to the Orthomyxoviridae family, and are classified into types A, B, and C based upon antigenic differences in their nucleoprotein (NP) and matrix protein (M1). Further subtyping into subtypes and even strains is commonly based upon assessing the type of antigen present in two virion glycoproteins, namely, hemagglutinin (HA; H) and neuraminidase (NA; N). HA and NP are virulence factors mediating attachment of the virion to the surface of host cells. Thus, H5N1, H1N1 and H3N2 are examples of subtypes of influenza A that are of interest. Within each subtype there are hundreds of strains. M1 protein is thought to function in virus assembly and budding, whereas NP functions in RNA replication and transcription. In addition to these virion proteins, two other non-structural, i.e., non-virion, proteins are expressed in virus infected cells which are referred to as non-structural proteins 1 and 2 (NS1; NS2). The non-structural viral protein NS1 has multiple functions including the regulation of splicing and nuclear export of cellular mRNAs and stimulation of translation, as well as the counteracting of host interferon ability.

Optionally, the detection assay involves the detection of an extracellular fraction of the target analyte. For example, the detection assay detects NS1 protein that is present outside cells (e.g., due to the lysis of infected cells). Optionally, the detection assay can comprise or exclude conditions in which any cells present in the sample undergo a significant level of lysis or breaking open.

A. NS1 Protein

Commonly owned patent publications WO2008/048276 and US2007/0161078 set out the general concept that NS1 protein of influenza protein is an abundant protein in subjects infected with influenza viruses and thus useful for detection of these viruses. The NS1 is optionally detected using an anti-NS1 antibody. US2007/0161078 also shows that the NS1 proteins of influenza A contain PL regions which can be readily detected using PDZ domains.

The NS1 protein has been identified and sequenced in influenza viruses and exemplary sequences can be found in the NCBI database. The NS1 proteins from influenza A, B and C do not in general show antigenic cross reactivity. Within a type (e.g., influenza A), there is considerable variation in sequence between subtypes, but some antigenic crossreactivity depending on which antibody is used. The GenBank accession numbers of some exemplary NS1 sequences from influenza type A, subtypes H1N1, H3N2 and H5N1 respectively, are CY003340 (SEQ ID NO:1003 AND SEQ ID NO:1004), CY003324 (SEQ ID NO:1005 AND SEQ ID NO:1006), and DQ266101 (SEQ ID NO:1007 AND SEQ ID NO:1008). The GenBank accession numbers of some exemplary NS1 sequences from influenza type B are AAA43690 (SEQ ID NO: 1009 AND SEQ ID NO: 1010) and BAD29872 (SEQ ID NO:1101 AND SEQ ID NO:1012). The NS1 protein in other strains of influenza either influenza type A, type B or type C, means a protein having the greatest sequence similarity to one of the proteins identified as an NS1 protein in known influenza strains of the same subtype, using as sequence for example, one of the GenBank accession numbers given above.

B. NP Protein

The NP protein has been identified and sequenced in many strains of influenza viruses and exemplary sequences can be found in the NCBI database. The GenBank accession numbers of some exemplary NP sequences from influenza type A for subtype H1N1 are NP 040982 (AAA43467) (SEQ ID NO:1013 AND SEQ ID NO:1014), for subtype H3N2 are AAZ38620 (YP308843) (SEQ ID NO: 1015 AND SEQ ID NO: 1016); and for subtype H5N1 are AY856864 (SEQ ID NO:1017 AND SEQ ID NO:1018) and AAF02400 (SEQ ID NO: 1019 AND SEQ ID NO: 1020). The GenBank accession numbers of some exemplary NP sequences from influenza type B are CAA32437 and ABF21293.

C. HA Protein

The HA protein has been identified and sequenced in many strains of influenza viruses and exemplary sequences can be found in the NCBI database. The GenBank accession numbers of some exemplary HA sequences from influenza type A for subtype H1N1 are AAB29091 and ABD59849, for subtype H3N2 are YP_308839 and AAZ38616; and for subtype H5N1 are AAW72226. The GenBank accession numbers of some exemplary HA sequences from influenza type B are BAA96844.

D. M1 Protein

The M1 protein has been identified and sequenced in many strains of influenza viruses and exemplary sequences can be found in the NCBI database. The GenBank accession numbers of some exemplary M1 sequences from influenza type A for subtype H1N1 are NP_040978.1, for subtype H3N2 are YP_308841.1, or AAZ38617.1; and for subtype H5N1 are AAG48228 and AA052905. The GenBank accession numbers of some exemplary M1 sequences from influenza type B are NP_056664.1.

E. NA Protein

The NA protein, generally associated with late phase of infection, has been identified and sequenced in many strains of influenza viruses and exemplary sequences can be found in the NCBI database. The GenBank accession numbers of some exemplary NA sequences from influenza type A for subtype H1N1 are ABD59870, for subtype H3N2 are ABD59878; and for subtype H5N1 are ABF93438 and AAW72227. The GenBank accession numbers of some exemplary NA sequences from influenza type B are AAB26739.

III. Characterization of Infection, e.g., Combination with Other Assays

The determination of the NS1:NP ratio can be done using any method that helps to characterize the infection further. Where desired, subtype-specific agents can be used, which bind to a specific subtype of influenza virus but not others. The use of one or more of subtype-specific agents can allow simultaneous diagnosis, subtyping and/or prognosis of infection. Any combinations of pan-specific, type-specific, subtype-specific and/or strain-specific detection agents can be used. For example, PDZ proteins can be used to not only detect influenza antigens but also to distinguish between pathogenic and seasonal strains of influenza as well (discussed below).

Similarly, the NS1:NP ratio can be determined in conjunction with any other test or assay that can provide useful information about the infection. For example, assays for other influenza antigens can provide useful information about an influenza infection. The HA and M antigens are useful in typing influenza virus, while the M1 and NP antigens are used for subtyping and identifying strains of influenza virus.

The amount of influenza antigens, such as HA, MA, NS1 and/or NP can be determined by a variety of ways. The amount of genomic RNA or mRNA of influenza virus antigens can be assessed for example by hybridization or amplification (e.g., RT-PCR). The amounts of influenza antigens can be determined by contacting the sample with one or more agents that bind specifically to the antigen and detecting specific binding, for example through the formation of a complex between the antigen and one or more agents that bind specifically to the antigen. As discussed below, binding agents include antibodies and/or PDZ proteins. Any combination of agents can be used. If the sample is contacted with two binding agents specific for two (or more) different strains or subtypes of influenza virus, the different strains or subtypes can be identified by the relative binding of the binding agents. For example, if one binding agent is specific for a protein of influenza A and another for influenza B, then higher binding of the agent specific for influenza A than the agent for influenza B indicates that the influenza virus infection is influenza A. Reference to the relative binding includes situations in which the binding of one of two agents being compared is not detectable above background.

1. Detection and/or Typing of Influenza with PDZ Proteins

As discussed herein, multiple PDZ proteins bind to influenza proteins including NS1 and NP. Such PDZ proteins can be used in addition to or in lieu of antibodies, to determine the amounts of influenza antigens such as HA, MA, NS1 and/or NP in a sample. Any combination of PDZ polypeptides, PDZ polypeptides and/or antibodies that bind to antigens such as NS1 and/or NP can be used. A preferred format uses one or more PDZ domain as a capture reagent and one or more pan-specific antibodies as the detection reagent, although the reverse strategy can also be used. Table 1 indicates various PDZ proteins that can be used to detect influenza antigens.

TABLE 1

PDZ-PL Interactions

| | | | |
|---|---|---|---|
| influenza A HA | 8486126 | RICI (SEQ ID NO: 13), NICI (SEQ ID NO: 11), TICI (SEQ ID NO: 12), | NOS1 (PDZ #1, 2, 3); MINT1 (PDZ #2); ZO-1 (PDZ #2); NSP; RIM2 |
| NS1 | 8486133 | ESEV (SEQ ID NO: 2), RSEV (SEQ ID NO: 7), RSKV (SEQ ID NO: 8), | NeDLG (PDZ #1, 2); LIM-RIL; Vartul (PDZ #1, 2); MAGI2; DLG2 (PDZ #1, 2); MAST2; DLG1 (PDZ #1, 2); P5D95 (PDZ #1, 2, 3); MAGI1; TIP1; MAGI 3; Outer membrane protein; MAST2; Syntrophin gamma 1; MUPP1 (PDZ #13); PTPL1 (PDZ #2); Syntrophin 1 alpha; ERBIN; KIAA1526; AIPC; LIM mystique; TIP43; TIP2 |
| influenza B HA | 8486153 | SICL (SEQ ID NO: 18), | NOS1 (PDZ #1, 2, 3); MINT1 (PDZ #2); ZO-1 (PDZ #2); NSP; RIM2; Novel serine protease; PICK1 |

TABLE 1-continued

| PDZ-PL Interactions | | | |
|---|---|---|---|
| NA | 8486155 | DMAL (SEQ ID NO: 14), DMTL (SEQ ID NO: 15), DIAL (SEQ ID NO: 16) | ZO-1 (PDZ #2); RIM2; Novel serine protease; MINT1 |
| M1 | 8486158 | RKYL (SEQ ID NO: 29), KKYL (SEQ ID NO: 30) | ZO-1 (PDZ #2) RIM2 d1 |
| NP | 8486160 | DLDY (SEQ ID NO: 17) | ZO-1 (PDZ #2) RIM2 d1; syntenin |

PDZ proteins can also be used to type or subtype influenza virus. Thus the claimed methods can include a test for distinguishing between pathogenic and seasonal subtypes of influenza A using. A more detailed description of the specificity of PDZ proteins for different types and subtypes of influenza virus is provided herein. PDZ proteins that binds strongly to NS1 include DLG1 d1,2, LIM mystique d1, DLG2 d3, Vartul d2, PSD95 d1, Magi3 d1, DLG1 d2, PTN-3 d1, DLG2 d1, NeDLG1 d1,2, Magi2 d5, DLG2 d2, and PSD95 d3 CS Bound, Magi2 d1, DLG1 d1, RhoGap10, Outer membrane, Magi1 d4, Tip 43, Tip1 d1, PSD95 d1,2,3, Tip33 d1, and PSD95 d2.

Other PDZ proteins that can be of use in the instant assays are described in PCT/US06/26155, filed Jul. 3, 2006, PCT/US06/41748 filed Oct. 21, 2006, PCT/US08/01123 filed on Jan. 28, 2008, as well as U.S. application Ser. Nos. 11/698,798 filed Jan. 26, 2007; 11/481,411 filed Jul. 3, 2006, each of which is incorporated by reference in its entirety.

NS1 from influenza A can contain a PL sequence that is specifically bound by various PDZ proteins. Table 2 below lists the PL sequences in NS1 of influenza A subtypes H5N1, H1N1 and H3N2. H5N1 is the most clinically relevant subtype of pathogenic strains. H1N1 and H3N2 are the most clinically relevant subtypes of seasonal influenza A. The table also indicates whether various PDZ domains bind to the indicated PL (as detailed further in Table 3). The table can be used to select PDZ domains for differential detection of pathogenic and seasonal subtypes of influenza A. For example, a PSD95 domain is useful for detecting pathogenic subtypes of influenza A, and INADL domain 8 is useful for detecting seasonal subtypes of influenza A. The PSD95 domain can be any of PDZ domains 1, 2, and 3 of PSD95, or combinations thereof. A preferred detection reagent is a protein formed from three copies of domain 2 of PSD95 in a PSD95. That is, three tandem copies interspersed by segments of PSD95 flanking its PDZ domains. In such a protein two of the copies of domain 2 of PSD95 effectively replace natural domains 1 and 3 of PSD95. Another preferred detection reagent is a protein containing PDZ domains 1, 2 and 3 of PSD95.

TABLE 2

| Influenza A subtypes | PL | PSD-95D2 | PSD95 D1, D2, D3 | INADL d8 |
|---|---|---|---|---|
| H5N1 | ESEV (SEQ ID NO: 2) | ++ | ++ | - |
| H1N1 | RSEV (SEQ ID NO: 7) | + | +- | ++ |
| H3N2 | RSKV (SEQ ID NO: 8) | - | - | ++ |

Assay conditions such as buffer and temperature can be used to modulate binding to favor detection of a particular strain or differentiation among the different strains. The symbols used in Table 2 mean as follows: ++ relatively strong binding, + detectable but relatively weak binding, +/− detectable but relatively weak binding or undetectable binding, − undetectable binding. Detectable binding means that the signal from binding is greater in a sample containing NS1 of the indicated subtype relative to a control lacking the NS1 of the indicated subtype to a significant extent taking into account random variation due to experimental error. Undetectable binding means that the signal from binding to a sample containing NS1 of the indicated subtype is within the margin of error from the signal in a control lacking NS1 of the indicated subtype.

TABLE 3

| Pathogen | Protein | C-terminus | PDZ Partners |
|---|---|---|---|
| influenza A | NS1 | ESEV (SEQ ID NO:2) | Outer Membrane; PSD95 (PDZ #2); PSD95 (PDZ #1, 2, 3); DLG1 (PDZ #1); DLG1 (PDZ #1 2); DLG1 (PDZ #2); DLG2 (PDZ #1); DLG2 (PDZ #2); Magi3 (PDZ #); PTN3 (PDZ #1); MAST2 (PDZ #1); NeDLG (PDZ #1, 2); Shank1 d1; Shank2 d1; Shank3 d1; Syntrophini alpha; Syntrophin gamma 1; Magi1 (PDZ #1); Magi1 (PDZ #4); Tip1; PTPL1 (PDZ#1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ#1); KIAA0313; DLG1 (PDZ #2); Syntenin (PDZ #2); Pick1 |
| | NS1 | EPEV (SEQ ID NO: 27) | PSD95 (PDZ #2) PSD95 (PDZ #1, 2, 3) |
| | NS1 | ESEI | Outer Membrane; PSD95 (PDZ #2); PSD95 (PDZ #1, 2, 3); |

TABLE 3-continued

| Pathogen | Protein | C-terminus | PDZ Partners |
|---|---|---|---|
| | | (SEQ ID NO: 3) | NeDLG (PDZ #1,2); DLG2 (PDZ #2); MAST2; PTN3 (PDZ #1) |
| | NS1 | ESKV (SEQ ID NO: 4) | PSD95 (PDZ #2); PSD95 (PDZ #1,2,3); MAST2; Magi3 (PDZ #1); NeDLG (PDZ #1, 2); NumBP (PDZ #4) |

PDZ proteins can optionally be used to detect or quantify NS1 from influenza. NS1 from influenza A contains C-terminal PL sequences such as ESEV (SEQ ID NO:2), RSEV (SEQ ID NO:7), RSKV (SEQ ID NO:8). NS1 has been observed to bind to PDZ proteins such as NeDLG (PDZ #1, 2); LIM-RIL; Vartul (PDZ #1,2); MAGI2; DLG2 (PDZ #1, 2); MAST2; DLG1 (PDZ # 1,2); PSD95 (PDZ # 1,2,3); MAG11; TIP1; MAGI 3; Outer membrane protein; MAST2; Syntrophin gamma 1; MUPP1 (PDZ #13); PTPL1 (PDZ #2); Syntrophin 1 alpha; ERBIN; KIAA1526; AIPC; LIM mystique; TIP43; and TIP2.

Similarly, PDZs that bind to NP from influenza A and/or influenza B can also be useful. For example, the influenza B NP contains the PL motif DLDY (SEQ ID NO:17), bound by ZO-1 (PDZ # 2), RIM2 domain 1; and syntenin. Other PL motifs in NP of influenza include: ACL (A/Duck/Shantou/2143/00(H9N2)), DNA (A/Quail/Hong Kong/G1/97 (H9N2)); ESA (A/Chicken/Hong Kong/NT16/99(H9N2)); LIL (A/swine/Boxte1/144# 15/97(H1N1)); DNA (A/swine/Italy/1509-6/97(H1N1)); ENA (A/Chicken/Hong Kong/KC12/99(H9N2)); DNA (A/Chicken/Hong Kong/739/94 (H9N2)); FDI (A/China); ENA (A/Silkie Chicken/Hong Kong/SF43/99(H9N2)); ENA (A/Chicken/Hong Kong/FY20/99(H9N2)); DNA (A/Chicken/Guangdong/10/00 (H9N2)); ENA (A/Chicken/Hong Kong/SF2/99(H9N2)); STL (A/Swine/Colorado/23619/99(H3N2)); SGA (A/Swine/NorthCarolina/16497/99(H3N2)); ESA (A/Pigeon/Hong Kong/FY6/99(H9N2)).

An exemplary strategy for subtyping influenza A uses a PDZ from PDS95 as shown in Table 2 in combination with an INADL PDZ domain 8. As a general rule, detectable binding of the PSD95 domain without binding of the INADL domain or significantly stronger (i.e., stronger beyond experimental error) binding of the PSD95 domain that that of the INADL domain is an indication that the influenza A subtype is H5N1 (pathogenic). Conversely, detectable binding of the INADL domain to the sample without detectable binding of the PSD95 domain to the sample or significantly stronger binding of the INADL domain to the sample than of the PSD95 to the sample is an indication that the sample contains an influenza A subtype H1N1 or H3N2 (both seasonal influenza). Detectable but weak binding of PSD95 domain 2 to the sample compared with undetectable binding distinguishes H1N1 from H3N2 as indicated in the table. Detectable but relatively weak binding of PSD95 domains 1, 2 and 3 to a sample compared with binding of INADL to the sample is also an indication that the subtype is H1N1.

The use of domain 2 or domains 1, 2 and 3 of PSD95 and/or domain 8 of INADL are preferred as PDZ domain subtyping reagents. Preferred panspecific antibodies for use with a PDZ capture reagent are a pan specific antibody F68 8E6 (or an antibody that competes therewith) or F68 4B2 (or an antibody that competes therewith) as the detection antibody. The same or different panspecific antibody can be used with different PDZ domains in the same assay.

2. Detection of Influenza A with Pan Specific Antibodies

The invention also provides methods of detecting influenza A or influenza B in a manner that does not necessarily distinguish between subtypes of influenza A but can distinguish between influenza A and influenza B (or C). For example, influenza A can be detected using at least two pan specific antibodies to the NS1 protein of influenza A binding to different epitopes. The two panspecific antibodies specifically bind to different epitopes defined numerically as described herein or can be selected from different competition groups. Detection is preferably performed using a sandwich or lateral flow format as described in more detail below. One preferred combination of antibodies for detecting influenza A is F64 3H3 (or antibody that competes therewith) as the capture antibody, and F80 3D5 (or an antibody that competes therewith) as the detection antibody. Another preferred combination is F68 4H9 (or an antibody that competes therewith) as the capture antibody and F68 8E6 (or an antibody that competes therewith) as the detection antibody.

Detecting of influenza A using two panspecific antibodies can be combined with differential detection of influenza A subtypes as described herein. Such an assay indicates both whether influenza A is present, and if so, whether a pathogenic or seasonal subtype is present. The non-subtype-specific and subtype-specific assays can be performed separately or combined. One suitable format for combining the assays is to attach subtype-specific PDZ sequences that bind to NS1 to a solid phase, for use in subtype-specific or non-subtype specific analysis. Binding of a PDZ domain to an NS1 protein in the sample can be detected using a panspecific detection antibody. The panspecific detection antibody used to detect binding of the PDZ domain to the NS1 protein can be the same or different as the panspecific antibody used for non-subtype specific analysis. Thus, in a preferred format, one or more subtype-specific PDZ polypeptides (such as a PSD95 domain and/or an INADL domain 8) and at least one panspecific capture antibody for influenza A are attached to different regions of a support, and a common panspecific detection antibody (binding to a different epitope than the panspecific capture antibody) is used to detect binding of each of the capture reagents to an influenza A NS1 protein if present in the sample.

3. Detection of Influenza B with Pan Specific Antibodies

Influenza B can be detected using first and second panspecific antibodies to the NS1 protein of influenza B in analogous fashion to the assays described for detecting the NS1 protein of influenza A, as described. Such methods are performed using at least two pan specific antibodies to the NS1 protein of influenza B binding to different epitopes. The two panspecific antibodies bind different epitopes defined numerically as described above or can be selected from different competition groups. Detection is preferably performed using a sandwich or lateral flow format as described in more detail below. A preferred combination of antibodies for detection of influenza B uses F89 6B5 (or an antibody that competes therewith) as the capture antibody and F94 3A1 (or an antibody that competes therewith) or F94 1F9 (or an antibody that competes therewith) as the detection or detection antibody. Competition of antibodies is determined by binding to an NS1 protein of influenza B.

4. Combined Detection of Influenza A and Influenza B

Any one or more of the assays described herein can effectively be combined to provide an assay capable of detecting influenza A (non-subtype specific), influenza B (non-subtype specific), influenza A (pathogenic subtype) and influenza A (seasonal subtype). The individual assays can be performed separately or together—for example, one or more individual assays can be combined into a single assay. One suitable format for combining the assays is to attach a panspecific capture antibody for the NS1 protein of influenza A, a panspecific capture antibody for the NS1 protein of influenza B, a PDZ domain for a PL of a pathogenic subtype of influenza A (e.g., a PSD95 domain as discussed above), and a PDZ domain for a PL of a seasonal subtype of influenza A (e.g., an INADL 8 domain) to a single support. The support is contacted with a sample from a subject and at least two panspecific detection antibodies. One detection antibody specifically binds to the NS1 protein of influenza A at an epitope different from the capture antibody to the NS1 protein of influenza A. The other detection antibody specifically binds to the NS1 protein of influenza B at an epitope different from the capture antibody to the NS1 protein of influenza B. The complexes that form indicate whether influenza A and/or B is present, and if influenza A is present whether the influenza A is pathogenic or seasonal.

IV. Binding Agents for Detection of Influenza Antigens

The binding agent can be pan-specific or subtype-specific or strain-specific. For example, the agent optionally binds influenza antigens such as NS1 or NP in a pan-specific manner to influenza A or influenza B or influenza C antigens. For example, a pan specific agent for influenza A specifically binds to NS1 or NP from at least 2, 3 or 5 or all or substantially all known strains of influenza A.

Although pan-specific antibodies are preferred for use in detecting the antigen, any binding agent with specific affinity for the influenza antigen can be used as an antibody surrogate. One especially useful type of binding agent for influenza antigens includes PDZ proteins, discussed below. Other agents includes peptides from randomized phage display libraries screened against antigen from influenza A or B, and aptamers (RNA or DNA molecules selected in vitro from vast populations of random sequence that recognize specific ligands by forming binding pockets). Optionally, a binding agent includes a combination of one or more binding agents described herein. Any combination of binding agents set forth below can be used in detection assays of the invention.

A. Antibodies

Antibodies are a useful type of NS1 and/or NP binding agent. Such antibodies can include antibodies, both intact and binding fragments thereof, such as Fabs and Fvs, which specifically bind to a NS1 and/or NP. Usually the antibody is a monoclonal antibody although polyclonal antibodies can also be used. Examples of antibodies that can be expressed include mouse antibodies, chimeric antibodies, humanized antibodies, veneered antibodies and human antibodies. Typically, fragments compete with the intact antibody from which they were derived for specific binding to an antigen fragment including separate heavy chains, light chains Fab, Fab' F(ab') 2, Fabc, and Fv. Fragments are produced by recombinant DNA techniques, or by enzymatic or chemical separation of intact immunoglobulins. The term "antibody" also includes one or more immunoglobulin chains that are chemically conjugated to other agents, or expressed as fusion proteins with other proteins. The term "antibody" also includes bispecific antibody. Unless otherwise indicated the antibodies described in the present application are mouse antibodies produced from hybridomas.

The agent can be an antibody that specifically binds to NS1 and/or NP. Optionally, the antibody is panspecific for different strains of influenza type A or B. Optionally, the antibody is subtype-specific or monospecific for a single strain of influenza type A or B. Optionally, the contacting step comprises, contacting the patient sample with first and second agents that specifically bind to different epitopes of NS1 and/or NP from influenza virus type A or B, and the first agent is immobilized on a support, and the detecting step detects a sandwich in which the first and second agents are specifically bound to the NS1 and/or NP protein to indicate presence of the virus. Optionally, the first and second agents are first and second antibodies. Optionally, the first and/or second agent is a polyclonal antibody. Optionally, the first and/or second agent is pan-specific for different strains of influenza type A or B.

Although antibodies are preferred for use in detecting the influenza antigen, any binding agent with specific affinity for the influenza antigen can be used as an antibody surrogate. Surrogates includes peptides from randomized phage display libraries screened against the antigen from influenza A or B. Surrogates also include aptamers. Aptamers are RNA or DNA molecules selected in vitro from vast populations of random sequence that recognize specific ligands by forming binding pockets. Aptamers can bind to nucleic acids, proteins, and even entire organisms. Aptamers are different from antibodies, yet they mimic properties of antibodies in a variety of diagnostic formats. Thus, aptamers can be used as a surrogate for panspecific antibodies.

1. NS1 antibodies

Monoclonal antibodies to NS1 of influenza A that can be used to determine the amount of NS1 are disclosed herein. Table 4A list various monoclonal antibodies to NS1 of influenza A, including subtype-specific antibodies and pan-specific antibodies, e.g., pan-specific antibodies for detection of influenza, particularly influenza A. A pan specific antibody for influenza A specifically binds to the NS1 protein from at least 2, 3 or 5 or all or substantially all known strains of influenza A. Likewise a pan specific antibody for influenza B specifically binds to the NS1 protein from at least 2, 3, 5 or all or substantially all known strains of influenza B.

TABLE 4A

| | | H1N1 | | | | | H3N2 | | | | | H5N1A |
|---|---|---|---|---|---|---|---|---|---|---|---|---|
| | | D | S[1] | R | L | Y[1] | D | S[2] | R | L | Y[2] | D |
| F63 | 1C6 | — | — | — | — | | D | — | R | — | | DDDD |
| | 1F9 | DD | — | | | | — | — | | | | DDD |
| | 3C1 | — | — | | | | — | — | | | | DDD |
| | 3G1 | DD | — | | | | D | — | R | — | | DDD |
| | 5E11 | — | — | | | | — | — | | | | DDD |
| | 2C3 | — | — | | | | — | — | | | | DDD |
| F64 | 1A10 | DDDD | — | RRR | LLL | | DDDD | — | RRR | LLL | | DDDD |
| | 1D6 | D | S | R | L | — | DDDD | — | R | — | — | — |
| | 3H3[4] | DDD | SSSS[4] | RRR | LLL | YY | DD | S | RR | — | — | DD |
| | 5B4 | D | S | R | — | — | D | — | — | — | — | — |
| | 6C1 | — | S | R | — | — | — | — | — | — | — | — |
| | 6G12 | D | SSS | RR | LL | — | DD | SS | RRR | LLL | Y | D |
| | 7A8[4] | DD | SSSS[4] | — | — | — | — | — | RR | — | — | — |
| | 7H2 | — | — | R | | — | — | — | — | | | — |
| | 2H6 | DD | SSS | — | | | — | — | — | | | — |
| | 4C4 | D | SS | R | | | — | — | — | | | DDD |
| | 5H10 | DD | SSS | R | | | — | — | — | | | D |
| | 7D1 | DDD | SSS | RRR | — | — | — | — | — | — | — | DDD |
| | 8B3 | D | S | RR | LL | — | — | — | — | L | — | — |
| | 2H9 | DD | SSS | | | | — | — | | | | — |
| | 5G12[4] | DDDD | SSSS[4] | RR | L | | — | — | — | — | | DDD |
| | 7B1 | — | — | | | | — | S | | | | — |
| | 7B5 | DDD | S | RRR | LLL | — | DDDD | — | RR | L | — | DDD |
| | 8C11 | — | — | | | | — | — | | | | — |
| | 5G8 | DDD | tbd | | | | DDD | — | | | | DDD |
| | 6B6 | — | tbd | | | | DDD | SSS | | | | DD |
| | 6H1 | DD | tbd | | | | DD | SS | | | | — |
| F68 | 4B2[4] | DD | SSSS[4] | RRR | LLL | Y | DDD | SSSS | RRR | — | Y | — |
| | 4H9 | DDD | SSS | RRR | LLL | Y | DDDD | SSSS | RR | — | Y | DDD |
| | 5B5 | DDDD | — | RRR | LLL | — | DDDD | — | RRR | LLL | — | DDD |
| | 6B7 | DDDD | S | RRR | LLL | — | DDDD | S | RRR | LL | — | DDDD |
| | 6D6 | DD | SSS | RRR | LLL | Y | DDD | SSS | RR | — | — | — |
| | 1D10 | DDDD | S | RRR | LLL | — | DDDD | S | RR | LL | — | DDDD |
| | 1E5 | DDD | SSS | | | | — | — | | | | — |
| | 3G5 | DDD | S | | | | — | — | | | | — |
| | 6A12 | DDD | S | RRR | LLL | — | DDD | — | RRR | LL | — | DDD |
| | 6C6 | DD | SSS | R | L | | DD | S | — | — | | D |
| | 7B10 | DDD | S | RRR | LLL | — | DDD | — | RRR | LLL | — | DDD |
| | 9A6 | DD | — | | | | — | — | | | | — |
| | 2C3 | — | — | | | | — | — | | | | DDDD |
| | 3H5 | DD | SS | | | | — | — | | | | — |
| | 4C1 | DDDD | SS | RRR | LLL | | — | — | — | — | | — |
| | 2H11 | DDDD | tbd | | | | DDD | — | | | | DDDD |
| | 4D6 | DDDD | tbd | RRR | LLL | | DDDD | SSSS | RRR | LLL | | DDDD |
| | 6A5 | DD | tbd | RRR | LLL | | DD | S | RRR | LL | | D |
| | 8A1 | DDDD | tbd | RRR | LLL | | DDDD | — | RRR | LLL | | DDDD |
| | 8E6 | DDDD | tbd | RRR | LLL | | DDDD | SSSS | RRR | LLL | | DDD |
| | 10A5 | DDDD | tbd | RRR | LLL | | DDDD | SSSS | RRR | LLL | | DDDD |
| F70 | 1A3 | DDD | — | R | L | | DDDD | — | R | L | | DDD |
| | 2C4 | DDDD | S | RRR | LLL | — | DDDD | S | RRR | LLL | — | DDDD |
| | 2G11 | DD | — | RR | L | | DDDD | — | RR | LL | | DDD |
| | 1B2 | — | — | | | | D | S | | | | — |
| | 2D12 | — | S | — | — | — | DD | SSSS | RR | LL | — | D |
| | 2H1 | DD | SS | RR | L | — | DD | SSSS | R | — | — | — |
| | 3A6 | D | — | | | | DDD | — | | | | — |
| | 3C2 | DD | — | RRR | LLL | | DDD | — | RR | LL | | DD |
| | 3F6 | DD | — | RR | — | | DDD | — | RR | — | | D |
| | 3G7 | — | S | — | — | — | D | SSS | — | — | — | — |
| | 4G9 | DD | — | RRR | LLL | | DD | — | RRR | LLL | | D |
| | 4H10 | DD | — | RR | L | | DD | — | RR | LL | | D |
| F72 | 1B11 | DDD | S | RRR | LLL | — | DDD | S | RRR | LLL | — | DD |
| | 1C1 | DDD | — | RRR | LLL | | DDD | — | RRR | LLL | | DD |
| | 1G4 | — | — | | | | — | — | | | | DDD |
| | 1H7 | DD | — | RR | LL | | DD | — | R | LL | | D |
| | 2A8 | DD | — | RRR | LLL | | DDD | — | RRR | LLL | | DD |
| | 3D7 | DDD | S | | | | — | — | | | | DD |
| | 1D9 | DDDD | tbd | | | | DDDD | — | | | | DDDD |
| | 2E7 | DDDD | tbd | RRR | LLL | | DDDD | — | RRR | LLL | | DDDD |
| | 2H7 | DD | tbd | | | | DDDD | S | | | | DDDD |
| F80 | 3A9 | — | tbd | | | | DDD | SSSS | | | | D |
| | 3E7 | DDD | tbd | RRR | LLL | | DDD | SSS | RRR | LLL | | DD |
| | 4E7 | DDD | tbd | RRR | LLL | | DDD | — | RRR | LL | | DD |
| | 5E7 | DDDD | tbd | | | | DDDD | — | | | | DDDD |
| | 7E7 | DDD | tbd | | | | DD | S | | | | DD |
| | 7H4 | DDDD | tbd | RRR | LLL | | DDDD | — | RRR | LLL | | DDDD |
| | 3D5 | DDD | tbd | RRR | LLL | | DDD | S | RRR | LLL | | DDD |

TABLE 4A-continued

| | | | | | | | | | | |
|---|---|---|---|---|---|---|---|---|---|---|
| | 5B12 | DD | tbd | | | DDDD | — | | | DDD |
| | 6G12 | DDDD | tbd | | | DDDD | — | | | DDDD |
| | 7E8 | DDD | tbd | RRR | LLL | DDDD | S | RRR | LLL | DDD |
| | 8F6 | DD | tbd | RR | LL | DDDD | SSS | RRR | LLL | DDD |
| | 9B1 | DD | tbd | RR | LL | DDDD | SSS | RRR | LLL | DDD |
| F81 | 1C12 | D | tbd | R | L | DDD | SSSS | R | L | DD |
| | 1F3 | DDDD | S | RRR | LLL | DD | S | RRR | LLL | DDDD |
| | 2B8 | DD | tbd | | | — | — | | | DDD |
| | 4D5 | DDD | tbd | RRR | ? | DDD | — | RRR | ? | DDD |

| | | H5N1A | | | | H5N1B[1] | | | | | H5N2 |
|---|---|---|---|---|---|---|---|---|---|---|---|
| | | S[3] | R | L | Y[3] | D | S[1] | R | L | Y[1] | D |
| F63 | 1C6 | N/A | RRR | LLL | N/A | — | — | — | — | | |
| | 1F9 | N/A | | | N/A | DDD | — | | | | |
| | 3C1 | N/A | | | N/A | D | — | | | | |
| | 3G1 | N/A | RRR | LLL | N/A | DDD | — | RRR | LLL | | — |
| | 5E11 | N/A | | | N/A | — | — | | | | |
| | 2C3 | N/A | | | N/A | — | — | | | | |
| F64 | 1A10 | N/A | RRR | LLL | N/A | DDDD | — | RRR | LLL | | DDDD |
| | 1D6 | N/A | — | — | N/A | DD | SSSS | R | — | YY | |
| | 3H3[4] | N/A | RR | L | N/A | DDDD | SSSS[4] | RR | LLL | YYYY | DDDD |
| | 5B4 | N/A | — | — | N/A | DD | SSS | R | — | Y | — |
| | 6C1 | N/A | — | — | N/A | D | SSS | — | — | — | |
| | 6G12 | N/A | RRR | LLL | N/A | DDD | SSSS | RRR | LL | YYYY | DDD |
| | 7A8[4] | N/A | — | — | N/A | DDDD | SSSS[4] | RRR | LL | YYYY | DDD |
| | 7H2 | N/A | | | N/A | D | S | RR | — | — | |
| | 2H6 | N/A | | | N/A | DD | SSSS | RR | — | | |
| | 4C4 | N/A | | | N/A | DDD | SSSS | RRR | LL | | |
| | 5H10 | N/A | | | N/A | DDD | SSSS | RRR | LL | | |
| | 7D1 | N/A | RRR | — | N/A | DDDD | SSSS | RRR | LLL | YYYY | |
| | 8B3 | N/A | — | LL | N/A | DD | SSSS | RRR | LLL | YYYY | |
| | 2H9 | N/A | | | N/A | DD | SSSS | | | | |
| | 5G12[4] | N/A | RRR | LL | N/A | DDDD | SSSS[4] | RR | LLL | | |
| | 7B1 | N/A | | | N/A | D | SSS | | | | |
| | 7B5 | N/A | RRR | LLL | N/A | DDD | S | RRR | LLL | — | — |
| | 8C11 | N/A | | | N/A | DD | SSSS | | | | |
| | 5G8 | N/A | | | N/A | DDD | — | | | | — |
| | 6B6 | N/A | | | N/A | DDDD | SSSS | | | | DDD |
| | 6H1 | N/A | | | N/A | DDD | SSSS | | | | DDD |
| F68 | 4B2[4] | N/A | — | — | N/A | D | SSSS[4] | RR | LL | YYYY | — |
| | 4H9 | N/A | R | L | N/A | DDDD | SSSS | R | L | YYYY | DDDD |
| | 5B5 | N/A | RRR | LLL | N/A | DDDD | — | RRR | LLL | — | DDDD |
| | 6B7 | N/A | RRR | LLL | N/A | DDDD | S | RRR | LLL | — | — |
| | 6D6 | N/A | R | L | N/A | DD | SSSS | R | L | YYYY | DDDD |
| | 1D10 | N/A | RRR | LLL | N/A | DDDD | S | RRR | LLL | — | — |
| | 1E5 | N/A | | | N/A | — | — | | | | |
| | 3G5 | N/A | | | N/A | — | SSSS | | | | |
| | 6A12 | N/A | RRR | LLL | N/A | DDD | S | RR | LLL | — | DDD |
| | 6C6 | N/A | — | — | N/A | DDD | SSSS | — | — | | DDD |
| | 7B10 | N/A | RRR | LLL | N/A | DDD | S | RRR | LLL | — | D |
| | 9A6 | N/A | | | N/A | — | — | | | | |
| | 2C3 | N/A | | | N/A | — | — | | | | |
| | 3H5 | N/A | | | N/A | DDD | SSSS | | | | |
| | 4C1 | N/A | — | — | N/A | — | — | — | — | | |
| | 2H11 | N/A | | | N/A | DDDD | — | | | | — |
| | 4D6 | N/A | RRR | LLL | N/A | DDDD | SSSS | RRR | LLL | | DDD |
| | 6A5 | N/A | R | L | N/A | DDD | SS | RRR | LLL | | DDD |
| | 8A1 | N/A | RRR | LLL | N/A | DDDD | — | RRR | LLL | | DDDD |
| | 8E6 | N/A | RR | LLL | N/A | DDDD | SSSS | RRR | LLL | | DDDD |
| | 10A5 | N/A | RRR | LLL | N/A | DDDD | SSSS | RRR | LLL | | DDDD |
| F70 | 1A3 | N/A | R | L | N/A | DDD | — | R | L | | DDDD |
| | 2C4 | N/A | RRR | LLL | N/A | DDDD | S | RRR | LLL | — | DDDD |
| | 2G11 | N/A | RR | LL | N/A | D | — | R | L | | DDD |
| | 1B2 | N/A | | | N/A | — | — | | | | |
| | 2D12 | N/A | RR | LL | N/A | DDD | SSSS | R | L | YY | — |
| | 2H1 | N/A | — | — | N/A | DDD | SSSS | — | — | YY | — |
| | 3A6 | N/A | | | N/A | D | — | | | | |
| | 3C2 | N/A | RRR | LLL | N/A | DDD | — | RRR | LLL | | — |
| | 3F6 | N/A | RR | — | N/A | D | — | — | — | | DDDD |
| | 3G7 | N/A | — | — | N/A | DDD | SSSS | — | — | Y | — |
| | 4G9 | N/A | RRR | LLL | N/A | DD | — | RRR | LLL | | DDDD |
| | 4H10 | N/A | RR | LL | N/A | DD | — | — | — | | DDDD |
| F72 | 1B11 | N/A | RRR | LLL | N/A | DDD | SS | RRR | LLL | — | — |
| | 1C1 | N/A | RRR | LLL | N/A | DDD | — | RR | LLL | | DDDD |
| | 1G4 | N/A | | | N/A | D | — | | | | DDD |
| | 1H7 | N/A | R | LLL | N/A | DD | — | — | LL | | DDDD |
| | 2A8 | N/A | RRR | LLL | N/A | DD | — | R | LLL | | DDDD |
| | 3D7 | N/A | | | N/A | DDD | S | | | | — |

TABLE 4A-continued

| | | | | | | | | | | |
|---|---|---|---|---|---|---|---|---|---|---|
| | 1D9 | N/A | | | N/A | DDDD | S | | | — |
| | 2E7 | N/A | RRR | LLL | N/A | DDDD | — | RRR | LLL | DDDD |
| | 2H7 | N/A | | | N/A | DDDD | SS | | | — |
| F80 | 3A9 | N/A | | | N/A | — | — | | | — |
| | 3E7 | N/A | — | — | N/A | DDD | SSSS | RR | LL | DDDD |
| | 4E7 | N/A | RRR | LLL | N/A | DDD | — | RR | LLL | DDDD |
| | 5E7 | N/A | | | N/A | DDDD | — | | | — |
| | 7E7 | N/A | | | N/A | DDD | S | | | — |
| | 7H4 | N/A | RRR | LLL | N/A | DDDD | — | RRR | LLL | DDDD |
| | 3D5 | N/A | RRR | LLL | N/A | DDDD | SSSS | RRR | LLL | DDDD |
| | 5B12 | N/A | | | N/A | DD | — | | | DD |
| | 6G12 | N/A | | | N/A | DDDD | — | | | D |
| | 7E8 | N/A | RRR | LLL | N/A | DDDD | S | RRR | LLL | DD |
| | 8F6 | N/A | RRR | LLL | N/A | DDDD | SSSS | RR | LL | DDD |
| | 9B1 | N/A | RRR | LLL | N/A | DDD | SSSS | RR | LL | DDD |
| F81 | 1C12 | N/A | R | L | N/A | DD | SSSS | R | L | D |
| | 1F3 | N/A | RRR | LLL | N/A | DDDD | — | RRR | LLL | DD |
| | 2B8 | N/A | | | N/A | DDD | — | | | — |
| | 4D5 | N/A | RRR | ? | N/A | DDD | S | RRR | ? | D |

[1]H1N1 and H5N1B were captured by PSD95 d1, 2, 3 in S2
[2]H3N2 was captured by INADL d8 in S2
[3]H5N1A does not have a PL so will not work in S2
[4]3H3 and 7A8 remain at OD = 4.0 on H5N1B until 80 ng/mL, but weaken to OD = 2.0 on H1N1 at 80 ng/mL
D = direct ELISA titer with MBP-NS1
— = OD450 of 0.0 to 0.4 at 160 ng/mL
D = OD450 of 0.4 to 0.8 at 160 ng/mL
DD = OD450 of 0.8 to 1.2 at 160 ng/mL
DDD = OD450 of 1.2 to 1.6 at 160 ng/mL
DDDD = OD450 of 1.6 and up at 160 ng/mL
Y = S2 ELISA with HA-NS1 lysate
— = OD450 of 0.0 to 0.5 at 160 ng/mL
Y = OD450 of 0.5 to 1.5 at 160 ng/mL
YY = OD450 of 1.5 to 2.5 at 160 ng/mL
YYY = OD450 of 2.5 to 3.5 at 160 ng/mL
YYYY = OD450 of 3.5 and up at 160 ng/mL
S = S2 ELISA titer with MBP-NS1
— = OD450 of 0.0 to 0.5 at 160 ng/mL
S = OD450 of 0.5 to 1.5 at 160 ng/mL
SS = OD450 of 1.5 to 2.5 at 160 ng/mL
SSS = OD450 of 2.5 to 3.5 at 160 ng/mL
SSSS = OD450 of 3.5 and up at 160 ng/mL
R = Western with GST-NS1
— = negative
R = very weakly positive
RR = positive
RRR = strongly positive
L = Western with HA-NS1 lysate
— = negative
L = very weakly positive
LL = positive
LLL = strongly positive Pan-specific antibodies can be defined by reference to either a numerically defined epitope or by a competition group defined by reference to an exemplary antibody. For influenza A, pan specific antibodies preferably specifically bind to an epitope within residues 8-21, 9-20, 29-38 or 45-49 of FIG. 1A (SEQ ID NO:998) or FIG. 2 (SEQ ID NO:1000). The X's in this sequence can be any amino acid but are preferably an amino acid occupying the corresponding position in an NS1 protein from a strain of influenza, and more preferably the consensus amino acid occupying the corresponding position from at least two or preferably all known strains of influenza A. A consensus sequence of influenza A is provided in FIG. 2 (SEQ ID NO: 1000). Some pan-specific antibodies specifically bind to an epitope within residues 9-11 or 13-16 of FIG. 1A (SEQ ID NO:998).

Pan specific antibodies can also be defined by a competition group; the antibodies within a competition group compete with one another for specific binding to the same antigen (i.e., an NS1 protein of influenza A or influenza B). Table 4B shows competition groups of panspecific antibodies binding to an NS1 protein of influenza A.

TABLE 4B

| Anti-Influenza A NS1 competition group | mAb Ref. | | |
|---|---|---|---|
| Group A | F64 3H3 | F68 4H9 | Comment: Partial competition |
| Group B | F68 8E6 | F80 3D5 | Comment: Slight/ partial competition |

Each group is defined by a prototypical antibody (in column 2) with which other antibodies (column 3) in the group compete. Groups A, B and C are preferred. All of these antibodies bind to the NS1 protein from at least strains H5N1, H1N1 and H3N2. The antibodies in different groups do not compete with each other.

Table 5 shows preferred antibodies for use in sandwich detection of the NS1 of H5N1 pathogenic strain of influenza A. In such assays, the detection agent is optionally an antibody preferably from Group A, or alternatively Group C or D. Optionally, the capture agent is a peptide comprising three copies of PSD95 domain 2 or PSD95 domains 1, 2 and 3.

TABLE 5

| Anti-Influenza A H5N1 NS1 competition group | Mab or PDZ Ref. |
|---|---|
| Group A | F68 4B2 F68 8E6 |
| Group B | PSD95(1, 2, 3) |
| Group C | F64 3H3 |

Table 6 shows competition groups for panspecific antibodies binding to the NS1 protein of influenza B.

TABLE 6

| Anti-Influenza B NS1 competiton group | mAb Ref. | | | | |
|---|---|---|---|---|---|
| Group A: F89-1F4 competitors | F89 1F4 | F89 6D11 | F89 6G1 | F89 6H3 | F89 6B5 |
| Group B: F94-3A1 competitors | F94 3A1 | F94 7G2 | | | |
| Group C | F94-1F8, F94-1F9 and F94-5E5 compete w/ each other | | | | |

Table 7 shows pairs of competing capture and detection antibodies. Detection antibodies are shown in the first row of the table and capture antibodies in the first column. Competition is shown with a C.

|  | F89-1F4 | F89-1G8 | F89-4D7 | F89-6B5 | F89-6D11 | F89-6G1 | F89-6H3 | F94-1F8 | F94-1F9 | F94-3A1 | F94-5E5 | F94-7A1 | F94-7G2 |
|---|---|---|---|---|---|---|---|---|---|---|---|---|---|
| F89-1F4 | C | | | C | C | C | C | | | | | | |
| F89-1G8 | | C | | | | | | | | | | | |
| F89-4D7 | | | C | | | | | | | | | | |
| F89-6B5 | C | | | C | | | | | | | | | |
| F89-6D11 | C | | | | C | | | | | | | | |
| F89-6G1 | C | | | | | C | | | | | | | |
| F89-6H3 | C | | | | | | C | | | | | | |
| F94-1F8 | | | | | | | | C | C | | C | | |
| F94-1F9 | | | | | | | | C | C | | C | | |
| F94-3A1 | | | | | | | | | | C | | | C |
| F94-5E5 | | | | | | | | C | C | | C | | |
| F94-7A1 | | | | | | | | | | | | C | |
| F94-7G2 | | | | | | | | | | C | | | C |

Antibodies (including pan-specific antibodies) for influenza type B can also be described by epitope specificity with reference to the consensus sequence of NS1 proteins from influenza B strains shown in FIG. 2 (SEQ ID NO: 1000). Preferred antibodies specifically bind to an epitope occurring within residues 10-28, 40-45, 50-57, 67-74, 84-100, 154-159, 169-173, 185-191, 212-224, 226-240 of FIG. 2, and particularly underlined regions thereof, which indicate residues that are invariable between different strains of influenza type B. Residues included in one of the above regions that are not underlined (i.e., vary between influenza type B strains) can be occupied by the consensus residue occupying that position shown in FIG. 2 or the residue occupying that position in any strain of influenza type B.

Figure 13:
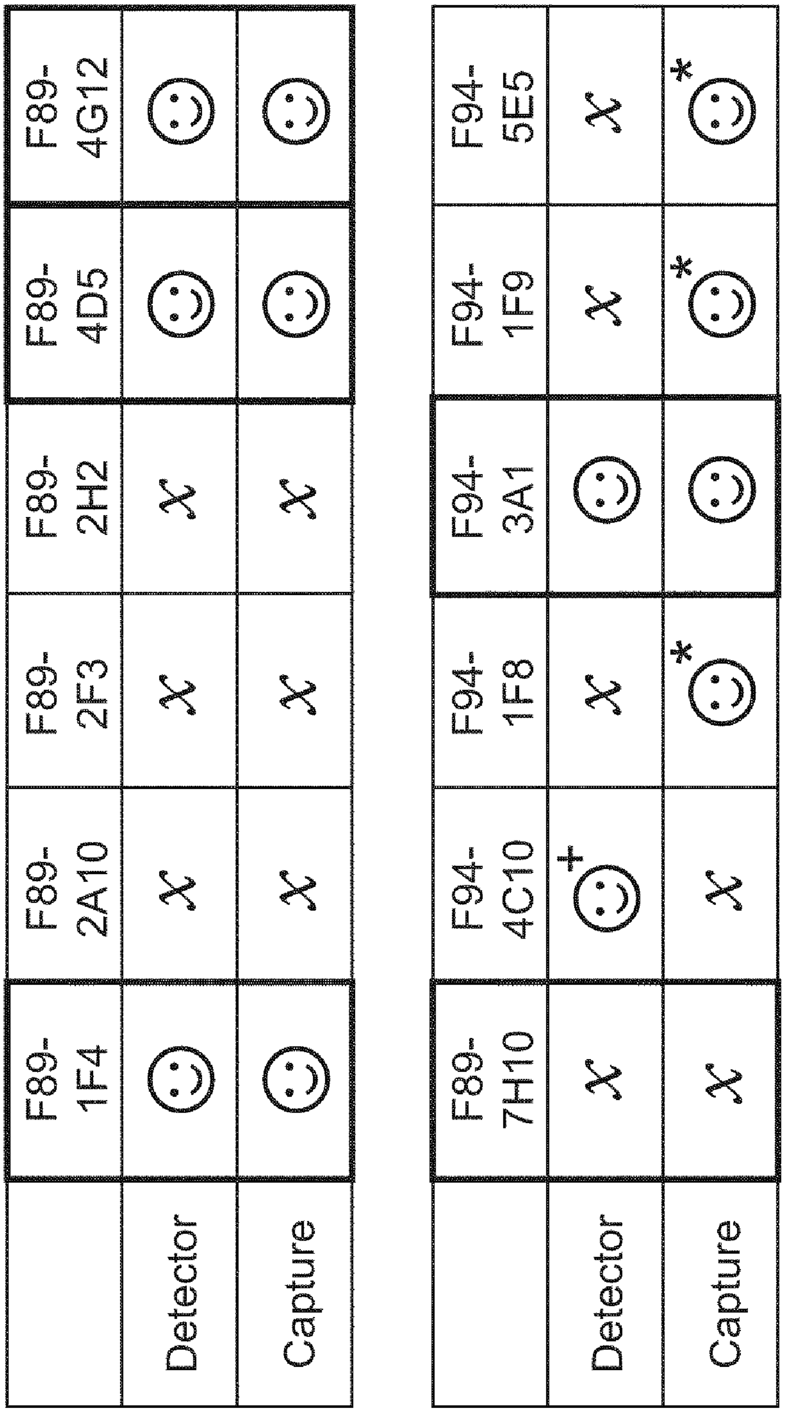
FIG. 13: Chart showing suitable combinations of capture and detection antibody for detection of NS1 from influenza B.

Some preferred combinations of antibodies to NS1 of influenza B for use in sandwich assays are indicated with a happy face in FIG. 13. For influenza A, the capture antibody is optionally F64 3H3, F68 4H9 and the corresponding detection antibody is F68 8E6 or F80 3D5. For influenza B, the capture antibodies is optionally F89 6B5 and the detection antibody is F94 1F9 or F94 3A 1. The detection antibody is optionally gold-conjugated. Antibodies reactive against seasonal and Avian Flu A NS1 can also be used to simultaneously determine pathogenicity.

Antibodies can be made from antigen-containing fragments of the protein by standard procedures according to the type of antibody (see, e.g., Kohler, et al., Nature, 256:495, (1975); and Harlow & Lane, Antibodies, A Laboratory Manual (C.S.H.P., NY, 1988) Queen et al., Proc. Natl. Acad. Sci. USA 86:10029-10033 (1989) and WO 90/07861; Dower et al., WO 91/17271 and McCafferty et al., WO 92/01047 (each of which is incorporated by reference for all purposes).

Immunization can be biased to generate panspecific antibodies by immunizing with multiple strains of influenza A or B, or by immunizing with one strain and boosting with another. Alternatively, one can use a fragment from a highly conserved region of influenza A (e.g., 8-21, 9-20, 29-38 or 45-49 or at least three contiguous amino acids of any of these of SEQ ID NO:998) or B NS1 (e.g., 10-28, 40-45, 50-57, 67-74, 84-100, 154-159, 169-173, 185-191, 212-224, or 226-240 of SEQ ID NO:1001 or subfragments of at least three contiguous amino acids thereof) as the immunogen. Conversely, to generate a monospecific antibody, immunization with NS1 of a single strain, or a fragment of NS1 from a nonconserved region (e.g., a PL region of influenza A) is preferred.

2. NP Antibodies

A variety of monoclonal antibodies against influenza A and influenza B NP are known and/or commercially available. See, e.g., J. A. López, M. Guillen, A. Sánchez-Fauquier, and J. A. Melero, J. Virol. Methods 13:255-264, 1986 (describing 3 anti-NP monoclonal antibodies). The Examples used herein make use of the Capilia immuno-diagnostic assay from Taun, Inc. (Japan).

V. Detection Formats

The invention provides diagnostic capture and detect reagents useful in assay methods for identifying influenza A and/or B viruses in a variety of different types of biological samples. Such formats include immunoprecipitation, Western blotting, ELISA, radioimmunoassay, competitive and immunometric assays. See Harlow & Lane, Antibodies, A Laboratory Manual (CSHP NY, 1988); U.S. Pat. Nos. 3,791, 932; 3,839,153; 3,850,752; 3,879,262; 4,034,074, 3,791,932;

3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Contemplated formats include a lateral flow test (e.g., cassette or dipstick), flow through test, ELISA, western blot, and/or a bead-type array (e.g., wherein NS1 and NP are on different color beads).

Immunometric or sandwich assays are a preferred format (see U.S. Pat. Nos. 4,376,110, 4,486,530, 5,914,241, and 5,965,375). A common type of "sandwich assay" optionally includes the use of a "capture" and a "detection" agent. Optionally, the capture and/or detection agent optionally comprises a combination of one or more binding agents described herein, e.g., an antibody, a PDZ, a population of antibodies and/or a population of PDZs. Optionally, a combination of capture agents for two or more different analytes is used. For example, the assays include capture agents for influenza NS1 and NP. Such assays optionally use one antibody or population of antibodies or a PDZ domain immobilized to a solid phase as a capture agent, and another antibody or population of antibodies or a PDZ domain in solution as detection agent. As discussed above, a combination of a capture PDZ domain and a detection antibody or vice versa is preferred for detection of influenza A. Typically, the detection agent is labeled (e.g., comprises a SGC that emits a detectable signal so that the presence and/or amount of the detection agent can be directly assessed without assessing the presence and/or amount of another detectable molecule). If an antibody population is used, the population typically contains antibodies binding to different epitope specificities within the target antigen. Accordingly, the same population can be used for both capture agent and detector agent. If monoclonal antibodies are used as detection and detection agents, first and second monoclonal antibodies having different binding specificities are used for the solid and solution phase.

Capture and detection agents can be contacted with target antigen in either order or simultaneously. If the capture agent is contacted first, the assay is referred to as being a forward assay. Conversely, if the detection agent is contacted first, the assay is referred to as being a reverse assay. If target is contacted with both capture agent and detection agent simultaneously, the assay is referred to as a simultaneous assay.

In the lateral flow format, the capture agent is optionally deposited (immobilized) on a solid support, e.g., a nitrocellulose membrane, onto a specified area—for example, shaped as a thin stripe, called a "test line." Where multiple capture agents are involved (e.g., NS1 antibody and NP antibody), various capture agent formats can be used. In one such format, the NS1 and NP capture agents were each deposited onto separate areas (two-area format). In the second format, both NS1 and NP capture agents can be deposited onto the same area (the single-area format). An immuno-diagnostic assay detecting two analytes, e.g., the NS1 and NP antigens from influenza A (or B), can show superior results to a test detecting only one of the antigens (either NS1 or NP alone). For example, the results presented herein show that the signal strength for NS1 levels in some cases exceeded NP levels, and vice-versa. Thus, the dual-antigen test could detect influenzavirus samples with overall low viral load in more instances than a single-antigen assay for each antigen separately—e.g., where NS1 levels were detectable and NP levels were not, and vice versa. In addition, where both NS1 and NP levels were so low that neither generated a detectable signal within the detection limit of an assay for either antigen alone, the combined signal strength of both antigens in a single-area format sometimes resulted in a combined detection signal above the detection threshold. Finally, even in cases where NS1 and NP levels were both detectable, the dual antigen test had the additional advantage of allowing the determination of disease stage based on the NS1/NP ratio, which could be determined by comparing the signals generated from NS1 and NP alone (e.g., when using a two-are format, or by using two different labels for NS1 and NP (e.g., when using a single-area format).

When a lateral flow format is used, the results can be read at a predetermined timepoint after a sample is added to the lateral flow device. For example, the results can be read at 15 minute, 30 minutes, 1 hour, 2-8 hours, or 1-3 days.

After contacting the sample with capture and detection antibodies, a sample is incubated for a period that e.g., from about 10 min to about 24 hr, such as about 1 hr. A wash step can then be performed to remove components of the sample not specifically bound to the detection agent. When capture and detection agents are bound in separate steps, a wash can be performed after either or both binding steps. After washing, binding is quantified, for example by detecting SGC associated with the solid phase through binding of labeled detection agent (e.g., antibody) in solution. Usually for a given pair of capture and detection agents and given reaction conditions, a calibration curve is prepared from samples containing known concentrations of target antigen. Concentrations of antigen in samples being tested are then read by interpolation from the calibration curve. Analyte can be measured either from the amount of labeled detection agent in solution bound at equilibrium or by kinetic measurements of bound labeled detection agent in solution at a series of time points before equilibrium is reached. The slope of such a curve is a measure of the concentration of target in a sample.

Competitive assays can also be used. In some methods, target antigen in a sample competes with exogenously supplied labeled target antigen for binding to an antibody or PDZ detection reagent. The amount of labeled target antigen bound to the detection reagent is inversely proportional to the amount of target antigen in the sample. The detection reagent can be immobilized to facilitate separation of the bound complex from the sample prior to detection (heterogeneous assays) or separation may be unnecessary as practiced in homogeneous assay formats. In other methods, the detection reagent is labeled. When the detection reagent is labeled, its binding sites compete for binding to the target antigen in the sample and an exogenously supplied form of the target antigen that can be, for example, the target antigen immobilized on a solid phase. Labeled detection reagent can also be used to detect antibodies in a sample that bind to the same target antigen as the labeled detection reagent in yet another competitive format. In each of the above formats, the detection reagent is present in limiting amounts roughly at the same concentration as the target that is being assayed.

Lateral flow devices are a preferred format. Similar to a home pregnancy test, lateral flow devices work by applying fluid to a test strip that has been treated with specific biologicals. Carried by the liquid sample, phosphors labeled with corresponding biologicals flow through the strip and can be captured as they pass into specific zones. The amount of phosphor signal found on the strip is proportional to the amount of the target analyte.

The lateral flow test can be designed by printing capture agents, for example a combination of anti-NS1 antibodies and anti-NP antibodies, onto a membrane. as either separate lines, or in combination in the same line.

A sample suspected of containing influenza is added to a lateral flow device, the sample is allowed to move by diffusion and a line or colored zone indicates the presence of influenza. The lateral flow typically contains a solid support (for example nitrocellulose membrane) that contains three specific areas: a sample addition area, a capture area containing one or more antibodies to NS1, and a read-out area that contains one or more zones, each zone containing one or more labels. The lateral flow can also include positive and negative controls. Thus, for example a lateral flow device can be used as follows: an influenza A and/or B NS1 protein is separated from other viral and cellular proteins in a biological sample by bringing an aliquot of the biological sample into contact with one end of a test strip, and then allowing the proteins to migrate on the test strip, e.g., by capillary action such as lateral flow. One or more antibodies, and/or aptamers are included as capture and/or detect reagents. Methods and devices for lateral flow separation, detection, and quantification are described by, e.g., U.S. Pat. Nos. 5,569,608; 6,297,020; and 6,403,383 incorporated herein by reference in their entirety. As an example, a test strip can comprise a proximal region for loading the sample (the sample-loading region) and a distal test region containing an antibody to an NS1 protein and buffer reagents and additives suitable for establishing binding interactions between the antibody any influenza B NS1 protein in the migrating biological sample. In another example, the test strip comprises two test regions that contain different antibodies to NS1 from two different subtypes of influenza B i.e., each is capable of specifically interacting with a different influenza B analyte.

The level of influenza B NS1 protein in a sample can be quantified and/or compared to controls. Suitable negative control samples are e.g. obtained from individuals known to be healthy, e.g., individuals known not to have an influenza viral infection. Specificity controls may be collected from individuals having known influenza A or influenza C infection, or individuals infected with viruses other than influenza. Control samples can be from individuals genetically related to the subject being tested, but can also be from genetically unrelated individuals. A suitable negative control sample can also be a sample collected from an individual at an earlier stage of infection, i.e., a time point earlier than the time point at which the test sample is taken. Recombinant NS1 of influenza B can be used as a positive control.

Western blots show that NS1 levels in biological samples are sufficient to allow detection of these antigens in a variety of different possible immunoassay formats. However, should the levels of NS1 in a particular biological sample prove to be limiting for detection in a particular immunoassay format, then, the live virus in a biological sample can be amplified by infecting cells in vitro, i.e., the NS1 protein in the virus-amplified sample should be detectable in about 6 hr to about 12 hr. The yield of NS1 antigen in biological samples and virus-amplified samples can also be improved by inclusion of protease inhibitors and proteasome inhibitors.

VI. Assay Sensitivity

As discussed above, the results of a test sample can be compared to that of a control sample to assess the amounts of NS1 and/or NP present. If so desired, the sensitivity of the detection assays of the invention can be assessed in comparison to the sensitivity of another "control" assay that is known to b sensitive enough to detect even very small amounts of the analyte (e.g., NS1 or NP) or entity of interest (e.g., influenzavirus). The control assay can for example be performed upon the same sample or organism in order to confirm the results of the detection assay. Alternatively, the control assay can be performed on different samples and/or different organisms the frequency of positive outcomes compared. The detection assay and control assay are optionally performed at the same timepoint—for example, both assays can be performed upon different samples taken from the same organism at the same timepoint. Optionally, the detection assay and control assay can be performed at different timepoints—for example, the control assay can be performed at a later timepoint, optionally after the organism displays at least one symptom of influenza.

Examples of useful control assays include isolation and cultivation in embryonated chicken eggs, identification of viral antigen in a commercial immunoassay test, immunodiffusion, hemagglutination and/or hemagglutination inhibition testing to identify the HA and/or NA subtype, RT-PCR detection of viral RNA or immunofluorescence detection of influenza A antigen in cells in respiratory specimens. A preferred control assay comprises RT-PCR for influenzaviral nucleic acid (e.g., genomic RNA within virions or mRNA within cells).

Positive predictive value, abbreviated PPV, can be measured as the percentage of samples that test positive in the instant methods and also test positive in a control assay for influenza virus. Optionally, PPV can be measured as the percentage of samples that test positive in the instant methods and also test positive in a control assay for an avian and/or pathogenic influenza virus. Preferably, the instant method has a PPV greater than about 20%, for example greater than about 40% or 60%, and most preferably greater than about 80%. Optionally, the assay is less sensitive than a PCR assay, for example the assay detects influenza in less than 95% of samples that test positive in an RT-PCR assay, or for example less than 90%, 80% or 70% of such samples.

Negative predictive value, abbreviated NPV, can be measured as the percentage of samples that test negative in both an assay of the invention and a control assay. Preferably, the instant method has an NPV greater than about 85% and most preferably greater than about 90%. The control assay used in determining positive or negative predictive value is usually an assay format among the most sensitive available formats, such as RT-PCR or immuno-PCR.

"True positive" means a sample or subject that is determined to be positive for influenza virus in a control assay. Similarly, "true positive avian influenza A" or "true positive highly pathogenic avian influenza A" indicates that the sample or subject was determined to be positive for avian or highly pathogenic influenza virus in a control assay. Conversely, "true negative" indicates a sample or subject that was determined to be negative for influenza virus in a control assay. Along the same lines, a "false positive" result indicates that the sample or subject was determined to be positive for the presence of an analyte or organism by an assay of the invention but was not determined to be positive in a control assay. Conversely, a "false negative" result optionally indicates that the sample or subject was determined to be negative for the presence of an analyte or organism in an assay of the invention, but was determined to be positive in a control assay.

"Background" can optionally be expressed as a percentage of false-positive or false-negative results.

Optionally, the detection limit of the assays of the present invention is above 0.1 pmoles, e.g., above about 1 pmole, sometimes above 10 pmole, for example about 100 pmoles, optionally above about 1 ng.

VII. Samples

Any biological sample from a subject can be used that contains or is thought might contain a detectable concentration of influenza proteins and preferably of NS1 and/or NP. For example, samples are often obtain from humans having or suspected of or at elevated risk of having influenza (e.g., through contact with others having influenza). Examples of samples that can be used are lung exudates, cell extracts (respiratory, epithelial lining nose), blood, mucous, and nasal swabs, for example. A high concentration of NS1 can be found in throat secretions and also in nasal and lung fluids. Thus, a preferred sample for identification of NS1 is a throat sample or a nasal sample. A nasal sample can includes materials such as fluids and/or tissues from the nasal cavity, the pharynx, nostrils and/or paranasal sinuses. Nasal fluid or tissue can be taken from the respiratory segment and/or the olfactory segment, such as conchae, the olfactory epithelium on the surface of the turbinates and the septum, and/or the vomeronasal organ, olfactory epithelium or olfactory mucosal cell types such as supporting (sustentacular) cells, basal cells, and Bowman's glands. Nasal samples can include lung fluids or tissues include those from the trachea, the primary bronchi and/or lungs, e.g., brochoalveolar fluid.

Binding of NS1 to an antibody occurs in the presence of up to 0.05% SDS, including 0.03% and 0.01%. Therefore, when the nasal, throat or other bodily secretion is not likely to easily be used in a lateral flow format, it can be treated with SDS. Preferably, the amount of SDS added is up to a final concentration of 0.01%, more preferably 0.03% and even more preferably, 0.05%.

VIII. Kits

Kits are provided for carrying out the present methods. The kits include one or more binding agents, typically antibodies or PDZ domains that specifically bind to NS1 of influenza A and/or B. The instant kit optionally contains one or more of the reagents, buffers or additive compositions or reagents disclosed in the examples. The kit can also include a means, such as a device or a system, for removing the influenza viral NS1 from other potential interfering substances in the biological sample. The instant kit can further include, if desired, one or more of various components useful in conducting an assay: e.g., one or more assay containers; one or more control or calibration reagents; one or more solid phase surfaces on which to conduct the assay; or, one or more buffers, additives or detection reagents or antibodies; one or more printed instructions detailing how to use the kit to detect influenza A and/or B, e.g. as package inserts and/or container labels, for indicating the quantities of the respective components that are to be used in performing the assay, as well as, guidelines for assessing the results of the assay. The instant kit can contain components useful for conducting a variety of different types of assay formats, including e.g. test strips, sandwich ELISA, Western blot assays, latex agglutination and the like.

IX. Antibody Arrays

The invention further provides arrays of antibodies and/or PDZ domains immobilized at different regions. Such arrays include a plurality of different antibodies and/or PDZ domains in different regions of the array, each with specificity for influenza proteins such as M1, HA, NA, NS1 or NP of influenza A and/or B. The different antibodies can be selected to have specificity for different subtypes and/or strains of influenza A and/or B. Antibodies that are panspecific for influenza A and/or B NS1 can also be included. Antibodies for influenza A or C NS1 proteins can also be included. Such arrays are useful for detection of influenza A and/or influenza B, and/or influenza C and distinguishing between subtypes and strains of these viruses.

Numerous formats for arrays have been proposed. U.S. Pat. No. 5,922,615 describes a device that utilizes multiple discrete zones of immobilized antibodies on membranes to detect multiple target antigens in an array. U.S. Pat. Nos. 5,458,852, 6,019,944, U.S. Pat. No. 6,143,576 and U.S. patent application Ser. No. 08/902,775 describe diagnostic devices with multiple discrete antibody zones immobilized in a device but not on a membrane for the assay of multiple target antigens. In U.S. Pat. No. 5,981,180, microspheres are again used to immobilize binders (including antibodies) and the microspheres are distinguished from one another without separating them from the sample by detecting the relative amounts of two different fluorophores that are contained in the microspheres in order to identify the specific binder attached to the microsphere.

All publications, and patent filings cited in this specification are herein incorporated by reference as if each individual publication or patent were specifically and individually indicated to be incorporated by reference. Genbank records referenced by Genbank identification (GID) or accession number, particularly any polypeptide sequence, polynucleotide sequences or annotation thereof, are incorporated by reference herein. If more than one version of a sequence has been associated with the same accession number at different times, reference to a deposit number should be construed as applying to the version in existence at the effective filing date of the application. Various changes may be made and equivalents may be substituted without departing from the true spirit and scope of the invention. For example, although the invention has been described primarily for influenza A and influenza B, a similar strategy can be used mutatis mutandis to detect influenza C. Unless otherwise apparent from the context, any feature, step or embodiment can be used in combination with any other feature, step or embodiment.

EXAMPLES

Example 1

NS1 Protein is Expressed in Human Clinical Specimens

Human nasal secretions were examined for the presence and amount of NS1 from Influenza A. Human nasal aspirates were collected and stored in M4 viral transport media (Remel, Inc, Lenexa, Kans.) at −80° C. Stored material was thawed and run on 10% SDS-PAGE. Western blot analysis was performed with monoclonal antibodies to NS1, 3H3 and 1A10 (Arbor Vita Corporation, Sunnyvale, Calif.). The results for six samples are shown in FIG. 4. The results show that NS1 is present in large amounts in nasal secretions.

To investigate the timeline of when NS1 was produced and secreted by cells infected with influenza A virus, MDCK cells were infected with human influenza ProteinPR/8 at a MOI of 0.1. Supernatant as well as cells were collected and lysed in 1% Triton X-100 and subjected to SDS-PAGE and western analysis with monoclonal antibody 3H3 which is pan-reactive to NS1. NS1 was detected in infected cells within 24 hours after infection and detected in the supernatant of infected cells within 48 hours (see FIG. 5). This suggests that a NS1 based diagnostic may be able to detect infection by influenza A within 48 hours and possibly within 24 hours.

Example 2

NS1 Interacts with PDZ in Cells

To verify that NS1 interacts with PDZ proteins in cells, a series of PDZ pull-down experiments were performed. 293

Figure 6:
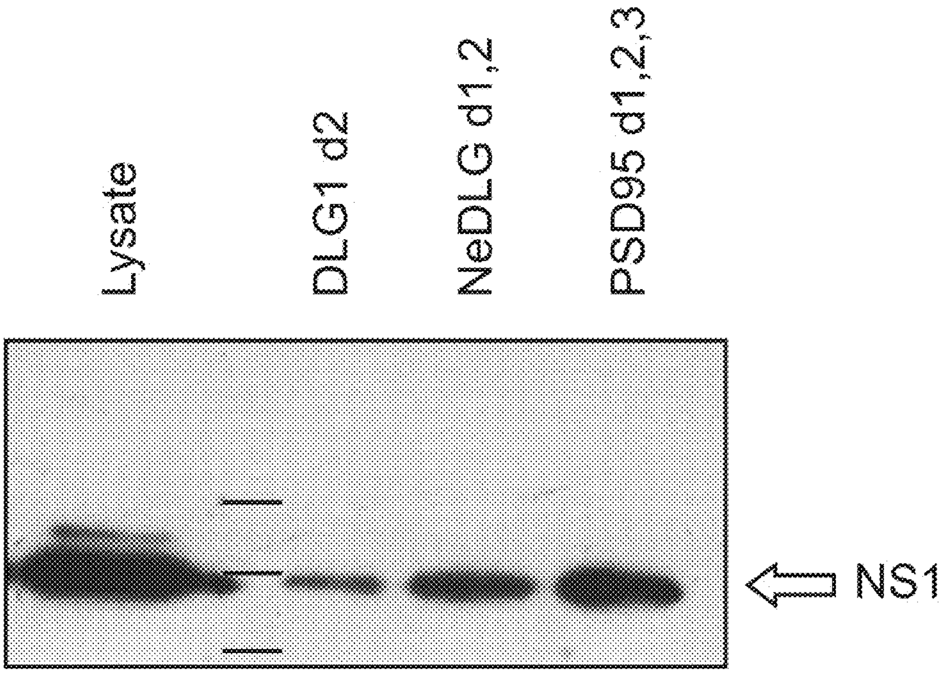
FIG. 6 shows that PDZ interacts with NS1 in cells.
Figure 7:
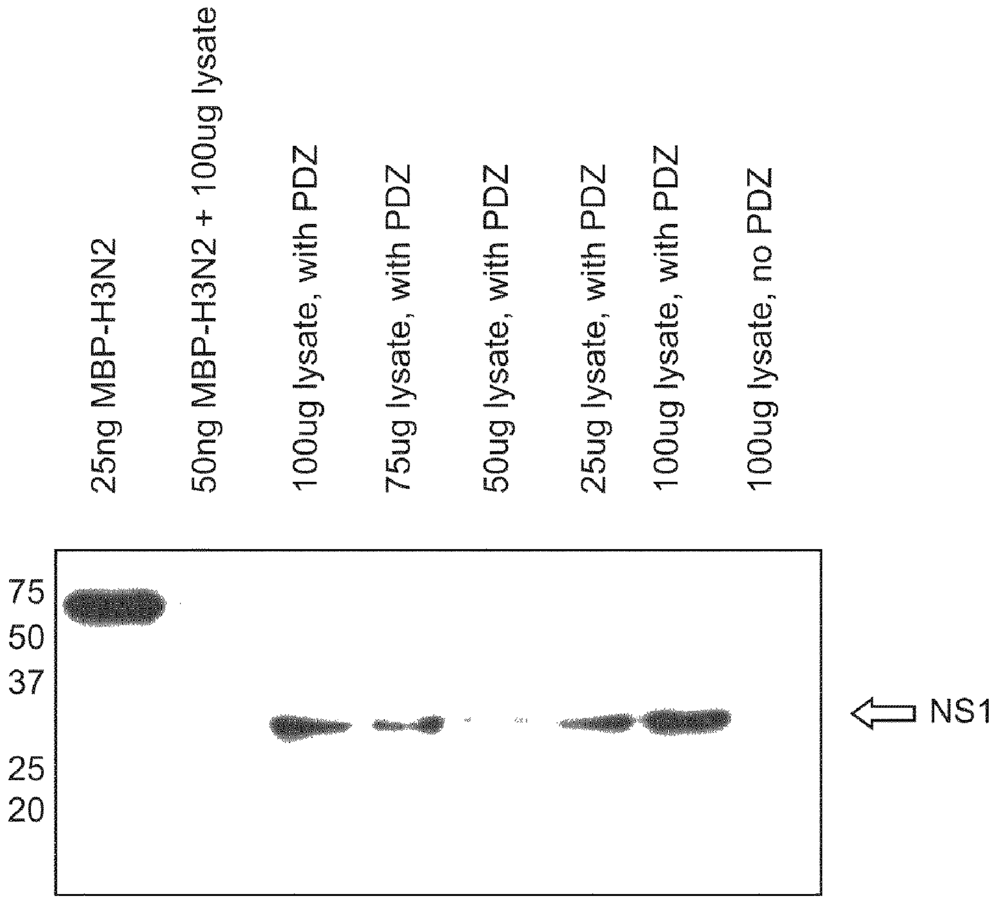
FIG. 7 shows that INADL d8 interacts with H3N2 NS1 in cells.

HEK cells were transfected with plasmids containing HA-NS1-H5N1B or with HA-NS1-H3N2. Lysates were prepared as described herein. Glutathione-sepharose-PDZ beads were prepared (10 ug of DLG1d1,2, 10 ug of NeDLGd1,2, and 10 ug PSD95d1,2,3) and used to pulldown 150 ug of lysate from transfected 293ET cells as shown in FIGS. 6 and 7. Following an overnight incubation at 4° C. and multiple washes with HNTG buffer, a membrane was prepared with the pulldowns. The membrane was probed with F63-3G1 supernatant (1:5). All 3 of the PDZs tested successfully pull-down NS1 from cell expressing HA-H5N1B (see FIG. 6).

Similarly, glutathione-sepharose-PDZ beads were prepared (40 ug of INADLd8) and used to pulldown 150 ug of lysate from 293ET cells transfected with H3N2. Following an overnight incubation at 4° C. and multiple washes with PBS, a western blot was prepared and probed a-HA (1:500) (Roche). INADL d8 successfully pulldown HA-H3N2 NS1 from cell lysate (FIG. 7).

The conclusion is that the NS1 PL is functional within the cell and can interact with PDZ domains as determined by the MATRIX assay.

Example 3

Monoclonal Antibodies to NS1

Monoclonal antibodies were prepared to specifically bind to subtype NS1 proteins (e.g., H5N1), NS1 PL classes (e.g., ESEV (SEQ ID NO:2)) and for pan-specificity (influenza A). The strategy for the generation of monoclonal antibodies to NS1 is as follows:

1. GST and MBP fusion proteins of NS1 were generated. The cloning vectors were obtained from Pharmacia (GST) or New England Biolabs (MBP). The NS1 coding regions were synthesized using overlapping oligonucleotides by DNA 2.0 (Menlo Park, Calif.).
2. Mice were immunized with MBP-NS1 fusion proteins at doses ranging from 10-100 ug per dose in CFA then IFA and PBS.
3. Splenocytes and lymphocytes were harvested 3 days after the last boost with the corresponding GST-NS1 fusion protein and fused with FOX-NY myeloma cells according to Kohler and Milstein (Nature 1975).
4. The hybridomas were screened first with MBP-NS1 in an ELISA. The positive wells were cloned and rescreened with a panel of MBP and GST NS1 and classified into pan-reactive or subtype reactive.
5. Further screenings were done using Western blots to verify the molecular weight of the target protein that is consistent with NS1.
6. An additional screening was performed using a S2 assay format (see Example 4) for compatibility with PDZ capture.
7. Steps 5 and 6 were repeated with eukaryotic expressed NS1 in the form of a cell lysate.
8. The antibodies are checked for compatibility with a lateral flow format described in Example 4.

Figure 20:
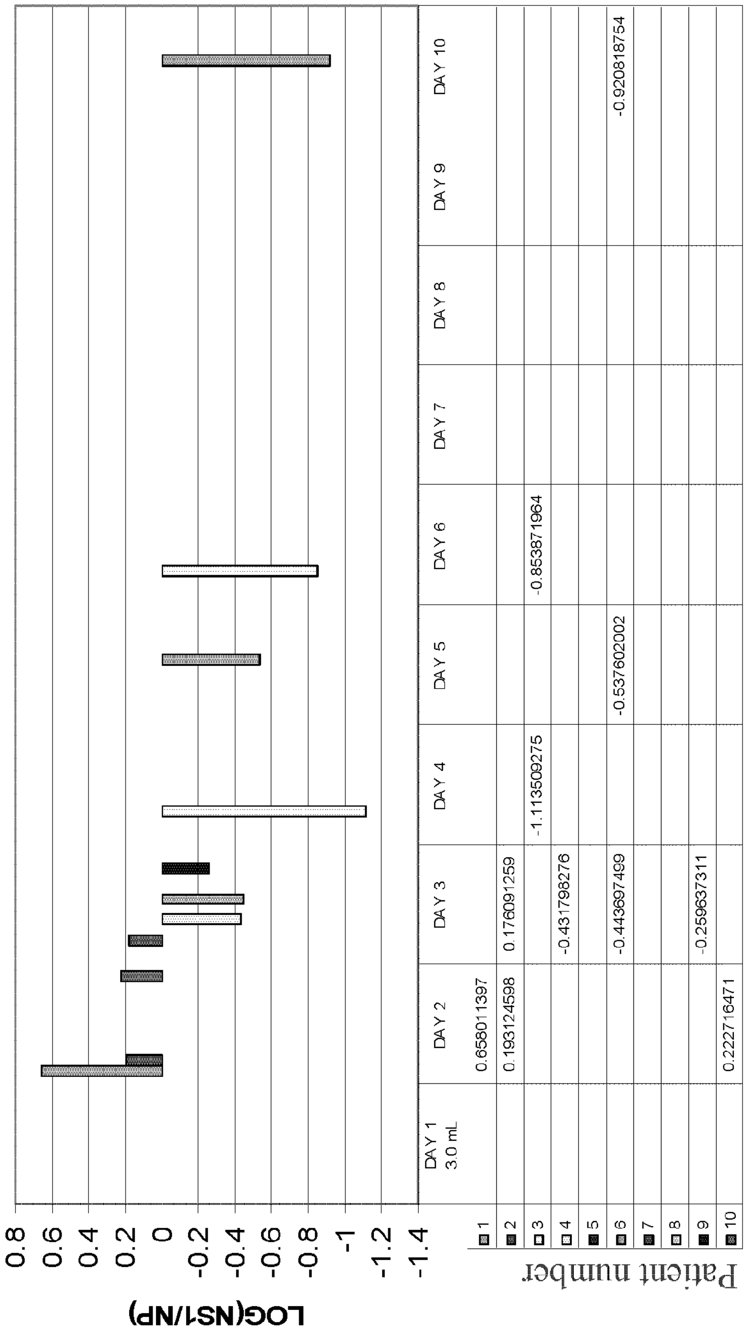
FIG. 20: Log ratio of NS1:NP over course of infection using nasal samples from three patients.

Finally, the antibodies are checked for the ability to detect NS1 in a clinical specimen. FIG. 20 shows the binding profile of a wide variety of monoclonal antibodies to NS1 from various subtypes of influenza A.

Example 4

Detection of NS1 Using a Lateral Flow Format

Figure 8:
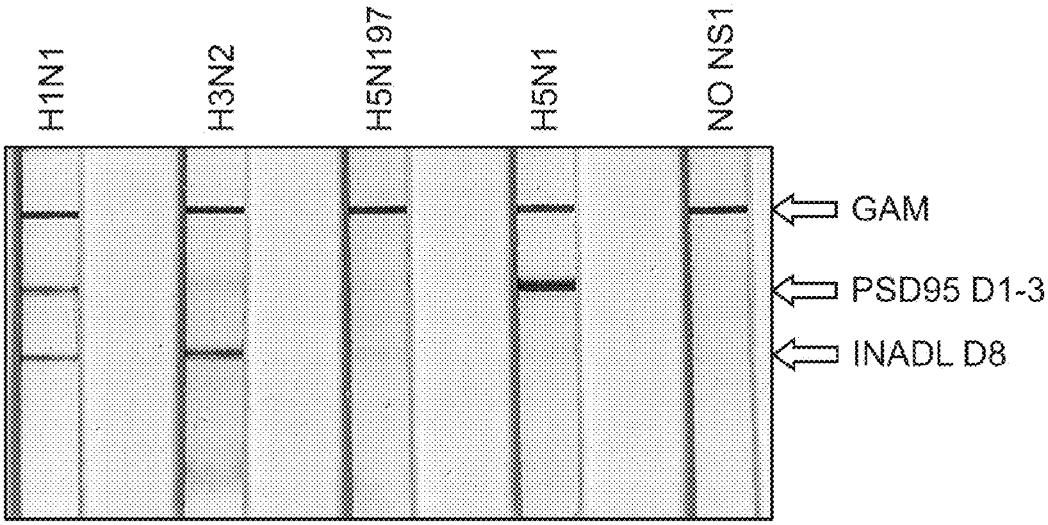
FIG. 8 shows a lateral flow format for an NS1 diagnostic using a PDZ capture agent and monoclonal antibody detect agent AU-4B2.

Examples of lateral flow formats for detection of NS1 are provided in FIGS. 8, 9 and 10A-F. FIG. 8 provides a lateral flow using PDZ capture followed by monoclonal antibody detection. For all cases, recombinant PDZ domain proteins or antibodies were deposited on RF120 Millipore membrane using a striper. For FIG. 8, the PDZ proteins PSD95D1-3, and INADL D8 were deposited at a concentration of 0.5 mg/ml. A control band was also deposited composed of goat anti-mouse antibody (GAM) also at 0.5 mg/ml. NS1 protein was combined with gold conjugated monoclonal anti-NS1 such as 4B2 in 100 ul volume in TBS-T buffer. The NS1 proteins used were from H1N1, H3N2, H5N197, H5N1, and a control lane did not contain NS1. In all cases, human nasal aspirates were diluted and stored in saline or M4, as indicated. The samples were directly mixed with gold conjugated antibody in the amounts described below.

The PDZ striped membrane was inserted into the NS1/anti-NS1 protein solution and flow initiated by capillary action and a wicking pad. NS1 was subtyped based on the pattern of PDZ reactivity; H1N1 binds to both PSD95 and INADL d8; H3N2 binds to INADL d8 only; H5N1 binds to PSD95 only. Influenza A subtyping was performed based on the results of the NS1 lateral flow using reactivity to PDZ and detection with a gold conjugated pan-reactive anti-NS1 monoclonal antibody.

Figure 9:
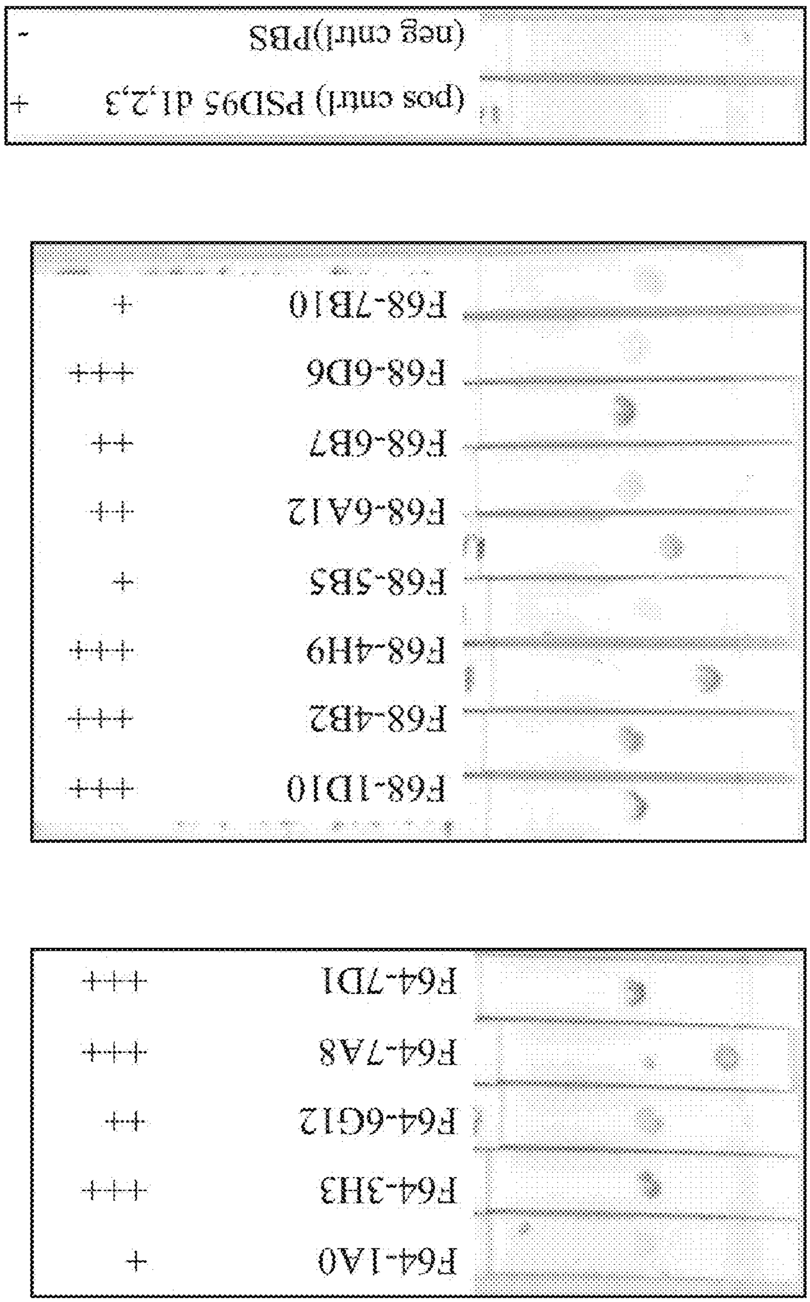
FIG. 9 shows a lateral flow format using a monoclonal antibody capture agent and a monoclonal antibody detect agent AU-4B2.

In FIG. 9, 13 different monoclonal antibodies were deposited on the lateral flow device. The 13 antibodies used were F64-1A0, F64-3H3, F64-6G12, F64-7A8, F64-7D1, F68-1D10, F68-4B2, F68-4H9, F68-6A12, F68-6B7, F68-6D6, F68-7B10. A subtype specific gold conjugated pan-NS1 antibody was added to a sample containing H1N1 influenza virus. The sample was applied to the lateral flow device and the results are shown in FIG. 9. The results show that a pan-specific antibody can be used for the test and the assay identified which antibodies were the best for binding to H1N1. The binding strength is quantified by using the following symbols: (−) for no binding, (+) for weak binding, (+++) for strong binding and (++) for moderate binding.

A lateral flow assay to identify pathogenic Influenza A in a patient sample is produced having pan-specific antibodies deposited on the membrane. The patient sample is admixed with a mixture of gold-labeled antibodies that recognize all NS1 PL's. The sample is applied to the lateral flow test strip and if a pathogenic strain of influenza A is present a line is formed on the strip.

The strip tests were run using the following protocol and materials: strips previously striped with goat anti-mouse/PSD95 d1,2,3/INADL d8; TBST/2% BSA/0.25% Tween 20 buffer; Stocks of NS1 proteins MBP-H1N1, MBP-H3N2, MBP-H5N1A, and MBP-H5N1B "old" (Jon's) fast gold-conjugated F68-4B2 antibody; and Maxisorp ELISA plates. The procedure was performed as follows:

1) Stock NS1 proteins were diluted down in TBST/2% BSA/0.25% Tween 20 to 100 ng/uL (using no less than 5 uL of proteins to perform the dilutions)

2.) The 100 ng/uL dilution was diluted down to 50 ng/uL by adding 10 uL of the protein to 10 uL of TBST/2% BSA/0.25% Tween 20

3.) A stock solution of gold-conjugated antibody in TBST/2% BSA/0.25% Tween 20 buffer was prepared. Four uL of the antibody was added to every 100 uL of the buffer, and enough buffer was prepared for 6 100 uL reactions (which provides extra dead volume).

4.) 98 uL of the antibody/buffer mix was added to separate wells in the ELISA plate 5.) 2 uL of the NS1 dilutions were added to the buffer-containing wells (one NS1 per well)

6.) One well was left with just antibody and buffer to serve as a negative "no NS1" control 7.) The ELISA plate was tapped several times to mix the contents of the wells 8.) The pre-striped strips were added to the wells and observed during development.

After approximately 15 minutes (when all of the liquid had been absorbed, but the strip was not yet dry) the strips were removed from the wells and scanned into the computer.

The test provided in FIGS. 10A and 10B was prepared as follows: a GST-PSD95 d1,2,3 protein was striped onto the membrane at 3 mg/mL for the avian test, or alternatively a mixture of two monoclonal antibodies can be used (1.1 mg/mL F64-3H3 and 0.075 mg/mL F68-4H9 for the pan-flu A test. A second line of 1 mg/mL polyclonal goat anti-mouse antibody was used for the test capture line. The steps are set out below.

1. Prepare cards with a sample membrane and sink pad.

2. Stripe membrane with the PDZ protein and/or antibodies (see above for conc.)

3. Dry the membrane overnight at 56 degrees, then cut the cards into strips 4.26 mm wide.

4. Attach a glass fiber sample pad to the bottom of the strip and place the entire strip inside a cassette for testing.

5. Thaw sample to be tested and add 80 μl of sample to 20 μl of buffer. Pipette up and down several times to mix.

6. Spike 8 μl of the gold-conjugated (Au-)detector mix into the sample/buffer solution. This detector mix is 4 μl of Au—F68-4B2 with 4 μl of Au—F68-3D5. Pipette up and down several times to mix.

7. Add 100 μl of the prepared sample to the sample well on the cassette.

8. Read the test and control lines on the cassette at 15 minutes post-addition of sample. The control line is clearly visible for any test results to be read reliably. Flu A positive samples are noted with (+). Flu A negative samples are noted with (−). The top arrow is pointing to the control and the bottom arrow is pointing to the test.

In both cases the top line is a control line (goat anti-mouse mAb), the second line down is the test line (mixture of F64-3H3 and F68-4H9 mAbs for the Pan-Flu A Test and PSD95 d1,2,3 for the Avian test). 2 ng of H5N1 protein was tested for the Avian test. The bottom circular spot is the sample well. In FIG. 10*a*, both test are positives.

Figure 10A:
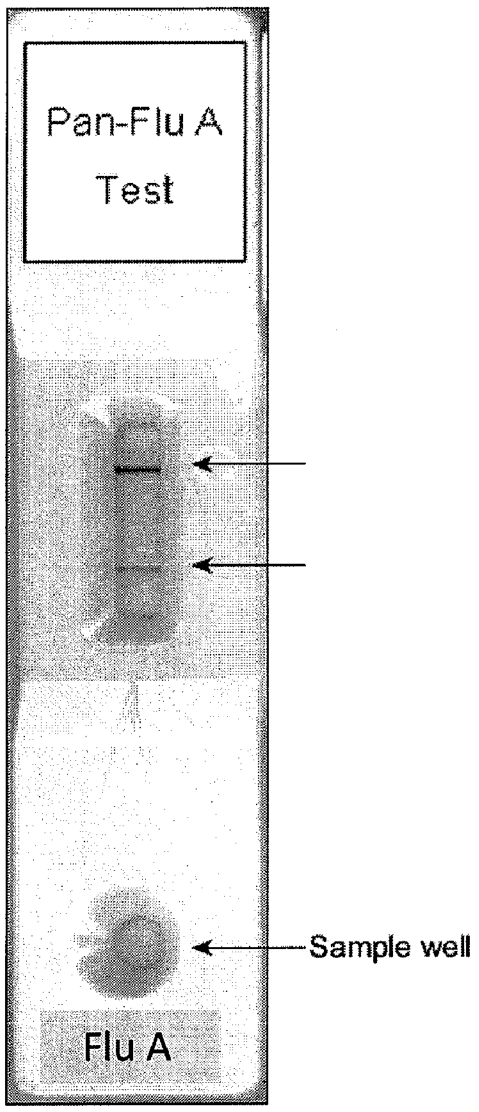
FIG. 10A-F exemplary lateral flow Influenza test formats.
Figure 10B:
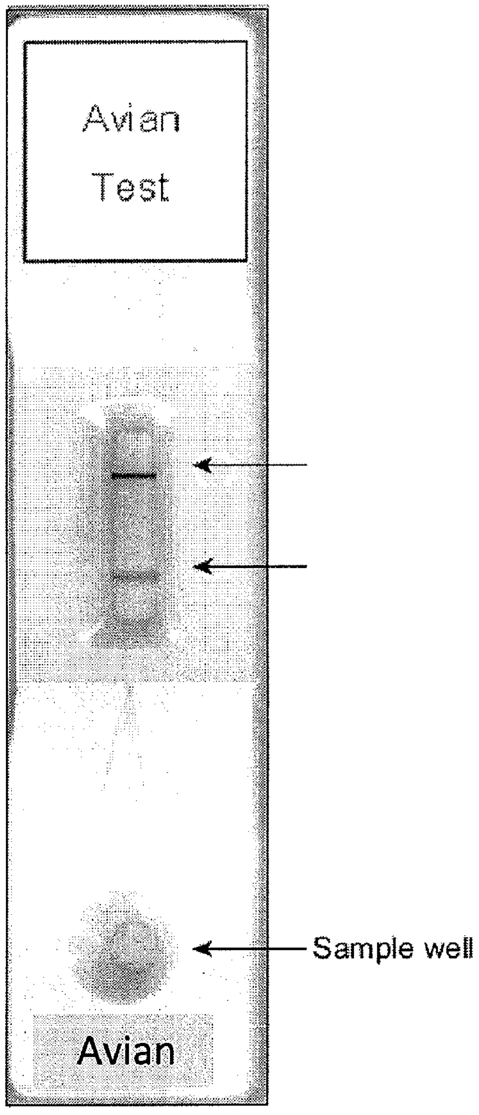
Figure 10C:
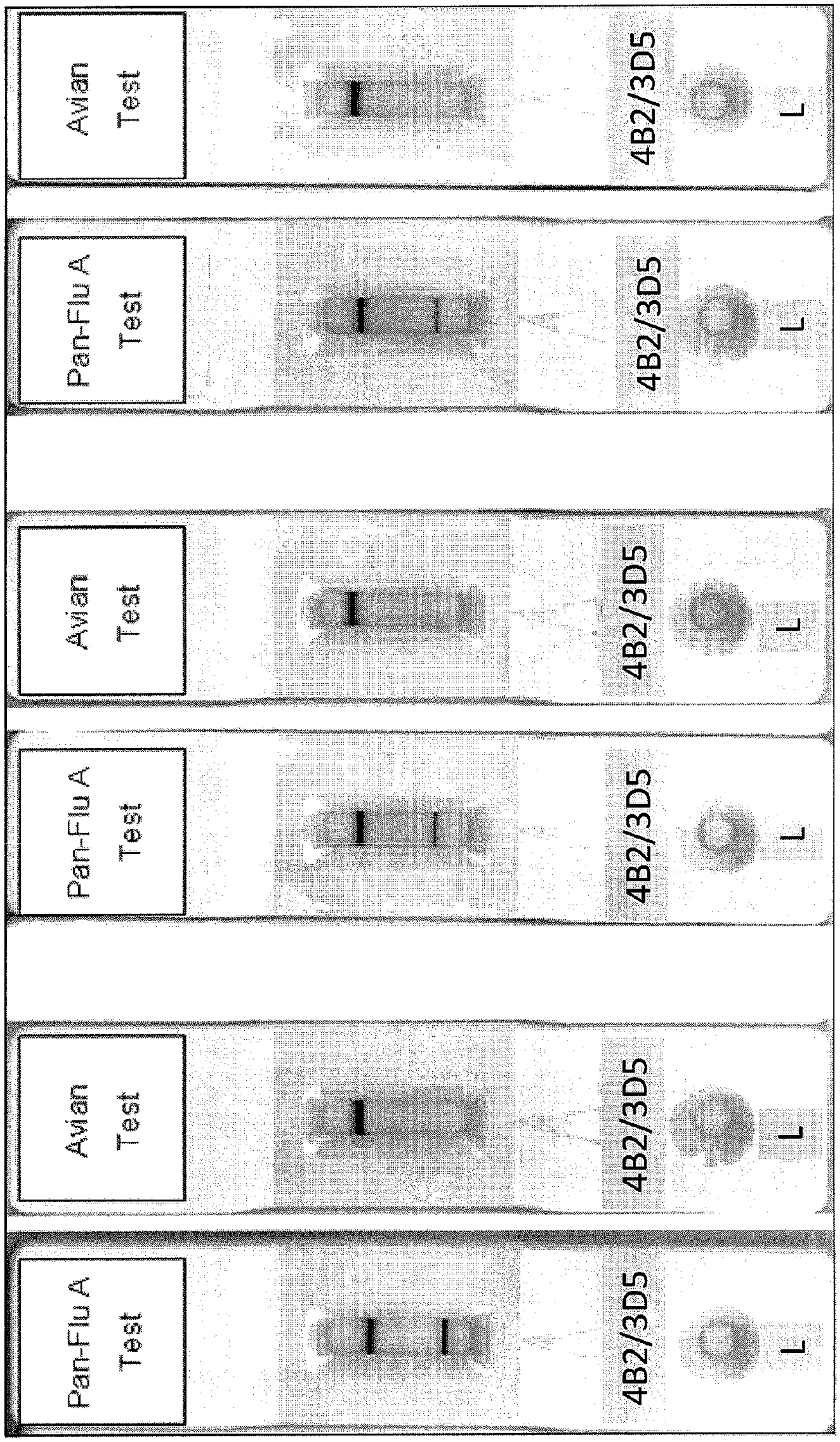
Figure 10D:
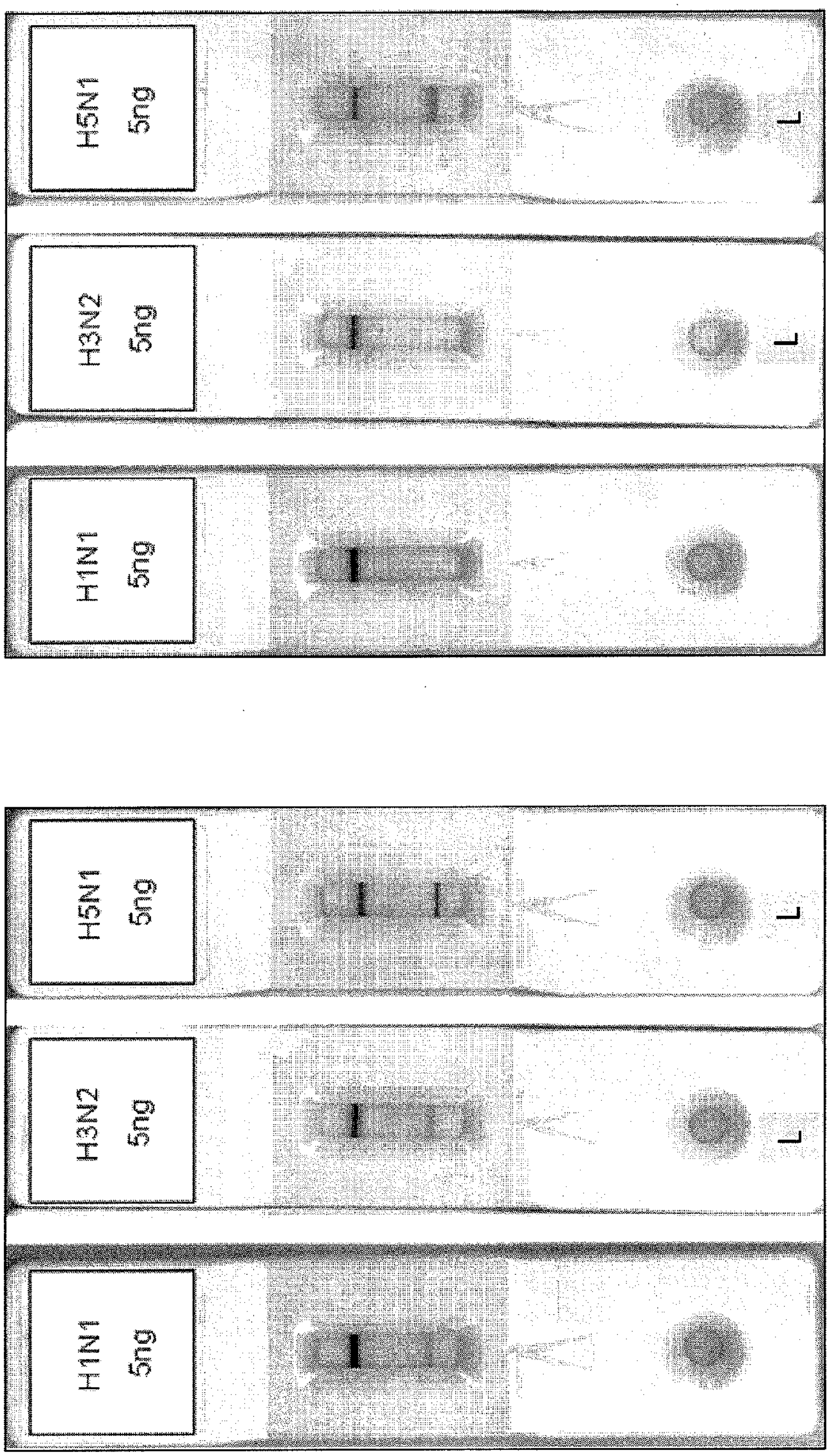

FIG. 10C shows three of twenty human samples that were tested with the format shown in FIGS. 10A and 10B. The samples showed a variety of outcomes, for example, Sample 1 was positive for Flu A, but negative for Avian Flu A (i.e., H5N1) and Sample 14 was negative for both (i.e., FluA and H5N1). FIG. 10*d* shows the same test for H1N1, H3N2, and H5N1 recombinant proteins. The Pan-FluA test was positive for all three. The Avian Flu test was positive for only H5N1.

Figure 10E:
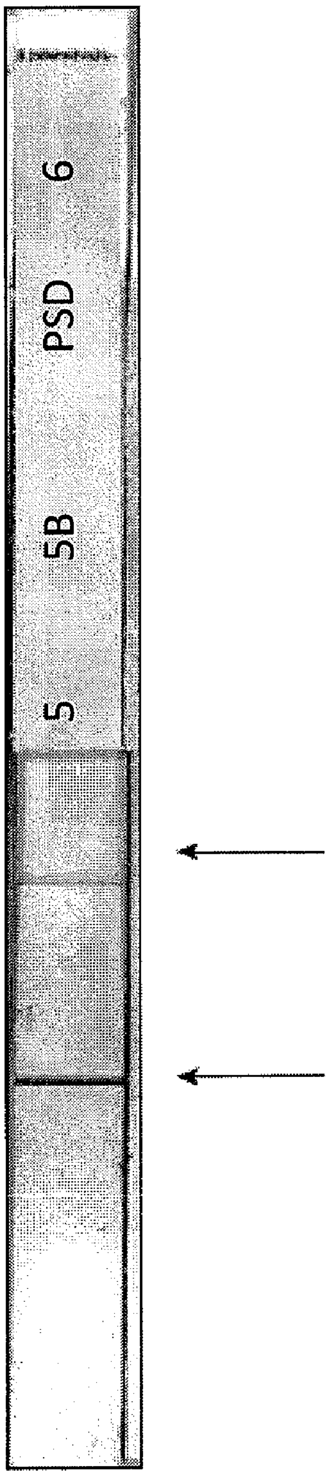

In FIG. 10E, Gold-conjugated PDZs were used as detectors and single or multiple mAbs were used for capture. FIG. 10E had liquid gold added in the form of Au—PSD95 d1,2,3 with a F68-4B2 mAb capture. 1.7 ng of NS1 H5N1 protein tested positively. This was an Avian Flu (i.e., H5N1) specific test.

Figure 10F:
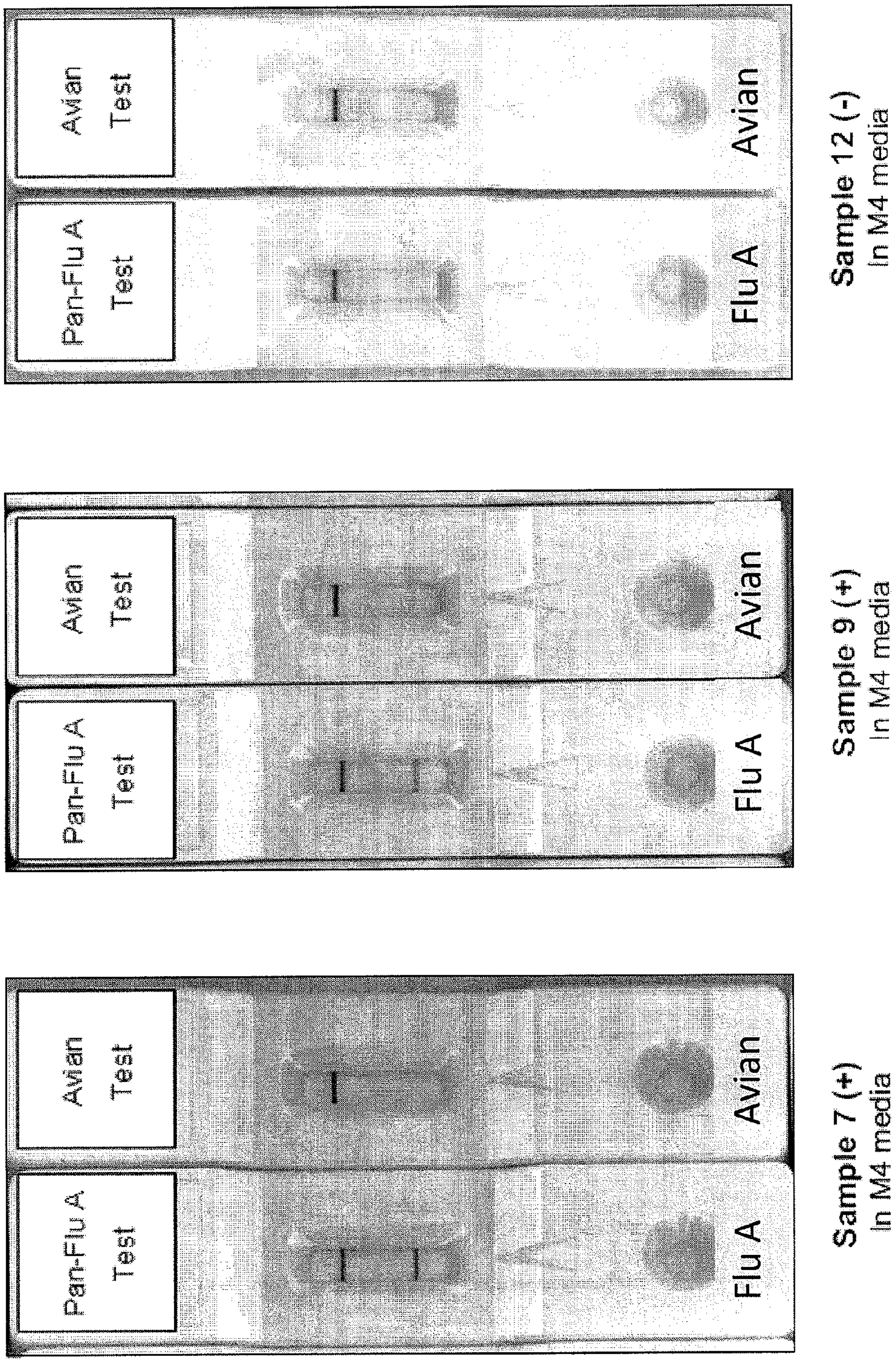

In FIG. 10F, a dried gold method was used. The cards were prepared as in the liquid gold protocol except the sample pad was affixed to the card before striping. When the captures were striped down, the gold-conjugated detector mix (which here also contained a conjugate diluent) was sprayed on the sample pad at the base of the card. The cards were dried, cut, and placed in cassettes as with the liquid test. When the human samples were prepared, they were treated with only the buffer solution before 100 μl was run on the cassette (no additional gold-conjugated detector mix was added). The Flu A positive samples are noted with a (+), the Flu A negative samples are noted with a (−). These cassettes were designed and read in the same way as the liquid gold cassettes. In FIG. 10F, Sample 7 and 9 were positive for both Flu A and Avian flu (i.e., H5N1) and sample 12 was negative for both Flu A and Avian flu (i.e., H5N1).

Example 5

Detection of Influenza B NS1 Using Panspecific Antibodies

Using anti-Influenza B NST1 monoclonal antibodies generated according to the above method, a lateral flow test was developed to detect Influenza B NS1. Monoclonal anti-influenza B NS1 antibodies were deposited on an HF075 Millipore membrane at a concentration of 0.7 mg/ml using a striper. Some examples of antibodies deposited as capture agents are among the following: F89 1F4, F94 3A1, F89 4D5. A control band was also deposited composed of goat anti-mouse antibody (GAM) also at 1 mg/ml. Flu B NS1 protein was combined with gold conjugated monoclonal anti-NS1 such as F94 3A1 (when F94 3A1 is not used as capture) in 100 μl volume of AVC Flu B buffer. The FluB NS1 proteins used were either recombinant AVC ID 522 (B/BA/78 NS1) and AVC ID 523 (B/YM/222/2002) or clinical samples of from patients known to be infected with influenza B.

The anti-Flu B NS1 antibody striped membrane was inserted into the FluB NS1/anti-NS1 protein solution and flow initiated by capillary action and a wicking pad.

Several combinations of anti-Flu B NS1 capture and detection agents were used in several experiments. The following is an example protocol. The strip tests were run using strips previously striped with goat anti-mouse/F89 1F4 anti-Flu B NS1 monoclonal antibody; 90% M4 viral transport media, 10% of a 10× AVC Flu B buffer; Stocks of NS1 proteins MBP-Flu B NS1 (AVC 522 and AVC 523); gold conjugated F94 3A1 antibody; and Maxisorp ELISA plates. The procedure was performed as follows:

1) Stock NS1 proteins were diluted down in 90% M4 viral transport media, 10% of a 10× AVC Flu B buffer 9.) The stock of NS1 was diluted down to 0.5 ng/μL by diluting with 90% M4/10% of a 10× AVC Flu B buffer.

10.) Four μL of the gold-conjugated antibody was added to every 100 μL of the buffer 11.) 98 μL of the antibody/buffer mix was added to separate wells in the ELISA plate 12.) 2 μL of the NS1 dilutions were added to the buffer-containing wells (one NS1 per well) to achieve the desired final protein concentration (example 1 ng Flu B NS1)

13.) One well was left with just antibody and buffer to serve as a negative "no NS1" control 14.) The ELISA plate was tapped several times to mix the contents of the wells 15.) The pre-striped strips were added to the wells and observed during development.

After approximately 15 minutes (when all of the liquid had been absorbed, but the strip was not yet dry) the strips were removed from the wells and scanned into the computer.

Figure 11:
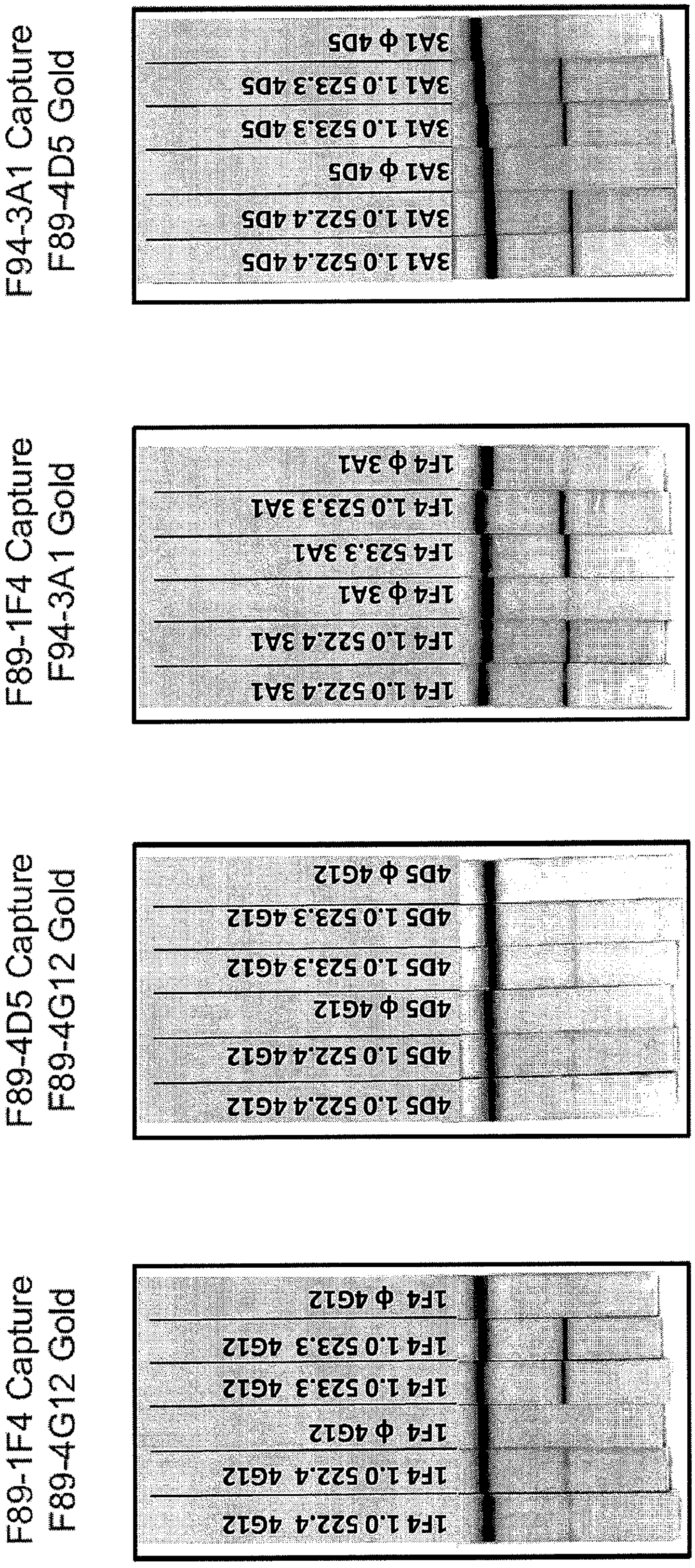
FIG. 11: Detection of recombinant NS1 from two strains of influenza B in a lateral flow assay using various combinations of capture and detection antibody.

FIG. 11 shows results from testing various pairs of monoclonal antibodies as capture and detection reagent on two strains of influenza B, B/BA78 (also known as strain 522), and B/Yagamata\222\2002, also known as strain 523). The four different panels show four combinations of antibodies. In each panel, tracks 3 and 6 are negative controls. Tracks 1 and 2 are recombinant NS1 from strain 522 and tracks 4 and 5 are recombinant NS1 from strain 523. The presence of additional bands in tracks 4 and 5 but not tracks 1 and 2 of the first panel shows that the F89-F4 capture antibody F89-4G12 detection antibody combination detects the 523 strain but does not detect the 522 strains. The other panels can be analyzed in the same way. The results from this experiment and other similar experiments are summarized in FIG. 13. FIG. 13 shows which antibodies can serve as a capture antibody and which as a detection antibody and whether the antibodies are panspecific for both strains of influenza B (522 and 523) or monospecific to 522 or 523. For example, the F89-1F4 antibody can serve as either a capture or detection antibody and is panspecific. F94-4C10 works as a detection antibody but not as a capture antibody and is specific for influenza B 523. F89-1F4 and F94-3A1 are preferred antibodies for use in lateral flow format.

Figure 12:
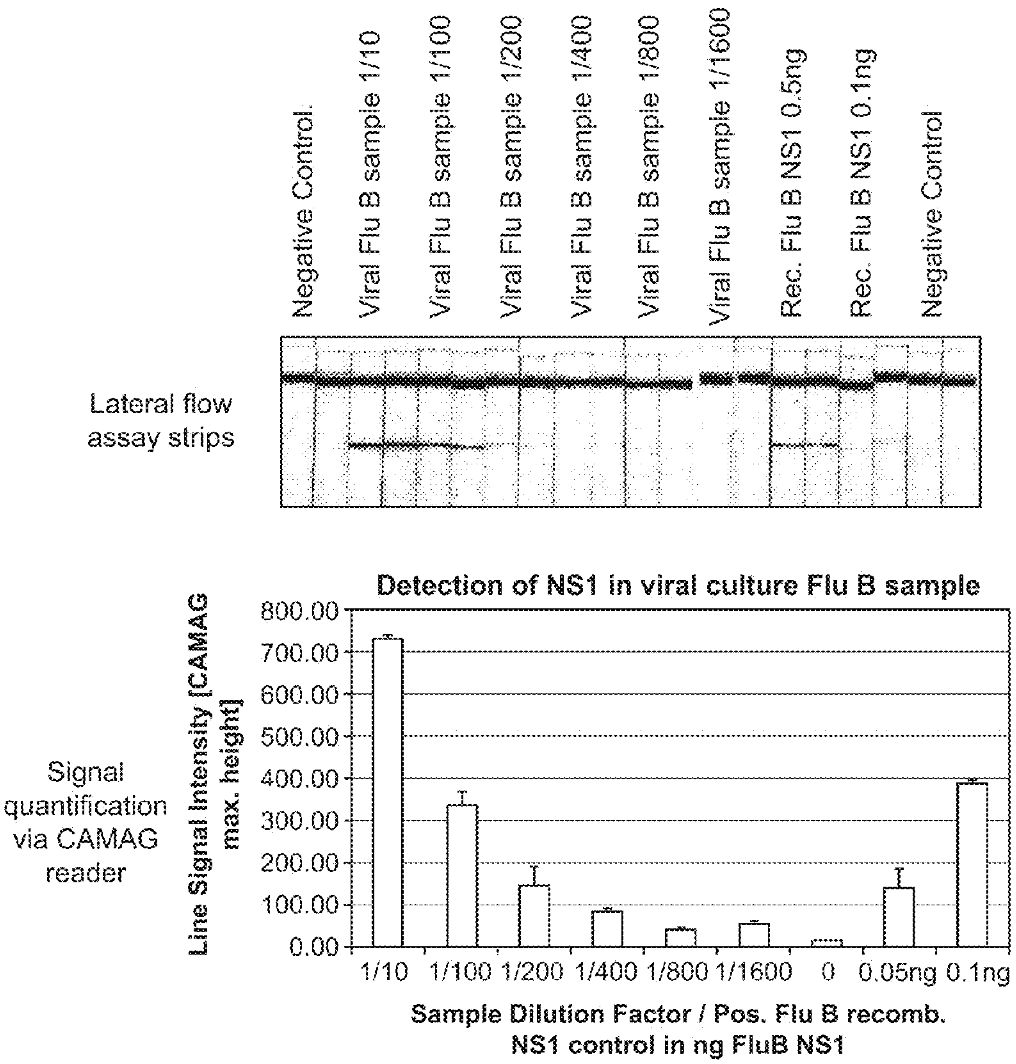
FIG. 12: Detection of NS1 from influenza B in clinical samples.

A lateral flow assay was used to identify Influenza B in a patient sample is produced having pan-specific antibodies deposited on the membrane. The patient sample was admixed with a mixture of gold-labeled antibodies that recognize all Influenza B NS1s. The sample was applied to the lateral flow test strip. Presence of influenza B is present a line is shown by a line formed on the strip. FIG. 12 shows the results from different dilutions of a patient sample compared with positive and negative controls. The upper part of the figure shows the actual appearance of lines indicating presence of influenza B. The lower part of the figure indicates the relative intensity of the bands. Influenza B was easily detectable up to a dilution of at least 400 fold.

Example 6

Figure 15:
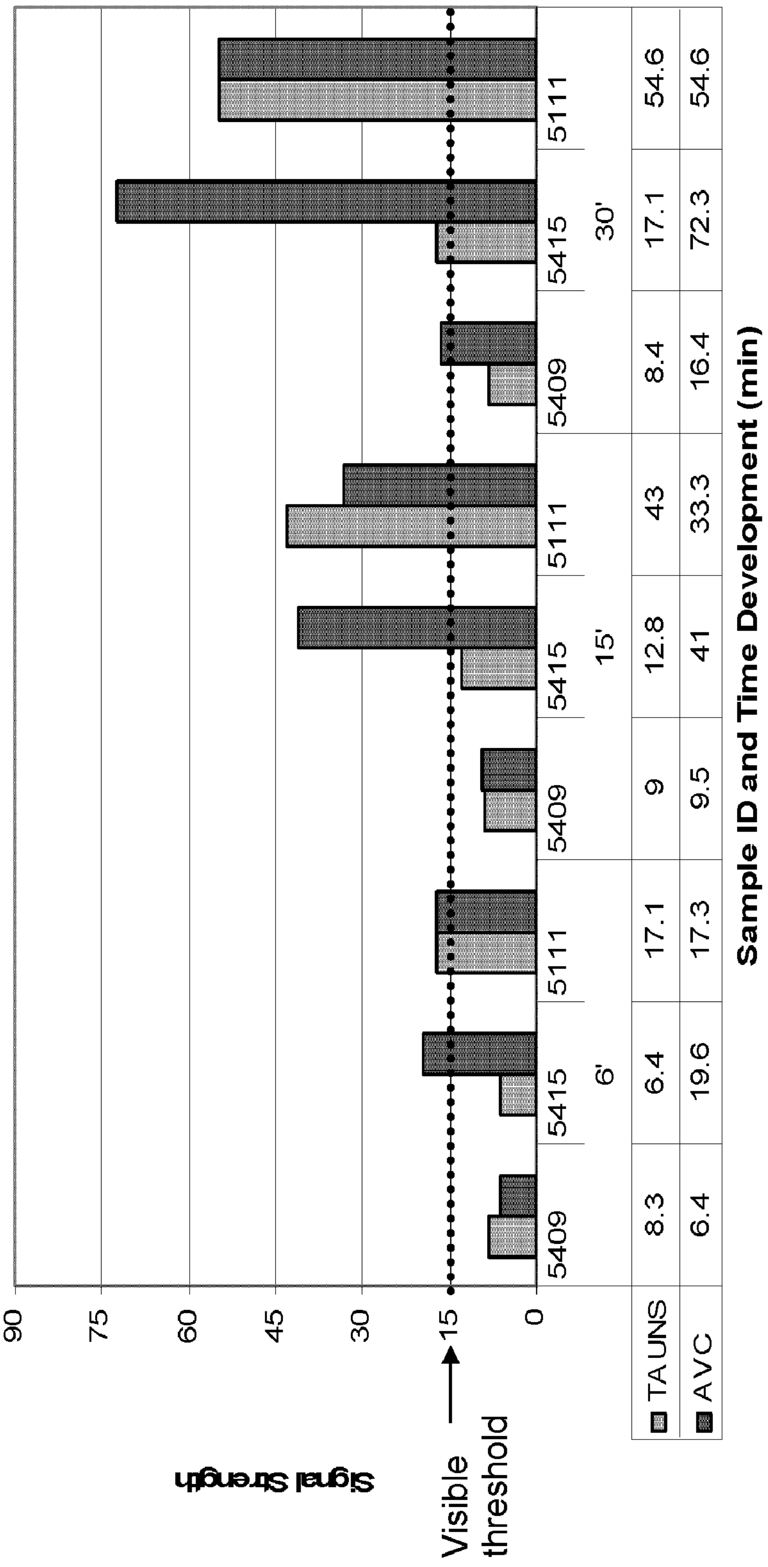
FIG. 15: Diagnostic testing of three diluted clinical samples for NS1 and NP antigens: results after 6, 15 and 30 minutes.

Detection of Influenza a in Clinical Samples Using Antibody-Based Assays for Both NS1 and NP A lateral flow assay was devised as described in Example 4, using a capture antibody that was pan-specific for influenza A NS1 and a second detection antibody that was similarly pan-specific for influenza A NS1 (hereafter called the "AVC Flu A/B" test). To assess the relative sensitivity of the AVC Flu A/B test, three human clinical samples collected in BD viral transport media were diluted down to the limit of detection (LOD) of the AVC Flu A/B test. Specifically, sample 5409 was diluted 2-fold, sample 5415 was diluted 800-fold and sample 5111 was diluted 40-fold. The diluted samples were then tested for the presence and/or levels of NS1 by the AVC Flu A/B test. The same samples were also tested for the presence of the NP antigen of influenza A by a commercially available rapid immunodiagnostic assay (Capiliarm Flu test from Tauns, Inc., Japan—hereafter, the "Tauns test") that uses an antibody for NP from influenza A. The results were read by an electronic reader (CAMAG) after about 6, 15 and 30 minutes. The visible threshold was determined to be 15 AU units. Samples were considered positive if the test readout is >15 AU units. If variations>30% between measurements, the data was discarded. FIG. 15 compares the results of the two assays. The AVC Flu A/B test detected NS1 in 2 of 3 diluted clinical specimens at the 15-minute timepoint, and 3 of 3 samples at 30 minutes. The Tauns test detected NP in only one of the three clinical specimens in 15 minutes, and in two of three samples at 30 minutes.

Figure 17:
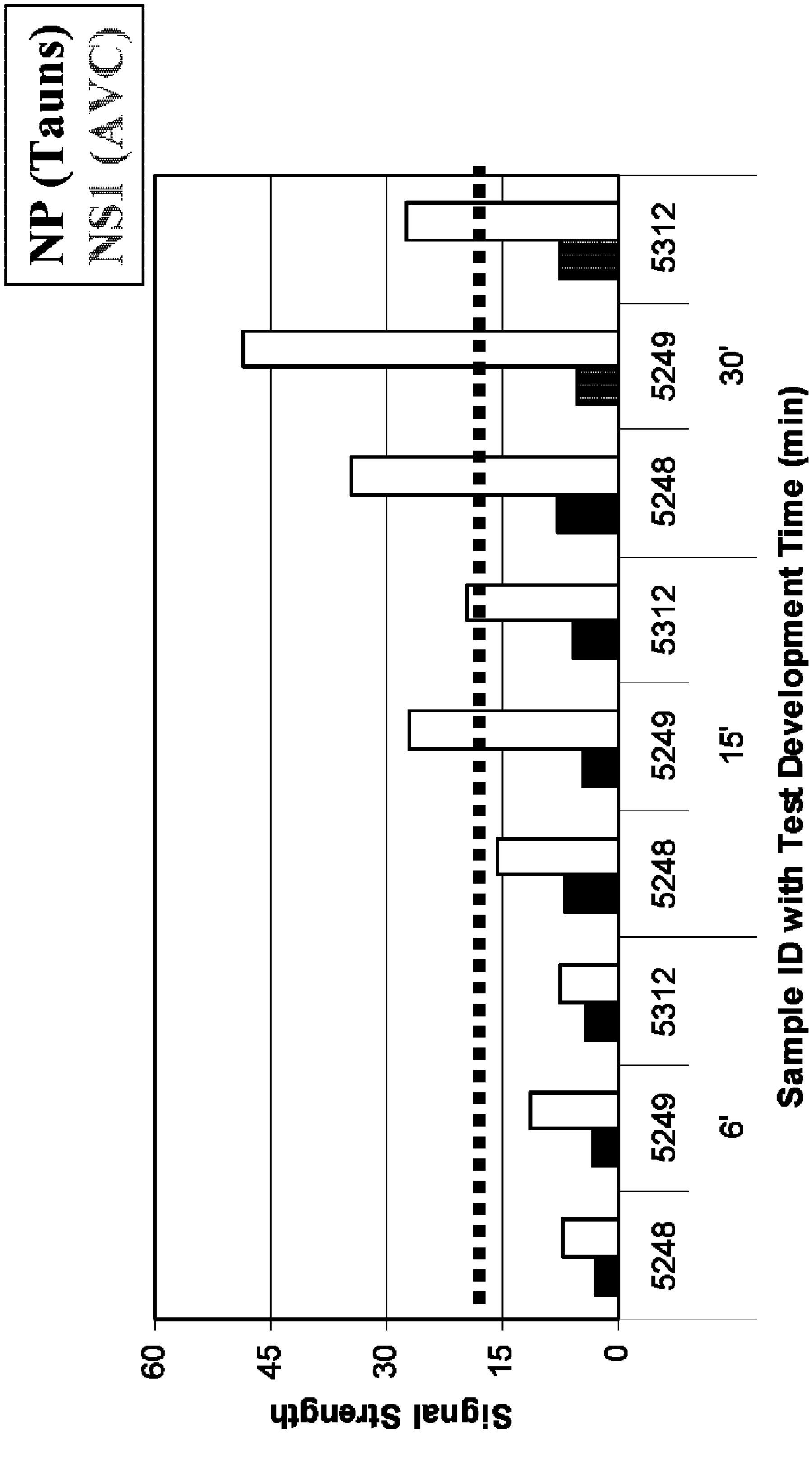
FIG. 17: Diagnostic testing of three diluted clinical samples for NS1 and NP antigens: results after 6, 15 and 30 minutes.

Similar results were also obtained for three new clinical samples. The samples were diluted in BD viral transport medium. Sample 5248 was diluted 80-fold, sample 5249 was diluted 20-fold, and sample 5312 was diluted 80-fold. The final buffer composition used in the three tests were as follows. For the Tauns test (NP, FLU7H101), the final buffer composition was 50% sample in BD VTM and 50% BL Tauns liquid extraction buffer. For the AVC NP test, the final buffer composition was 50% sample in BD VTM and 50% AVC Buffer 1. For the AVC Flu A/B test (NS1) the final buffer composition was 50% sample in BD VTM and 50% AVC Buffer 1. The tests were allowed to develop for about 6, 15 and 30 minutes. As shown in FIG. 17, the AVC Flu A/B detected NS1 in all 3 clinical specimens in 15 minutes, while the Tauns test failed to detect NP in any of the three samples.

Figure 16:
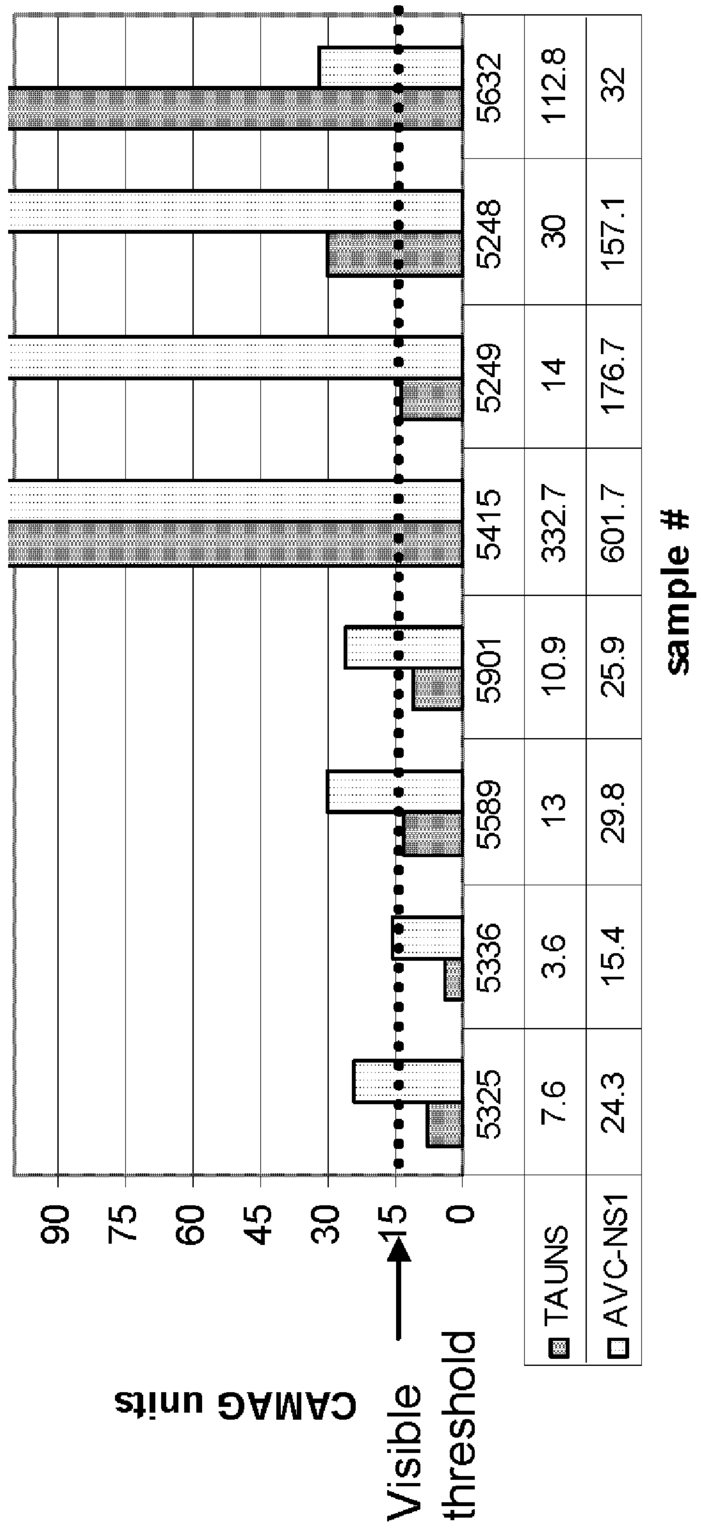
FIG. 16: Diagnostic testing of eight diluted clinical samples for NS1 and NP antigens: results after 15 minutes.

To confirm these results, eight new clinical samples were similarly diluted and tested. As shown in FIG. 16, the AVC Flu A/B test detected NS1 in 8 out of 8 clinical specimens in 15 minutes. The Tauns test detected NP in 3 out of the 8 samples in 15 minutes. The results at 15 and 30 minutes are summarized in Tables 8A and 8B below.

TABLE 8A

| Comparison of influenza A test results at 15 minutes (highly diluted samples) | | | | |
|---|---|---|---|---|
| Sample ID | Dilution factor | Sample Type* | Tauns NP Test | AVC NS1 Test |
| 5325 | 1/800 | A-Positive | − | + |
| 5336 | 1/80 | A-Positive | − | + |
| 5589 | 1/25 | A-Positive | − | + |
| 5901 | 1/20 | A-Positive | − | + |
| 5415 | 1/10 | A-Positive | + | + |
| 5249 | 1/2 | A-Positive | − | + |
| 5248 | 1/5 | A-Positive | + | + |
| 5632 | 1/2 | A-Positive | + | + |
| Neg. Control | | Negative | − | − |
| Concordance with PCR: | | | 38% | 100% |

*A-Positive by PCR

TABLE 8B

| Comparison of influenza A test results at 30 minutes (highly diluted samples) | | | | |
|---|---|---|---|---|
| Sample ID | Dilution factor | Sample Status* | Tauns NP Test | AVC NS1 Test |
| 5325 | 1/800 | A-Positive | − | + |
| 5336 | 1/80 | A-Positive | − | + |
| 5589 | 1/25 | A-Positive | + | + |
| 5901 | 1/20 | A-Positive | + | + |
| 5415 | 1/10 | A-Positive | + | + |
| 5249 | 1/2 | A-Positive | + | + |
| 5248 | 1/5 | A-Positive | + | + |
| 5632 | 1/2 | A-Positive | + | + |
| Neg. Control | | Negative | − | − |
| Concordance with PCR for Flu A+: | | | 75% | 100% |

*A-Positive by PCR

Tables 8C and 8D summarize results at high concentrations.

TABLE 8C

| Comparison of influenza A test results at 15 minutes (concentrated samples) | | | | |
|---|---|---|---|---|
| Sample ID | Dilution factor | Sample Status* | Tauns NP Test | AVC NS1 Test |
| 5409 | 1/2 | A-Positive | − | − |
| 5111 | " | A-Positive | + | + |
| 5581 | " | A-Positive | − | − |
| 5634 | " | A-Positive | − | + |
| 5349 | " | A-Positive | − | + |
| 5411 | " | A-Positive | − | + |
| 5312 | 1/5 | A-Positive | + | + |
| 5336 | " | A-Positive | + | + |
| 5589 | " | A-Positive | + | + |

TABLE 8C-continued

| Comparison of influenza A test results at 15 minutes (concentrated samples) | | | | |
|---|---|---|---|---|
| Sample ID | Dilution factor | Sample Status* | Tauns NP Test | AVC NS1 Test |
| Neg. Control | | Negative | – | – |
| Concordance with PCR for Flu A+: | | | 44% | 77% |

*A-Positive by PCR

TABLE 8D

| Comparison of influenza A test results at 30 minutes (concentrated samples): | | | | |
|---|---|---|---|---|
| Sample ID | Dilution factor | Sample Status* | Tauns NP Test | AVC NS1 Test |
| 5409 | ½ | A-Positive | – | + |
| 5111 | " | A-Positive | + | + |
| 5581 | " | A-Positive | – | + |
| 5634 | " | A-Positive | – | + |
| 5349 | " | A-Positive | – | + |
| 5411 | " | A-Positive | + | + |
| 5312 | ⅕ | A-Positive | + | + |
| 5336 | " | A-Positive | + | + |
| 5589 | " | A-Positive | + | + |
| Neg. Control | | Negative | – | – |
| Concordance with PCR for Flu A+: | | | 55% | 100% |

*A-Positive by PCR

Tables 8E and 8F give a more quantitative summary of signal strengths observed for more concentrated samples. At 15 minutes, 6 of 8 total samples tested positive using the AVC Flu A/B test, while 2 of the 8 samples tested positive using the Tauns test. At 30 minutes, all 8 samples tested positive using the AVC Flu A/B test, while 4 of the 8 samples tested positive using the Tauns test.

TABLE 8E

Sensitivity of both diagnostic tests with less diluted samples

| | | 15' | | 30' | |
|---|---|---|---|---|---|
| sample# | final % | tauns | AVC | tauns | AVC |
| 5409 | 50% | 9 | 9.5 | 8.4 | 16.4 |
| | 50% | 5.3 | 11.5 | 6.5 | 23.1 |
| 5111 | 50% | 459.5 | 439.4 | 544.7 | 567.7 |
| 5249 | 50% | 14 | 176.7 | 21.3 | 282.9 |
| 5581 | 50% | 1.8 | 12.8 | 2.7 | 19.4 |
| | 50% | 7.4 | 8.4 | 3.8 | 17.2 |
| 5632 | 50% | 119.4 | 27.5 | 145.5 | 56 |
| | 50% | 112.8 | 32 | 139.2 | 57.5 |
| 5634 | 50% | 2.4 | 23.4 | 6.7 | 42.3 |
| | 50% | 7.7 | 22.8 | 5.4 | 38.9 |
| 5349 | 50% | 8.9 | 68.4 | 8.3 | 122.8 |
| 5411 | 50% | 13.8 | 60.9 | 17.4 | 113.4 |
| total 8 | | AVC 6/8 positive, tauns 2/8 positive | | AVC 8/8 positive, tauns 4/8 positive | |

TABLE 8F

Overall summary of both diagnostic tests with less diluted samples

| | AVC Flu A/B Test | Tauns Test | NP or NS1 |
|---|---|---|---|
| Read after 15 minutes | | | |
| True Positives | 6 | 2 | 6 |
| False negatives | 2 | 6 | 2 |
| Sensitivity | 75% | 25% | 75% |
| Specificity | 100% | 100% | |
| Read after 30 minutes | | | |
| True Positives | 8 | 4 | 8 |
| False negatives | 0 | 4 | 0 |
| Sensitivity | 100% | 50% | 100% |
| Specificity | 100% | 100% | |

Tables 8G and 8H summarize the test sensitivity (by comparison of signal strengths) for samples diluted to near the limit of detection of the AVC Flu A/B Test.

TABLE 8G

Sensitivity of both diagnostic tests with more diluted samples

| | | 15' | | 30' | |
|---|---|---|---|---|---|
| sample# | final % | tauns | AVC | tauns | AVC |
| 5409 | 50% | 9 | 9.5 | 8.4 | 16.4 |
| | 50% | 5.3 | 11.5 | 6.5 | 23.1 |
| 5415 | 0.13% | 12.8 | 41 | 17.1 | 72.3 |
| 5111 | 2.50% | 43 | 33.3 | 54.6 | 54.6 |
| 5248 | 1.25% | 6.9 | 15.7 | 7.9 | 34.7 |
| 5249 | 5% | 4.5 | 27.1 | 5.2 | 48.6 |
| 5312 | 0.13% | 6 | 19.5 | 7.4 | 27.5 |
| 5581 | 50.00% | 1.8 | 12.8 | 2.7 | 19.4 |
| | 50.00% | 7.4 | 8.4 | 3.8 | 17.2 |
| 5632 | 50.00% | 119.4 | 27.5 | 145.5 | 56 |
| | 50.00% | 112.8 | 32 | 139.2 | 57.5 |
| 5634 | 50.00% | 2.4 | 23.4 | 6.7 | 42.3 |
| | 50.00% | 7.7 | 22.8 | 5.4 | 38.9 |
| 5349 | 12.50% | 6.3 | 12.5 | 4 | 21 |
| 5411 | 12.50% | 3.7 | 7 | 3.1 | 16.1 |
| 5900 | 5% | 53.2 | 23.4 | 72.5 | 44.2 |
| 5325 | 0.13% | 7.6 | 24.3 | 8.7 | 39.4 |
| 5336 | 1.25% | 3.6 | 15.4 | 5 | 24.8 |
| 5589 | 4% | 13 | 29.8 | 19 | 50.2 |
| 5901 | 5% | 10.9 | 25.9 | 17.8 | 42.1 |
| total 16 | | AVC 12/16 positive, tauns 3/16 positive | | AVC 16/16 positive, tauuns 6/16 positive | |

TABLE 8H

Overall summary of both diagnostic tests with more diluted samples

| | AVC Flu A/B Test | Tauns Test | NP or NS1 |
|---|---|---|---|
| Read after 15 minutes | | | |
| True Positives | 12 | 3 | 12 |
| False negatives | 4 | 13 | 4 |
| Sensitivity | 75% | 19% | 75% |
| Specificity | 100% | 100% | |
| Read after 30 minutes | | | |
| True Positives | 16 | 6 | 16 |
| False negatives | 0 | 10 | 0 |
| Sensitivity | 100% | 38% | 100% |
| Specificity | 100% | 100% | |

In summary, the AVC Flu A/B test using pan-specific antibodies for the NS1 antigen was generally more sensitive in detecting influenza A in clinical samples than NP-directed tests such as the Tauns test and the AVC NP test (Tables 8A-H). However, as also seen from Tables 8A-H above, some samples showed detectable amounts of NP, but not NS1, at 15 and/or 30 minutes. Thus, combining an NS1 assay such as the AVC Flu A/B test with an NP assay increases the overall sensitivity and reliability of diagnosis of infection. Tables 8I and 8J compares the specificity of both diagnostic tests after 15 minutes and 30 minutes respectively. Neither the Tauns NP test nor the AVC Flu A/B test gave any false-positive results with influenza B-infected samples.

TABLE 8I

Results after 15 minutes (2-fold dilution)

| Sample ID | Dilution factor | Sample status | Tauns NP test | AVC NS1 test |
|---|---|---|---|---|
| 1655 | ½ | B-positive | – | – |
| 3614 | ½ | B-positive | – | – |
| 4924 | ½ | B-positive | – | – |
| 7145 | ½ | B-positive | – | – |
| 7815 | ½ | B-positive | – | – |
| 97 | ½ | negative | – | – |
| 99 | ½ | negative | – | – |
| 100 | ½ | negative | – | – |
| 108 | ½ | negative | – | – |
| 103 | ½ | negative | – | – |
| Flu A Specificity: | | | 100% | 100% |

TABLE 8J

Results after 30 minutes (2-fold dilution)

| Sample ID | Dilution factor | Sample status | Tauns NP test | AVC NS1 test |
|---|---|---|---|---|
| 1655 | ½ | B-positive | – | – |
| 3614 | ½ | B-positive | – | – |
| 4924 | ½ | B-positive | – | – |
| 7145 | ½ | B-positive | – | – |
| 7815 | ½ | B-positive | – | – |
| 97 | ½ | negative | – | – |
| 99 | ½ | negative | – | – |
| 100 | ½ | negative | – | – |
| 108 | ½ | negative | – | – |
| 103 | ½ | negative | – | – |
| Flu A Specificity | | | 100% | 100% |

Example 7

Detection of Influenza B in Clinical Samples Using Antibody-Based Assays for Both NS1 and NP The AVC Flu A/B test was modified to detect influenza B by using a capture antibody that was pan-specific for influenza B NS1 and a second detection antibody that was similarly pan-specific for influenza B NS1 (hereafter called the "AVC Flu A/B" test). The sensitivity of the influenza B-specific AVC Flu A/B test was compared with sensitivity of the Tauns assay for the NP antigen of influenza B. The sample test conditions and final buffer compositions were as described in Example 6.

Tables 9A and 9B compare the sensitivity of both diagnostic tests after 15 minutes and 30 minutes respectively.

TABLE 9A

Results for influenza B samples after 15 minutes

| Sample ID | Dilution factor | Sample status | Tauns NP test | AVC NS1 test |
|---|---|---|---|---|
| 1655 | ½ | B-positive | – | + |
| 3614 | ½ | B-positive | – | – |
| 4924 | ½ | B-positive | + | – |
| 7145 | ½ | B-positive | + | + |
| 7815 | ½ | B-positive | + | + |
| 97 | ½ | negative | – | – |
| 99 | ½ | negative | – | – |
| 100 | ½ | negative | – | – |
| 108 | ½ | negative | – | – |
| 103 | ½ | negative | – | – |
| Flu B Sensitivity: | | | 60% | 60% |
| Flu B Specificity: | | | 100% | 100% |

TABLE 9B

Results for influenza B samples after 30 minutes

| Sample ID | Dilution factor | Sample status | Tauns NP test | AVC NS1 test |
|---|---|---|---|---|
| 1655 | ½ | B-positive | – | + |
| 3614 | ½ | B-positive | – | – |
| 4924 | ½ | B-positive | + | – |
| 7145 | ½ | B-positive | + | + |
| 7815 | ½ | B-positive | + | + |
| 97 | ½ | negative | – | – |
| 99 | ½ | negative | – | – |
| 100 | ½ | negative | – | – |
| 108 | ½ | negative | – | – |
| 103 | ½ | negative | – | – |
| Flu B Sensitivity: | | | 60% | 60% |
| Flu B Specificity: | | | 100% | 100% |

As seen, the AVC Flu A/B Test based on NS1 and BL Tauns Test based on NP have comparable sensitivity for Influenza B. Because the NS1 assay could detect influenza B in some samples that showed negative for the presence of NP, and visa versa, a combined NS1/NP test has increased sensitivity.

Example 8

Disease Prognosis from Absolute and/or Relative Quantities of NS1 and NP

Figure 19:
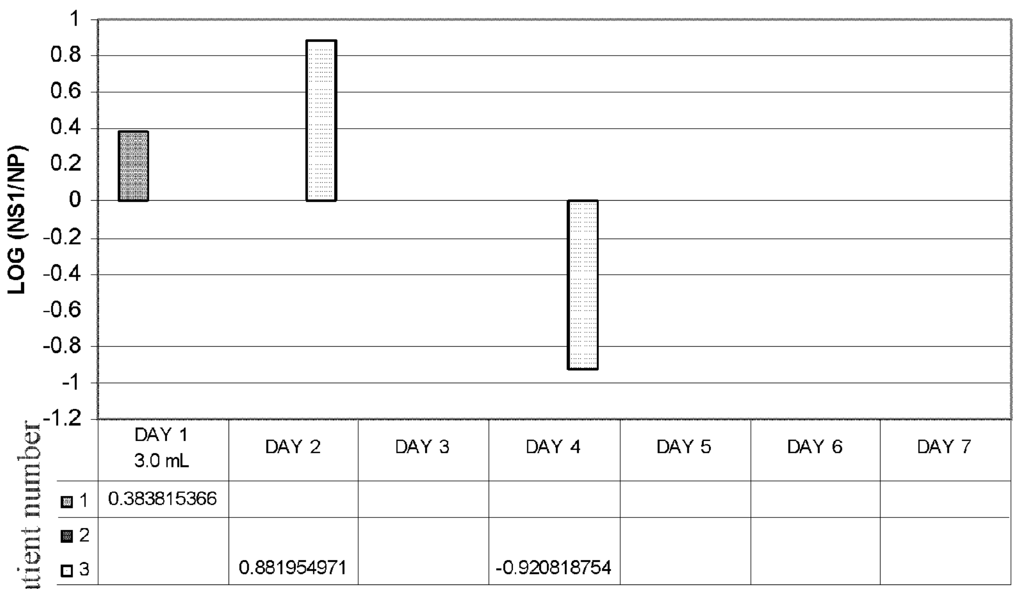
FIG. 19: Log ratio of NS1:NP over course of infection using throat samples from three patients.

The relative quantities of NS1 and NP were determined at various time points in infected subjects. A throat sample or a nasal sample obtained from individual suspected of having influenza was taken at different days (wherein day 1 represents the day of onset of at least one symptom of influenza, e.g., sore throat, sneezing, runny nose, fever, chills, tiredness, dry cough, headache, body aches and/or stomach symptoms such as nausea, vomiting and diarrhea). The swab was extracted in 3 ml of M4 viral transport media. The sample was tested using the AVC Flu A/B test (for NS1) and an AVC Flu A NP Test (an antibody-based test for influenza A NP). 67 μl of the sample was admixed with 331 μl AVC Flu A/B Buffer. The sample was tested as described in Example 4, and results read after 30 minutes. The test line intensity for both tests was quantified with an instrument, and the log(NS1_intensity/NP_intensity) was calculated. Results are shown in FIGS. 19 and 20. As seen, a higher NS1/NP ratio is observed at earlier stages of infection compared to later stages in both throat (FIG. 19) and nasal (FIG. 20) samples. In both cases, the log ratio went from positive to negative around the third day post infection. FIG. 21 gives CAMAG Absorbance Unit Values for AVC Flu A/B Tests (NS1) and AVC Flu A NP Tests of patients as a function of time.

Example 9

Figure 18:
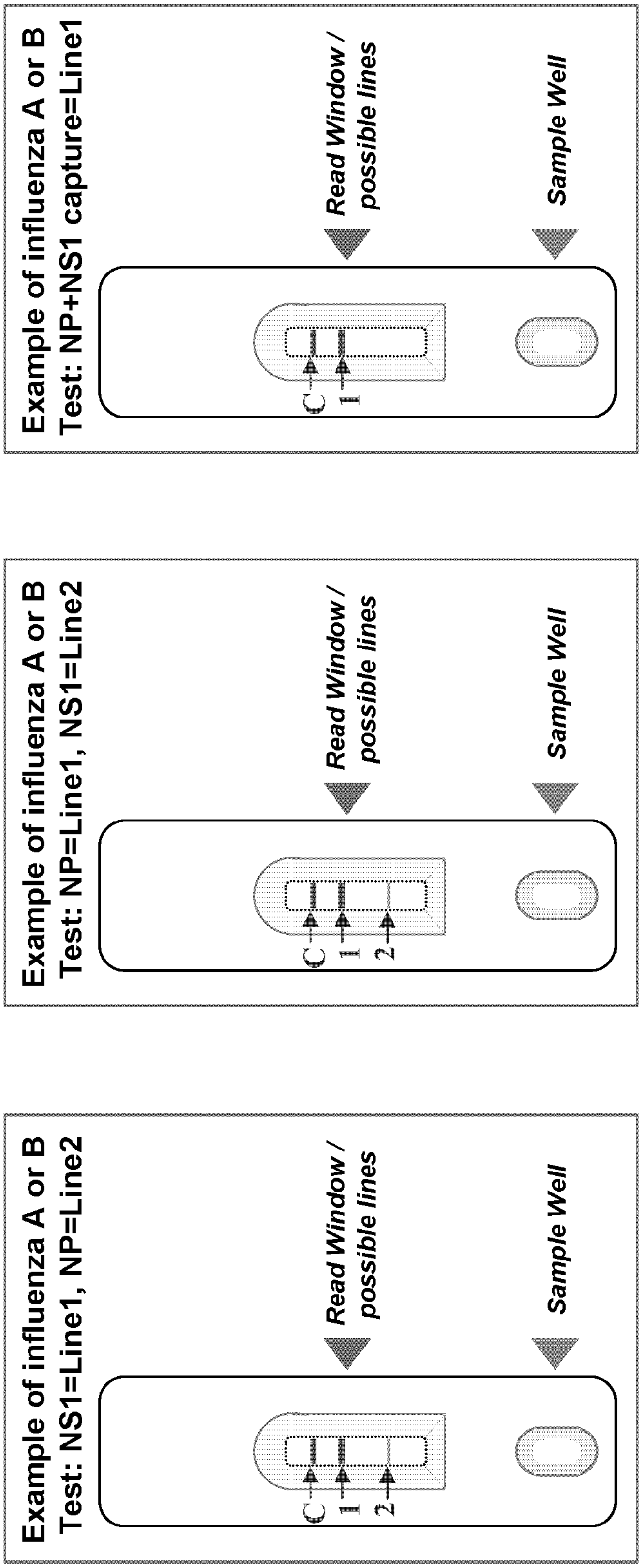
FIG. 18: Schematic of a NS1/NP lateral flow test format. The left and middle panels depict a format in which the NS1-capture agent and the NP-capture agent are deposited as separate lines, with the NS1 capture line situated between the NP capture line and the control line (left panel) or vice versa (middle panel). The right panel depicts a format in which the NS1-capture agent and the NP-capture agent are deposited together as a single line.

Performance of a Rapid Dual-Antigen (NS1 and NP) Diagnostic Test for Influenza a on Human Clinical Samples A rapid influenza A diagnostic test based on detection of the NS1 and NP antigens was evaluated using human clinical samples. The test was performed in a lateral flow assay format using different monoclonal antibodies as capture agent and detection agent. In the lateral flow format, the capture agent was deposited (immobilized) on a solid support, e.g., a nitrocellulose membrane, onto an area shaped as a thin stripe, called a "test line." Two different capture agent formats were evaluated. In one format, the NS1 and NP capture agents were each deposited onto separate test lines (hereafter, the "NS1 and NP" format). In the second format, both NS1 and NP capture agents were deposited onto the same test line (hereafter, the "NS1/NP" format). The assembled dipstick was enclosed in a cassette. The detection agent was a combination of gold conjugated anti-influenza A NS1 monoclonal antibodies as well as a gold-conjugated anti-influenza A NP monoclonal antibody. The different test formats for capture agent are shown schematically in FIG. 18. The second and third format were employed in this Example (FIG. 18, middle and right sections).

In further detail, 100 µl of a clinical sample was added to a tube with Lysis buffer (dried buffer), and after 5-10 minutes, 50 µl of Sample Buffer was added to the tube. The gold-mAb detection agents was added to the treated sample and 100 µl of the final sample was transferred with additives to the cassette well of the lateral flow device. Results were read at 30 minutes.

Samples collected were nasopharyngeal swabs extracted in 3 ml of BD Universal Transport Medium from symptomatic patients in the 2007-2008 Flu season in Northern California were analyzed by PCR (Prodessee RT-PCR assay) for presence or absence of Influenza A. Residual sample was stored frozen and subsequently analyzed by AVC using a prototype dual antigen assay. The dual-antigen assay independently detects NS1 and NP using a monoclonal antibody sandwich assay in a lateral flow strip format. Analysis of sixty Influenza A PCR-positive specimens and sixty PCR-negative specimens was undertaken to understand the relative performance for the two antigens (NS1 and NP).

Test Sensitivity:

Of the 60 PCR positive samples, 37 were positive for both antigens, 7 were positive for NS1 only, and an additional 3 for NP1 only. The two antigens are detected in many of the same Flu A positive samples (i.e. 37) but also each antigen is detected alone in a small but significant number (10) of Flu A positive samples not detected by the other. Thus the use of the two antigens significantly increases the detection of Flu A positive samples over the use of either antigen alone. As summarized in Table 10, the sensitivity of the dual-antigen assay in both the two-line "NS1 or NP" test format and the single-line "NS1/NP" test format is 78%, which is significantly improved over the NS1-alone sensitivity of 73% or the NP-alone sensitivity of 67%.

Test Specificity:

Of the 60 PCR negative samples, 1 was a false positive for both antigens, and three were false positives for the NP antigen alone. This leads to a specificity of 98% for NS1 alone, 93% for NP alone, as well as 93% specificity for "NS1 or NP" and "NS1/NP" test formats.

TABLE 10

AVC Flu A Test Results measuring 60 Influenza A positive samples (PCR method used as reference)

| Test Lines | 30' Test Counts |
|---|---|
| NS1+NP+ | 37 |
| NS1+NP− | 7 |
| NS1−NP+ | 3 |
| NS1−NS1− | 13 |
| (NS1/NP)+ | 47 |

| | NS1 | NP | NS1 or NP | NS1/NP |
|---|---|---|---|---|
| % Sensitivity, 30' | 73 | 67 | 78 | 78 |

AVC Flu A Test Results measuring 60 Influenza A negative samples (PCR method used as reference)

| Test Lines | 30' Test Counts |
|---|---|
| NS1+NP+ | 1 |
| NS1+NP− | 0 |
| NS1−NP+ | 3 |
| NS1−NP− | 56 |
| (NS1/NP)− | 56 |

| | NS1 | NP | NS1 or NP | NS1/NP |
|---|---|---|---|---|
| % Specificity, 30' | 98 | 93 | 93 | 93 |

Example 10

Comparison of a Lateral Flow Assay for Influenza B NS1 with an Immunoassay for NP on Human Clinical Samples A rapid influenza B diagnostic test based on detection of the influenza B NS1 was devised and its performance evaluated in comparison with a commercially available Influenza A/B rapid test on human B-positive and negative clinical samples. An influenza B NS1 capture monoclonal antibody was striped in a nitrocellulose membrane. The detection system comprised a combination of two gold conjugated anti-influenza B NS1 monoclonal antibodies. Samples were collected and the assay performed as in Example 9. Influenza B positive samples collected were nasopharyngeal swabs extracted in 3 ml of BD Universal Transport Medium from symptomatic patients in the 2007-2008 Flu season in Northern California which tested positive by PCR (Prodessee RT-PCR assay) for presence of Influenza B. Residual sample was stored frozen and analyzed by the influenza B NS1 and the commercially available influenza A/B NP test. Results were read at 15 and 30 minutes.

TABLE 11a

Results read at 15 minutes

| Sample ID | Dilution factor | Sample status | NP test | AVC NS1 test |
|---|---|---|---|---|
| 1655 | ½ | B-positive | − | + |
| 3614 | ½ | B-positive | − | − |
| 4924 | ½ | B-positive | + | − |
| 7145 | ½ | B-positive | + | + |
| 7815 | ½ | B-positive | + | + |
| 97 | ½ | negative | − | − |
| 99 | ½ | negative | − | − |
| 100 | ½ | negative | − | − |

TABLE 11a-continued

| Results read at 15 minutes | | | | |
|---|---|---|---|---|
| Sample ID | Dilution factor | Sample status | NP test | AVC NS1 test |
| 108 | ½ | negative | – | – |
| 103 | ½ | negative | – | – |
| Flu B Sensitivity: | | | 60% | 60% |
| Flu B Specificity: | | | 100% | 100% |

TABLE 11b

| results read at 30 minutes | | | | |
|---|---|---|---|---|
| Sample ID | Dilution factor | Sample status | NP test | AVC NS1 test |
| 1655 | ½ | B-positive | – | + |
| 3614 | ½ | B-positive | – | – |
| 4924 | ½ | B-positive | + | – |
| 7145 | ½ | B-positive | + | + |
| 7815 | ½ | B-positive | + | + |
| 97 | ½ | negative | – | – |
| 99 | ½ | negative | – | – |
| 100 | ½ | negative | – | – |
| 108 | ½ | negative | – | – |
| 103 | ½ | negative | – | – |
| Flu B Sensitivity: | | | 60% | 60% |
| Flu B Specificity: | | | 100% | 100% |

Test Sensitivity

Of the five influenza B positive samples, 2 were positive for both antigens, one was positive for NS1 alone, one was positive for NP alone, and 2 were negative for NS1 and two were negative for NP. Each antigen is detected alone in one Flu B positive sample not detected by the other. The sensitivity based on NS1 alone or NP alone was 60%. However, the use of the two antigens increases the sensitivity from 60% to 80%. This confirmed that combining the NS1 and NP markers can increase the sensitivity of the diagnostic relative to the individual antigens.

Test Specificity

The overall specificity was 100% for the NS1 and the NP markers (n=5 samples).

Example 11

Performance of a Rapid Dual-Antigen (NS1 and NP) Diagnostic Test for Influenza B on Human Clinical Samples A dual-antigen test that simultaneously assayed a single sample for NS1 and NP protein of influenza B was designed, similar to that of Example 9. Again, two formats were used. In one format, the NS1 and NP test lines were separated (designated the "NS1 or NP" test), as shown in the middle section of FIG. 18. In a second format, the anti-NS1 and anti-NP antibody captures were deposited together in one line (NS1/NP), as shown in the right section of FIG. 18. The NS1 capture test line contained anti-influenza B NS1 monoclonal antibody striped in a nitrocellulose membrane. The NP capture line contained an anti-influenza B NP monoclonal antibody striped in a nitrocellulose membrane. The membrane was enclosed in a cassette. The detection agent was a combination of gold conjugated anti-influenza B NS1 monoclonal antibodies as well as a gold-conjugated anti-influenza B NP monoclonal antibody.

Figure 22:
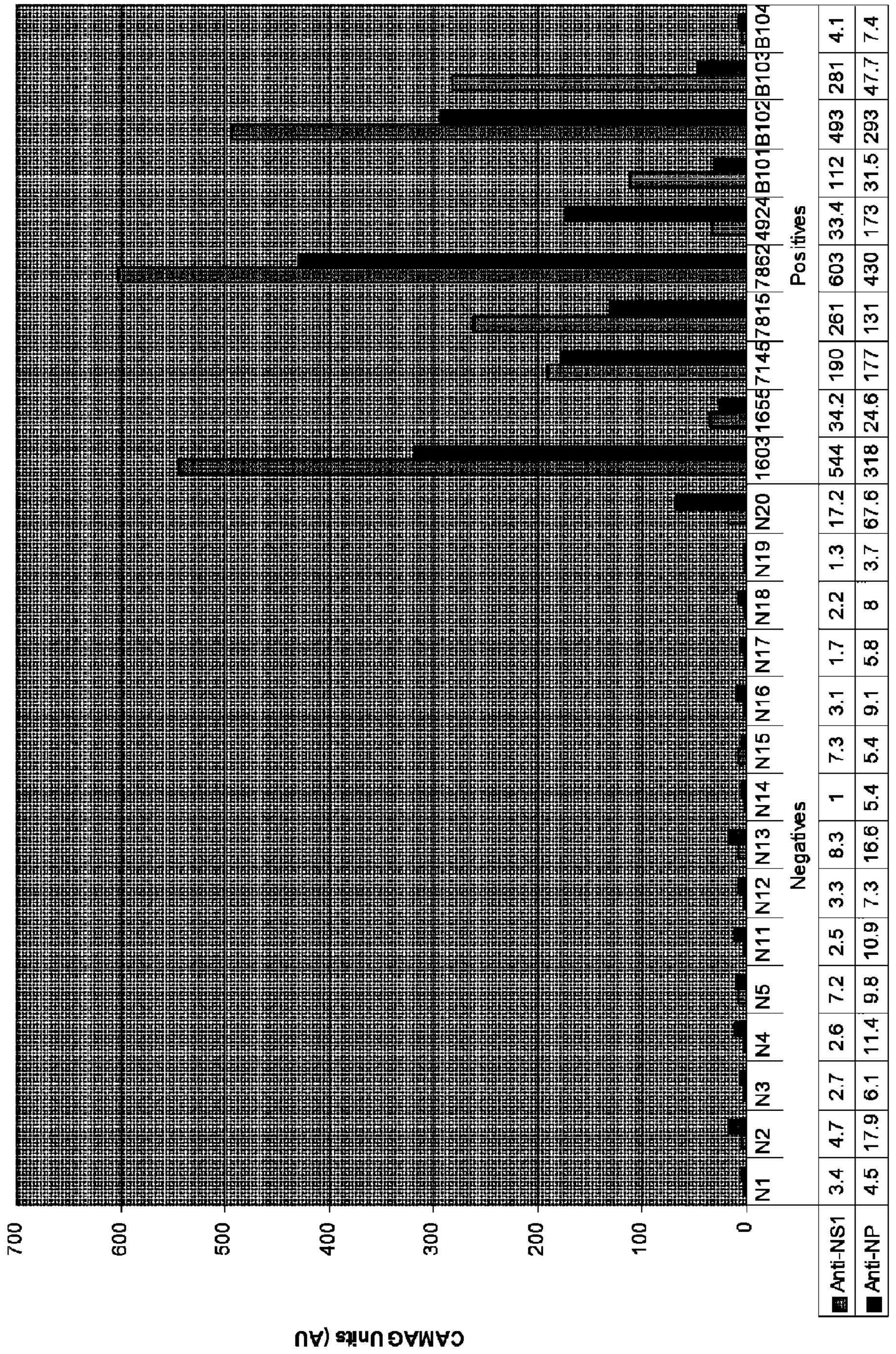
FIG. 22: Summary of influenza B virus detection in human clinical nasal samples in a "double-line" lateral flow format.

Samples were collected and the assay performed as in Example 9. Results are shown in FIG. 22.

Relative NS1/NP Test Sensitivity:

Of the 10 PCR positive samples measured, 9 were positive for both antigens. Two of the specimens had similar NS1 and NP line intensities, six of the samples had NS1 line intensities greater than NP line intensities, and one sample had an NP line intensity greater than NS1. These results demonstrate that a combined assay for both NS1 and NP influenza B antigen has improved performance over the NS1 or NP test alone.

Flu B Negative Sample Measurements:

Most of the influenza-negative samples were visually negative at the NS1 and NP lines. Samples N13 and N20 had a false positive line at the visible threshold for NP and NS1 respectively. Sample N20 had a readily visible line at the NP line.

These results indicate that an immuno-diagnostic assay detecting the NS1 and NP antigens from influenza A (or B) were superior to a test detecting only one of the antigens (either NS1 or NP alone). For example, the results presented show that the signal strength for NS1 levels in some cases exceeded NP levels, and vice-versa. Thus, samples with overall low viral load favored the dual antigen test in multiple instances, for example where NS1 levels were detectable and NP levels were not, and vice versa. In addition, in some cases where both NS1 and NP levels were so low that neither generated a detectable signal within the detection limit of an assay for either antigen alone, the combined signal strength of both antigens in a single-line NS1/NP format resulted in a combined detection signal above the detection threshold.

Even in cases where NS1 and NP levels were both detectable, the dual antigen test had the additional advantage of allowing the determination of disease stage based on the NS1/NP ratio where the NS1 and NP test lines were separated.

As used in the description of the invention and the appended claims, the singular forms "a", "an" and "the" are intended to indicate the plural forms as well as the single form. The term "about," as used herein when referring to a measurable value such as an amount of a compound, dose, time, temperature, and the like, is meant to encompass variations of 20%, 10%, 5%, 1%, 0.5%, or even 0.1% of the specified amount. In addition, if any aspect which is indicated to be optional (e.g., through terminology such as "optionally" or "can" or "for example," then variations which explicitly exclude the optional feature are also contemplated.

The disclosures of all United States patent references, other publications, GenBank citations and the like cited herein are hereby incorporated by reference to the extent they are consistent with the disclosures herein. If a Genbank citation is associated with more than variant of a sequence, the variant of the sequence assigned the GenBank ID No. at the filing date of the application or priority application (if disclosed in the priority application) is meant.

What is claimed is:

1. A method of assessing an influenza virus infection, comprising:

(a) determining an amount of influenza virus non-structural 1 (NS1) protein in a test sample from a subject, (b) determining an amount of influenza virus nucleoprotein (NP) protein in the test sample, and (c) comparing the amount of NS1 protein to the amount of NP protein, wherein a ratio of the amount of NS1 protein to the amount of NP protein indicates a prognosis of the subject, and wherein the method is performed at two or more different timepoints, wherein changes in the ratio with time provide an indication of the course of infection.

2. A method of assessing an influenza virus infection, comprising:

(a) determining an amount of influenza virus non-structural 1 (NS1) protein in a test sample from a subject, (b) determining an amount of influenza virus nucleoprotein (NP) protein in the test sample, (c) comparing the amount of NS1 protein to the amount of NP protein, and (d) comparing the amount of NS1 protein and the amount of NP protein in the test sample, or the ratio of NS1 protein to NP protein in the test sample, to that measured in a control sample, wherein a ratio of the amount of NS1 protein to the amount of NP protein in the test sample indicates a prognosis of the subject.

3. The method of claim 1 or 2, wherein the prognosis includes stage of infection, progress of infection over time, severity of infection, outcome of infection under a treatment of interest, or amenability to treatment.

4. The method of claim 1 or 2, further comprising determining the stage of infection from the ratio, a relatively higher ratio indicating a relatively earlier stage of infection.

5. The method of claim 4 further comprising selecting a treatment regime from the ratio, a relatively high ratio favoring administering an anti-viral agent that inhibits viral reproduction or isolating the patient.

6. The method of claim 2, wherein the method is performed at two or more different timepoints, wherein changes in the ratio with time provide an indication of the course of infection.

7. The method of claim 1 or 2, wherein determining the amount of NS1 protein or the amount of NP Protein comprises:

contacting the sample with at least one antibody that specifically binds to NS1 or NP protein, and determining the amount of a complex of the at least one antibody specifically bound to the NS1 or NP protein, wherein the amount of the complex is an indication of the amount of NS1 protein or the amount of NP protein in the sample.

8. The method of claim 1 or 2, wherein the amount of NS1 and NP protein is determined by:

contacting the sample with first and second binding agents that bind to different epitopes of NS1 protein, and with first and second binding agents that bind to different epitopes of NP protein; and determining the amount of NS1 and NP protein in the sample, wherein the first and second binding agents are selected from an agent that is pan specific for NS1 or NP protein; an antibody; and a Post synaptic density protein 95 (PSD95), Drosophila discs large tumor suppressor (DlgA), or Zonula occludens 1 protein (ZO1) (PDZ) polypeptide that can bind specifically to NS1 or NP protein.

9. The method of claim 8, wherein, when the first or second binding agent is a pan-specific antibody for NS1 protein, the antibody binds to an epitope within residues selected from the group consisting of 8-21, 9-20, 29-38 or 45-49 of NS1 protein.

10. The method of claim 1 or 2, wherein the determining is performed using a lateral flow format.

11. The method of claim 1 or 2, wherein the test sample is a nasal or throat sample.

12. The method of claim 1 or 2, wherein the amount of NS1 protein is determined using at least one Post synaptic density protein 95 (PSD95), Drosophila discs large tumor suppressor (DlgA), or Zonula occludens 1 protein (ZO1) (PDZ) polypeptide that binds specifically to NS1.

13. The method of claim 12, wherein the at least one PDZ polypeptide that binds specifically to NS1 protein is selected from the group consisting of post synaptic density protein 95 (PSD95) domain 2, InaD like (1NADL) domain 8, and a combination thereof.

14. The method of claim 2, further comprising detecting the amount of NS1 protein using at least one NS1 antibody.

15. The method of claim 1 or 2, wherein the method is performed on samples from a test subject and a control subject, the test subject being treated with a test agent, and the control subject being untreated with the test agent, and the method further comprises comparing the change in the NS1:NP ratio in the two subjects over time, wherein a quicker decrease in NS1:NP ratio over time in one or more test subjects kept in the presence of the test agent indicates that the test agent is effective in treating influenza during the early stages of infection.

16. The method of claim 1 or 2, wherein step (a) comprises contacting the sample with post synaptic density protein 95 (PSD95) and InaD like (INADL) polypeptides and the method further comprises determining relative binding of PSD95 and INADL polypeptides to NS1 protein in the sample and typing the influenza virus infection as pathogenic or nonpathogenic from the relative binding.

17. The method of claim 1 or 2, wherein step (a) or (b) comprises contacting the sample with first and second binding agents specific for NS1 or NP protein of influenza A and influenza B, the method further comprising determining relative binding of the first and second binding agents, and characterizing the influenza virus infection as A or B based on the relative binding.

18. The method of claim 1 or 2, wherein the amount of NS1 and NP protein or the NS1:NP ratio in the test sample is compared to that measured in a control sample.

19. The method of claim 18, where the control subject is at:

(i) an early stage of infection, infected within the last 72 hours, or (ii) a late stage of infection, infected at least 1 week ago.

20. The method of claim 18, wherein the amount of NS1 and NP protein or the NS1:NP ratio in the test sample is compared to that measured in multiple control samples taken at different timepoints of an influenza virus infection in a control subject.

21. The method of claim 18, wherein the amount of NS1 and NP protein in the test sample and control sample is measured by contacting the test sample and control sample with the same solution of an NS1-binding agent and/or an NP-binding agent.

22. The method of claim 18, wherein the amount of NS1 and NP protein in the test sample is measured using a lateral flow assay in which an NS1-capture agent and an NP-capture agent are both immobilized within the same area of a solid support.

* * * * *